US011248026B2

(12) United States Patent
Anderson et al.

(10) Patent No.: US 11,248,026 B2
(45) Date of Patent: Feb. 15, 2022

(54) COMPOSITIONS AND METHODS FOR TREATMENT OF CYTOMEGALOVIRUS

(71) Applicants: Variation Biotechnologies Inc., Ottawa (CA); Sorbonne Université, Paris (FR)

(72) Inventors: David E. Anderson, Newton, MA (US); Anne-Catherine Fluckiger, Saint Genis les Ollières (FR); David Klatzmann, Paris (FR); Charlotte Dalba-Fribert, Gothenburg (SE)

(73) Assignees: Variation Biotechnologies Inc., Ottawa (CA); Sorbonne Université, Paris (FR)

( * ) Notice: Subject to any disclaimer, the term of this patent is extended or adjusted under 35 U.S.C. 154(b) by 0 days.

(21) Appl. No.: 15/683,355

(22) Filed: Aug. 22, 2017

(65) Prior Publication Data

US 2017/0349634 A1   Dec. 7, 2017

Related U.S. Application Data

(63) Continuation of application No. 14/357,423, filed as application No. PCT/IB2012/002854 on Nov. 9, 2012.

(Continued)

(51) Int. Cl.
*A61K 39/12*   (2006.01)
*A61P 31/22*   (2006.01)
(Continued)

(52) U.S. Cl.
CPC .......... *C07K 14/005* (2013.01); *A61K 39/245* (2013.01); *A61K 2039/5258* (2013.01);
(Continued)

(58) Field of Classification Search
None
See application file for complete search history.

(56) References Cited

U.S. PATENT DOCUMENTS 4,694,074 A   9/1987   Uemura et al.
6,440,730 B1   8/2002   Von Laer et al.
(Continued)

FOREIGN PATENT DOCUMENTS

RU   2290204 C1   12/2006
WO   WO-89/07143 A1   8/1989
(Continued)

OTHER PUBLICATIONS

Baker et al., Protein Structure Predication and Structural Genomics, Science (2001) vol. 294, No. 5540, pp. 93-96 (Year: 2001).*
(Continued)

*Primary Examiner* — Michelle S Horning
(74) *Attorney, Agent, or Firm* — Choate, Hall & Stewart LLP; Rolando Medina

(57) ABSTRACT

The present disclosure provides compositions and methods useful for treating HCMV infection. As described herein, the compositions and methods are based on development of immunogenic compositions that include virus-like particles (VLPs) which comprise one or more Moloney Murine leukemia virus (MMLV) core proteins and include one or more HCMV epitopes, such as, for example, from HCMV envelope glycoproteins gB and/or gH and/or tegument protein pp65. Among other things, the present invention encompasses the recognition that a combination of antigens (e.g., envelope glycoproteins and structural proteins) can lead to beneficial immune responses, for example that include both a humoral response (e.g., production of neutralizing antibodies) and a cellular response (e.g., T-cell activation).

20 Claims, 17 Drawing Sheets

Specification includes a Sequence Listing.

Related U.S. Application Data

(60) Provisional application No. 61/654,157, filed on Jun. 1, 2012, provisional application No. 61/558,800, filed on Nov. 11, 2011.

(51) Int. Cl.
  *C07K 14/005* (2006.01)
  *A61K 39/245* (2006.01)
  *A61K 39/00* (2006.01)

(52) U.S. Cl.
  CPC ...... *A61K 2039/70* (2013.01); *C07K 2319/00* (2013.01); *C07K 2319/03* (2013.01); *C12N 2710/16134* (2013.01); *C12N 2740/13023* (2013.01); *C12N 2760/20234* (2013.01)

(56) References Cited

U.S. PATENT DOCUMENTS

| | | | |
|---|---|---|---|
| 8,673,612 | B2 | 3/2014 | Klatzmann et al. |
| 9,777,043 | B2 * | 10/2017 | Anderson ............ C07K 14/005 |
| 2004/0071661 | A1 | 4/2004 | Klatzmann et al. |
| 2006/0216702 | A1 | 9/2006 | Compans et al. |
| 2009/0123494 | A1 | 5/2009 | Staplin et al. |
| 2010/0047266 | A1 | 2/2010 | Haynes |
| 2011/0250675 | A1 | 10/2011 | Bennett |
| 2014/0308308 | A1 | 10/2014 | Anderson et al. |

FOREIGN PATENT DOCUMENTS

| | | |
|---|---|---|
| WO | WO-2008/094200 A2 | 8/2008 |
| WO | WO-2009/120883 A2 | 10/2009 |
| WO | WO-2010/128338 A2 | 11/2010 |
| WO | WO-2013/068847 A2 | 5/2013 |

OTHER PUBLICATIONS

Attwood, T. The Babel of Bioinformatics, Science (2000) vol. 290, No. 5491, pp. 471-473 (Year: 2000).*

Broer, R. et al., Important Role for the Transmembrane Domain of Severe Acute Respiratory Syndrome Coronavirus Spike Protein during Entry, Journal of Virology, 80(3):1302-1310 (2006).

Garrone, P. et al., A Prime-Boost Strategy Using Virus-Like Particles Pseudotyped for HCV Proteins Triggers Broadly Neutralizing Antibodies in Macaques, Sci. Transl. Med., 3(94): 94ra71 1-9 (2011).

Garry, C.E. and Garry, R.F., Proteomics computational analyses suggest that baculovirus GP64 superfamily proteins are class III penetrenes, Virology Journal 5(28): 1-11 (2008).

Gonczol, E. and Plotkin, S., Development of a cytomegalovirus vaccine: lessons from recent clinical trials, Expert Opinion on Biological Therapy, 1(3): 401-412 (2001).

International Search Report for PCT/IB2012/002854, 6 pages (dated Apr. 15, 2013).

Kirchmeier, M. et al., Enveloped virus-like particle expression of human Cytomegalovirus Glycoprotein B Antigen induces antibodies with potent and broad neutralizing activity, Clinical and Vaccine Immunology, 21(2): 174-180 (2014).

Lagging, L.M. et al., Functional Role of Hepatitis C Virus Chimeric Glycoproteins in the Infectivity of Pseudotyped Virus, Journal of Virology, 72(5): 3539-3546 (1998).

UniProtKB/Swiss-Prot: B9VXM1 (2009) HCMV sequence.
UniProtKB/Swiss-Prot: B9VXM4 (2009) HCMV sequence.
UniProtKB/Swiss-Prot: B9VXP1 (2009) HCMV sequence.
UniProtKB/Swiss-Prot: P03332 (1986) MLV gag.
UniProtKB/Swiss-Prot: Q86131 (1996) VSV-G.

Written Opinion for PCT/IB2012/002854, 10 pages (dated Apr. 15, 2013).

Baraniak, I. et al, Epitope-Specific Humoral Responses to Human Cytomegalovirus Glycoprotein-B Vaccine With MF59: Anti-AD2 Levels Correlate With Protection From Viremia, The Journal of Infectious Diseases, 217(12): 1907-1917 (2018).

GenBank Accession No. ACM48044.1, envelope glycoprotein B [Human betaherpesvirus 5], published on Dec. 17, 2009), retrieved from <<http://www.ncbi.nlm.nih.gov/protein/222354496>>, accessed on Oct. 2, 2018.

GenBank Accession No. ADX53329.1, G protein precursor [Vesicular stomatitis Indiana virus], published on Jun. 21, 2011, retrieved from <<https://www.ncbi.nlm.nih.gov/protein/ADX53329>>, accessed on Oct. 2, 2018.

Baraniak, I. et al., Seronegative patients vaccinated with cytomegalovirus gB-MF59 vaccine have evidence of neutralising antibody responses against gB early post-transplantation, EbioMedicine, 50:45-54 (2019).

GenBank Accession No. ACM48061.1, tegument protein pp65 [Human herpesvirus 5], Sep. 17, 2009.

Sampson, J. H. et al., Brain immunology and immunotherapy in brain tumours, Nat Rev Cancer, 20(1):12-25 (2020).

Berencsi, K. et al., A Canarypox Vector-Expressing Cytomegalovir (CMV) Phosphoprotein 65 Induces Long-Lasting Cytotoxic T Cell Responses in Human CMV-Seronegative Subjects, Journal of Infectious Diseases, 183(8):1171-1179 (2001).

Bernstein, D. et al., Effect of previous or simultaneous immunization with canarypox expressing cytomegalovirus (CMV) glycoprotein B (GB) on response to subunit GB vaccine plus MF59 in healthy CMV-seronegative adults, Journal of Infectious Diseases, 185(5):686-690 (2002).

* cited by examiner 10L gB-G AEX

B 10L gB-G Diafiltration Retentate Flowthrough (6.5x conc)

A

SEQUENCE LISTING

```
<160> NUMBER OF SEQ ID NOS: 22

<210> SEQ ID NO 1
<211> LENGTH: 538
<212> TYPE: PRT
<213> ORGANISM: Murine leukemia virus
<220> FEATURE:
<221> NAME/KEY: MISC_FEATURE
<222> LOCATION: (1)..(538)
<223> OTHER INFORMATION: MMLV Gag Amino Acid Sequence

<400> SEQUENCE: 1

Met Gly Gln Thr Val Thr Thr Pro Leu Ser Leu Thr Leu Gly His Trp
1               5                   10                  15

Lys Asp Val Glu Arg Ile Ala His Asn Gln Ser Val Asp Val Lys Lys
            20                  25                  30

Arg Arg Trp Val Thr Phe Cys Ser Ala Glu Trp Pro Thr Phe Asn Val
        35                  40                  45

Gly Trp Pro Arg Asp Gly Thr Phe Asn Arg Asp Leu Ile Thr Gln Val
    50                  55                  60

Lys Ile Lys Val Phe Ser Pro Gly Pro His Gly His Pro Asp Gln Val
65                  70                  75                  80

Pro Tyr Ile Val Thr Trp Glu Ala Leu Ala Phe Asp Pro Pro Trp
                85                  90                  95

Val Lys Pro Phe Val His Pro Lys Pro Pro Pro Pro Leu Pro Pro Ser
```

-continued

```
            100                 105                 110
Ala Pro Ser Leu Pro Leu Glu Pro Pro Arg Ser Thr Pro Arg Ser
            115                 120                 125
Ser Leu Tyr Pro Ala Leu Thr Pro Ser Leu Gly Ala Lys Pro Lys Pro
        130                 135                 140
Gln Val Leu Ser Asp Ser Gly Gly Pro Leu Ile Asp Leu Leu Thr Glu
145                 150                 155                 160
Asp Pro Pro Tyr Arg Asp Pro Arg Pro Pro Ser Asp Arg Asp
                165                 170                 175
Gly Asn Gly Gly Glu Ala Thr Pro Ala Gly Glu Ala Pro Asp Pro Ser
            180                 185                 190
Pro Met Ala Ser Arg Leu Arg Gly Arg Glu Pro Pro Val Ala Asp
        195                 200                 205
Ser Thr Thr Ser Gln Ala Phe Pro Leu Arg Ala Gly Gly Asn Gly Gln
    210                 215                 220
Leu Gln Tyr Trp Pro Phe Ser Ser Ser Asp Leu Tyr Asn Trp Lys Asn
225                 230                 235                 240
Asn Asn Pro Ser Phe Ser Glu Asp Pro Gly Lys Leu Thr Ala Leu Ile
                245                 250                 255
Glu Ser Val Leu Ile Thr His Gln Pro Thr Trp Asp Asp Cys Gln Gln
            260                 265                 270
Leu Leu Gly Thr Leu Leu Thr Gly Glu Glu Lys Gln Arg Val Leu Leu
        275                 280                 285
Glu Ala Arg Lys Ala Val Arg Gly Asp Asp Gly Arg Pro Thr Gln Leu
    290                 295                 300
Pro Asn Glu Val Asp Ala Ala Phe Pro Leu Glu Arg Pro Asp Trp Asp
305                 310                 315                 320
Tyr Thr Thr Gln Ala Gly Arg Asn His Leu Val His Tyr Arg Gln Leu
                325                 330                 335
Leu Leu Ala Gly Leu Gln Asn Ala Gly Arg Ser Pro Thr Asn Leu Ala
            340                 345                 350
Lys Val Lys Gly Ile Thr Gln Gly Pro Asn Glu Ser Pro Ser Ala Phe
        355                 360                 365
Leu Glu Arg Leu Lys Glu Ala Tyr Arg Arg Tyr Thr Pro Tyr Asp Pro
    370                 375                 380
Glu Asp Pro Gly Gln Glu Thr Asn Val Ser Met Ser Phe Ile Trp Gln
385                 390                 395                 400
Ser Ala Pro Asp Ile Gly Arg Lys Leu Glu Arg Leu Glu Asp Leu Lys
                405                 410                 415
Asn Lys Thr Leu Gly Asp Leu Val Arg Glu Ala Glu Lys Ile Phe Asn
            420                 425                 430
Lys Arg Glu Thr Pro Glu Glu Arg Glu Arg Ile Arg Arg Glu Thr
        435                 440                 445
Glu Glu Lys Glu Glu Arg Arg Thr Glu Asp Glu Gln Lys Glu Lys
    450                 455                 460
Glu Arg Asp Arg Arg Arg His Arg Glu Met Ser Lys Leu Leu Ala Thr
465                 470                 475                 480
Val Val Ser Gly Gln Lys Gln Asp Arg Gln Gly Gly Glu Arg Arg
                485                 490                 495
Ser Gln Leu Asp Arg Asp Gln Cys Ala Tyr Cys Lys Glu Lys Gly His
            500                 505                 510
Trp Ala Lys Asp Cys Pro Lys Lys Pro Arg Gly Pro Arg Gly Pro Arg
        515                 520                 525
```

```
Pro Gln Thr Ser Leu Leu Thr Leu Asp Asp
    530                 535

<210> SEQ ID NO 2
<211> LENGTH: 1614
<212> TYPE: DNA
<213> ORGANISM: Murine leukemia virus
<220> FEATURE:
<221> NAME/KEY: misc_feature
<222> LOCATION: (1)..(1614)
<223> OTHER INFORMATION: MMLV Gag Nucleotide Sequence

<400> SEQUENCE: 2
atgggccaga ctgttaccac tcccttaagt ttgaccttag gtcactggaa agatgtcgag      60
cggatcgctc acaaccagtc ggtagatgtc aagaagagac gttgggttac cttctgctct     120
gcagaatggc caacctttaa cgtcggatgg ccgcgagacg gcacctttaa ccgagacctc     180
atcacccagg ttaagatcaa ggtcttttca cctggcccgc atggacaccc agaccaggtc     240
ccctacatcg tgacctggga agccttggct tttgaccccc ctccctgggt caagcccttt     300
gtacacccta agcctccgcc tcctcttcct ccatccgccc cgtctctccc ccttgaacct     360
cctcgttcga ccccgcctcg atcctccctt tatccagccc tcactccttc tctaggcgcc     420
aaacctaaac ctcaagttct ttctgacagt gggggccgc tcatcgacct acttacagaa      480
gaccccccgc cttatagggc cccaagacca cccccttccg acaggacgg aaatggtgga      540 gaagcgaccc ctgcgggaga ggcaccggac ccctccccaa tggcatctcg cctacgtggg     600
agacgggagc cccctgtggc cgactccact acctcgcagg cattcccccct ccgcgcagga     660 ggaaacggac agcttcaata ctggccgttc tcctcttctg acctttacaa ctggaaaaat     720 aataacccctt ctttttctga agatccaggt aaactgacag ctctgatcga gtctgttctc     780
atcacccatc agcccacctg gacgactgt cagcagctgt tggggactct gctgaccgga     840
gaagaaaaac aacgggtgct cttagaggct agaaaggcgg tgcggggcga tgatgggcgc     900
cccactcaac tgcccaatga agtcgatgcc gcttttcccc tcgagcgccc agactgggat     960
tacaccaccc aggcaggtag gaaccaccta gtccactatc gccagttgct cctagcgggt    1020
ctccaaaacg cgggcagaag ccccaccaat ttggccaagg taaaaggaat aacacaaggg    1080
cccaatgagt ctccctcggc cttcctagag agacttaagg aagcctatcg caggtacact    1140
ccttatgacc ctgaggaccc agggcaagaa actaatgtgt ctatgtcttt catttggcag    1200
tctgccccag acattgggag aaagttagag aggttagaag atttaaaaaa caagacgctt    1260
ggagatttgg ttagagaggc agaaaagatc tttaataaac gagaaacccc ggaagaaaga    1320
gaggaacgta tcaggagaga acagaggaa aagaagaac gccgtaggac agaggatgag    1380
cagaaagaga agaaagaga tcgtaggaga catagagaga tgagcaagct attggccact    1440
gtcgttagtg acagaaaca ggatagacag ggagagaac gaaggaggtc ccaactcgat    1500
cgcgaccagt gtgcctactg caaagaaag gggcactggg ctaaagattg tcccaagaaa    1560
ccacgaggac ctcggggacc aagaccccag acctccctcc tgaccctaga tgac         1614

<210> SEQ ID NO 3
<211> LENGTH: 1614
<212> TYPE: DNA
<213> ORGANISM: Murine leukemia virus
<220> FEATURE:
<221> NAME/KEY: misc_feature
<222> LOCATION: (1)..(1614)
<223> OTHER INFORMATION: Codon Optimized MMLV Gag Nucleotide Sequence
```

-continued

<400> SEQUENCE: 3

| | |
|---|---|
| atgggacaga cagtcactac acccctgagc ctgacactgg gacattggaa agacgtggag | 60 |
| aggattgcac ataaccagag cgtggacgtg aagaaacgga gatgggtcac cttttgctcc | 120 |
| gccgagtggc caacattcaa tgtgggatgg ccccgagatg gcaccttcaa ccgggacctg | 180 |
| atcactcagg tgaagatcaa ggtcttctct ccaggacccc acggccatcc agatcaggtg | 240 |
| ccctacatcg tcacctggga ggctctggca tttgaccccc ctccatgggt gaagcctttc | 300 |
| gtccacccaa aaccacctcc accactgcct ccatctgccc ctagtctgcc actggaaccc | 360 |
| cctcggtcaa ccccacccag aagctccctg tatcccgcac tgacacctag cctgggggcc | 420 |
| aagcctaaac cacaggtgct gtctgatagt ggcgggcctc tgatcgatct gctgaccgag | 480 |
| gaccctccac cataccgcga cccacgacct ccaccaagcg accgggacgg aaacggagga | 540 |
| gaggctacac ccgcaggcga agcccccgat cctagtccaa tggcatcaag gctgcgcggg | 600 |
| aggcgcgaac tccagtggcc gactcaacc acaagccagg catttccact gagggccggg | 660 |
| ggaaatggac agctccagta ttggcccttc tctagttcag atctgtacaa ctggaagaac | 720 |
| aataacccta gcttcagcga ggacccaggc aaactgaccg ccctgatcga atccgtgctg | 780 |
| attccccacc agcccacatg ggacgattgt cagcagctcc tgggcacccc tgctgaccgga | 840 |
| gaggaaaagc agagagtgct gctggaggct aggaaagcag tccgcgggga cgatggaagg | 900 |
| ccaacacagc tccccaatga ggtggatgcc gctttccctc tggaacggcc agattgggac | 960 |
| tatactaccc aggctggacg caaccaccgt gtgcattacc ggcagctcct gctggctgga | 1020 |
| ctgcagaatg cagggcgcag ccccactaac ctggccaagg tgaaaggaat cacccagggc | 1080 |
| cccaatgagt cccttctgc attcctggag cggctgaagg aagcctaccg acggtatact | 1140 |
| ccctacgatc ctgaggaccc aggccaggaa accaacgtga gtatgagctt catctggcag | 1200 |
| tccgctcctg acattggccg aaaactggag cggctgaag atctgaagaa caagaccctg | 1260 |
| ggcgacctgg tgcgggaggc agaaaagatc ttcaacaaaa gggagactcc agaggaacgg | 1320 |
| gaggaaagaa ttagaaggga aacagaggaa aggaggaac gccgacggac tgaggatgaa | 1380 |
| cagaaggaga agaaaagaga ccggcggcgg caccgggaga tgtctaagct gctggccacc | 1440 |
| gtggtcagtg ccagaaaaca ggatcgacag ggaggagagc gacggagaag ccagctcgat | 1500 |
| cgggaccagt gcgcctattg taaggaaaaa gggcattggg ctaaggactg ccccaagaaa | 1560 |
| cccagaggcc cacgcgggcc ccgacctcag acttccctgc tgaccctgga cgat | 1614 |

<210> SEQ ID NO 4
<211> LENGTH: 1099
<212> TYPE: PRT
<213> ORGANISM: Murine leukemia virus
<220> FEATURE:
<221> NAME/KEY: MISC_FEATURE
<222> LOCATION: (1)..(538)
<223> OTHER INFORMATION: MMLV Gag amino acid sequence
<220> FEATURE:
<221> NAME/KEY: MISC_FEATURE
<222> LOCATION: (539)..(1099)
<223> OTHER INFORMATION: CMV pp65 amino acid sequence

<400> SEQUENCE: 4

Met Gly Gln Thr Val Thr Thr Pro Leu Ser Leu Thr Leu Gly His Trp
1               5                   10                  15

Lys Asp Val Glu Arg Ile Ala His Asn Gln Ser Val Asp Val Lys Lys
            20                  25                  30

-continued

Arg Arg Trp Val Thr Phe Cys Ser Ala Glu Trp Pro Thr Phe Asn Val
         35                  40                  45

Gly Trp Pro Arg Asp Gly Thr Phe Asn Arg Asp Leu Ile Thr Gln Val
 50                  55                  60

Lys Ile Lys Val Phe Ser Pro Gly Pro His Gly His Pro Asp Gln Val
 65                  70                  75                  80

Pro Tyr Ile Val Thr Trp Glu Ala Leu Ala Phe Asp Pro Pro Trp
                     85                  90                  95

Val Lys Pro Phe Val His Pro Lys Pro Pro Pro Leu Pro Pro Ser
             100                 105                 110

Ala Pro Ser Leu Pro Leu Glu Pro Arg Ser Thr Pro Pro Arg Ser
         115                 120                 125

Ser Leu Tyr Pro Ala Leu Thr Pro Ser Leu Gly Ala Lys Pro Lys Pro
         130                 135                 140

Gln Val Leu Ser Asp Ser Gly Gly Pro Leu Ile Asp Leu Leu Thr Glu
145                 150                 155                 160

Asp Pro Pro Pro Tyr Arg Asp Pro Arg Pro Pro Ser Asp Arg Asp
                 165                 170                 175

Gly Asn Gly Gly Glu Ala Thr Pro Ala Gly Glu Ala Pro Asp Pro Ser
             180                 185                 190

Pro Met Ala Ser Arg Leu Arg Gly Arg Arg Glu Pro Pro Val Ala Asp
         195                 200                 205

Ser Thr Thr Ser Gln Ala Phe Pro Leu Arg Ala Gly Gly Asn Gly Gln
         210                 215                 220

Leu Gln Tyr Trp Pro Phe Ser Ser Ser Asp Leu Tyr Asn Trp Lys Asn
225                 230                 235                 240

Asn Asn Pro Ser Phe Ser Glu Asp Pro Gly Lys Leu Thr Ala Leu Ile
                 245                 250                 255

Glu Ser Val Leu Ile Thr His Gln Pro Thr Trp Asp Asp Cys Gln Gln
                 260                 265                 270

Leu Leu Gly Thr Leu Leu Thr Gly Glu Glu Lys Gln Arg Val Leu Leu
             275                 280                 285

Glu Ala Arg Lys Ala Val Arg Gly Asp Asp Gly Arg Pro Thr Gln Leu
         290                 295                 300

Pro Asn Glu Val Asp Ala Ala Phe Pro Leu Glu Arg Pro Asp Trp Asp
305                 310                 315                 320

Tyr Thr Thr Gln Ala Gly Arg Asn His Leu Val His Tyr Arg Gln Leu
                 325                 330                 335

Leu Leu Ala Gly Leu Gln Asn Ala Gly Arg Ser Pro Thr Asn Leu Ala
             340                 345                 350

Lys Val Lys Gly Ile Thr Gln Gly Pro Asn Glu Ser Pro Ser Ala Phe
         355                 360                 365

Leu Glu Arg Leu Lys Glu Ala Tyr Arg Arg Tyr Thr Pro Tyr Asp Pro
370                 375                 380

Glu Asp Pro Gly Gln Glu Thr Asn Val Ser Met Ser Phe Ile Trp Gln
385                 390                 395                 400

Ser Ala Pro Asp Ile Gly Arg Lys Leu Glu Arg Leu Glu Asp Leu Lys
                 405                 410                 415

Asn Lys Thr Leu Gly Asp Leu Val Arg Glu Ala Glu Lys Ile Phe Asn
             420                 425                 430

Lys Arg Glu Thr Pro Glu Glu Arg Glu Arg Ile Arg Arg Glu Thr
         435                 440                 445

Glu Glu Lys Glu Glu Arg Arg Arg Thr Glu Asp Glu Gln Lys Glu Lys

```
            450                 455                 460
Glu Arg Asp Arg Arg His Arg Glu Met Ser Lys Leu Leu Ala Thr
465                 470                 475                 480

Val Val Ser Gly Gln Lys Gln Asp Arg Gln Gly Gly Glu Arg Arg
                    485                 490                 495

Ser Gln Leu Asp Arg Asp Gln Cys Ala Tyr Cys Lys Glu Lys Gly His
            500                 505                 510

Trp Ala Lys Asp Cys Pro Lys Lys Pro Arg Gly Pro Arg Gly Pro Arg
                515                 520                 525

Pro Gln Thr Ser Leu Leu Thr Leu Asp Asp Cys Glu Ser Arg Gly Arg
            530                 535                 540

Arg Cys Pro Glu Met Ile Ser Val Leu Gly Pro Ile Ser Gly His Val
545                 550                 555                 560

Leu Lys Ala Val Phe Ser Arg Gly Asp Thr Pro Val Leu Pro His Glu
                565                 570                 575

Thr Arg Leu Leu Gln Thr Gly Ile His Val Arg Val Ser Gln Pro Ser
            580                 585                 590

Leu Ile Leu Val Ser Gln Tyr Thr Pro Asp Ser Thr Pro Cys His Arg
            595                 600                 605

Gly Asp Asn Gln Leu Gln Val Gln His Thr Tyr Phe Thr Gly Ser Glu
610                 615                 620

Val Glu Asn Val Ser Val Asn Val His Asn Pro Thr Gly Arg Ser Ile
625                 630                 635                 640

Cys Pro Ser Gln Glu Pro Met Ser Ile Tyr Val Tyr Ala Leu Pro Leu
                645                 650                 655

Lys Met Leu Asn Ile Pro Ser Ile Asn Val His His Tyr Pro Ser Ala
                660                 665                 670

Ala Glu Arg Lys His Arg His Leu Pro Val Ala Asp Ala Val Ile His
            675                 680                 685

Ala Ser Gly Lys Gln Met Trp Gln Ala Arg Leu Thr Val Ser Gly Leu
            690                 695                 700

Ala Trp Thr Arg Gln Gln Asn Gln Trp Lys Glu Pro Asp Val Tyr Tyr
705                 710                 715                 720

Thr Ser Ala Phe Val Phe Pro Thr Lys Asp Val Ala Leu Arg His Val
                725                 730                 735

Val Cys Ala His Glu Leu Val Cys Ser Met Glu Asn Thr Arg Ala Thr
                740                 745                 750

Lys Met Gln Val Ile Gly Asp Gln Tyr Val Lys Val Tyr Leu Glu Ser
                755                 760                 765

Phe Cys Glu Asp Val Pro Ser Gly Lys Leu Phe Met His Val Thr Leu
770                 775                 780

Gly Ser Asp Val Glu Asp Leu Thr Met Thr Arg Asn Pro Gln Pro
785                 790                 795                 800

Phe Met Arg Pro His Glu Arg Asn Gly Phe Thr Val Leu Cys Pro Lys
                805                 810                 815

Asn Met Ile Ile Lys Pro Gly Lys Ile Ser His Ile Met Leu Asp Val
                820                 825                 830

Ala Phe Thr Ser His Glu His Phe Gly Leu Leu Cys Pro Lys Ser Ile
            835                 840                 845

Pro Gly Leu Ser Ile Ser Gly Asn Leu Leu Met Asn Gly Gln Gln Ile
            850                 855                 860

Phe Leu Glu Val Gln Ala Ile Arg Glu Thr Val Glu Leu Arg Gln Tyr
865                 870                 875                 880
```

```
Asp Pro Val Ala Ala Leu Phe Phe Phe Asp Ile Asp Leu Leu Leu Gln
                885                 890                 895

Arg Gly Pro Gln Tyr Ser Glu His Pro Thr Phe Thr Ser Gln Tyr Arg
            900                 905                 910

Ile Gln Gly Lys Leu Glu Tyr Arg His Thr Trp Asp Arg His Asp Glu
        915                 920                 925

Gly Ala Ala Gln Gly Asp Asp Asp Val Trp Thr Ser Gly Ser Asp Ser
    930                 935                 940

Asp Glu Glu Leu Val Thr Thr Glu Arg Lys Thr Pro Arg Val Thr Gly
945                 950                 955                 960

Gly Gly Ala Met Ala Gly Ala Ser Thr Ser Ala Gly Arg Lys Arg Lys
                965                 970                 975

Ser Ala Ser Ser Ala Thr Ala Cys Thr Ala Gly Val Met Thr Arg Gly
            980                 985                 990

Arg Leu Lys Ala Glu Ser Thr Val  Ala Pro Glu Glu Asp  Thr Asp Glu
        995                 1000                 1005

Asp Ser  Asp Asn Glu Ile His  Asn Pro Ala Val Phe  Thr Trp Pro
    1010                 1015                 1020

Pro Trp  Gln Ala Gly Ile Leu  Ala Arg Asn Leu Val  Pro Met Val
    1025                 1030                 1035

Ala Thr  Val Gln Gly Gln Asn  Leu Lys Tyr Gln Glu  Phe Phe Trp
    1040                 1045                 1050

Asp Ala  Asn Asp Ile Tyr Arg  Ile Phe Ala Glu Leu  Glu Gly Val
    1055                 1060                 1065

Trp Gln  Pro Ala Ala Gln Pro  Lys Arg Arg Arg His  Arg Gln Asp
    1070                 1075                 1080

Ala Leu  Pro Gly Pro Cys Ile  Ala Ser Thr Pro Lys  Lys His Arg
    1085                 1090                 1095

Gly
```

<210> SEQ ID NO 5
<211> LENGTH: 3300
<212> TYPE: DNA
<213> ORGANISM: Murine leukemia virus
<220> FEATURE:
<221> NAME/KEY: misc_feature
<222> LOCATION: (1)..(1614)
<223> OTHER INFORMATION: MMLV Gag nucleotide sequence
<220> FEATURE:
<221> NAME/KEY: misc_feature
<222> LOCATION: (1615)..(3300)
<223> OTHER INFORMATION: CMV pp65 nucleotide sequence

<400> SEQUENCE: 5

```
atgggccaga ctgttaccac tcccttaagt ttgaccttag gtcactggaa agatgtcgag      60
cggatcgctc acaaccagtc ggtagatgtc aagaagagac gttgggttac cttctgctct     120
gcagaatggc caacctttaa cgtcggatgg ccgcgagacg caccttta ccgagacctc       180 atcacccagg ttaagatcaa ggtctttca cctggcccgc atggacaccc agaccaggtc      240
ccctacatcg tgacctggga agccttggct tttgaccccc ctccctgggt caagccctt      300 gtacacccta agcctccgcc tcctcttcct ccatccgccc cgtctctccc ccttgaacct     360
cctcgttcga ccccgcctcg atcctccctt tatccagccc tcactccttc tctaggcgcc     420
aaacctaaac ctcaagttct ttctgacagt gggggggccgc tcatcgacct acttacagaa    480 gacccccccgc cttataggga cccaagacca ccccccttccg acaggacgg aaatggtgga    540
```

```
gaagcgaccc ctgcgggaga ggcaccggac ccctccccaa tggcatctcg cctacgtggg    600
agacgggagc ccctgtggc cgactccact acctcgcagg cattccccct ccgcgcagga     660
ggaaacggac agcttcaata ctggccgttc tcctcttctg acctttacaa ctggaaaaat    720 aataacccctt cttttctga agatccaggt aaactgacag ctctgatcga gtctgttctc    780
atcacccatc agcccacctg gacgactgt cagcagctgt tggggactct gctgaccgga     840
gaagaaaaac aacgggtgct cttagaggct agaaaggcgg tgcggggcga tgatgggcgc    900
cccactcaac tgcccaatga agtcgatgcc gcttttcccc tcgagcgccc agactgggat    960
tacaccaccc aggcaggtag gaaccaccta gtccactatc gccagttgct cctagcgggt    1020
ctccaaaacg cgggcagaag ccccaccaat ttggccaagg taaaaggaat aacacaaggg    1080
cccaatgagt ctccctcggc cttcctagag agacttaagg aagcctatcg caggtacact    1140
ccttatgacc ctgaggaccc agggcaagaa actaatgtgt ctatgtcttt catttggcag    1200
tctgccccag acattgggag aaagttagag aggttagaag atttaaaaaa caagacgctt    1260
ggagatttgg ttagagaggc agaaaagatc tttaataaac gagaaacccc ggaagaaaga    1320
gaggaacgta tcaggagaga aacagaggaa aaagaagaac gccgtaggac agaggatgag    1380
cagaaagaga agaaagaga tcgtaggaga catagagaga tgagcaagct attggccact    1440
gtcgttagtg gacagaaaca ggatagacag ggaggagaac gaaggaggtc ccaactcgat    1500
cgcgaccagt gtgcctactg caaagaaaag gggcactggg ctaaagattg tcccaagaaa    1560
ccacgaggac ctcggggacc aagaccccag acctccctcc tgaccctaga tgactgtgag    1620
tcgcgcggtc gccgttgtcc cgaaatgata tccgtactgg gtcccatttc ggggcacgtg    1680
ctgaaagccg tgtttagtcg cggcgacacg ccggtgctgc cgcacgagac gcgactcctg    1740
cagacgggta tccacgtgcg cgtgagccag ccctcgctga tcctggtgtc gcagtacacg    1800
cccgactcga cgccatgcca ccgcggcgac aatcagctgc aggtgcagca cacgtacttt    1860
acgggcagcg aggtggagaa cgtgtcggtc aacgtgcaca ccccacgggc cggagcatc    1920 tgccccagcc aagagcccat gtcgatctat gtgtacgcgc tgccgctcaa gatgctgaac    1980
atccccagca tcaacgtgca ccactacccg tcggcggccg agcgcaaaca ccgacacctg    2040
cccgtagctg acgctgtgat tcacgcgtcg ggcaagcaga tgtggcaggc gcgtctcacg    2100
gtctcgggac tggcctggac gcgtcagcag aaccagtgga agagcccga cgtctactac    2160 acgtcagcgt tcgtgtttcc caccaaggac gtggcactgc ggcacgtggt gtgcgcgcac    2220
gagctggttt gctccatgga gaacacgcgc gcaaccaaga tgcaggtgat aggtgaccag    2280
tacgtcaagg tgtacctgga gtccttctgc gaggacgtgc cctccggcaa gctctttatg    2340
cacgtcacgc tgggctctga cgtggaagag gacctgacga tgacccgcaa cccgcaaccc    2400
ttcatgcgcc cccacgagcg caacggcttt acggtgttgt gtcccaaaaa tatgataatc    2460
aaaccgggca agatctcgca catcatgctg gatgtggctt ttacctcaca cgagcatttt    2520
gggctgctgt gtcccaagag catcccgggc ctgagcatct caggtaacct attgatgaac    2580
gggcagcaga tcttcctgga ggtgcaagcg atacgcgaga ccgtggaact gcgtcagtac    2640
gatcccgtgg ctgcgctctt cttttcgat atcgacttgc tgctgcagcg cgggcctcag    2700
tacagcgaac accccacctt caccagccag tatcgcatcc agggcaagct tgagtaccga    2760
cacacctggg accggcacga cgagggtgcc gcccagggcg acgacgacgt ctggaccagc    2820
ggatcggact ccgacgagga actcgtaacc accgagcgca agacgccccg cgttaccggc    2880
ggcggcgcca tggcgggcgc ctccacttcc gcgggccgca aacgcaaatc agcatcctcg    2940
```

```
gcgacggcgt gcacggcggg cgttatgaca cgcggccgcc ttaaggccga gtccaccgtc    3000
gcgcccgaag aggacaccga cgaggattcc gacaacgaaa tccacaatcc ggccgtgttc    3060
acctggccgc cctggcaggc cggcatcctg gcccgcaacc tggtgcccat ggtggctacg    3120
gttcagggtc agaatctgaa gtaccaggag ttcttctggg acgccaacga catctaccgc    3180
atcttcgccg aattggaagg cgtatggcag cccgctgcgc aacccaaacg tcgccgccac    3240
cggcaagacg ccttgcccgg gccatgcatc gcctcgacgc ccaaaaagca ccgaggttag    3300

<210> SEQ ID NO 6
<211> LENGTH: 3300
<212> TYPE: DNA
<213> ORGANISM: Murine leukemia virus
<220> FEATURE:
<221> NAME/KEY: misc_feature
<222> LOCATION: (1)..(1614)
<223> OTHER INFORMATION: Codon Optimized MMLV Gag nucleotide sequence
<220> FEATURE:
<221> NAME/KEY: misc_feature
<222> LOCATION: (1615)..(3300)
<223> OTHER INFORMATION: Codon Optimized CMV pp65  nucleotide sequence

<400> SEQUENCE: 6
atgggacaga cagtcactac acccctgagc ctgacactgg acattggaa agacgtggag      60 aggattgcac ataaccagag cgtggacgtg aagaaacgga gatgggtcac cttttgctcc    120
gccgagtggc caacattcaa tgtgggatgg ccccgagatg gcaccttcaa ccgggacctg    180
atcactcagg tgaagatcaa ggtcttctct ccaggacccc acggccatcc agatcaggtg    240
ccctacatcg tcacctggga ggctctggca tttgaccccc ctccatgggt gaagcctttc    300
gtccacccaa aaccacctcc accactgcct ccatctgccc ctagtctgcc actggaaccc    360
cctcggtcaa ccccacccag aagctccctg tatcccgcac tgacacctag cctggggggcc    420 aagcctaaac cacaggtgct gtctgatagt ggcgggcctc tgatcgatct gctgaccgag    480
gaccctccac cataccgcga cccacgacct ccaccaagcg accgggacgg aaacggagga    540
gaggctacac ccgcaggcga agcccccgat cctagtccaa tggcatcaag gctgcgcggg    600
aggcgcgaac ctccagtggc cgactcaacc acaagccagg catttccact gagggccggg    660
ggaaatggac agctccagta ttggcccttc tctagttcag atctgtacaa ctggaagaac    720
aataacccta gcttcagcga ggaccaggc aaactgaccg ccctgatcga atccgtgctg    780
attacccacc agcccacatg ggacgattgt cagcagctcc tgggcaccct gctgaccgga    840
gaggaaaagc agagagtgct gctggaggct aggaaagcag tccgcgggga cgatggaagg    900
ccaacacagc tccccaatga ggtggatgcc gctttccctc tggaacggcc agattgggac    960
tatactaccc aggctggacg caaccacctg gtgcattacc ggcagctcct gctggctgga    1020
ctgcagaatg cagggcgcag ccccactaac ctggccaagg tgaaggaat cacccagggc   1080 cccaatgagt ccccttctgc attcctggag cggctgaagg aagcctaccg acggtatact    1140
ccctacgatc ctgaggaccc aggccaggaa accaacgtga gtatgagctt catctggcag    1200
tccgctcctg acattggccg aaaactggag cggctggaag atctgaagaa caagaccctg    1260
ggcgacctgt gcggaggc agaaaagatc ttcaacaaaa gggagactcc agaggaacgg    1320
gaggaaagaa ttagaaggga acagaggaa aaggaggaac gccgacggac tgaggatgaa    1380
cagaaggaga agaaaagaga ccggcggcgg caccggagaa tgtctaagct gctggccacc    1440
gtggtcagtg gccagaaaca ggatcgacag ggaggagagc gacggagaag ccagctcgat    1500
```

```
cgggaccagt gcgcctattg taaggaaaaa gggcattggg ctaaggactg ccccaagaaa    1560
cccagaggcc cacgcgggcc ccgacctcag acttccctgc tgaccctgga cgattgcgag    1620
agccggggcc ggcggtgccc agaaatgatc tctgtgctgg ggcccattag tggacatgtg    1680
ctgaaggccg tcttctccag gggagacacc cccgtgctgc ctcacgagac tcgactgctg    1740
cagaccggca tccatgtgcg ggtctcccag ccctctctga ttctggtgtc acagtataca    1800
ccagatagca ctccctgcca cagaggagac aatcagctcc aggtgcagca tacctacttt    1860
acaggctccg aggtcgaaaa cgtgtctgtc aatgtgcaca ccctaccgg caggagcatc    1920 tgtcctagcc aggagccaat gagcatctac gtgtacgccc tgcctctgaa gatgctgaat    1980
atcccatcaa ttaacgtcca ccattaccct agcgcagccg aacggaagca cagacatctg    2040
ccagtggccg acgctgtcat ccatgccagc ggcaaacaga tgtggcaggc aagactgacc    2100
gtgtccgggc tggcctggac aaggcagcag aatcagtgga aggagcccga cgtgtactat    2160
accagcgcct tcgtgttccc taccaaagac gtggccctga catgtggt gtgcgcacat    2220 gagctggtgt gcagcatgga aaacactagg gccaccaaga tgcaggtcat cggcgatcag    2280
tatgtcaaag tgtacctgga gagttttttgc gaagacgtgc catcagggaa gctgttcatg    2340
catgtgaccc tgggcagcga tgtcgaggaa gacctgacca tgacaagaaa tccacagccc    2400
tttatgagac cccacgagag gaatgggttc actgtgctgt gccccaagaa catgatcatt    2460
aagcctggaa aaatcagtca tattatgctg gatgtggcct ttacatcaca cgagcatttc    2520
ggactgctgt gccccaaatc catccctgga ctgagcattt ccggcaatct gctgatgaac    2580
ggccagcaga tcttcctgga agtgcaggcc atccgggaga ccgtcgaact gcgacagtat    2640
gacccagtgg ctgcactgtt cttttttcgac atcgacctgc tgctgcagcg aggaccacag    2700
tacagcgagc accctacttt tacctcccag tatcggattc aggggaagct ggagtacagg    2760
cacacctggg atcgccatga cgaaggagcc gctcagggg acgatgacgt gtggacatct    2820
ggcagtgatt cagacgagga actggtgaca actgagcgaa aaaccccccg ggtgacagga    2880 ggagggggcaa tggcaggggc cagcaccagc gcagggcgga agcgaaaaag cgccagcagc    2940
gccacagcat gtaccgccgg cgtgatgact agaggaaggc tgaaggccga gtctacagtc    3000
gctcccgagg aagatactga cgaggatagt gacaatgaaa tccacaaccc cgccgtgttc    3060
acctggccac cttggcaggc agggattctg gctcgcaacc tggtccccat ggtggcaacc    3120
gtccagggac agaatctgaa gtatcaggag tttttctggg atgctaacga catctaccgg    3180 attttttgcag agctggaagg cgtgtggcag ccagcagccc agcccaaacg acggagacat    3240
cgacaggacg ctctgccagg accttgtatc gccagcacac caaagaagca caggggctaa    3300
```

<210> SEQ ID NO 7
<211> LENGTH: 907
<212> TYPE: PRT
<213> ORGANISM: Human cytomegalovirus
<220> FEATURE:
<221> NAME/KEY: MISC_FEATURE
<222> LOCATION: (1)..(907)
<223> OTHER INFORMATION: HCMV gB Amino Acid Sequence
<220> FEATURE:
<221> NAME/KEY: MISC_FEATURE
<222> LOCATION: (751)..(907)
<223> OTHER INFORMATION: TM and CD

<400> SEQUENCE: 7

Met Glu Ser Arg Ile Trp Cys Leu Val Val Cys Val Asn Leu Cys Ile
1               5                   10                  15

-continued

```
Val Cys Leu Gly Ala Ala Val Ser Ser Ser Thr Arg Gly Thr Ser
            20                  25                  30

Ala Thr His Ser His His Ser Ser His Thr Thr Ser Ala Ala His Ser
        35                  40                  45

Arg Ser Gly Ser Val Ser Gln Arg Val Thr Ser Ser Gln Thr Val Ser
    50                  55                  60

His Gly Val Asn Glu Thr Ile Tyr Asn Thr Thr Leu Lys Tyr Gly Asp
65                  70                  75                  80

Val Val Gly Val Asn Thr Thr Lys Tyr Pro Tyr Arg Val Cys Ser Met
                85                  90                  95

Ala Gln Gly Thr Asp Leu Ile Arg Phe Glu Arg Asn Ile Val Cys Thr
            100                 105                 110

Ser Met Lys Pro Ile Asn Glu Asp Leu Asp Glu Gly Ile Met Val Val
        115                 120                 125

Tyr Lys Arg Asn Ile Val Ala His Thr Phe Lys Val Arg Val Tyr Gln
130                 135                 140

Lys Val Leu Thr Phe Arg Arg Ser Tyr Ala Tyr Ile His Thr Thr Tyr
145                 150                 155                 160

Leu Leu Gly Ser Asn Thr Glu Tyr Val Ala Pro Pro Met Trp Glu Ile
                165                 170                 175

His His Ile Asn Ser His Ser Gln Cys Tyr Ser Ser Tyr Ser Arg Val
            180                 185                 190

Ile Ala Gly Thr Val Phe Val Ala Tyr His Arg Asp Ser Tyr Glu Asn
        195                 200                 205

Lys Thr Met Gln Leu Met Pro Asp Asp Tyr Ser Asn Thr His Ser Thr
210                 215                 220

Arg Tyr Val Thr Val Lys Asp Gln Trp His Ser Arg Gly Ser Thr Trp
225                 230                 235                 240

Leu Tyr Arg Glu Thr Cys Asn Leu Asn Cys Met Val Thr Ile Thr Thr
                245                 250                 255

Ala Arg Ser Lys Tyr Pro Tyr His Phe Ala Thr Ser Thr Gly Asp
            260                 265                 270

Val Val Asp Ile Ser Pro Phe Tyr Asn Gly Thr Asn Arg Asn Ala Ser
        275                 280                 285

Tyr Phe Gly Glu Asn Ala Asp Lys Phe Phe Ile Phe Pro Asn Tyr Thr
290                 295                 300

Ile Val Ser Asp Phe Gly Arg Pro Asn Ser Ala Leu Glu Thr His Arg
305                 310                 315                 320

Leu Val Ala Phe Leu Glu Arg Ala Asp Ser Val Ile Ser Trp Asp Ile
                325                 330                 335

Gln Asp Glu Lys Asn Val Thr Cys Gln Leu Thr Phe Trp Glu Ala Ser
            340                 345                 350

Glu Arg Thr Ile Arg Ser Glu Ala Glu Asp Ser Tyr His Phe Ser Ser
        355                 360                 365

Ala Lys Met Thr Ala Thr Phe Leu Ser Lys Lys Gln Glu Val Asn Met
370                 375                 380

Ser Asp Ser Ala Leu Asp Cys Val Arg Asp Glu Ala Ile Asn Lys Leu
385                 390                 395                 400

Gln Gln Ile Phe Asn Thr Ser Tyr Asn Gln Thr Tyr Glu Lys Tyr Gly
                405                 410                 415

Asn Val Ser Val Phe Glu Thr Thr Gly Gly Leu Val Val Phe Trp Gln
            420                 425                 430

Gly Ile Lys Gln Lys Ser Leu Val Glu Leu Glu Arg Leu Ala Asn Arg
```

```
                435                 440                 445
Ser Ser Leu Asn Leu Thr His Asn Arg Thr Lys Arg Ser Thr Asp Gly
450                 455                 460

Asn Asn Ala Thr His Leu Ser Asn Met Glu Ser Val His Asn Leu Val
465                 470                 475                 480

Tyr Ala Gln Leu Gln Phe Thr Tyr Asp Thr Leu Arg Gly Tyr Ile Asn
                485                 490                 495

Arg Ala Leu Ala Gln Ile Ala Glu Ala Trp Cys Val Asp Gln Arg Arg
                500                 505                 510

Thr Leu Glu Val Phe Lys Glu Leu Ser Lys Ile Asn Pro Ser Ala Ile
                515                 520                 525

Leu Ser Ala Ile Tyr Asn Lys Pro Ile Ala Arg Phe Met Gly Asp
530                 535                 540

Val Leu Gly Leu Ala Ser Cys Val Thr Ile Asn Gln Thr Ser Val Lys
545                 550                 555                 560

Val Leu Arg Asp Met Asn Val Lys Glu Ser Pro Gly Arg Cys Tyr Ser
                565                 570                 575

Arg Pro Val Val Ile Phe Asn Phe Ala Asn Ser Ser Tyr Val Gln Tyr
                580                 585                 590

Gly Gln Leu Gly Glu Asp Asn Glu Ile Leu Leu Gly Asn His Arg Thr
                595                 600                 605

Glu Glu Cys Gln Leu Pro Ser Leu Lys Ile Phe Ile Ala Gly Asn Ser
610                 615                 620

Ala Tyr Glu Tyr Val Asp Tyr Leu Phe Lys Arg Met Ile Asp Leu Ser
625                 630                 635                 640

Ser Ile Ser Thr Val Asp Ser Met Ile Ala Leu Asp Ile Asp Pro Leu
                645                 650                 655

Glu Asn Thr Asp Phe Arg Val Leu Glu Leu Tyr Ser Gln Lys Glu Leu
                660                 665                 670

Arg Ser Ile Asn Val Phe Asp Leu Glu Glu Ile Met Arg Glu Phe Asn
                675                 680                 685

Ser Tyr Lys Gln Arg Val Lys Tyr Val Glu Asp Lys Val Val Asp Pro
690                 695                 700

Leu Pro Pro Tyr Leu Lys Gly Leu Asp Asp Leu Met Ser Gly Leu Gly
705                 710                 715                 720

Ala Ala Gly Lys Ala Val Gly Val Ala Ile Gly Ala Val Gly Gly Ala
                725                 730                 735

Val Ala Ser Val Val Glu Gly Val Ala Thr Phe Leu Lys Asn Pro Phe
                740                 745                 750

Gly Ala Phe Thr Ile Ile Leu Val Ala Ile Ala Val Ile Ile Ile
                755                 760                 765

Tyr Leu Ile Tyr Thr Arg Gln Arg Arg Leu Cys Met Gln Pro Leu Gln
770                 775                 780

Asn Leu Phe Pro Tyr Leu Val Ser Ala Asp Gly Thr Thr Val Thr Ser
785                 790                 795                 800

Gly Asn Thr Lys Asp Thr Ser Leu Gln Ala Pro Pro Ser Tyr Glu Glu
                805                 810                 815

Ser Val Tyr Asn Ser Gly Arg Lys Gly Pro Gly Pro Pro Ser Ser Asp
                820                 825                 830

Ala Ser Thr Ala Ala Pro Pro Tyr Thr Asn Glu Gln Ala Tyr Gln Met
                835                 840                 845

Leu Leu Ala Leu Val Arg Leu Asp Ala Glu Gln Arg Ala Gln Gln Asn
850                 855                 860
```

```
Gly Thr Asp Ser Leu Asp Gly Gln Thr Gly Thr Gln Asp Lys Gly Gln
865                 870                 875                 880

Lys Pro Asn Leu Leu Asp Arg Leu Arg His Arg Lys Asn Gly Tyr Arg
                885                 890                 895

His Leu Lys Asp Ser Asp Glu Glu Glu Asn Val
            900                 905

<210> SEQ ID NO 8
<211> LENGTH: 2724
<212> TYPE: DNA
<213> ORGANISM: Human cytomegalovirus
<220> FEATURE:
<221> NAME/KEY: misc_feature
<222> LOCATION: (1)..(2724)
<223> OTHER INFORMATION: HCMV gB Nucleotide Sequence
<220> FEATURE:
<221> NAME/KEY: misc_feature
<222> LOCATION: (2253)..(2724)
<223> OTHER INFORMATION: TM and CD

<400> SEQUENCE: 8
```

| | | | | | |
|---|---|---|---|---|---|
| atggaatcca | ggatctggtg | cctggtagtc | tgcgttaact | tgtgtatcgt | ctgtctgggt | 60 |
| gctgcggttt | cctcatcttc | tactcgtgga | acttctgcta | ctcacagtca | ccattcctct | 120 |
| catacgacgt | ctgctgctca | ttctcgatcc | ggttcagtct | ctcaacgcgt | aacttcttcc | 180 |
| caaacggtca | gccatggtgt | taacgagacc | atctacaaca | ctaccctcaa | gtacggagat | 240 |
| gtggtggggg | tcaacaccac | caagtacccc | tatcgcgtgt | gttctatggc | acagggtacg | 300 |
| gatcttattc | gctttgaacg | taatatcgtc | tgcacctcga | tgaagcccat | caatgaagac | 360 |
| ctggacgagg | gcatcatggt | ggtctacaaa | cgcaacatcg | tcgcgcacac | ctttaaggta | 420 |
| cgagtctacc | agaaggtttt | gacgtttcgt | cgtagctacg | cttacatcca | ccccacttat | 480 |
| ctgctgggca | gcaacacgga | atacgtggcg | cctcctatgt | gggagattca | tcatatcaac | 540 |
| agtcacagtc | agtgctacag | ttcctacagc | cgcgttatag | caggcacggt | tttcgtggct | 600 |
| tatcataggg | acagctatga | aaacaaaacc | atgcaattaa | tgcccgacga | ttattccaac | 660 |
| acccacagta | cccgttacgt | gacggtcaag | gatcaatggc | acagccgcgg | cagcaccctgg | 720 |
| ctctatcgtg | agacctgtaa | tctgaattgt | atggtgacca | tcactactgc | gcgctccaag | 780 |
| tatcccatat | cattttttcgc | aacttccacg | ggtgatgtgg | ttgacatttc | tcctttctac | 840 |
| aacggaacta | atcgcaatgc | cagctatttt | ggagaaaacg | ccgacaagtt | tttcattttt | 900 |
| ccgaactaca | ctatcgtctc | cgactttgga | agaccgaatt | ctgcgttaga | gacccacagg | 960 |
| ttggtggctt | ttcttgaacg | tgcggactca | gtgatctcct | gggatataca | ggacgagaag | 1020 |
| aatgttactt | gtcaactcac | tttctgggaa | gcctcggaac | gcaccattcg | ttccgaagcc | 1080 |
| gaggactcgt | atcactttcc | ttctgccaaa | atgaccgcca | ctttcttatc | taagaagcaa | 1140 |
| gaggtgaaca | tgtccgactc | tgcgctggac | tgtgtacgtg | atgaggccat | aaataagtta | 1200 |
| cagcagattt | tcaatacttc | atacaatcaa | acatatgaaa | aatatggaaa | cgtgtccgtc | 1260 |
| tttgaaacca | ctggtggttt | ggtggtgttc | tggcaaggta | tcaagcaaaa | atctctggtg | 1320 |
| gaactcgaac | gtttggccaa | ccgctccagt | ctgaatctta | tcataatag | aaccaaaaga | 1380 |
| agtacagatg | gcaacaatgc | aactcattta | tccaacatgg | agtcggtgca | aatctggtc | 1440 |
| tacgcccagc | tgcagttcac | ctatgacacg | ttgcgcggtt | acatcaaccg | ggcgctggcg | 1500 |
| caaatcgcag | aagcctggtg | tgtggatcaa | cggcgcaccc | tagaggtctt | caaggaactt | 1560 |
| agcaagatca | cccgtcagc | tattctctcg | gccatctaca | acaaaccgat | tgccgcgcgt | 1620 |

```
ttcatgggtg atgtcctggg tctggccagc tgcgtgacca ttaaccaaac cagcgtcaag    1680
gtgctgcgtg atatgaatgt gaaggaatcg ccaggacgct gctactcacg accagtggtc    1740
atctttaatt tcgccaacag ctcgtacgtg cagtacggtc aactgggcga ggataacgaa    1800
atcctgttgg gcaaccaccg cactgaggaa tgtcagcttc ccagcctcaa gatcttcatc    1860
gccggcaact cggcctacga gtacgtggac tacctcttca aacgcatgat tgacctcagc    1920
agcatctcca ccgtcgacag catgatcgcc ctagacatcg acccgctgga aaacaccgac    1980
ttcagggtac tggaacttta ctcgcagaaa gaattgcgtt ccatcaacgt ttttgatctc    2040
gaggagatca tgcgcgagtt caattcgtat aagcagcggg taaagtacgt ggaggacaag    2100
gtagtcgacc cgctgccgcc ctacctcaag gtctggacg acctcatgag cggcctgggc    2160
gccgcgggaa aggccgttgg cgtagccatt ggggccgtgg gtggcgcggt ggcctccgtg    2220
gtcgaaggcg ttgccaccct cctcaaaaac cccttcggag ccttcaccat catcctcgtg    2280
gccatagccg tcgtcattat catttatttg atctatactc gacagcggcg tctctgcatg    2340
cagccgctgc agaacctctt tccctatctg gtgtccgccg acgggaccac cgtgacgtcg    2400
ggcaacacca agacacgtc gttacaggct ccgccttcct acgaggaaag tgtttataat    2460
tctggtcgca aaggaccggg accaccgtcg tctgatgcat ccacggcggc tccgccttac    2520
accaacgagc aggcttacca gatgcttctg gccctggtcc gtctggacgc agagcagcga    2580
gcgcagcaga acggtacaga ttctttggac ggacagactg gcacgcagga caagggacag    2640
aagcccaacc tgctagaccg actgcgacac cgcaaaaacg gctaccgaca cttgaaagac    2700
tccgacgaag aagagaacgt ctga                                           2724
```

<210> SEQ ID NO 9
<211> LENGTH: 2724
<212> TYPE: DNA
<213> ORGANISM: Human cytomegalovirus
<220> FEATURE:
<221> NAME/KEY: misc_feature
<222> LOCATION: (1)..(2724)
<223> OTHER INFORMATION: Codon Optimized HCMV gB Nucleotide Sequence
<220> FEATURE:
<221> NAME/KEY: misc_feature
<222> LOCATION: (2253)..(2724)
<223> OTHER INFORMATION: TM and CD

<400> SEQUENCE: 9

```
atggagtcaa ggatttggtg cctggtcgtg tgcgtcaatc tgtgcatcgt ctgtctgggg      60
gctgccgtgt catcaagttc tacaagaggc accagcgcca cccactcaca ccatagctcc     120
cataccacat ccgccgctca ctcccggtct ggcagcgtga gccagagagt cacatctagt     180
cagaccgtga gccacggggt caacgagacc atctacaata ctaccctgaa gtatggcgac     240
gtggtcgggg tgaacacaac taaataccca tagggtctt gcagtatggc cagggcact     300 gatctgatta gatcgaaag gaacatcgtg tgcaccagca tgaagcccat taatgaggac     360
ctggatgaag ggatcatggt ggtctacaaa cgcaatattg tggcccatac cttcaaggtg     420
cgagtctatc agaaagtgct gacatttcgg agatcttacg catatatcca caccacatac     480
ctgctgggga gtaacaccga gtatgtggct ccccctatgt gggaaattca ccatatcaat     540
agccattccc agtgctactc aagctacagc agagtgatcg ctggaacagt gttcgtcgca     600
taccacagag actcttatga gaacaagact atgcagctca tgcccgacga ttacagcaat     660
acacattcca ctagatatgt gacagtcaaa gatcagtggc actcaagggg cagcaccctgg     720
```

```
ctgtaccgcg agacatgcaa cctgaattgt atggtgacta tcactaccgc tagatccaag      780 taccccatc  acttctttgc aacttccacc ggggacgtgg tcgatatttc tccttttctac    840 aacggcacaa accggaatgc atcttatttt ggggagaacg ccgacaagtt ctttatttc      900 ccaaattaca ccatcgtgtc tgattttggc agacccaaca gtgccctgga gacacatcga    960
ctggtggcat tcctggaacg ggccgactcc gtcatttctt gggacatcca ggatgagaag   1020
aatgtgacct gccagctcac cttctgggag gccagcgaac gcaccatccg atccgaggct   1080
gaagattctt accacttctc ctctgccaaa atgacagcta cttttctgag caagaaacag   1140
gaggtgaaca tgtctgacag tgctctggat tgcgtgcggg acgaagcaat taataagctg   1200
cagcagatct caacacatc  atacaaccag acttacgaga agtacggaaa cgtgagcgtc   1260
ttcgaaacaa ctggcgggct ggtggtcttt tggcagggca tcaagcagaa atccctggtg   1320
gagctggaaa ggctggccaa tcgcagttca ctgaacctga ctcataatcg gaccaagaga   1380
tctacagacg gaaacaatgc cacacatctg tctaacatgg agagtgtgca caatctggtc   1440
tacgctcagc tccagtttac ctacgacaca ctgagaggct atattaacag ggcactggcc   1500
cagatcgctg aagcatggtg cgtggatcag aggcgcaccc tggaggtctt caaggaactg   1560
tccaaaatca cccttcagc  aattctgagc gccatctaca ataagccaat gcagccagg    1620 tttatgggag acgtgctggg cctggccagt tgcgtcacta tcaaccagac ctcagtgaag   1680
gtcctgcgcg atatgaatgt gaaagagagt cccggcagat gctattcacg gcctgtggtc   1740
atcttcaact tgctaatag  ctcctacgtg cagtatggac agctcggcga ggacaacgaa   1800
attctgctgg ggaatcacag gaccgaggaa tgtcagctcc ctagcctgaa gattttcatc   1860
gctggaaaac tccgcatacga gtatgtggat tacctgttca gcggatgat  tgacctgtct   1920 agtatctcca ctgtggattc tatgattgcc ctggacatcg atccactgga aaataccgac   1980
ttcagggtgc tggagctgta tagccagaag gaactgcgct ccatcaacgt gttcgatctg   2040
gaggaaatta tgagagagtt taatagctac aagcagaggg tgaaatatgt cgaagataag   2100
gtggtcgacc ccctgccacc ctacctgaaa ggcctggacg atctgatgag cgggctggga   2160
gctgcaggga aggcagtggg agtcgctatc ggcgcagtgg aggagccgt  ggccagcgtg   2220 gtcgagggag tggcaacatt cctgaaaaac cccttcgggg ccttcaccat cattctggtg   2280
gcaatcgccg tggtcatcat tatctacctg atctacacaa ggcagcggcg gctgtgcatg   2340
cagcctctgc agaacctgtt tccataccctg gtgagcgccg acgggaccac agtcacctca   2400
ggaaatacta aggataccct tctgcaggcc cccccaagtt acgaggaatc agtgtataac   2460
agcggcagaa aaggaccagg accaccttca agcgacgcca gcactgccgc tccaccctac   2520
accaatgagc aggcctatca gatgctgctg gctctggtgc gcctggatgc cgaacagcga   2580
gctcagcaga acgggaccga ctccctggat ggacagaccg gaacacagga caagggacag   2640
aaacctaatc tgctggatcg gctgcggcac agaaaaaacg ggtataggca cctgaaggac   2700
tccgacgaag aagaaaatgt ctaa                                          2724
```

<210> SEQ ID NO 10
<211> LENGTH: 795
<212> TYPE: PRT
<213> ORGANISM: Human cytomegalovirus
<220> FEATURE:
<221> NAME/KEY: MISC_FEATURE
<222> LOCATION: (1)..(795)
<223> OTHER INFORMATION: HCMV gB-G Amino Acid Sequence
<220> FEATURE:
<221> NAME/KEY: MISC_FEATURE
<222> LOCATION: (751)..(795)
<223> OTHER INFORMATION: TM and CTD

<400> SEQUENCE: 10

Met Glu Ser Arg Ile Trp Cys Leu Val Val Cys Val Asn Leu Cys Ile
1               5                   10                  15

Val Cys Leu Gly Ala Ala Val Ser Ser Ser Thr Arg Gly Thr Ser
            20                  25                  30

Ala Thr His Ser His His Ser Ser His Thr Thr Ser Ala Ala His Ser
            35                  40                  45

Arg Ser Gly Ser Val Ser Gln Arg Val Thr Ser Ser Gln Thr Val Ser
        50                  55                  60

His Gly Val Asn Glu Thr Ile Tyr Asn Thr Thr Leu Lys Tyr Gly Asp
65                  70                  75                  80

Val Val Gly Val Asn Thr Thr Lys Tyr Pro Tyr Arg Val Cys Ser Met
                85                  90                  95

Ala Gln Gly Thr Asp Leu Ile Arg Phe Glu Arg Asn Ile Val Cys Thr
            100                 105                 110

Ser Met Lys Pro Ile Asn Glu Asp Leu Asp Glu Gly Ile Met Val Val
        115                 120                 125

Tyr Lys Arg Asn Ile Val Ala His Thr Phe Lys Val Arg Val Tyr Gln
        130                 135                 140

Lys Val Leu Thr Phe Arg Arg Ser Tyr Ala Tyr Ile His Thr Thr Tyr
145                 150                 155                 160

Leu Leu Gly Ser Asn Thr Glu Tyr Val Ala Pro Pro Met Trp Glu Ile
                165                 170                 175

His His Ile Asn Ser His Ser Gln Cys Tyr Ser Ser Tyr Ser Arg Val
            180                 185                 190

Ile Ala Gly Thr Val Phe Val Ala Tyr His Arg Asp Ser Tyr Glu Asn
        195                 200                 205

Lys Thr Met Gln Leu Met Pro Asp Asp Tyr Ser Asn Thr His Ser Thr
        210                 215                 220

Arg Tyr Val Thr Val Lys Asp Gln Trp His Ser Arg Gly Ser Thr Trp
225                 230                 235                 240

Leu Tyr Arg Glu Thr Cys Asn Leu Asn Cys Met Val Thr Ile Thr Thr
                245                 250                 255

Ala Arg Ser Lys Tyr Pro Tyr His Phe Phe Ala Thr Ser Thr Gly Asp
            260                 265                 270

Val Val Asp Ile Ser Pro Phe Tyr Asn Gly Thr Asn Arg Asn Ala Ser
        275                 280                 285

Tyr Phe Gly Glu Asn Ala Asp Lys Phe Phe Ile Phe Pro Asn Tyr Thr
        290                 295                 300

Ile Val Ser Asp Phe Gly Arg Pro Asn Ser Ala Leu Glu Thr His Arg
305                 310                 315                 320

Leu Val Ala Phe Leu Glu Arg Ala Asp Ser Val Ile Ser Trp Asp Ile
                325                 330                 335

Gln Asp Glu Lys Asn Val Thr Cys Gln Leu Thr Phe Trp Glu Ala Ser
            340                 345                 350

Glu Arg Thr Ile Arg Ser Glu Ala Glu Asp Ser Tyr His Phe Ser Ser
        355                 360                 365

Ala Lys Met Thr Ala Thr Phe Leu Ser Lys Lys Gln Glu Val Asn Met
        370                 375                 380

Ser Asp Ser Ala Leu Asp Cys Val Arg Asp Glu Ala Ile Asn Lys Leu
385                 390                 395                 400

```
Gln Gln Ile Phe Asn Thr Ser Tyr Asn Gln Thr Tyr Glu Lys Tyr Gly
                405                 410                 415

Asn Val Ser Val Phe Glu Thr Thr Gly Gly Leu Val Val Phe Trp Gln
            420                 425                 430

Gly Ile Lys Gln Lys Ser Leu Val Glu Leu Glu Arg Leu Ala Asn Arg
        435                 440                 445

Ser Ser Leu Asn Leu Thr His Asn Arg Thr Lys Arg Ser Thr Asp Gly
    450                 455                 460

Asn Asn Ala Thr His Leu Ser Asn Met Glu Ser Val His Asn Leu Val
465                 470                 475                 480

Tyr Ala Gln Leu Gln Phe Thr Tyr Asp Thr Leu Arg Gly Tyr Ile Asn
                485                 490                 495

Arg Ala Leu Ala Gln Ile Ala Glu Ala Trp Cys Val Asp Gln Arg Arg
            500                 505                 510

Thr Leu Glu Val Phe Lys Glu Leu Ser Lys Ile Asn Pro Ser Ala Ile
        515                 520                 525

Leu Ser Ala Ile Tyr Asn Lys Pro Ile Ala Ala Arg Phe Met Gly Asp
    530                 535                 540

Val Leu Gly Leu Ala Ser Cys Val Thr Ile Asn Gln Thr Ser Val Lys
545                 550                 555                 560

Val Leu Arg Asp Met Asn Val Lys Glu Ser Pro Gly Arg Cys Tyr Ser
                565                 570                 575

Arg Pro Val Val Ile Phe Asn Phe Ala Asn Ser Ser Tyr Val Gln Tyr
            580                 585                 590

Gly Gln Leu Gly Glu Asp Asn Glu Ile Leu Leu Gly Asn His Arg Thr
        595                 600                 605

Glu Glu Cys Gln Leu Pro Ser Leu Lys Ile Phe Ile Ala Gly Asn Ser
    610                 615                 620

Ala Tyr Glu Tyr Val Asp Tyr Leu Phe Lys Arg Met Ile Asp Leu Ser
625                 630                 635                 640

Ser Ile Ser Thr Val Asp Ser Met Ile Ala Leu Asp Ile Asp Pro Leu
                645                 650                 655

Glu Asn Thr Asp Phe Arg Val Leu Glu Leu Tyr Ser Gln Lys Glu Leu
            660                 665                 670

Arg Ser Ile Asn Val Phe Asp Leu Glu Glu Ile Met Arg Glu Phe Asn
        675                 680                 685

Ser Tyr Lys Gln Arg Val Lys Tyr Val Glu Asp Lys Val Val Asp Pro
    690                 695                 700

Leu Pro Pro Tyr Leu Lys Gly Leu Asp Asp Leu Met Ser Gly Leu Gly
705                 710                 715                 720

Ala Ala Gly Lys Ala Val Gly Val Ala Ile Gly Ala Val Gly Gly Ala
                725                 730                 735

Val Ala Ser Val Val Glu Gly Val Ala Thr Phe Leu Lys Asn Pro Phe
            740                 745                 750

Phe Phe Ile Ile Gly Leu Ile Ile Gly Leu Phe Leu Val Leu Arg Val
        755                 760                 765

Gly Ile His Leu Cys Ile Lys Leu Lys His Thr Lys Lys Arg Gln Ile
    770                 775                 780

Tyr Thr Asp Ile Glu Met Asn Arg Leu Gly Lys
785                 790                 795

<210> SEQ ID NO 11
<211> LENGTH: 2388
```

<212> TYPE: DNA
<213> ORGANISM: Human cytomegalovirus
<220> FEATURE:
<221> NAME/KEY: misc_feature
<222> LOCATION: (1)..(2388)
<223> OTHER INFORMATION: HCMV gB - G Nucleotide Sequence
<220> FEATURE:
<221> NAME/KEY: misc_feature
<222> LOCATION: (2253)..(2388)
<223> OTHER INFORMATION: TM and CTD

<400> SEQUENCE: 11

```
atggaatcca ggatctggtg cctggtagtc tgcgttaact tgtgtatcgt ctgtctgggt      60
gctgcggttt cctcatcttc tactcgtgga acttctgcta ctcacagtca ccattcctct     120
catacgacgt ctgctgctca ttctcgatcc ggttcagtct ctcaacgcgt aacttcttcc     180
caaacggtca gccatggtgt taacgagacc atctacaaca ctaccctcaa gtacggagat     240
gtggtggggg tcaacaccac caagtacccc tatcgcgtgt gttctatggc acagggtacg     300
gatcttattc gctttgaacg taatatcgtc tgcacctcga tgaagcccat caatgaagac     360
ctggacgagg gcatcatggt ggtctacaaa cgcaacatcg tcgcgcacac ctttaaggta     420
cgagtctacc agaaggtttt gacgtttcgt cgtagctacg cttacatcca ccaccacttat    480
ctgctgggca gcaacacgga atacgtggcg cctcctatgt gggagattca tcatatcaac     540
agtcacagtc agtgctacag ttcctacagc gcgttatag caggcacggt tttcgtggct     600
tatcataggg acagctatga aaacaaaacc atgcaattaa tgcccgacga ttattccaac     660
acccacagta cccgttacgt gacggtcaag gatcaatggc acagccgcgg cagcaccctgg    720
ctctatcgtg agacctgtaa tctgaattgt atggtgacca tcactactgc gcgctccaag     780
tatccctatc attttttcgc aacttccacg ggtgatgtgg ttgacatttc tcctttctac     840
aacggaacta atcgcaatgc cagctatttt ggagaaaacg ccgacaagtt tttcattttt     900
ccgaactaca ctatcgtctc gactttggga agaccgaatt ctgcgttaga cccacagg      960
ttggtggctt ttcttgaacg tgcggactca gtgatctcct gggatataca ggacgagaag    1020
aatgttactt gtcaactcac tttctgggaa gcctcggaac gcaccattcg ttccgaagcc    1080
gaggactcgt atcactttct tctgccaaa atgaccgcca ctttcttatc taagaagcaa     1140
gaggtgaaca tgtccgactc tgcgctggac tgtgtacgtg atgaggccat aaataagtta    1200
cagcagattt tcaatacttc atacaatcaa acatatgaaa aatatggaaa cgtgtccgtc    1260
tttgaaacca ctggtggttt ggtggtgttc tggcaaggta tcaagcaaaa atctctggtg    1320
gaactcgaac gtttggccaa ccgctccagt ctgaatctta ctcataatag aaccaaaaga    1380
agtacagatg caacaatgc aactcattta tccaacatgg agtcggtgca atctggtc       1440
tacgcccagc tgcagttcac ctatgacacg ttgcgcggtt acatcaaccg ggcgctggcg    1500
caaatcgcag aagcctggtg tgtggatcaa cggcgcaccc tagaggtctt caaggaactt    1560
agcaagatca cccgtcagc tattctctcg gccatctaca caaaccgat gccgcgcgt      1620
ttcatgggtg atgtcctggg tctggccagc tgcgtgacca ttaaccaaac cagcgtcaag    1680
gtgctgcgtg atatgaatgt gaaggaatcg ccaggacgct gctactcacg accagtggtc    1740
atctttaatt tcgccaacag ctcgtacgtg cagtacggtc aactgggcga ggataacgaa    1800
atcctgttgg gcaaccaccg cactgaggaa tgtcagcttc ccagcctcaa gatcttcatc    1860
gccggcaact cggcctacga gtacgtggac tacctcttca aacgcatgat tgacctcagc    1920
agcatctcca ccgtcgacag catgatcgcc ctagacatcg acccgctgga aaacaccgac    1980
```

```
ttcagggtac tggaacttta ctcgcagaaa gaattgcgtt ccatcaacgt ttttgatctc    2040
gaggagatca tgcgcgagtt caattcgtat aagcagcggg taaagtacgt ggaggacaag    2100
gtagtcgacc cgctgccgcc ctacctcaag gtctggacg acctcatgag cggcctgggc     2160
gccgcgggaa aggccgttgg cgtagccatt ggggccgtgg gtggcgcggt ggcctccgtg    2220
gtcgaaggcg ttgccacctt cctcaaaaac ccctttttct ttatcatagg gttaatcatt    2280
ggactattct tggttctccg agttggtatc catctttgca ttaaattaaa gcacaccaag    2340
aaaagacaga tttatacaga catagagatg aaccgacttg gaaagtaa                 2388
```

<210> SEQ ID NO 12
<211> LENGTH: 2388
<212> TYPE: DNA
<213> ORGANISM: Human cytomegalovirus
<220> FEATURE:
<221> NAME/KEY: misc_feature
<222> LOCATION: (1)..(2388)
<223> OTHER INFORMATION: Codon Optimized HCMV gB - G Nucleotide Sequence
<220> FEATURE:
<221> NAME/KEY: misc_feature
<222> LOCATION: (2253)..(2388)
<223> OTHER INFORMATION: TM and CTD

<400> SEQUENCE: 12

```
atggagtcaa ggatttggtg tctggtcgtc tgcgtcaacc tgtgcattgt ctgcctggga     60
gccgccgtct catcatcatc tacccgaggc acatccgcca ctcactctca ccatagctcc    120
cataccacat ccgccgctca ctcaagaagc gggtccgtgt ctcagagggt cacatctagt    180
cagaccgtga gccatggagt caacgagaca atctacaata ctaccctgaa gtatggagac    240
gtggtcggcg tgaacacaac taaataccc tataggtct gctctatggc cagggaca         300 gatctgatcc gatttgaacg gaacatcgtg tgcactagca tgaagcctat caatgaggac    360
ctggatgaag gaattatggt ggtctacaaa cgaaatatcg tggcccatac ttttaaggtg    420
agagtctatc agaaagtgct gaccttccgg agaagctacg cttatattca caccacatac    480 ctgctgggt ccaacaccga gtatgtggca ccccctatgt gggaaatcca ccatattaat      540
agtcattcac agtgctactc aagctacagc agagtgatcg ctggaaccgt gttcgtcgca    600
taccacagag acagttatga gaacaagaca atgcagctca tgcccgacga ttacagtaat    660
acccattcaa caagatatgt gaccgtcaaa gatcagtggc actctcgcgg cagtacctgg    720
ctgtaccgag agacatgcaa cctgaattgt atggtgacaa ttactaccgc cagaagcaag    780
tacccttatc acttctttgc tacctcaaca ggggacgtgg tcgacatcag cccttctac      840 aacggaacaa accggaatgc ctcctatttc ggcgagaacg ctgacaaatt ctttatcttc    900
cccaactaca ctatcgtgag cgatttcggc agacctaaca gtgccctgga cccatcgg       960 ctggtggcat ttctggaaag agccgacagc gtgatctcct gggacattca ggatgagaag    1020
aatgtgacct gccagctcac cttctgggag gccagcgaaa gaaccatcag gtccgaggca    1080
gaagattctt accactttc ctctgcaaaa atgactgcca ccttcctgtc caagaaacag      1140
gaggtgaaca tgagcgactc cgcactggat tgcgtgcggg acgaagccat caataagctg    1200
cagcagatct tcaacacatc ttacaaccag acttacgaga gtacggcaa cgtgagtgtc     1260 tttgaaacaa ctggcgggct ggtggtcttc tggcagggga tcaagcagaa atctctggtg    1320
gagctggaac ggctggccaa tagaagttca ctgaacctga ctcataatcg caccaagcga    1380
tccacagacg gaaacaatgc aactcatctg agcaacatgg agtccgtgca caatctggtc    1440
tacgcccagc tccagttcac ttacgacacc ctgcgaggct atatcaaccg ggccctggct    1500
```

-continued

```
cagattgcag aagcctggtg cgtggatcag aggcgcaccc tggaggtctt taaggaactg    1560
agcaaaatta acccatctgc tatcctgagt gcaatctaca ataagcccat cgcagccagg    1620
ttcatggggg acgtgctggg actggcctcc tgcgtcacta tcaaccagac ctctgtgaag    1680
gtcctgcgcg atatgaatgt gaaagagagt cctggcaggt gttattcacg cccagtggtc    1740
atcttcaact cgctaatag ctcctacgtg cagtatggcc agctcgggga ggacaacgaa     1800
atcctgctgg gaaatcacag gaccgaggaa tgtcagctcc caagtctgaa gatctttatt    1860
gccggcaact cagcttacga gtatgtggat tacctgttca aacgcatgat cgacctgtct    1920
agtatttcaa cagtggatag catgatcgcc ctggacattg atcccctgga aaatactgac    1980
ttcagggtgc tggagctgta tagccagaag gaactgcgct ccattaacgt gtttgatctg    2040
gaggaaatca tgagggagtt caattcctac aagcagcgcg tgaaatatgt cgaagataag    2100
gtggtcgacc ctctgccacc ctacctgaaa ggcctggacg atctgatgag cgggctggga    2160
gctgcaggca aggcagtggg agtcgccatc ggagctgtgg gaggcgctgt cgcatccgtg    2220
gtcgagggag tggctacctt tctgaagaac ccattctttt tcatcatcgg cctgatcatt    2280
gggctgttcc tggtgctgag agtcggcatc cacctgtgca ttaagctgaa gcacaccaag    2340
aagaggcaga tctacaccga tattgaaatg aacagactgg gcaagtga                2388
```

```
<210> SEQ ID NO 13
<211> LENGTH: 742
<212> TYPE: PRT
<213> ORGANISM: Human cytomegalovirus
<220> FEATURE:
<221> NAME/KEY: MISC_FEATURE
<222> LOCATION: (1)..(742)
<223> OTHER INFORMATION: HCMV gH Amino Acid Sequence
<220> FEATURE:
<221> NAME/KEY: MISC_FEATURE
<222> LOCATION: (717)..(742)
<223> OTHER INFORMATION: TM and CTD

<400> SEQUENCE: 13

Met Arg Pro Gly Leu Pro Ser Tyr Leu Ile Val Leu Ala Val Cys Leu
1               5                   10                  15

Leu Ser His Leu Leu Ser Ser Arg Tyr Gly Ala Glu Ala Ile Ser Glu
                20                  25                  30

Pro Leu Asp Lys Ala Phe His Leu Leu Leu Asn Thr Tyr Gly Arg Pro
            35                  40                  45

Ile Arg Phe Leu Arg Glu Asn Thr Thr Gln Cys Thr Tyr Asn Ser Ser
        50                  55                  60

Leu Arg Asn Ser Thr Val Val Arg Glu Asn Ala Ile Ser Phe Asn Phe
65                  70                  75                  80

Phe Gln Ser Tyr Asn Gln Tyr Tyr Val Phe His Met Pro Arg Cys Leu
                85                  90                  95

Phe Ala Gly Pro Leu Ala Glu Gln Phe Leu Asn Gln Val Asp Leu Thr
            100                 105                 110

Glu Thr Leu Glu Arg Tyr Gln Gln Arg Leu Asn Thr Tyr Ala Leu Val
        115                 120                 125

Ser Lys Asp Leu Ala Ser Tyr Arg Ser Phe Ser Gln Gln Leu Lys Ala
    130                 135                 140

Gln Asp Ser Leu Gly Glu Gln Pro Thr Thr Val Pro Pro Pro Ile Asp
145                 150                 155                 160

Leu Ser Ile Pro His Val Trp Met Pro Pro Gln Thr Thr Pro His Gly
                165                 170                 175
```

-continued

```
Trp Thr Glu Ser His Thr Thr Ser Gly Leu His Arg Pro His Phe Asn
            180                 185                 190

Gln Thr Cys Ile Leu Phe Asp Gly His Asp Leu Leu Phe Ser Thr Val
        195                 200                 205

Thr Pro Cys Leu His Gln Gly Phe Tyr Leu Ile Asp Glu Leu Arg Tyr
    210                 215                 220

Val Lys Ile Thr Leu Thr Glu Asp Phe Phe Val Val Thr Val Ser Ile
225                 230                 235                 240

Asp Asp Asp Thr Pro Met Leu Leu Ile Phe Gly His Leu Pro Arg Val
                245                 250                 255

Leu Phe Lys Ala Pro Tyr Gln Arg Asp Asn Phe Ile Leu Arg Gln Thr
            260                 265                 270

Glu Lys His Glu Leu Leu Val Leu Val Lys Lys Asp Gln Leu Asn Arg
        275                 280                 285

His Ser Tyr Leu Lys Asp Pro Asp Phe Leu Asp Ala Ala Leu Asp Phe
    290                 295                 300

Asn Tyr Leu Asp Leu Ser Ala Leu Leu Arg Asn Ser Phe His Arg Tyr
305                 310                 315                 320

Ala Val Asp Val Leu Lys Ser Gly Arg Cys Gln Met Leu Asp Arg Arg
                325                 330                 335

Thr Val Glu Met Ala Phe Ala Tyr Ala Leu Ala Leu Phe Ala Ala Ala
            340                 345                 350

Arg Gln Glu Glu Ala Gly Ala Gln Val Ser Val Pro Arg Ala Leu Asp
        355                 360                 365

Arg Gln Ala Ala Leu Leu Gln Ile Gln Glu Phe Met Ile Thr Cys Leu
    370                 375                 380

Ser Gln Thr Pro Pro Arg Thr Thr Leu Leu Tyr Pro Thr Ala Val
385                 390                 395                 400

Asp Leu Ala Lys Arg Ala Leu Trp Thr Pro Asn Gln Ile Thr Asp Ile
                405                 410                 415

Thr Ser Leu Val Arg Leu Val Tyr Ile Leu Ser Lys Gln Asn Gln Gln
            420                 425                 430

His Leu Ile Pro Gln Trp Ala Leu Arg Gln Ile Ala Asp Phe Ala Leu
        435                 440                 445

Lys Leu His Lys Thr His Leu Ala Ser Phe Leu Ser Ala Phe Ala Arg
    450                 455                 460

Gln Glu Leu Tyr Leu Met Gly Ser Leu Val His Ser Met Leu Val His
465                 470                 475                 480

Thr Thr Glu Arg Arg Glu Ile Phe Ile Val Glu Thr Gly Leu Cys Ser
                485                 490                 495

Leu Ala Glu Leu Ser His Phe Thr Gln Leu Leu Ala His Pro His His
            500                 505                 510

Glu Tyr Leu Ser Asp Leu Tyr Thr Pro Cys Ser Ser Gly Arg Arg
        515                 520                 525

Asp His Ser Leu Glu Arg Leu Thr Arg Leu Phe Pro Asp Ala Thr Val
    530                 535                 540

Pro Thr Thr Val Pro Ala Ala Leu Ser Ile Leu Ser Thr Met Gln Pro
545                 550                 555                 560

Ser Thr Leu Glu Thr Phe Pro Asp Leu Phe Cys Leu Pro Leu Gly Glu
                565                 570                 575

Ser Phe Ser Ala Leu Thr Val Ser Glu His Val Ser Tyr Val Val Thr
            580                 585                 590
```

```
Asn Gln Tyr Leu Ile Lys Gly Ile Ser Tyr Pro Val Ser Thr Thr Val
            595                 600                 605

Val Gly Gln Ser Leu Ile Ile Thr Gln Thr Asp Ser Gln Thr Lys Cys
610                 615                 620

Glu Leu Thr Arg Asn Met His Thr Thr His Ser Ile Thr Ala Ala Leu
625                 630                 635                 640

Asn Ile Ser Leu Glu Asn Cys Ala Phe Cys Gln Ser Ala Leu Leu Glu
                645                 650                 655

Tyr Asp Asp Thr Gln Gly Val Ile Asn Ile Met Tyr Met His Asp Ser
            660                 665                 670

Asp Asp Val Leu Phe Ala Leu Asp Pro Tyr Asn Glu Val Val Val Ser
            675                 680                 685

Ser Pro Arg Thr His Tyr Leu Met Leu Leu Lys Asn Gly Thr Val Leu
            690                 695                 700

Glu Val Thr Asp Val Val Asp Ala Thr Asp Ser Arg Leu Leu Met
705                 710                 715                 720

Met Ser Val Tyr Ala Leu Ser Ala Ile Ile Gly Ile Tyr Leu Leu Tyr
                725                 730                 735

Arg Met Leu Lys Thr Cys
            740

<210> SEQ ID NO 14
<211> LENGTH: 2229
<212> TYPE: DNA
<213> ORGANISM: Human cytomegalovirus
<220> FEATURE:
<221> NAME/KEY: misc_feature
<222> LOCATION: (1)..(2229)
<223> OTHER INFORMATION: HCMV gH Nucleotide Sequence
<220> FEATURE:
<221> NAME/KEY: misc_feature
<222> LOCATION: (2151)..(2229)
<223> OTHER INFORMATION: TM and CTD

<400> SEQUENCE: 14
atgcggccag gcctcccctc ctacctcatc gtcctcgccg tctgtctcct cagccaccta      60
ctttcgtcac gatatggcgc agaagccata tccgaaccgc tggacaaagc gtttcaccta     120
ctgctcaaca cctacgggag acccatccgc ttcctgcgtg aaaacaccac ccagtgtacc     180
tacaatagca gcctccgtaa cagcacggtc gtcagggaaa acgccatcag tttcaacttt     240
ttccaaagct ataatcaata ctatgtattc catatgcctc gatgtctttt tgcgggtcct     300
ctggcggagc agtttctgaa ccaggtagat ctgaccgaaa ccctggaaag ataccaacag     360
agacttaaca cttacgcgct ggtatccaaa gacctggcca gctaccgatc ttttttcgcag    420 cagctaaagg cacaggacag cctaggtgaa cagcccacca ctgtgccacc acccattgac     480
ctgtcaatac ctcacgtttg atgccaccg caaaccactc cacacggctg acagaatca      540 cataccacct caggactaca ccgaccacac tttaaccaga cctgtatcct ctttgatgga     600
cacgatctac tattcagcac cgtcacacct tgtttgcacc aaggctttta cctcatcgac     660
gaactacgtt acgttaaaat aacactgacc gaggacttct tcgtagttac ggtgtccata     720
gacgacgaca cacccatgct gcttatcttc ggccatcttc cacgcgtact ctttaaagcg     780
ccctatcaac gcgacaactt tatactacga caaactgaaa acacgagct cctggtgcta     840 gttaagaaag atcaactgaa ccgtcactct tatctcaaag accggactt tcttgacgcc     900 gcacttgact tcaactacct ggacctcagc gcactactac gtaacagctt tcaccgttac     960
gccgtggatg tactcaaaag cggtcgatgt cagatgctgg accgccgcac ggtagaaatg    1020
```

```
gccttcgcct acgcattagc actgttcgca gcagcccgac aagaagaggc cggcgcccaa    1080
gtctccgtcc cacgggccct agaccgccag gccgcactct acaaataca gaatttatg      1140 atcacctgcc tctcacaaac accaccacgc accacgttgc tgctgtatcc cacggccgtg    1200
gacctggcca acgagccct ttggacaccg aatcagatca ccgacatcac cagcctcgta     1260
cgcctggtct acatactctc taaacagaat cagcaacatc tcatccccca gtgggcacta    1320
cgacagatcg ccgactttgc cctaaaacta cacaaaacgc acctggcctc ttttctttca    1380
gccttcgcgc gtcaagaact ctacctcatg ggcagcctcg tccactccat gctagtacat    1440
acgacggaga gacgcgaaat cttcatcgta gaaacgggcc tctgttcatt agccgagcta    1500
tcacacttta cgcagttgct agctcatccg caccacgaat acctcagcga cctgtacaca    1560
ccctgttcca gtagcgggcg acgcgatcac tcgctcgaac gcctcacacg tctcttcccc    1620
gatgccaccg tccccactac cgttcccgcc gccctctcca tcctatctac catgcaacca    1680
agcacgctag aaaccttccc cgacctgttt tgtctgccgc tcggcgaatc cttctccgcg    1740
ctgaccgtct ccgaacacgt cagttatgtc gtaacaaacc agtacctgat caaaggtatc    1800
tcctaccctg tctccaccac cgtcgtaggc cagagcctca tcatcaccca gacgacagt    1860 caaactaaat gcgaactgac gcgcaacatg cataccacac acagcatcac agcggcgctc    1920
aacatttccc tagaaaactg cgccttttgc caaagcgccc tactagaata cgacgacacg    1980
caaggcgtca tcaacatcat gtacatgcac gactcggacg acgtcctttt cgccctggat    2040
ccctacaacg aagtggtggt ctcatctccg cgaactcact acctcatgct tttgaaaaac    2100
ggtacggtcc tagaagtaac tgacgtcgtc gtggacgcta ccgacagtcg tctcctcatg    2160
atgtccgtct acgcgctatc ggccatcatc ggcatctatc tgctctaccg catgctcaag    2220
acatgctga                                                            2229
```

<210> SEQ ID NO 15
<211> LENGTH: 2229
<212> TYPE: DNA
<213> ORGANISM: Human cytomegalovirus
<220> FEATURE:
<221> NAME/KEY: misc_feature
<222> LOCATION: (1)..(2229)
<223> OTHER INFORMATION: Codon Optimized HCMV gH Nucleotide Sequence
<220> FEATURE:
<221> NAME/KEY: misc_feature
<222> LOCATION: (2151)..(2229)
<223> OTHER INFORMATION: TM and CTD

<400> SEQUENCE: 15

```
atgagacctg gactgccttc ttatctgatt gtgctggccg tctgcctgct gtcacatctg    60
ctgagttcac gctatgggc tgaggctatc tccgagccac tggacaaggc ttttcacctg    120
ctgctgaaca cctacgggag acccattagg ttcctgcgcg agaataccac acagtgcaca    180
tataacagct ccctgcggaa cagcactgtg gtccgcgaaa acgccatctc ttttaatttc    240
tttcagagtt acaaccagta ctacgtgttc catatgccac gctgtctgtt tgcaggaccc    300
ctggccgagc agttcctgaa ccaggtggac ctgaccgaga cactggaaag ataccagcag    360
aggctgaata cctatgccct ggtgagtaag gatctggctt catatcggtc tttcagtcag    420
cagctcaagg cccaggactc actgggcgag cagcctacta ccgtgccccc tccaatcgat    480
ctgagcattc acacgtctg gatgccccct cagacaactc cccacggctg gaccgaaagc    540
cataccacat ccgggctgca cagaccccat ttcaaccaga catgcatcct gtttgatggg    600
```

| | |
|---|---|
| cacgacctgc tgttcagcac tgtgaccect tgtctgcatc agggattcta cctgatcgat | 660 |
| gagctgagat atgtgaaaat tacactgact gaagacttct ttgtggtcac cgtgagcatc | 720 |
| gacgatgaca caccaatgct gctgattttt ggacacctgc cccgggtgct gttcaaggcc | 780 |
| ccctaccagc gagacaactt tattctgcgg cagaccgaga acacgaact gctggtgctg | 840 |
| gtcaagaaag atcagctcaa caggcatagc tatctgaagg ccccgactt tctggatgcc | 900 |
| gctctggact caactacct ggacctgtca gcactgctgc ggaatagctt ccacagatat | 960 |
| gccgtggatg tcctgaaatc cggaagatgc cagatgctgg accggagaac cgtggagatg | 1020 |
| gcatttgcct acgctctggc actgttcgca gccgctaggc aggaggaagc aggcgctcag | 1080 |
| gtgtccgtcc ctcgcgcact ggatcgacag gcagccctgc tgcagatcca ggagttcatg | 1140 |
| attacctgtc tgtctcagac accaccaga actaccctgc tgctgtaccc cactgccgtg | 1200 |
| gacctggcta agagggcact gtggacccct aaccagatca ctgatattac ctctctggtg | 1260 |
| cgcctggtct atatcctgag taaacagaat cagcagcacc tgatcccaca gtgggccctg | 1320 |
| cgacagattg ccgacttcgc tctgaagctg cacaaaaccc atctggcttc cttcctgtct | 1380 |
| gcatttgccc gccaggagct gtacctgatg ggctctctgg tgcacagtat gctggtccat | 1440 |
| acaactgaga ggcgcgaaat ctttattgtg gagacagggc tgtgcagcct ggctgaactg | 1500 |
| tcccacttca ctcagctcct ggcccatcct caccatgagt acctgtccga tctgtatacc | 1560 |
| ccatgttcta gttcaggccg acgggaccac tctctggaac gactgactcg gctgtttcct | 1620 |
| gatgcaaccg tgcctaccac cgtgcccgcc gccctgagta tcctgtcaac aatgcagcca | 1680 |
| agcacactgg agactttccc cgacctgttt tgcctgcctc tgggggagtc attcagcgcc | 1740 |
| ctgaccgtgt cagaacatgt cagctacgtg gtcacaaacc agtatctgat caagggaatt | 1800 |
| tcctaccccg tgtctactac cgtggtcggc cagagtctga tcattaccca gacagattca | 1860 |
| cagactaaat gtgagctgac ccggaatatg cacacaactc atagcatcac cgccgctctg | 1920 |
| aacatttccc tggagaattg cgcttttttgt cagagtgcac tgctggaata cgatgacaca | 1980 |
| cagggcgtga tcaacattat gtatatgcac gatagcgatg acgtgctgtt cgctctggac | 2040 |
| ccctacaacg aggtggtcgt gagctcccct cgcactcatt atctgatgct gctgaagaat | 2100 |
| ggaacagtgc tggaagtcac tgatgtcgtg gtcgatgcca cagactcccg gctgctgatg | 2160 |
| atgtctgtgt acgcactgtc cgccatcatc ggcatctatc tgctgtatcg aatgctgaaa | 2220 |
| acctgttga | 2229 |

<210> SEQ ID NO 16
<211> LENGTH: 761
<212> TYPE: PRT
<213> ORGANISM: Human cytomegalovirus
<220> FEATURE:
<221> NAME/KEY: MISC_FEATURE
<222> LOCATION: (1)..(761)
<223> OTHER INFORMATION: HCMV gH - G Amino Acid Sequence
<220> FEATURE:
<221> NAME/KEY: MISC_FEATURE
<222> LOCATION: (717)..(761)
<223> OTHER INFORMATION: TM and CTD

<400> SEQUENCE: 16

Met Arg Pro Gly Leu Pro Ser Tyr Leu Ile Val Leu Ala Val Cys Leu
1               5                   10                  15

Leu Ser His Leu Leu Ser Ser Arg Tyr Gly Ala Glu Ala Ile Ser Glu
            20                  25                  30

Pro Leu Asp Lys Ala Phe His Leu Leu Leu Asn Thr Tyr Gly Arg Pro

-continued

```
                35                  40                  45
Ile Arg Phe Leu Arg Glu Asn Thr Thr Gln Cys Thr Tyr Asn Ser Ser
 50                  55                  60
Leu Arg Asn Ser Thr Val Val Arg Glu Asn Ala Ile Ser Phe Asn Phe
 65                  70                  75                  80
Phe Gln Ser Tyr Asn Gln Tyr Val Phe His Met Pro Arg Cys Leu
                 85                  90                  95
Phe Ala Gly Pro Leu Ala Glu Gln Phe Leu Asn Gln Val Asp Leu Thr
                100                 105                 110
Glu Thr Leu Glu Arg Tyr Gln Gln Arg Leu Asn Thr Tyr Ala Leu Val
                115                 120                 125
Ser Lys Asp Leu Ala Ser Tyr Arg Ser Phe Ser Gln Gln Leu Lys Ala
                130                 135                 140
Gln Asp Ser Leu Gly Glu Gln Pro Thr Thr Val Pro Pro Ile Asp
145                 150                 155                 160
Leu Ser Ile Pro His Val Trp Met Pro Pro Gln Thr Thr Pro His Gly
                165                 170                 175
Trp Thr Glu Ser His Thr Thr Ser Gly Leu His Arg Pro His Phe Asn
                180                 185                 190
Gln Thr Cys Ile Leu Phe Asp Gly His Asp Leu Leu Phe Ser Thr Val
                195                 200                 205
Thr Pro Cys Leu His Gln Gly Phe Tyr Leu Ile Asp Glu Leu Arg Tyr
                210                 215                 220
Val Lys Ile Thr Leu Thr Glu Asp Phe Phe Val Val Thr Val Ser Ile
225                 230                 235                 240
Asp Asp Asp Thr Pro Met Leu Leu Ile Phe Gly His Leu Pro Arg Val
                245                 250                 255
Leu Phe Lys Ala Pro Tyr Gln Arg Asp Asn Phe Ile Leu Arg Gln Thr
                260                 265                 270
Glu Lys His Glu Leu Leu Val Leu Val Lys Lys Asp Gln Leu Asn Arg
                275                 280                 285
His Ser Tyr Leu Lys Asp Pro Asp Phe Leu Asp Ala Ala Leu Asp Phe
                290                 295                 300
Asn Tyr Leu Asp Leu Ser Ala Leu Leu Arg Asn Ser Phe His Arg Tyr
305                 310                 315                 320
Ala Val Asp Val Leu Lys Ser Gly Arg Cys Gln Met Leu Asp Arg Arg
                325                 330                 335
Thr Val Glu Met Ala Phe Ala Tyr Ala Leu Ala Leu Phe Ala Ala Ala
                340                 345                 350
Arg Gln Glu Glu Ala Gly Ala Gln Val Ser Val Pro Arg Ala Leu Asp
                355                 360                 365
Arg Gln Ala Ala Leu Leu Gln Ile Gln Glu Phe Met Ile Thr Cys Leu
                370                 375                 380
Ser Gln Thr Pro Pro Arg Thr Thr Leu Leu Tyr Pro Thr Ala Val
385                 390                 395                 400
Asp Leu Ala Lys Arg Ala Leu Trp Thr Pro Asn Gln Ile Thr Asp Ile
                405                 410                 415
Thr Ser Leu Val Arg Leu Val Tyr Ile Leu Ser Lys Gln Asn Gln Gln
                420                 425                 430
His Leu Ile Pro Gln Trp Ala Leu Arg Gln Ile Ala Asp Phe Ala Leu
                435                 440                 445
Lys Leu His Lys Thr His Leu Ala Ser Phe Leu Ser Ala Phe Ala Arg
                450                 455                 460
```

```
Gln Glu Leu Tyr Leu Met Gly Ser Leu Val His Ser Met Leu Val His
465                 470                 475                 480

Thr Thr Glu Arg Arg Glu Ile Phe Ile Val Glu Thr Gly Leu Cys Ser
                485                 490                 495

Leu Ala Glu Leu Ser His Phe Thr Gln Leu Leu Ala His Pro His His
            500                 505                 510

Glu Tyr Leu Ser Asp Leu Tyr Thr Pro Cys Ser Ser Gly Arg Arg
        515                 520                 525

Asp His Ser Leu Glu Arg Leu Thr Arg Leu Phe Pro Asp Ala Thr Val
    530                 535                 540

Pro Thr Thr Val Pro Ala Ala Leu Ser Ile Leu Ser Thr Met Gln Pro
545                 550                 555                 560

Ser Thr Leu Glu Thr Phe Pro Asp Leu Phe Cys Leu Pro Leu Gly Glu
                565                 570                 575

Ser Phe Ser Ala Leu Thr Val Ser Glu His Val Ser Tyr Val Val Thr
            580                 585                 590

Asn Gln Tyr Leu Ile Lys Gly Ile Ser Tyr Pro Val Ser Thr Thr Val
        595                 600                 605

Val Gly Gln Ser Leu Ile Ile Thr Gln Thr Asp Ser Gln Thr Lys Cys
    610                 615                 620

Glu Leu Thr Arg Asn Met His Thr Thr His Ser Ile Thr Ala Ala Leu
625                 630                 635                 640

Asn Ile Ser Leu Glu Asn Cys Ala Phe Cys Gln Ser Ala Leu Leu Glu
                645                 650                 655

Tyr Asp Asp Thr Gln Gly Val Ile Asn Ile Met Tyr Met His Asp Ser
            660                 665                 670

Asp Asp Val Leu Phe Ala Leu Asp Pro Tyr Asn Glu Val Val Val Ser
        675                 680                 685

Ser Pro Arg Thr His Tyr Leu Met Leu Leu Lys Asn Gly Thr Val Leu
    690                 695                 700

Glu Val Thr Asp Val Val Asp Ala Thr Asp Ser Arg Phe Phe Phe
705                 710                 715                 720

Ile Ile Gly Leu Ile Ile Gly Leu Phe Leu Val Leu Arg Val Gly Ile
                725                 730                 735

His Leu Cys Ile Lys Leu Lys His Thr Lys Lys Arg Gln Ile Tyr Thr
            740                 745                 750

Asp Ile Glu Met Asn Arg Leu Gly Lys
        755                 760

<210> SEQ ID NO 17
<211> LENGTH: 2286
<212> TYPE: DNA
<213> ORGANISM: Human cytomegalovirus
<220> FEATURE:
<221> NAME/KEY: misc_feature
<222> LOCATION: (1)..(2286)
<223> OTHER INFORMATION: HCMV gH - G Nucleotide Sequence
<220> FEATURE:
<221> NAME/KEY: misc_feature
<222> LOCATION: (2151)..(2286)
<223> OTHER INFORMATION: TM and CTD

<400> SEQUENCE: 17
atgcggccag gcctcccctc ctacctcatc gtcctcgccg tctgtctcct cagccaccta      60
ctttcgtcac gatatggcgc agaagccata tccgaaccgc tggacaaagc gtttcaccta     120
ctgctcaaca cctacgggag acccatccgc ttcctgcgtg aaaacaccac ccagtgtacc     180
```

```
tacaatagca gcctccgtaa cagcacggtc gtcagggaaa acgccatcag tttcaacttt     240
ttccaaagct ataatcaata ctatgtattc catatgcctc gatgtctttt tgcgggtcct     300
ctggcggagc agtttctgaa ccaggtagat ctgaccgaaa ccctggaaag ataccaacag     360
agacttaaca cttacgcgct ggtatccaaa gacctggcca gctaccgatc tttttcgcag     420
cagctaaagg cacaggacag cctaggtgaa cagcccacca ctgtgccacc acccattgac     480
ctgtcaatac ctcacgtttg gatgccaccg caaaccactc cacacggctg acagaatca     540 cataccacct caggactaca ccgaccacac tttaaccaga cctgtatcct ctttgatgga     600
cacgatctac tattcagcac cgtcacacct tgtttgcacc aaggctttta cctcatcgac     660
gaactacgtt acgttaaaat aacactgacc gaggacttct tcgtagttac ggtgtccata     720
gacgacgaca cacccatgct gcttatcttc ggccatcttc cacgcgtact ctttaaagcg     780
ccctatcaac gcgacaactt tatactacga caaactgaaa acacgagct cctggtgcta     840 gttaagaaag atcaactgaa ccgtcactct tatctcaaag acccggactt tcttgacgcc     900
gcacttgact tcaactacct ggacctcagc gcactactac gtaacagctt tcaccgttac     960
gccgtggatg tactcaaaag cggtcgatgt cagatgctgg accgccgcac ggtagaaatg    1020
gccttcgcct acgcattagc actgttcgca gcagcccgac aagaagaggc cggcgcccaa    1080
gtctccgtcc cacgggccct agaccgccag gccgcactct acaaatacag aaatttatg     1140 atcacctgcc tctcacaaac accaccacgc accacgttgc tgctgtatcc cacggccgtg    1200
gacctggcca acgagccct ttggacaccg aatcagatca ccgacatcac cagcctcgta     1260
cgcctggtct acatactctc taaacagaat cagcaacatc tcatccccca gtgggcacta    1320
cgacagatcg ccgactttgc cctaaaacta cacaaaacgc acctggcctc ttttctttca    1380
gccttcgcgc gtcaagaact ctacctcatg ggcagcctcg tccactccat gctagtacat    1440
acgacggaga gacgcgaaat cttcatcgta gaaacgggcc tctgttcatt agccgagcta    1500 tcacactttta cgcagttgct agctcatccg caccacgaat acctcagcga cctgtacaca    1560
ccctgttcca gtagcgggcg acgcgatcac tcgctcgaac gcctcacacg tctcttcccc    1620
gatgccaccg tccccactac cgttcccgcc gccctctcca tcctatctac catgcaacca    1680
agcacgctag aaaccttccc cgacctgttt tgtctgccgc tcggcgaatc cttctccgcg    1740
ctgaccgtct ccgaacacgt cagttatgtc gtaacaaacc agtacctgat caaaggtatc    1800
tcctaccctg tctccaccac cgtcgtaggc cagagcctca tcatcaccca gacggacagt    1860
caaactaaat gcgaactgac gcgcaacatg cataccacac acagcatcac agcggcgctc    1920
aacatttccc tagaaaactg cgccttttgc caaagcgccc tactagaata cgacgacacg    1980
caaggcgtca tcaacatcat gtacatgcac gactcggacg acgtcctttt cgccctggat    2040
ccctacaacg aagtggtggt ctcatctccg cgaactcact acctcatgct tttgaaaaac    2100
ggtacggtcc tagaagtaac tgacgtcgtc gtggacgcta ccgacagtcg tttttttcttt    2160 atcataggt taatcattgg actattcttg gttctccgag ttggtatcca tctttgcatt     2220
aaattaaagc acaccaagaa aagacagatt tatacagaca tagagatgaa ccgacttgga    2280
aagtaa                                                                2286
```

<210> SEQ ID NO 18
<211> LENGTH: 2286
<212> TYPE: DNA
<213> ORGANISM: Human cytomegalovirus
<220> FEATURE:

```
<221> NAME/KEY: misc_feature
<222> LOCATION: (2151)..(2286)
<223> OTHER INFORMATION: TM and CTD
<220> FEATURE:
<221> NAME/KEY: misc_feature
<222> LOCATION: (2151)..(2286)
<223> OTHER INFORMATION: Codon Optimized HCMV gH - G Nucleotide Sequence

<400> SEQUENCE: 18
```

| | | | |
|---|---|---|---|
| atgcgacccg gactgccaag ctacctgatt gtcctggctg tctgtctgct gtcacacctg | 60 | | |
| ctgagttcaa gatatggggc cgaagccatc agcgagccac tggacaaggc tttccacctg | 120 | | |
| ctgctgaaca cctacggcag acccattagg tttctgcgcg agaataccac acagtgcaca | 180 | | |
| tataacagct ccctgaggaa tagcactgtg gtccgcgaaa acgccatctc tttcaatttc | 240 | | |
| tttcagagtt acaaccagta ctacgtgttc catatgccac gctgtctgtt cgcaggaccc | 300 | | |
| ctggccgagc agtttctgaa ccaggtggac ctgaccgaga cactggaaag ataccagcag | 360 | | |
| aggctgaata cctatgccct ggtgagtaag gatctggctt catatcggtc tttcagtcag | 420 | | |
| cagctcaagg cccaggactc tctgggagag cagcctacta ccgtgccccc tccaatcgat | 480 | | |
| ctgagtattc acacgtctg gatgccccct cagacaactc ccacggatg accgaaagc | 540 | | |
| cataccacat ccggcctgca cagacccac ttcaaccaga catgcatcct gttcgatggc | 600 | | |
| cacgacctgc tgttttccac tgtgaccccc tgtctgcatc aggggttcta cctgatcgat | 660 | | |
| gagctgagat atgtgaagat tacactgact gaagacttct tgtggtcac cgtgtctatc | 720 | | |
| gacgatgaca caccaatgct gctgattttc ggacacctgc ccgggtgct gttcaaggcc | 780 | | |
| ccctaccagc gagacaactt catcctgcgg cagaccgaga acacgaact gctggtgctg | 840 | | |
| gtcaagaaag atcagctcaa ccggcattcc tatctgaagg accccgactt cctggatgcc | 900 | | |
| gctctggact ttaactacct ggacctgtca gcactgctgc ggaatagctt cacagatat | 960 | | |
| gccgtggatg tcctgaaatc tgggcgctgc cagatgctgg accggagaac cgtggagatg | 1020 | | |
| gcattcgcct acgctctggc actgtttgca gccgctcggc aggaggaagc aggagctcag | 1080 | | |
| gtgagtgtcc ctcgcgcact ggatcgacag gcagccctgc tgcagatcca ggagttcatg | 1140 | | |
| attacctgtc tgagccagac accacccaga actaccctgc tgctgtaccc cactgccgtg | 1200 | | |
| gacctggcta agagggcact gtggaccct aaccagatca ctgatattac cagcctggtg | 1260 | | |
| agactggtct atatcctgtc caaacagaat cagcagcacc tgatcccaca gtgggccctg | 1320 | | |
| aggcagattg ccgactttgc tctgaagctg cacaaaaccc atctggcttc ctttctgtct | 1380 | | |
| gcattcgcca gacaggagct gtacctgatg ggatctctgg tgcacagtat gctggtccat | 1440 | | |
| acaactgaga ggcgcgaaat cttcattgtg agacaggcc tgtgcagcct ggctgaactg | 1500 | | |
| tcccacttta ctcagctcct ggcccatcct caccatgagt acctgtcaga tctgtatacc | 1560 | | |
| ccatgttcta gttcaggacg acgggaccac agcctggaac gactgactcg gctgttccct | 1620 | | |
| gatgcaaccg tgcctaccac cgtgcccgcc gccctgagta cctgtcaac aatgcagcca | 1680 | | |
| agcacactgg agacttttcc cgacctgttc tgcctgcctc tgggcgagag cttcagcgcc | 1740 | | |
| ctgaccgtga gcgaacatgt cagctacgtg gtcacaaaacc agtatctgat caggggatt | 1800 | | |
| tcctaccccg tgtctactac cgtggtcgga cagtccctga tcattaccca gacagattct | 1860 | | |
| cagactaaat gtgagctgac cagaaatatg cacacaactc atagtatcac cgccgctctg | 1920 | | |
| aacatttcac tggagaattg cgcttttctgt cagtccgcac tgctggaata cgatgacaca | 1980 | | |
| cagggcgtga tcaacattat gtatatgcac gattctgatg acgtgctgtt tgctctggac | 2040 | | |
| ccctacaacg aggtggtcgt gagctccccc agaactcatt atctgatgct gctgaagaat | 2100 | | |

```
ggcacagtgc tggaagtcac tgatgtcgtg gtcgatgcca cagactcccg cttcttttc    2160 atcattggcc tgatcattgg gctgttcctg gtgctgcgag tcggcatcca cctgtgcatc    2220
aagctgaagc atacaaagaa gagacagatc tacaccgata ttgaaatgaa caggctgggc    2280
aaatga                                                               2286

<210> SEQ ID NO 19
<211> LENGTH: 4895
<212> TYPE: DNA
<213> ORGANISM: Artificial Sequence
<220> FEATURE:
<223> OTHER INFORMATION: Propol II Expression Plasmid
<220> FEATURE:
<221> NAME/KEY: misc_feature
<222> LOCATION: (1)..(4895)
<223> OTHER INFORMATION: Propol II Expression Plasmid Nucleotide
      Sequence

<400> SEQUENCE: 19
ctagagagct tggcccattg catacgttgt atccatatca taatatgtac atttatattg      60
gctcatgtcc aacattaccg ccatgttgac attgattatt gactagttat taatagtaat    120
caattacggg gtcattagtt catagcccat atatggagtt ccgcgttaca taacttacgg    180
taaatggccc gcctggctga ccgcccaacg acccccgccc attgacgtca ataatgacgt    240
atgttcccat agtaacgcca atagggactt tccattgacg tcaatgggtg gagtatttac    300
ggtaaactgc ccacttggca gtacatcaag tgtatcatat gccaagtacg ccccctattg    360
acgtcaatga cggtaaatgg cccgcctggc attatgccca gtacatgacc ttatgggact    420
ttcctacttg gcagtacatc tacgtattag tcatcgctat taccatggtg atgcggtttt    480
ggcagtacat caatgggcgt ggatagcggt ttgactcacg gggatttcca agtctccacc    540
ccattgacgt caatgggagt ttgttttggc accaaaatca acgggacttt ccaaaatgtc    600
gtaacaactc cgccccattg acgcaaatgg gcggtaggcg tgtacggtgg gaggtctata    660
taagcagagc tcgtttagtg aaccgtcaga tcgcctggag acgccatcca cgctgttttg    720
acctccatag aagacaccgg gaccgatcca gcctccggtc gaccgatcct gagaacttca    780
gggtgagttt ggggacccct tgattgttct tctttttcgc tattgtaaaa ttcatgttat    840
atggaggggg caaagttttc agggtgttgt ttagaatggg aagatgtccc ttgtatcacc    900
atggaccctc atgataaatt tgtttctttc actttctact ctgttgacaa ccattgtctc    960
ctcttatttt cttttcattt tcttgtaact tttcgttaa actttagctt gcatttgtaa   1020
cgaattttta aattcacttt tgtttatttg tcagattgta agtactttct ctaatcactt   1080 tttttcaag gcaatcaggg tatattatat tgtacttcag cacagtttta gagaacaatt   1140
gttataatta aatgataagg tagaatattt ctgcatataa attctggctg gcgtggaaat   1200
attcttattg gtagaaacaa ctacatcctg gtcatcatcc tgcctttctc tttatggtta   1260
caatgatata cactgtttga gatgaggata aatactctg agtccaaacc gggcccctct   1320
gctaaccatg ttcatgcctt cttctttttc ctacagctcc tgggcaacgt gctggttatt   1380
gtgctgtctc atcattttgg caaagaattc ctcgagcgta cgcctagggg atccagcgct   1440
atttaaatgc tagcatgcat gttaaccctg caggggtacc gcggccgcaa gcttagatcc   1500
gtcgaggaat tcactcctca ggtgcaggct gcctatcaga aggtggtggc tggtgtggcc   1560
aatgccctgg ctcacaaata ccactgagat cttttttccct ctgccaaaaa ttatggggac   1620
atcatgaagc cccttgagca tctgacttct ggctaataaa ggaaatttat tttcattgca   1680
```

```
atagtgtgtt ggaattttt gtgtctctca ctcggaagga catatgggag ggcaaatcat    1740
ttaaaacatc agaatgagta tttggtttag agtttggcaa catatgccca tatgctggct    1800
gccatgaaca aaggttggct ataaagaggt catcagtata tgaaacagcc ccctgctgtc    1860
cattccttat tccatagaaa agccttgact tgaggttaga ttttttttat attttgtttt    1920
gtgttatttt tttctttaac atccctaaaa ttttccttac atgttttact agccagattt    1980
ttcctcctct cctgactact cccagtcata gctgtccctc ttctcttatg agatccctc     2040
gacggatcgg ccgcaattcg taatcatgtc atagctgttt cctgtgtgaa attgttatcc    2100
gctcacaatt ccacacaaca tacgagccgg aagcataaag tgtaaagcct ggggtgccta    2160
atgagtgagc taactcacat taattgcgtt gcgctcactg cccgctttcc agtcgggaaa    2220
cctgtcgtgc cagctgcatt aatgaatcgg ccaacgcgcg gggagaggcg tttgcgtat     2280
tgggcgctct tccgcttcct cgctcactga ctcgctgcgc tcggtcgttc ggctgcggcg    2340
agcggtatca gctcactcaa aggcggtaat acggttatcc acagaatcag gggataacgc    2400
aggaaagaac atgtgagcaa aaggccagca aaaggccagg aaccgtaaaa aggccgcgtt    2460
gctggcgttt ttccataggc tccgcccccc tgacgagcat cacaaaaatc gacgctcaag    2520
tcagaggtgg cgaaacccga caggactata aagataccag gcgtttcccc ctggaagctc    2580
cctcgtgcgc tctcctgttc cgaccctgcc gcttaccgga tacctgtccg cctttctccc    2640
ttcgggaagc gtggcgcttt ctcatagctc acgctgtagg tatctcagtt cggtgtaggt    2700
cgttcgctcc aagctgggct gtgtgcacga accccccgtt cagcccgacc gctgcgcctt    2760
atccggtaac tatcgtcttg agtccaaccc ggtaagacac gacttatcgc cactggcagc    2820
agccactggt aacaggatta gcagagcgag gtatgtaggc ggtgctacag agttcttgaa    2880
gtggtggcct aactacggct acactagaag aacagtattt ggtatctgcg ctctgctgaa    2940
gccagttacc ttcggaaaaa gagttggtag ctcttgatcc ggcaaacaaa ccaccgctgg    3000
tagcggtggt ttttttgttt gcaagcagca gattacgcgc agaaaaaaag gatctcaaga    3060
agatcctttg atcttttcta cggggtctga cgctcagtgg aacgaaaact cacgttaagg    3120
gattttggtc atgagattat caaaaaggat cttcacctag atcctttaa attaaaaatg     3180
aagttttaaa tcaatctaaa gtatatatga gtaaacttgg tctgacagtt accaatgctt    3240
aatcagtgag gcacctatct cagcgatctg tctatttcgt tcatccatag ttgcctgact    3300
ccccgtcgtg tagataacta cgatacggga gggcttacca tctggcccca gtgctgcaat    3360
gataccgcga gacccacgct caccggctcc agatttatca gcaataaacc agccagccgg    3420
aagggccgag cgcagaagtg gtcctgcaac tttatccgcc tccatccagt ctattaattg    3480
ttgccgggaa gctagagtaa gtagttcgcc agttaatagt ttgcgcaacg ttgttgccat    3540
tgctacaggc atcgtggtgt cacgctcgtc gtttggtatg gcttcattca gctccggttc    3600
ccaacgatca aggcgagtta catgatcccc catgttgtgc aaaaaagcgg ttagctcct     3660
tcggtcctcc gatcgttgtc agaagtaagt tggccgcagt gttatcactc atggttatgg    3720
cagcactgca taattctctt actgtcatgc catccgtaag atgcttttct gtgactggtg    3780
agtactcaac caagtcattc tgagaatagt gtatgcggcg accgagttgc tcttgcccgg    3840
cgtcaatacg ggataatacc gcgccacata gcagaacttt aaaagtgctc atcattggaa    3900
aacgttcttc ggggcgaaaa ctctcaagga tcttaccgct gttgagatcc agttcgatgt    3960
aacccactcg tgcacccaac tgatcttcag catcttttac tttcaccagc gtttctgggt    4020
```

```
gagcaaaaac aggaaggcaa aatgccgcaa aaaagggaat aagggcgaca cggaaatgtt    4080
gaatactcat actcttcctt tttcaatatt attgaagcat ttatcagggt tatttgtctca    4140 tgagcggata catatttgaa tgtatttaga aaaataaaca aataggggtt ccgcgcacat    4200
ttccccgaaa agtgccacct aaattgtaag cgttaatatt ttgttaaaat tcgcgttaaa    4260
tttttgttaa atcagctcat tttttaacca ataggccgaa atcggcaaaa tcccttataa    4320
atcaaaagaa tagaccgaga tagggttgag tgttgttcca gtttggaaca agagtccact    4380
attaaagaac gtggactcca acgtcaaagg gcgaaaaacc gtctatcagg gcgatggccc    4440
actacgtgaa ccatcaccct aatcaagttt ttgggggtcg aggtgccgta aagcactaaa    4500
tcggaaccct aaagggagcc cccgatttag agcttgacgg ggaaagccgg cgaacgtggc    4560
gagaaaggaa gggaagaaag cgaaaggagc gggcgctagg gcgctggcaa gtgtagcggt    4620
cacgctgcgc gtaaccacca cacccgccgc gcttaatgcg ccgctacagg gcgcgtccca    4680
ttcgccattc aggctgcgca actgttggga agggcgatcg tgcgggcct cttcgctatt    4740 acgccagctg gcgaaagggg gatgtgctgc aaggcgatta agttgggtaa cgccagggtt    4800
ttcccagtca cgacgttgta aaacgacggc cagtgagcgc gcgtaatacg actcactata    4860
gggcgaattg gagctccacc gcggtggcgg ccgct                                4895

<210> SEQ ID NO 20
<211> LENGTH: 2622
<212> TYPE: DNA
<213> ORGANISM: Human cytomegalovirus
<220> FEATURE:
<221> NAME/KEY: sig_peptide
<222> LOCATION: (1)..(69)
<223> OTHER INFORMATION: gH peptide signal
<220> FEATURE:
<221> NAME/KEY: misc_feature
<222> LOCATION: (1)..(2622)
<223> OTHER INFORMATION: HCMV gH - HCMV gB TM/CTD Nucleotide Sequence
<220> FEATURE:
<221> NAME/KEY: misc_feature
<222> LOCATION: (2151)..(2622)
<223> OTHER INFORMATION: gB TM-CTD

<400> SEQUENCE: 20
atgcggccag gcctcccctc ctacctcatc gtcctcgccg tctgtctcct cagccaccta      60
ctttcgtcac gatatggcgc agaagccata tccgaaccgc tggacaaagc gtttcaccta    120
ctgctcaaca cctacgggag acccatccgc ttcctgcgtg aaaacaccac ccagtgtacc    180
tacaatagca gcctccgtaa cagcacggtc gtcaggaaaa cgccatcag tttcaacttt    240 ttccaaagct ataatcaata ctatgtattc catatgcctc gatgtctttt tgcgggtcct    300
ctggcggagc agtttctgaa ccaggtagat ctgaccgaaa ccctggaaag ataccaacag    360
agacttaaca cttacgcgct ggtatccaaa gacctggcca gctaccgatc tttttcgcag    420
cagctaaagg cacaggacag cctaggtgaa cagcccacca ctgtgccacc acccattgac    480
ctgtcaatac ctcacgtttg gatgccaccg caaaccactc acacggctg acagaatca    540 cataccacct caggactaca ccgaccacac tttaaccaga cctgtatcct ctttgatgga    600
cacgatctac tattcagcac cgtcacacct gtttgcacc aaggcttta cctcatcgac    660 gaactacgtt acgttaaaat aacactgacc gaggacttct tcgtagttac ggtgtccata    720
gacgacgaca cacccatgct gcttatcttc ggccatcttc cacgcgtact ctttaaagcg    780
ccctatcaac gcgacaactt atactacgca caaactgaaa acacgagct cctggtgcta    840 gttaagaaag atcaactgaa ccgtcactct tatctcaaag acccggactt tcttgacgcc    900
```

```
gcacttgact tcaactacct ggacctcagc gcactactac gtaacagctt tcaccgttac      960
gccgtggatg tactcaaaag cggtcgatgt cagatgctgg accgccgcac ggtagaaatg     1020
gccttcgcct acgcattagc actgttcgca gcagcccgac aagaagaggc cggcgcccaa     1080
gtctccgtcc cacgggccct agaccgccag gccgcactct tacaaataca gaatttatg     1140 atcacctgcc tctcacaaac accaccacgc accacgttgc tgctgtatcc cacggccgtg     1200
gacctggcca acgagccct ttggacaccg aatcagatca ccgacatcac cagcctcgta     1260
cgcctggtct acatactctc taaacagaat cagcaacatc tcatccccca gtgggcacta     1320
cgacagatcg ccgactttgc cctaaaacta cacaaaacgc acctggcctc ttttctttca     1380
gccttcgcgc gtcaagaact ctacctcatg ggcagcctcg tccactccat gctagtacat     1440
acgacggaga gacgcgaaat cttcatcgta gaaacgggcc tctgttcatt agccgagcta     1500
tcacacttta cgcagttgct agctcatccg caccacgaat acctcagcga cctgtacaca     1560
ccctgttcca gtagcgggcg acgcgatcac tcgctcgaac gcctcacacg tctcttcccc     1620
gatgccaccg tccccactac cgttcccgcc gccctctcca tcctatctac catgcaacca     1680
agcacgctag aaaccttccc cgacctgttt tgtctgccgc tcggcgaatc cttctccgcg     1740
ctgaccgtct ccgaacacgt cagttatgtc gtaacaaacc agtacctgat caaaggtatc     1800
tcctaccctg tctccaccac cgtcgtaggc cagagcctca tcatcaccca gacgacagt     1860 caaactaaat gcgaactgac gcgcaacatg cataccacac acagcatcac agcggcgctc     1920
aacatttccc tagaaaactg cgccttttgc caaagcgccc tactagaata cgacgacacg     1980
caaggcgtca tcaacatcat gtacatgcac gactcggacg acgtccttttt cgccctggat     2040 ccctacaacg aagtggtggt ctcatctccg cgaactcact acctcatgct tttgaaaaac     2100
ggtacggtcc tagaagtaac tgacgtcgtc gtggacgcta ccgacagtcg tttcggagcc     2160
ttcaccatca tcctcgtggc catagccgtc gtcattatca tttatttgat ctatactcga     2220
cagcggcgtc tctgcatgca gccgctgcag aacctctttc cctatctggt gtccgccgac     2280
gggaccaccg tgacgtcggg caacaccaaa gacacgtcgt tacaggctcc gccttcctac     2340
gaggaaagtg tttataattc tggtcgcaaa ggaccgggac caccgtcgtc tgatgcatcc     2400
acggcggctc cgccttacac caacgagcag gcttaccaga tgcttctggc cctggtccgt     2460
ctggacgcag agcagcgagc gcagcagaac ggtacagatt ctttggacgg acagactggc     2520
acgcaggaca agggacagaa gcccaacctg ctagaccgac tgcgacaccg caaaaacggc     2580
taccgacact tgaaagactc cgacgaagaa gagaacgtct ga                       2622
```

<210> SEQ ID NO 21
<211> LENGTH: 1614
<212> TYPE: DNA
<213> ORGANISM: Murine leukemia virus
<220> FEATURE:
<221> NAME/KEY: misc_feature
<222> LOCATION: (1)..(1614)
<223> OTHER INFORMATION: Codon Optimized MMLV Gag Nucleotide Sequence

<400> SEQUENCE: 21

```
atgggacaga ccgtcacaac acccctgagc ctgaccctgg acattggaa agacgtggag       60 aggatcgcac ataaccagag cgtggacgtg aagaaacgga gatgggtcac attctgcagt     120
gctgagtggc caacttttaa tgtgggatgg ccccgagacg gcactttcaa cagggatctg     180
atcacccagg tgaagatcaa ggtctttagc ccaggacctc acggacatcc agaccaggtg     240
```

```
ccttatatcg tcacctggga ggcactggcc ttcgatcccc ctccatgggt gaagccattt      300
gtccacccaa aaccacctcc accactgcct ccaagtgccc cttcactgcc actggaacca      360
ccccggagca caccaccccg cagctccctg tatcctgctc tgactccatc tctgggcgca      420
aagccaaaac cacaggtgct gagcgactcc ggaggaccac tgattgacct gctgacagag      480 gacccccac  cataccgaga tcctcggcct ccaccaagcg accgcgatgg aaatggagga      540
gaggctactc ctgccggcga agccctgac  ccatctccaa tggctagtag gctgcgcggc      600
aggcgcgagc ctccagtggc agatagcacc acatcccagg ccttccctct gagggctggg      660
ggaaatgggc agctccagta ttggccattt tctagttcag acctgtacaa ctggaagaac      720
aataacccct ctttcagtga ggaccccggc aaactgaccg ccctgatcga atccgtgctg      780
attacccatc agcccacatg ggacgattgt cagcagctcc tggcacccct gctgaccgga      840
gaggaaaagc agcgcgtgct gctggaggct cgcaaagcag tccgagggga cgatggacgg      900
cccacacagc tccctaatga ggtggacgcc gcttttccac tggaaagacc cgactgggat      960
tatactaccc aggcagggag aaaccacctg gtccattaca gcagctcct  gctggcaggc     1020 ctgcagaatg ccgggagatc ccccaccaac ctggccaagg tgaaaggcat cacacagggg     1080
cctaatgagt caccaagcgc ctttctggag aggctgaagg aagcttaccg acggtatacc     1140
ccatacgacc ctgaggaccc cggacaggaa acaaacgtct ccatgtcttt catctggcag     1200
tctgccccag acattgggcg gaagctggag agactggaag acctgaagaa caagaccctg     1260
ggcgacctgg tgcgggaggc tgaaaagatc ttcaacaaac gggagacccc cgaggaaaga     1320
gaggaaagga ttagaaggga aactgaggaa aaggaggaac gccgacggac cgaggacgaa     1380
cagaaggaga aagaacgaga tcggcggcgg caccgggaga tgtcaaagct gctggccacc     1440
gtggtcagcg acagaaaca  ggacagacag ggaggagagc gacggagaag ccagctcgac     1500
agggatcagt gcgcatactg taaggaaaaa ggccattggg ccaaggattg ccccaaaaag     1560
ccaagaggac caagaggacc aagaccacag acatcactgc tgaccctgga cgac           1614
```

<210> SEQ ID NO 22
<211> LENGTH: 3300
<212> TYPE: DNA
<213> ORGANISM: Murine leukemia virus
<220> FEATURE:
<221> NAME/KEY: misc_feature
<222> LOCATION: (1)..(1614)
<223> OTHER INFORMATION: Codon Optimized MMLV Gag nucleotide sequence
<220> FEATURE:
<221> NAME/KEY: misc_feature
<222> LOCATION: (1615)..(3300)
<223> OTHER INFORMATION: Codon Optimized CMV pp65  nucleotide sequence

<400> SEQUENCE: 22

```
atgggacaga ccgtcacaac accctgagc ctgaccctgg acattggaa  agacgtggag       60 aggatcgcac ataaccagag cgtggacgtg aagaaacgga gatgggtcac attctgcagt      120
gctgagtggc caacttttaa tgtgggatgg ccccgagacg cactttcaa  cagggatctg      180 atcacccagg tgaagatcaa ggtctttagc ccaggacctc acggacatcc agaccaggtg      240
ccttatatcg tcacctggga ggcactggcc ttcgatcccc ctccatgggt gaagccattt      300
gtccacccaa aaccacctcc accactgcct ccaagtgccc cttcactgcc actggaacca      360
ccccggagca caccaccccg cagctccctg tatcctgctc tgactccatc tctgggcgca      420
aagccaaaac cacaggtgct gagcgactcc ggaggaccac tgattgacct gctgacagag      480 gacccccac  cataccgaga tcctcggcct ccaccaagcg accgcgatgg aaatggagga      540
```

```
gaggctactc ctgccggcga agccctgac ccatctccaa tggctagtag gctgcgcggc    600
aggcgcgagc ctccagtggc agatagcacc acatcccagg ccttccctct gagggctggg    660
ggaaatgggc agctccagta ttggccattt tctagttcag acctgtacaa ctggaagaac    720
aataacccct ctttcagtga ggaccccggc aaactgaccg ccctgatcga atccgtgctg    780
attacccatc agcccacatg ggacgattgt cagcagctcc tgggcaccct gctgaccgga    840
gaggaaaagc agcgcgtgct gctggaggct cgcaaagcag tccgagggga cgatggacgg    900
cccacacagc tccctaatga ggtggacgcc gcttttccac tggaaagacc cgactgggat    960
tatactaccc aggcagggag aaaccacctg gtccattaca ggcagctcct gctggcaggc   1020
ctgcagaatg ccgggagatc ccccaccaac ctggccaagg tgaaaggcat cacacagggg   1080
cctaatgagt caccaagcgc ctttctggag aggctgaagg aagcttaccg acggtatacc   1140
ccatacgacc ctgaggaccc cggacaggaa acaaacgtct ccatgtcttt catctggcag   1200
tctgccccag acattgggcg gaagctggag agactggaag acctgaagaa caagaccctg   1260
ggcgacctgg tgcgggaggc tgaaaagatc ttcaacaaac gggagacccc cgaggaaaga   1320
gaggaaagga ttagaaggga aactgaggaa aaggaggaac gccgacggac cgaggacgaa   1380
cagaaggaga agaacgaga tcggcggcgg caccgggaga tgtcaaagct gctggccacc   1440
gtggtcagcg gacagaaaca ggacagacag ggaggagagc gacggagaag ccagctcgac   1500
agggatcagt gcgcatactg taaggaaaaa ggccattggg ccaaggattg ccccaaaaag   1560
ccaagaggac caagaggacc aagaccacag acatcactgc tgaccctgga cgactgcgag   1620
agccggggcc ggcggtgccc agaaatgatc tctgtgctgg ggcccattag tggacatgtg   1680
ctgaaggccg tcttctccag gggagacacc ccgtgctgc ctcacgagac tcgactgctg   1740
cagaccggca tccatgtgcg ggtctcccag ccctctctga ttctggtgtc acagtataca   1800
ccagatagca ctccctgcca cagaggagac aatcagctcc aggtgcagca tacctacttt   1860
acaggctccg aggtcgaaaa cgtgtctgtc aatgtgcaca ccctaccgg caggagcatc   1920 tgtcctagcc aggagccaat gagcatctac gtgtacgccc tgcctctgaa gatgctgaat   1980
atcccatcaa ttaacgtcca ccattaccct agcgcagccg aacggaagca cagacatctg   2040
ccagtggccg acgctgtcat ccatgccagc ggcaaacaga tgtggcaggc aagactgacc   2100
gtgtccgggc tggcctggac aaggcagcag aatcagtgga aggagcccga cgtgtactat   2160
accagcgcct tcgtgttccc taccaaagac gtggccctga cacatgtggt gtgcgcacat   2220
gagctggtgt gcagcatgga aaacactagg gccaccaaga tgcaggtcat cggcgatcag   2280
tatgtcaaag tgtacctgga gagtttttgc gaagacgtgc catcagggaa gctgttcatg   2340
catgtgaccc tgggcagcga tgtcgaggaa gacctgacca tgacaagaaa tccacagccc   2400
tttatgagac cccacgagag gaatgggttc actgtgctgt gccccaagaa catgatcatt   2460
aagcctggaa aaatcagtca tattatgctg gatgtggcct ttacatcaca cgagcatttc   2520
ggactgctgt gccccaaatc catccctgga ctgagcattt ccggcaatct gctgatgaac   2580
ggccagcaga tcttcctgga agtgcaggcc atccgggaga ccgtcgaact gcgacagtat   2640
gacccagtgg ctgcactgtt ctttttcgac atcgacctgc tgctgcagcg aggaccacag   2700
tacagcgagc ccctactttt tacctcccag tatcggattc aggggaagct ggagtacagg   2760
cacacctggg atcgccatga cgaaggagcc gctcaggggg acgatgacgt gtggacatct   2820
ggcagtgatt cagacgagga actggtgaca actgagcgaa aaaccccccg ggtgacagga   2880
```

```
ggagggcaa tggcaggggc cagcaccagc gcagggcgga agcgaaaaag cgccagcagc    2940
gccacagcat gtaccgccgg cgtgatgact agaggaaggc tgaaggccga gtctacagtc    3000
gctcccgagg aagatactga cgaggatagt gacaatgaaa tccacaaccc cgccgtgttc    3060
acctggccac cttggcaggc agggattctg gctcgcaacc tggtccccat ggtggcaacc    3120
gtccagggac agaatctgaa gtatcaggag tttttctggg atgctaacga catctaccgg    3180
atttttgcag agctggaagg cgtgtggcag ccagcagccc agcccaaacg acggagacat    3240
cgacaggacg ctctgccagg accttgtatc gccagcacac caaagaagca caggggctaa    3300
```

COMPOSITIONS AND METHODS FOR TREATMENT OF CYTOMEGALOVIRUS

CROSS REFERENCE TO RELATED APPLICATIONS

The present application is a continuation of U.S. application Ser. No. 14/357,423, filed May 9, 2014, which is the National Stage of International Application PCT/IB12/02854, filed Nov. 9, 2012, which claims the benefit of U.S. Provisional Application No. 61/558,800, filed Nov. 11, 2011, and of U.S. Provisional Application No. 61/654,157, filed Jun. 1, 2012, the contents of all of which are herein incorporated by reference in their entirety.

REFERENCE TO SEQUENCE LISTING

The specification includes a Sequence Listing in the form of an ASCII compliant text file named "2007801-0086_VBI-025-PC_ST25.txt", which was created on May 2, 2013 and has a size of 98.8 KB, the contents of which are hereby incorporated by reference in their entirety.

BACKGROUND

Human cytomegalovirus (HCMV), a β-herpesvirus, is a ubiquitously occurring pathogen. In an immunocompetent person, HCMV infection is normally unnoticed, having at most mild and nonspecific symptoms. By contrast, certain risk groups, for example in immunosuppressed patients such as AIDS patients or transplant recipients, and after prenatal infection, HCMV infection has serious manifestations (Staras S A et al., 2006 Clin Infect Dis 43(9):1143-51; Hebart H et al., 2004 Hum Immunol 65(5):432-6; Rowshani A T et al., 2005 Transplantation 79(4):381-6). Existing therapies include the use of immunoglobulins and anti-viral agents such as ganciclovir and its derivatives, which are most effective when used prophylactically or very early during infection in at risk populations. However, existing therapies are characterized by significant toxicity and limited efficacy, especially for late-onset disease (Boeckh M., 2004 Pediatr Transplant 8(Suppl. 5):19-27; Limaye A P., 2004 Transplantation 78(9):1390-6), and they have not had an impact on congenital HCMV disease. Development of an effective vaccine to protect against HCMV disease is recognized as an important public health priority (Arvin A M et al., 2004 Clin Infect Dis 39(2):233-9).

SUMMARY

Among other things, the present invention provides methods and compositions useful for prophylaxis, treatment, and/or study of human cytomegalovirus (HCMV) infection. In some embodiments, the present invention provides virus-like particles (VLPs) which comprise one or more Moloney Murine leukemia virus (MMLV) core proteins and include one or more HCMV epitopes, such as, for example, from HCMV envelope glycoproteins gB and/or gH and/or tegument protein pp65. Among other things, the present invention encompasses the recognition that a combination of antigens (e.g., envelope glycoproteins and structural proteins) can lead to improved induction of beneficial immune responses, for example that include both a humoral response (e.g., production of neutralizing antibodies) and a cellular response (e.g., T-cell activation). Provided VLPs may be characterized in that they contain no viral DNA and are non-infectious.

In some embodiments, provided VLPs are surrounded by a lipid membrane, optionally containing one or more epitopes from viral envelope glycoproteins (e.g., gB and/or gH) which are antigens that play a role in induction of virus-neutralizing antibodies.

In some embodiments, provided VLPs contain one or more epitopes from viral structural proteins (e.g., pp65) which are antigens that play a role in induction of cellular immune responses (e.g., T-cell response). In some embodiments, utilized viral structural proteins (e.g., pp65) both stimulate formation of T-helper cells and also induce cytotoxic T lymphocytes (CTL) against HCMV.

In some embodiments, the present invention provides variants of viral envelope glycoproteins (e.g., gB and/or gH). In some embodiments, a variant viral envelope glycoprotein is or comprises a fusion protein. In some embodiments, a variant of a viral glycoprotein comprises a heterologous protein domain (e.g., a transmembrane and/or cytoplasmic domain from a different protein). In some embodiments, a variant of a viral structural protein comprises a heterologous antigen or epitope. In some embodiments, the present invention provides VLPs comprising variants of viral structural proteins. In some embodiments, a variant of a viral structural protein is or comprises a fusion protein.

As used in this application, the terms "about" and "approximately" are used as equivalents. Any numerals used in this application with or without about/approximately are meant to cover any normal fluctuations appreciated by one of ordinary skill in the relevant art.

Other features, objects, and advantages of the present invention are apparent in the detailed description that follows. It should be understood, however, that the detailed description, while indicating embodiments of the present invention, is given by way of illustration only, not limitation. Various changes and modifications within the scope of the invention will become apparent to those skilled in the art from the detailed description.

BRIEF DESCRIPTION OF THE DRAWINGS

The drawings are for illustration purposes only, not for limitation.

DEFINITIONS

Figure 1:
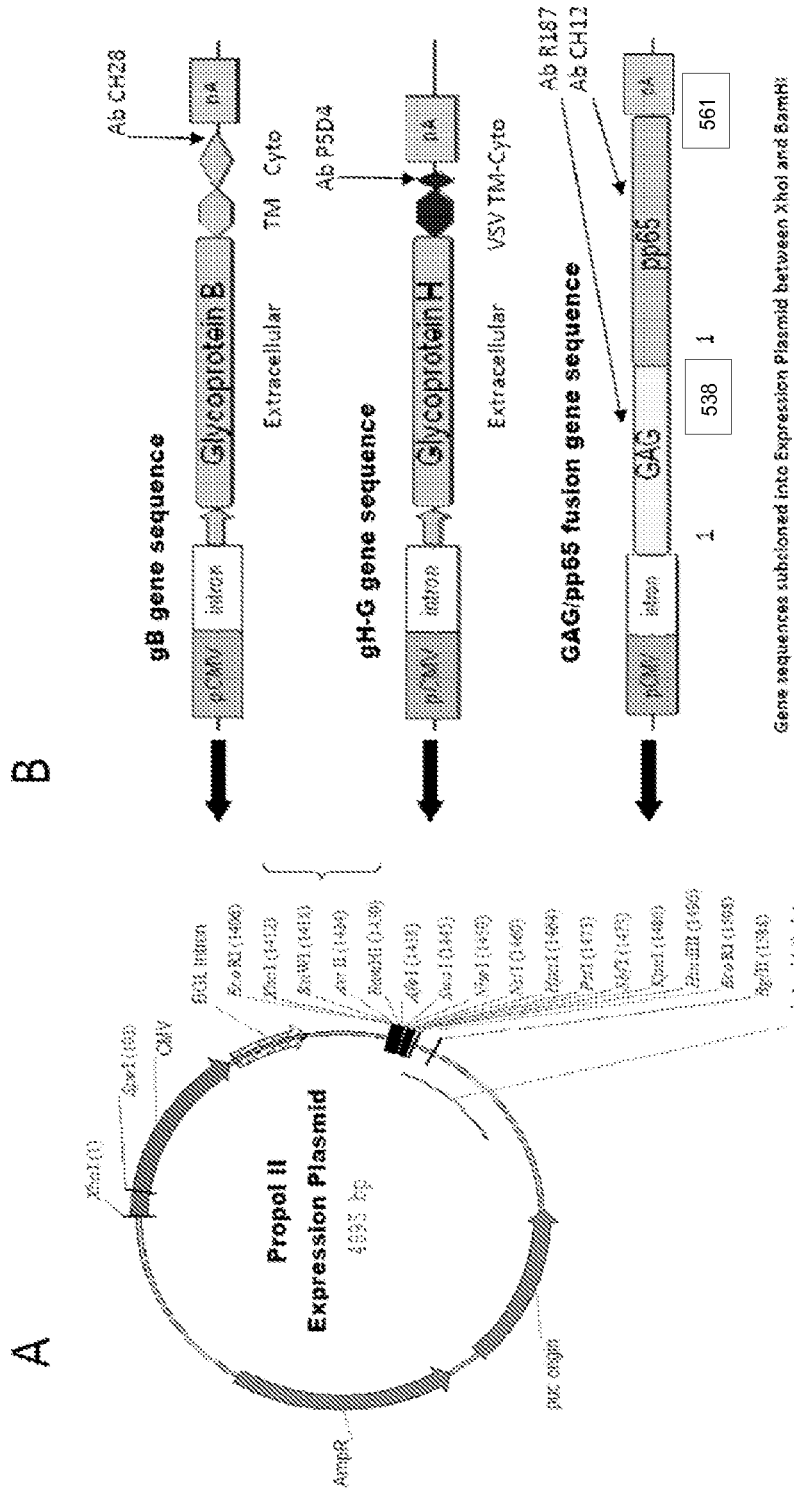
FIG. 1 shows the DNA expression plasmid map (A) and construction of exemplary recombinant expression plasmids (B).

In order for the present invention to be more readily understood, certain terms are first defined below. Additional definitions for the following terms and other terms are set forth throughout the specification.

Amino acid: As used herein, term "amino acid," in its broadest sense, refers to any compound and/or substance that can be incorporated into a polypeptide chain. In some embodiments, an amino acid has the general structure $H_2N$—C(H)(R)—COOH. In some embodiments, an amino acid is a naturally occurring amino acid. In some embodiments, an amino acid is a synthetic amino acid; in some embodiments, an amino acid is a d-amino acid; in some embodiments, an amino acid is an l-amino acid. "Standard amino acid" refers to any of the twenty standard l-amino acids commonly found in naturally occurring peptides. "Nonstandard amino acid" refers to any amino acid, other than the standard amino acids, regardless of whether it is prepared synthetically or obtained from a natural source. As used herein, "synthetic amino acid" encompasses chemically modified amino acids, including but not limited to salts, amino acid derivatives (such as amides), and/or substitutions. Amino acids, including carboxy- and/or amino-terminal amino acids in peptides, can be modified by methylation, amidation, acetylation, protecting groups, and/or substitution with other chemical groups that can change the peptide's circulating half-life without adversely affecting their activity. Amino acids may participate in a disulfide bond. Amino acids may comprise one or posttranslational modifications, such as association with one or more chemical entities (e.g., methyl groups, acetate groups, acetyl groups, phosphate groups, formyl moieties, isoprenoid groups, sulfate groups, polyethylene glycol moieties, lipid moieties, carbohydrate moieties, biotin moieties, etc.). The term "amino acid" is used interchangeably with "amino acid residue," and may refer to a free amino acid and/or to an amino acid residue of a peptide. It will be apparent from the context in which the term is used whether it refers to a free amino acid or a residue of a peptide.

Antigen: As used herein, the term "antigen" refers to a substance containing one or more epitopes (either linear, conformational or both) that are recognized by antibodies. In certain embodiments, an antigen is or comprises a virus or a viral polypeptide. In some embodiments, the term "antigen" refers to a subunit antigen (i.e., an antigen which is separate and discrete from a whole virus with which the antigen is associated in nature; e.g., an antigen which is associated with a virus-like particle). Alternatively or additionally, in some embodiments, the term "antigen" refers to killed, attenuated or inactivated viruses. In certain embodiments, an antigen is an "immunogen."

Approximately or about: As used herein, the term "approximately" or "about," as applied to one or more values of interest, refers to a value that is similar to a stated reference value. In certain embodiments, the term "approximately" or "about" refers to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

Amelioration: As used herein, the term "amelioration" is meant the prevention, reduction or palliation of a state, or improvement of the state of a subject. Amelioration includes, but does not require complete recovery or complete prevention of a disease, disorder or condition (e.g., HCMV infection). The term "prevention" refers to a delay of onset of a disease, disorder or condition. Prevention may be considered complete when onset of a disease, disorder or condition has been delayed for a predefined period of time.

Characteristic portion: As used herein, the term a "characteristic portion" of a substance, in the broadest sense, is one that shares a designated degree of structural identity with intact substance. In certain embodiments, a characteristic portion shares at least one functional characteristic with the intact substance. For example, a "characteristic portion" of a protein or polypeptide is one that contains a continuous stretch of amino acids, or a collection of continuous stretches of amino acids, that together are characteristic of a protein or polypeptide. In some embodiments, each such continuous stretch generally contains at least 2, 5, 10, 15, 20, 50, or more amino acids. In general, a characteristic portion of a substance (e.g., of a protein, antibody, etc.) is one that, in addition to the sequence and/or structural identity specified above, shares at least one functional characteristic with the relevant intact substance. In some embodiments, a characteristic portion may be biologically active.

Characteristic sequence: A "characteristic sequence" is a sequence that is found in all members of a family of polypeptides or nucleic acids, and therefore can be used by those of ordinary skill in the art to define members of the family.

Cytoplasmic domain: As is known in the art, polypeptides sometimes have transmembrane, cytoplasmic, and/or extracellular domains. In general, a "cytoplasmic domain", as used herein, refers to a domain that has an attribute of being present in the cytoplasm. As will be appreciated, it is not required that every amino acid in a cytoplasmic domain be present in the cytoplasm. For example, in some embodiments, a cytoplasmic domain is characterized in that a designated stretch or portion of a protein is substantially located in the cytoplasm. As is well known in the art, amino acid or nucleic acid sequences may be analyzed using a variety of algorithms to predict protein subcellular localization (e.g., cytoplasmic localization). Exemplary such programs include psort (PSORT.org), Prosite (prosite.expasy.org), among others.

Dosage form: As used herein, the terms "dosage form" and "unit dosage form" refer to a physically discrete unit of a therapeutic agent for the patient to be treated. Each unit contains a predetermined quantity of active material calculated to produce the desired therapeutic effect. It will be understood, however, that the total dosage of the composition will be decided by the attending physician within the scope of sound medical judgment.

Dosing regimen: A "dosing regimen" (or "therapeutic regimen"), as that term is used herein, is a set of unit doses (typically more than one) that are administered individually to a subject, typically separated by periods of time. In some embodiments, a given therapeutic agent has a recommended dosing regimen, which may involve one or more doses. In some embodiments, a dosing regimen comprises a plurality of doses each of which are separated from one another by a time period of the same length; in some embodiments, a dosing regimen comprises a plurality of doses and at least two different time periods separating individual doses.

Expression: As used herein, "expression" of a nucleic acid sequence refers to one or more of the following events: (1) production of an RNA template from a DNA sequence (e.g., by transcription); (2) processing of an RNA transcript (e.g., by splicing, editing, 5' cap formation, and/or 3' end formation); (3) translation of an RNA into a polypeptide or protein; and/or (4) post-translational modification of a polypeptide or protein.

Extracellular domain: As is known in the art, polypeptides sometimes have transmembrane, cytoplasmic, and/or extracellular domains. In general, an "extracellular domain", as used herein, refers to a domain that has an attribute of being present outside a cell. As will be appreciated, it is not required that every amino acid in an extracellular domain be present outside the cell. For example, in some embodiments, an extracellular domain is characterized in that a designated stretch or portion of a protein is substantially located outside the cell. As is well known in the art, amino acid or nucleic acid sequences may be analyzed using a variety of algorithms to predict protein subcellular localization (e.g., extracellular localization). Exemplary such programs include psort (PSORT.org), Prosite (prosite.expasy.org), among others.

Fusion protein: As used herein, the term "fusion protein" generally refers to a polypeptide including at least two segments, each of which shows a high degree of amino acid identity to a peptide moiety that (1) occurs in nature, and/or (2) represents a functional domain of a polypeptide. Typically, a polypeptide containing at least two such segments is considered to be a fusion protein if the two segments are moieties that (1) are not included in nature in the same peptide, and/or (2) have not previously been linked to one another in a single polypeptide, and/or (3) have been linked to one another through action of the hand of man.

Gene: As used herein, the term "gene" has its meaning as understood in the art. It will be appreciated by those of ordinary skill in the art that the term "gene" may include gene regulatory sequences (e.g., promoters, enhancers, etc.) and/or intron sequences. It will further be appreciated that definitions of gene include references to nucleic acids that do not encode proteins but rather encode functional RNA molecules such as tRNAs, RNAi-inducing agents, etc. For the purpose of clarity we note that, as used in the present application, the term "gene" generally refers to a portion of a nucleic acid that encodes a protein; the term may optionally encompass regulatory sequences, as will be clear from context to those of ordinary skill in the art. This definition is not intended to exclude application of the term "gene" to non-protein—coding expression units but rather to clarify that, in most cases, the term as used in this document refers to a protein-coding nucleic acid.

Gene product or expression product: As used herein, the term "gene product" or "expression product" generally refers to an RNA transcribed from the gene (pre- and/or post-processing) or a polypeptide (pre- and/or post-modification) encoded by an RNA transcribed from the gene.

Heterologous: As used herein, the term "heterologous" with respect to a protein or a polypeptide refers to a protein or polypeptide that is non-naturally occurring in a particular organism, such as a retrovirus or VLP. In some embodiments, a heterologous protein or polypeptide is non-naturally occurring in a particular retrovirus virion. As used herein, the term "heterologous" with respect to a protein domain generally refers to a protein domain that is non-naturally occurring in a particular protein.

Immunogenic: As used herein, the term "immunogenic" means capable of producing an immune response in a host animal against a non-host entity (e.g., an HCMV antigen). In certain embodiments, this immune response forms the basis of the protective immunity elicited by a vaccine against a specific infectious organism (e.g., an HCMV).

Immune response: As used herein, the term "immune response" refers to a response elicited in an animal. An immune response may refer to cellular immunity, humoral immunity or may involve both. An immune response may also be limited to a part of the immune system. For example, in certain embodiments, an immunogenic composition may induce an increased IFNγ response. In certain embodiments, an immunogenic composition may induce a mucosal IgA response (e.g., as measured in nasal and/or rectal washes). In certain embodiments, an immunogenic composition may induce a systemic IgG response (e.g., as measured in serum). In certain embodiments, an immunogenic composition may induce virus-neutralizing antibodies or a neutralizing antibody response.

Improve, increase, or reduce: As used herein, the terms "improve," "increase" or "reduce," or grammatical equivalents, indicate values that are relative to a baseline measurement, such as a measurement in the same individual prior to initiation of the treatment described herein, or a measurement in a control individual (or multiple control individuals) in the absence of the treatment described herein.

Individual, subject, patient: As used herein, the terms "subject," "individual" or "patient" refer to a human or a non-human mammalian subject. In some embodiments, the individual (also referred to as "patient" or "subject") being treated is an individual (fetus, infant, child, adolescent, or adult) suffering from a disease, for example, HCMV infection. In some embodiments, the subject is at risk for HCMV infection. In some embodiments, the subject is an immunosuppressed subject. For example, in some embodiments, the immunosuppressed subject is selected from the group consisting of an HIV-infected subject, an AIDS patient, a transplant recipient, a pediatric subject, and a pregnant subject. In some embodiments, the subject has been exposed to HCMV infection. In some embodiments, the subject is a human.

Isolated: As used herein, the term "isolated" refers to a substance and/or entity that has been (1) separated from at least some of the components with which it was associated when initially produced (whether in nature and/or in an experimental setting), and/or (2) produced, prepared, and/or manufactured by the hand of man. Isolated substances and/or entities may be separated from about 10%, about 20%, about 30%, about 40%, about 50%, about 60%, about 70%, about 80%, about 90%, about 91%, about 92%, about 93%, about 94%, about 95%, about 96%, about 97%, about 98%, about 99%, or more than about 99% of the other components with which they were initially associated. In some embodiments, isolated agents are about 80%, about 85%, about 90%, about 91%, about 92%, about 93%, about 94%, about 95%, about 96%, about 97%, about 98%, about 99%, or more than about 99% pure. As used herein, a substance is "pure" if it is substantially free of other components. As used herein, calculation of percent purity of isolated substances and/or entities should not include excipients (e.g., buffer, solvent, water, etc.).

Linker: As used herein, the term "linker" refers to, e.g., in a fusion protein, an amino acid sequence of an appropriate length other than that appearing at a particular position in the natural protein and is generally designed to be flexible and/or to interpose a structure, such as an α-helix, between two protein moieties. In general, a linker allows two or more domains of a fusion protein to retain 50%, 55%, 60%, 65%, 70%, 75%, 80%, 85%, 90%, 95% or more of the biological activity of each of the domains. A linker may also be referred to as a spacer.

Nucleic acid: As used herein, the term "nucleic acid," in its broadest sense, refers to any compound and/or substance that is or can be incorporated into an oligonucleotide chain. In some embodiments, a nucleic acid is a compound and/or substance that is or can be incorporated into an oligonucleotide chain via a phosphodiester linkage. In some embodiments, "nucleic acid" refers to individual nucleic acid residues (e.g., nucleotides and/or nucleosides). In some embodiments, "nucleic acid" refers to an oligonucleotide chain comprising individual nucleic acid residues. As used herein, the terms "oligonucleotide" and "polynucleotide" can be used interchangeably. In some embodiments, "nucleic acid" encompasses RNA as well as single and/or double-stranded DNA and/or cDNA. Furthermore, the terms "nucleic acid," "DNA," "RNA," and/or similar terms include nucleic acid analogs, i.e., analogs having other than a phosphodiester backbone. For example, the so-called "peptide nucleic acids," which are known in the art and have peptide bonds instead of phosphodiester bonds in the backbone, are considered within the scope of the present invention. The term "nucleotide sequence encoding an amino acid sequence" includes all nucleotide sequences that are degenerate versions of each other and/or encode the same amino acid sequence. Nucleotide sequences that encode proteins and/or RNA may include introns. Nucleic acids can be purified from natural sources, produced using recombinant expression systems and optionally purified, chemically synthesized, etc. Where appropriate, e.g., in the case of chemically synthesized molecules, nucleic acids can comprise nucleoside analogs such as analogs having chemically modified bases or sugars, backbone modifications, etc. A nucleic acid sequence is presented in the 5' to 3' direction unless otherwise indicated. The term "nucleic acid segment" is used herein to refer to a nucleic acid sequence that is a portion of a longer nucleic acid sequence. In many embodiments, a nucleic acid segment comprises at least 3, 4, 5, 6, 7, 8, 9, 10, or more residues. In some embodiments, a nucleic acid is or comprises natural nucleosides (e.g., adenosine, thymidine, guanosine, cytidine, uridine, deoxyadenosine, deoxythymidine, deoxyguanosine, and deoxycytidine); nucleoside analogs (e.g., 2-aminoadenosine, 2-thiothymidine, inosine, pyrrolo-pyrimidine, 3-methyl adenosine, 5-methylcytidine, C-5 propynyl-cytidine, C-5 propynyl-uridine, 2-aminoadenosine, C5-bromouridine, C5-fluorouridine, C5-iodouridine, C5-propynyl-uridine, C5-propynyl-cytidine, C5-methylcytidine, 2-aminoadenosine, 7-deazaadenosine, 7-deazaguanosine, 8-oxoadenosine, 8-oxoguanosine, O(6)-methylguanine, and 2-thiocytidine); chemically modified bases; biologically modified bases (e.g., methylated bases); intercalated bases; modified sugars (e.g., 2'-fluororibose, ribose, 2'-deoxyribose, arabinose, and hexose); and/or modified phosphate groups (e.g., phosphorothioates and 5'-N-phosphoramidite linkages). In some embodiments, the present invention is specifically directed to "unmodified nucleic acids," meaning nucleic acids (e.g., polynucleotides and residues, including nucleotides and/or nucleosides) that have not been chemically modified in order to facilitate or achieve delivery.

Pharmaceutically acceptable: The term "pharmaceutically acceptable" as used herein, refers to substances that, within the scope of sound medical judgment, are suitable for use in contact with the tissues of human beings and animals without excessive toxicity, irritation, allergic response, or other problem or complication, commensurate with a reasonable benefit/risk ratio.

Polypeptide: As used herein, a "polypeptide", generally speaking, is a string of at least two amino acids attached to one another by a peptide bond. In some embodiments, a polypeptide may include at least 3-5 amino acids, each of which is attached to others by way of at least one peptide bond. Those of ordinary skill in the art will appreciate that polypeptides sometimes include "non-natural" amino acids or other entities that nonetheless are capable of integrating into a polypeptide chain, optionally.

Polyprotein: As used herein, the term "polyprotein", generally refers to a protein that, after synthesis, may be cleaved to produce several functionally distinct polypeptides. A polyprotein is typically encoded by a single amino acid sequence. In some embodiments, an uncleaved polyprotein retains biological activity of its component parts. Some viruses produce such polyproteins, e.g., a Gag polyprotein, which can be retained as a functional polyprotein or can be processed into several functionally distinct polypeptides. Functionally, the Gag polyprotein is divided into three domains: the membrane binding domain, which targets the Gag polyprotein to the cellular membrane; the interaction domain which promotes Gag polymerization; and the late domain which facilitates release of nascent virions from the host cell. In general, the form of the Gag protein that mediates viral particle assembly is the polyprotein.

Self-assembling portion: In general, a "self-assembling portion", as used herein, refers to a relevant stretch of an entity that adopts a defined arrangement without guidance or management from an outside source. In some embodiments, the entity is a protein. In some embodiments, the entity is a polyprotein. In some such embodiments, the relevant stretch is at least 10, 15, 20, 25, 30, 35, 40, 45, 50, 55, 60, 65, 70, 75, 80, 85, 90, 95, 100, 125, 150, 175, 200, 225, 250, 275, 300, 325, 350, 375, 400, 425, 450, 475, 500 or more residues. Self-assembly may be exhibited, for example, within the context of a cell (e.g., in vivo). Alternatively or additionally, self-assembly may be exhibited outside the context of a cell (e.g., in vitro). Self-assembly may be intramolecular (e.g., folding) and/or intermolecular. In some embodiments, self-assembly may be macromolecular whereby entities self-assemble into a complex and/or extended macromolecular structure. Self-assembled entities may exhibit a wide range of structural motifs, including, but not limited to particles, fibers, sheets, and ribbons. In some embodiments, self-assembly of an entity is important for a biological function of the entity. For example, in some embodiments, self assembly of a lipid leads to formation of a cell membrane structure. In some embodiments, self assembly of a protein (e.g., a viral structural protein) in a cellular context leads to formation of a particle structure (e.g., a viral particle structure). For example, a viral structural polyprotein may contain a targeting sequence that is capable of directing its localization to a cellular membrane of its host cell (e.g., plasma membrane, endosome, etc.) from which the viral structural polyprotein may bud out to form a VLP that contains host cellular membranous material surrounding the viral structural polyprotein.

Substantial homology: The phrase "substantial homology" is used herein to refer to a comparison between amino acid or nucleic acid sequences. As will be appreciated by those of ordinary skill in the art, two sequences are generally considered to be "substantially homologous" if they contain homologous residues in corresponding positions. Homologous residues may be identical residues. Alternatively, homologous residues may be non-identical residues with appropriately similar structural and/or functional characteristics. For example, as is well known by those of ordinary skill in the art, certain amino acids are typically classified as "hydrophobic" or "hydrophilic" amino acids, and/or as having "polar" or "non-polar" side chains. Substitution of one amino acid for another of the same type may often be considered a "homologous" substitution.

As is well known in this art, amino acid or nucleic acid sequences may be compared using any of a variety of algorithms, including those available in commercial computer programs such as BLASTN for nucleotide sequences and BLASTP, gapped BLAST, and PSI-BLAST for amino acid sequences. Exemplary such programs are described in Altschul, et al., Basic local alignment search tool, *J. Mol. Biol.*, 215(3): 403-410, 1990; Altschul, et al., *Methods in Enzymology* 266:460-480 (1996); Altschul, et al., "Gapped BLAST and PSI-BLAST: a new generation of protein database search programs", *Nucleic Acids Res.* 25:3389-3402, 1997; Baxevanis, et al., *Bioinformatics: A Practical Guide to the Analysis of Genes and Proteins*, Wiley, 1998; and Misener, et al., (eds.), *Bioinformatics Methods and Protocols* (Methods in Molecular Biology, Vol. 132), Humana Press, 1999. In addition to identifying homologous sequences, the programs mentioned above typically provide an indication of the degree of homology. In some embodiments, two sequences are considered to be substantially homologous if at least 50%, 55%, 60%, 65%, 70%, 75%, 80%, 85%, 90%, 91%, 92%, 93%, 94%, 95%, 96%, 97%, 98%, 99% or more of their corresponding residues are homologous over a relevant stretch of residues. In some embodiments, the relevant stretch is a complete sequence. In some embodiments, the relevant stretch is at least 10, 15, 20, 25, 30, 35, 40, 45, 50, 55, 60, 65, 70, 75, 80, 85, 90, 95, 100, 125, 150, 175, 200, 225, 250, 275, 300, 325, 350, 375, 400, 425, 450, 475, 500 or more residues.

Substantial identity: The phrase "substantial identity" is used herein to refer to a comparison between amino acid or nucleic acid sequences. As will be appreciated by those of ordinary skill in the art, two sequences are generally considered to be "substantially identical" if they contain identical residues in corresponding positions. As is well known in this art, amino acid or nucleic acid sequences may be compared using any of a variety of algorithms, including those available in commercial computer programs such as BLASTN for nucleotide sequences and BLASTP, gapped BLAST, and PSI-BLAST for amino acid sequences. Exemplary such programs are described in Altschul, et al., Basic local alignment search tool, *J. Mol. Biol.*, 215(3): 403-410, 1990; Altschul, et al., *Methods in Enzymology* 266:460-480 (1996); Altschul et al., *Nucleic Acids Res.* 25:3389-3402, 1997; Baxevanis et al., *Bioinformatics: A Practical Guide to the Analysis of Genes and Proteins*, Wiley, 1998; and Misener, et al., (eds.), *Bioinformatics Methods and Protocols* (Methods in Molecular Biology, Vol. 132), Humana Press, 1999. In addition to identifying identical sequences, the programs mentioned above typically provide an indication of the degree of identity. In some embodiments, two sequences are considered to be substantially identical if at least 50%, 55%, 60%, 65%, 70%, 75%, 80%, 85%, 90%, 91%, 92%, 93%, 94%, 95%, 96%, 97%, 98%, 99% or more of their corresponding residues are identical over a relevant stretch of residues. In some embodiments, the relevant stretch is a complete sequence. In some embodiments, the relevant stretch is at least 10, 15, 20, 25, 30, 35, 40, 45, 50, 55, 60, 65, 70, 75, 80, 85, 90, 95, 100, 125, 150, 175, 200, 225, 250, 275, 300, 325, 350, 375, 400, 425, 450, 475, 500 or more residues.

Suffering from: An individual who is "suffering from" a disease, disorder, or condition (e.g., HCMV infection) has been diagnosed with and/or exhibits one or more symptoms of the disease, disorder, or condition.

Susceptible to: An individual who is "susceptible to" a disease, disorder, or condition (e.g., HCMV infection) is at risk for developing the disease, disorder, or condition. In some embodiments, an individual who is susceptible to a disease, disorder, or condition does not display any symptoms of the disease, disorder, or condition. In some embodiments, an individual who is susceptible to a disease, disorder, or condition has not been diagnosed with the disease, disorder, and/or condition. In some embodiments, an individual who is susceptible to a disease, disorder, or condition is an individual who has been exposed to conditions associated with development of the disease, disorder, or condition (e.g., the individual has been exposed to HCMV).

Symptoms are reduced: According to the present invention, "symptoms are reduced" when one or more symptoms of a particular disease, disorder or condition is reduced in magnitude (e.g., intensity, severity, etc.) or frequency. For purposes of clarity, a delay in the onset of a particular symptom is considered one form of reducing the frequency of that symptom. It is not intended that the present invention be limited only to cases where the symptoms are eliminated. The present invention specifically contemplates treatment such that one or more symptoms is/are reduced (and the condition of the subject is thereby "improved"), albeit not completely eliminated.

Therapeutically effective amount: As used herein, the term "therapeutically effective amount" refers to an amount sufficient to confer a therapeutic effect on the treated subject, at a reasonable benefit/risk ratio applicable to any medical treatment. The therapeutic effect may be objective (i.e., measurable by some test or marker) or subjective (i.e., subject gives an indication of or feels an effect). In particular, the "therapeutically effective amount" refers to an amount of a therapeutic protein or composition effective to treat, ameliorate, or prevent a desired disease or condition, or to exhibit a detectable therapeutic or preventative effect, such as by ameliorating symptoms associated with the disease, preventing or delaying the onset of the disease, and/or also lessening the severity or frequency of symptoms of the disease. A therapeutically effective amount is commonly administered in a dosing regimen that may comprise multiple unit doses. For any particular immunogenic composition, a therapeutically effective amount (and/or an appropriate unit dose within an effective dosing regimen) may vary, for example, depending on route of administration, on combination with other pharmaceutical agents. Also, the specific therapeutically effective amount (and/or unit dose) for any particular patient may depend upon a variety of factors including the disorder being treated and the severity of the disorder; the activity of the specific pharmaceutical agent employed; the specific composition employed; the age, body weight, general health, sex and diet of the patient; the time of administration, route of administration, and/or rate of excretion or metabolism of the specific immunogenic composition employed; the duration of the treatment; and like factors as is well known in the medical arts.

Transmembrane domain: As is known in the art, polypeptides sometimes have transmembrane, cytoplasmic, and/or extracellular domains. In general, a "transmembrane domain", as used herein, refers to a domain having an attribute of being present in the membrane (e.g., spanning a portion or all of a cellular membrane). As will be appreciated, it is not required that every amino acid in a transmembrane domain be present in the membrane. For example, in some embodiments, a transmembrane domain is characterized in that a designated stretch or portion of a protein is substantially located in the membrane. As is well known in the art, amino acid or nucleic acid sequences may be analyzed using a variety of algorithms to predict protein subcellular localization (e.g., transmembrane localization). Exemplary such programs include psort (PSORT.org), Prosite (prosite.expasy.org), among others.

Treatment: As used herein, the term "treatment" (also "treat" or "treating") refers to any administration of an immunogenic composition that partially or completely alleviates, ameliorates, relieves, inhibits, delays onset of, reduces severity of and/or reduces incidence of one or more symptoms or features of a particular disease, disorder, and/or condition (e.g., HCMV infection) or the predisposition toward the disease. Such treatment may be of a subject who does not exhibit signs of the relevant disease, disorder and/or condition and/or of a subject who exhibits only early signs of the disease, disorder, and/or condition. Alternatively or additionally, such treatment may be of a subject who exhibits one or more established signs of the relevant disease, disorder and/or condition. In certain embodiments, the term "treating" refers to the vaccination of a patient.

Vaccination: As used herein, the term "vaccination" refers to the administration of a composition intended to generate an immune response, for example to a disease-causing agent (e.g., HCMV). For the purposes of the present invention, vaccination can be administered before, during, and/or after exposure to a disease-causing agent, and in certain embodiments, before, during, and/or shortly after exposure to the agent. In some embodiments, vaccination includes multiple administrations, appropriately spaced in time, of a vaccinating composition.

Vector: As used herein, "vector" refers to a nucleic acid molecule capable of transporting another nucleic acid to which it is associated. In some embodiments, vectors are capable of extra-chromosomal replication and/or expression of nucleic acids to which they are linked in a host cell such as a eukaryotic and/or prokaryotic cell. Vectors capable of directing the expression of operatively linked genes are referred to herein as "expression vectors."

DETAILED DESCRIPTION OF CERTAIN EMBODIMENTS

Among other things, the present invention provides methods and compositions useful for prophylaxis, treatment, and/or study of human cytomegalovirus (HCMV) infection. In some embodiments, the present invention provides virus-like particles (VLPs) which comprise one or more Moloney Murine leukemia virus (MMLV) core proteins and include one or more HCMV epitopes, such as, for example, from HCMV envelope glycoproteins gB and/or gH and/or tegument protein pp65. Among other things, the present invention encompasses the recognition that a combination of antigens (e.g., envelope glycoproteins and structural proteins) can lead to improved induction of beneficial immune responses, for example that include both a humoral response (e.g., production of neutralizing antibodies) and a cellular response (e.g., T-cell activation). Provided VLPs may be characterized in that they contain no viral RNA or DNA and are non-infectious. In some embodiments, provided VLPs do contain viral RNA or DNA and are infectious. In some such embodiments, provided VLPs are useful as a DNA vaccine.

In some embodiments, the humoral immune response in a subject is sustained for at least about 1 month, at least about 2 months, at least about 3 months, at least about 4 months, at least about 5 months, at least about 6 months, at least about 7 months, at least about 8 months, at least about 9 months, at least about 10 months, at least about 11 months, at least about 12 months, at least about 13 months, at least about 14 months, at least about 15 months, at least about 16 months, at least about 17 months, at least about 18 months, at least about 19 months, at least about 20 months, at least about 21 months, at least about 22 months, at least about 23 months, at least about 24 months, at least about 28 months, at least about 32 months, at least about 36 months, at least about 40 months, at least about 44 months, at least about 48 months, or longer. In some embodiments, the cellular immune response in a subject is sustained for at least about 1 month, at least about 2 months, at least about 3 months, at least about 4 months, at least about 5 months, at least about 6 months, at least about 7 months, at least about 8 months, at least about 9 months, at least about 10 months, at least about 11 months, or at least 12 months.

In some embodiments, provided VLPs are surrounded by a lipid membrane, optionally containing one or more epitopes from viral envelope glycoproteins (e.g., gB and/or gH) which are antigens that play a role in induction of virus-neutralizing antibodies.

In some embodiments, provided VLPs contain one or more epitopes from viral structural proteins (e.g., pp65) which are antigens that play a role in induction of cellular immune responses (e.g., T-cell response). In some embodiments, utilized viral structural proteins (e.g., pp65) both stimulate formation of T-helper cells ($T_H$) and also induce cytotoxic T lymphocytes (CTL) against HCMV.

In some embodiments, the present invention provides variants of viral envelope glycoproteins (e.g., gB and/or gH). In some embodiments, a variant viral envelope glycoprotein is or comprises a fusion protein. In some embodiments, a variant of a viral glycoprotein comprises a heterologous protein domain (e.g., a transmembrane and/or cytoplasmic domain from a different protein). In some embodiments, a variant of a viral structural protein comprises a heterologous antigen or epitope. In some embodiments, the present invention provides VLPs comprising variants of viral structural proteins. In some embodiments, a variant of a viral structural protein is or comprises a fusion protein.

I. Virus-Like Particles (VLPs)

Retroviruses are enveloped RNA viruses that belong to the family Retroviridae. After infection of a host cell by a retrovirus, RNA is transcribed into DNA via the enzyme reverse transcriptase. DNA is then incorporated into the host cell's genome by an integrase enzyme and thereafter replicates as part of the host cell's DNA. The Retroviridae family includes the following genus *Alpharetrovirus, Betaretrovirus, Gammearetrovirus, Deltaretrovirus, Epsilonretrovirus, Lentivirus* and *Spumavirus*. The hosts for this family of retroviruses generally are vertebrates. Retroviruses produce an infectious virion containing a spherical nucleocapsid (the viral genome in complex with viral structural proteins) surrounded by a lipid bilayer derived from the host cell membrane.

Retroviral vectors can be used to generate enveloped virions that are infectious and either replication-competent or replication-defective. Replication-competent infectious retroviral vectors contain all of the necessary genes for virion synthesis and continue to propagate themselves once infection of the host cell occurs. Replication-defective infectious retroviral vectors do not spread after the initial infection. This is accomplished by replacement of most of the coding regions of the retrovirus with genes or nucleotide sequences to be transferred; so that the vector is incapable of making proteins required for additional rounds of replication.

Alternatively or additionally, retroviral vectors can be used to generate virus-like particles (VLPs) that lack a retrovirus-derived genome and are both non-infectious and non-replicating. Because of VLPs advantageous properties, VLPs may be utilized as an antigen delivery system. Furthermore, because VLPs are non-infectious, they can be administered safely as an immunogenic composition (e.g., a vaccine). VLPs are generally structurally similar to enveloped virions described above, but lack a retrovirus-derived genome, making it unlikely that viral replication will occur. Expression of capsid proteins (e.g., Gag) of some viruses (e.g., murine leukemia viruses, such as Moloney Murine leukemia virus (MMLV)) leads to self-assembly into particles similar to the corresponding native virus, which particles are free of viral genetic material.

A wide variety of VLPs have been prepared. For example, VLPs including single or multiple capsid proteins either with or without envelope proteins and/or surface glycoproteins have been prepared. In some cases, VLPs are non-enveloped and assemble by expression of just one major capsid protein, as shown for VLPs prepared from hepadnaviruses (e.g., Engerix™, GSK and Recombivax HB™, Merck), papillomaviruses (e.g., Cervarix™, GSK and Gardasil™, Merck), paroviruses, or polyomaviruses. In some embodiments, VLPs are enveled and can comprise multiple antigenic proteins found in the corresponding native virus. VLPs typically resemble their corresponding native virus and can be multivalent particulate structures. In some embodiments, antigenic proteins may be presented internally within the VLP, as a component of the VLP structure, and/or on the surface of the VLP. The present invention encompasses the recognition that presentation of an antigen in the context of a VLP is advantageous for induction of neutralizing antibodies against the antigen as compared to other forms of antigen presentation, e.g., soluble antigens not associated with a VLP. Neutralizing antibodies most often recognize tertiary or quarternary structures; this often requires presenting antigenic proteins, like envelope glycoproteins, in their native viral conformation. Alternatively or additionally, VLPs may be useful for presenting antigens in a context which induces cellular immunity (e.g., T cell response). The present invention further encompasses the insight that use of antigen combinations in VLP systems can generate improved immune response.

A. Structural Proteins

In some embodiments, the present invention utilizes VLPs comprised of one or more retroviral structural proteins (e.g., Gag). In some embodiments, a structural protein for use in accordance with the present invention is Alpharetrovirus (e.g., Avian Leukosis Virus), Betaretrovirus (Mouse Mammary Tumor Virus), Gammcarctrovirus (Murine Leukemia Virus), Deltaretrovirus (Bovine Leukemia Virus), Epsilonretrovirus (Walley Dermal Sarcoma Virus), Lentivirus (Human Immunodeficiency Virus 1) or Spumavirus (Chimpanzee Foamy Virus) structural protein. In certain embodiments, a structural polyprotein is a Murine Leukemia Virus (MLV) structural protein. Genomes of these retroviruses are readily available in databases. The Gag genes of all these retroviruses have an overall structural similarity and within each group of retroviruses are conserved at the amino acid level. Retroviral Gag proteins primarily function in viral assembly. The Gag gene in the form of a polyprotein gives rise to the core structural proteins of the VLP. The MLV Gag gene encodes a 65 kDa polyprotein precursor which is proteolytically cleaved into 4 structural proteins (Matrix (MA); p12; Capsid (CA); and Nucleocapsid (NC)), by MLV protease, in the mature virion. Retroviruses assemble immature capsid composed of the Gag polyprotein formed from the Gag polypeptide but devoid of other viral elements like viral protease with Gag as the structural protein of the immature virus particle. Functionally, the Gag polyprotein is divided into three domains: the membrane binding domain, which targets the Gag polyprotein to the cellular membrane; the interaction domain which promotes Gag polymerization; and the late domain which facilitates release of nascent virions from the host cell. The form of the Gag protein that mediates viral particle assembly is the polyprotein.

In some embodiments, a retroviral structural protein for use in accordance with the present invention is a Gag polypeptide. As used herein, the term "Gag polypeptide" is the retrovirus derived structural polypeptide that is responsible for formation of the VLPs described herein and refers to a polypeptide sequence whose amino acid sequence includes at least one characteristic sequence of Gag. A wide variety of Gag sequences from various retroviruses are known in the art and those of ordinary skill in the art, referring to such sequences, can readily identify sequences that are characteristic of Gag proteins generally, and/or of particular Gag polypeptides.

An exemplary Gag polypeptide for use in accordance with the present invention is shown as SEQ ID NO:1 below. In some embodiments, a suitable Gag polypeptide is substantially homologous to a known retroviral Gag polypeptide. For example, a Gag polypeptide may be a modified retroviral Gag polypeptide containing one or more amino acid substitutions, deletions, and/or insertions as compared to a wild-type or naturally-occurring Gag polypeptide (e.g., SEQ ID NO:1), while retaining substantial self-assembly activity. Thus, in some embodiments, a Gag polypeptide suitable for the present invention is substantially homologous to an MMLV Gag polypeptide (SEQ ID NO:1). In some embodiments, a Gag polypeptide suitable for the present invention has an amino acid sequence at least 50%, 55%, 60%, 65%, 70%, 75%, 80%, 85%, 90%, 91%, 92%, 93%, 94%, 95%, 96%, 97%, 98%, 99% or more homologous to SEQ ID NO:1. In some embodiments, a Gag polypeptide suitable for the present invention is substantially identical to an MMLV Gag polypeptide (SEQ ID NO:1). In some embodiments, a Gag polypeptide suitable for the present invention has an amino acid sequence at least 50%, 55%, 60%, 65%, 70%, 75%, 80%, 85%, 90%, 91%, 92%, 93%, 94%, 95%, 96%, 97%, 98%, 99% or more identical to SEQ ID NO:1.

MMLV Gag Amino Acid Sequence (SEQ ID NO: 1)

(SEQ ID NO: 1)

```
MGQTVTTPLSLTLGHWKDVERIAHNQSVDVKKRRWVTFCSAEWPTFNVGWPRDGTFN
RDLITQVKIKVFSPGPHGHPDQVPYIVTWEALAFDPPPWVKPFVHPKPPPPLPPSAPSLPL
EPPRSTPPRSSLYPALTPSLGAKPKPQVLSDSGGPLIDLLTEDPPPYRDPRPPPSDRDGNGG
EATPAGEAPDPSPMASRLRGRREPPVADSTTSQAFPLRAGGNGQLQYWPFSSSDLYNW
KNNNPSFSEDPGKLTALIESVLITHQPTWDDCQQLLGTLLTGEEKQRVLLEARKAVRGD
DGRPTQLPNEVDAAFPLERPDWDYTTQAGRNHLVHYRQLLLAGLQNAGRSPTNLAKV
KGITQGPNESPSAFLERLKEAYRRYTPYDPEDPGQETNVSMSFIWQSAPDIGRKLERLED
LKNKTLGDLVREAEKIFNKRETPEEREERIRRETEEKEERRRTEDEQKEKERDRRRHREM
SKLLATVVSGQKQDRQGGERRRSQLDRDQCAYCKEKGHWAKDCPKKPRGPRGPRPQT
SLLTLDD
```

MMLV Gag Nucleotide Sequence (SEQ ID NO: 2)

(SEQ ID NO: 2)

```
ATGGGCCAGACTGTTACCACTCCCTTAAGTTTGACCTTAGGTCACTGGAAAGATGTC
GAGCGGATCGCTCACAACCAGTCGGTAGATGTCAAGAAGAGACGTTGGGTTACCTT
CTGCTCTGCAGAATGGCCAACCTTTAACGTCGGATGGCCGCGAGACGGCACCTTTAA
CCGAGACCTCATCACCCAGGTTAAGATCAAGGTCTTTTCACCTGGCCCGCATGGACA
CCCAGACCAGGTCCCCTACATCGTGACCTGGGAAGCCTTGGCTTTTGACCCCCCTCC
CTGGGTCAAGCCCTTTGTACACCCTAAGCCTCCGCCTCCTCTTCCTCCATCCGCCCCG
TCTCTCCCCCTTGAACCTCCTCGTTCGACCCCGCCTCGATCCTCCCTTTATCCAGCCC
TCACTCCTTCTCTAGGCGCCAAACCTAAACCTCAAGTTCTTTCTGACAGTGGGGGGC
CGCTCATCGACCTACTTACAGAAGACCCCCCGCCTTATAGGGACCCAAGACCACCCC
CTTCCGACAGGGACGGAAATGGTGGAGAAGCGACCCCTGCGGGAGAGGCACCGGA
CCCCTCCCCAATGGCATCTCGCCTACGTGGGAGACGGGAGCCCCCTGTGGCCGACTC
CACTACCTCGCAGGCATTCCCCCTCCGCGCAGGAGGAAACGGACAGCTTCAATACT
GGCCGTTCTCCTCTTCTGACCTTTACAACTGGAAAAATAATAACCCTTCTTTTTCTGA
AGATCCAGGTAAACTGACAGCTCTGATCGAGTCTGTTCTCATCACCCATCAGCCCAC
CTGGGACGACTGTCAGCAGCTGTTGGGGACTCTGCTGACCGGAGAAGAAAAACAAC
GGGTGCTCTTAGAGGCTAGAAAGGCGGTGCGGGGCGATGATGGGCGCCCCACTCAA
CTGCCCAATGAAGTCGATGCCGCTTTTCCCCTCGAGCGCCCAGACTGGGATTACACC
ACCCAGGCAGGTAGGAACCACCTAGTCCACTATCGCCAGTTGCTCCTAGCGGGTCTC
CAAAACGCGGGCAGAAGCCCCACCAATTTGGCCAAGGTAAAAGGAATAACACAAG
GGCCCAATGAGTCTCCCTCGGCCTTCCTAGAGAGACTTAAGGAAGCCTATCGCAGGT
ACACTCCTTATGACCCTGAGGACCCAGGGCAAGAAACTAATGTGTCTATGTCTTTCA
TTTGGCAGTCTGCCCCAGACATTGGGAGAAAGTTAGAGAGGTTAGAAGATTTAAAA
AACAAGACGCTTGGAGATTTGGTTAGAGAGGCAGAAAAGATCTTTAATAAACGAGA
AACCCCGGAAGAAAGAGAGGAACGTATCAGGAGAGAAACAGAGGAAAAAGAAGA
ACGCCGTAGGACAGAGGATGAGCAGAAAGAGAAAGAAAGAGATCGTAGGAGACAT
AGAGAGATGAGCAAGCTATTGGCCACTGTCGTTAGTGGACAGAAACAGGATAGACA
GGGAGGAGAACGAAGGAGGTCCCAACTCGATCGCGACCAGTGTGCCTACTGCAAAG
```

-continued

AAAAGGGGCACTGGGCTAAAGATTGTCCCAAGAAACCACGAGGACCTCGGGGACC

AAGACCCCAGACCTCCCTCCTGACCCTAGATGAC

Codon Optimized MMLV Gag Nucleotide Sequence (SEQ ID NO: 3)

(SEQ ID NO: 3)

ATGGGACAGACAGTCACTACACCCCTGAGCCTGACACTGGGACATTGGAAAGACGT

GGAGAGGATTGCACATAACCAGAGCGTGGACGTGAAGAAACGGAGATGGGTCACCT

TTTGCTCCGCCGAGTGGCCAACATTCAATGTGGGATGGCCCCGAGATGGCACCTTCA

ACCGGGACCTGATCACTCAGGTGAAGATCAAGGTCTTCTCTCCAGGACCCCACGGCC

ATCCAGATCAGGTGCCCTACATCGTCACCTGGGAGGCTCTGGCATTTGACCCCCCTC

CATGGGTGAAGCCTTTCGTCCACCCAAAACCACCTCCACCACTGCCTCCATCTGCCC

CTAGTCTGCCACTGGAACCCCCTCGGTCAACCCCACCCAGAAGCTCCCTGTATCCCG

CACTGACACCTAGCCTGGGGGCCAAGCCTAAACCACAGGTGCTGTCTGATAGTGGC

GGGCCTCTGATCGATCTGCTGACCGAGGACCCTCCACCATACCGCGACCCACGACCT

CCACCAAGCGACCGGGACGGAAACGGAGGAGAGGCTACACCCGCAGGCGAAGCCC

CCGATCCTAGTCCAATGGCATCAAGGCTGCGCGGGAGGCGCGAACCTCCAGTGGCC

GACTCAACCACAAGCCAGGCATTTCCACTGAGGGCCGGGGGAAATGGACAGCTCCA

GTATTGGCCCTTCTCTAGTTCAGATCTGTACAACTGGAAGAACAATAACCCTAGCTT

CAGCGAGGACCCAGGCAAACTGACCGCCCTGATCGAATCCGTGCTGATTACCCACC

AGCCCACATGGGACGATTGTCAGCAGCTCCTGGGCACCCTGCTGACCGGAGAGGAA

AAGCAGAGAGTGCTGCTGGAGGCTAGGAAAGCAGTCCGCGGGGACGATGGAAGGC

CAACACAGCTCCCCAATGAGGTGGATGCCGCTTTCCCTCTGGAACGGCCAGATTGGG

ACTATACTACCCAGGCTGGACGCAACCACCTGGTGCATTACCGGCAGCTCCTGCTGG

CTGGACTGCAGAATGCAGGGCGCAGCCCCACTAACCTGGCCAAGGTGAAAGGAATC

ACCCAGGGCCCCAATGAGTCCCCTTCTGCATTCCTGGAGCGGCTGAAGGAAGCCTAC

CGACGGTATACTCCCTACGATCCTGAGGACCCAGGCCAGGAAACCAACGTGAGTAT

GAGCTTCATCTGGCAGTCCGCTCCTGACATTGGCCGAAAACTGGAGCGGCTGGAAG

ATCTGAAGAACAAGACCCTGGGCGACCTGGTGCGGGAGGCAGAAAAGATCTTCAAC

AAAAGGGAGACTCCAGAGGAACGGGAGGAAAGAATTAGAAGGGAAACAGAGGAA

AAGGAGGAACGCCGACGGACTGAGGATGAACAGAAGGAGAAAGAAAGAGACCGGC

GGCGGCACCGGGAGATGTCTAAGCTGCTGGCCACCGTGGTCAGTGGCCAGAAACAG

GATCGACAGGGAGGAGAGCGACGGAGAAGCCAGCTCGATCGGGACCAGTGCGCCT

ATTGTAAGGAAAAAGGGCATTGGGCTAAGGACTGCCCCAAGAAACCCAGAGGCCCA

CGCGGGCCCCGACCTCAGACTTCCCTGCTGACCCTGGACGAT

Codon Optimized MMLV Gag Nucleotide Sequence (SEQ ID NO: 21)

(SEQ ID NO: 21)

ATGGGACAGACCGTCACAACACCCCTGAGCCTGACCCTGGGACATTGGAAAGACGT

GGAGAGGATCGCACATAACCAGAGCGTGGACGTGAAGAAACGGAGATGGGTCACA

TTCTGCAGTGCTGAGTGGCCAACTTTTAATGTGGGATGGCCCCGAGACGGCACTTTC

AACAGGGATCTGATCACCCAGGTGAAGATCAAGGTCTTTAGCCCAGGACCTCACGG

ACATCCAGACCAGGTGCCTTATATCGTCACCTGGGAGGCACTGGCCTTCGATCCCCC

TCCATGGGTGAAGCCATTTGTCCACCCAAAACCACCTCCACCACTGCCTCCAAGTGC

CCCTTCACTGCCACTGGAACCACCCCGGAGCACACCACCCCGCAGCTCCCTGTATCC

TGCTCTGACTCCATCTCTGGGCGCAAAGCCAAAACCACAGGTGCTGAGCGACTCCG

```
GAGGACCACTGATTGACCTGCTGACAGAGGACCCCCCACCATACCGAGATCCTCGG

CCTCCACCAAGCGACCGCGATGGAAATGGAGGAGAGGCTACTCCTGCCGGCGAAGC

CCCTGACCCATCTCCAATGGCTAGTAGGCTGCGCGGCAGGCGCGAGCCTCCAGTGG

CAGATAGCACCACATCCCAGGCCTTCCCTCTGAGGGCTGGGGGAAATGGGCAGCTC

CAGTATTGGCCATTTTCTAGTTCAGACCTGTACAACTGGAAGAACAATAACCCCTCT

TTCAGTGAGGACCCCGGCAAACTGACCGCCCTGATCGAATCCGTGCTGATTACCCAT

CAGCCCACATGGGACGATTGTCAGCAGCTCCTGGGCACCCTGCTGACCGGAGAGGA

AAAGCAGCGCGTGCTGCTGGAGGCTCGCAAAGCAGTCCGAGGGGACGATGGACGG

CCCACACAGCTCCCTAATGAGGTGGACGCCGCTTTTCCACTGGAAAGACCCGACTGG

GATTATACTACCCAGGCAGGGAGAAACCACCTGGTCCATTACAGGCAGCTCCTGCT

GGCAGGCCTGCAGAATGCCGGGAGATCCCCCACCAACCTGGCCAAGGTGAAAGGCA

TCACACAGGGGCCTAATGAGTCACCAAGCGCCTTTCTGGAGAGGCTGAAGGAAGCT

TACCGACGGTATACCCCATACGACCCTGAGGACCCCGGACAGGAAACAAACGTCTC

CATGTCTTTCATCTGGCAGTCTGCCCCAGACATTGGGCGGAAGCTGGAGAGACTGGA

AGACCTGAAGAACAAGACCCTGGGCGACCTGGTGCGGGAGGCTGAAAAGATCTTCA

ACAAACGGGAGACCCCCGAGGAAAGAGAGGAAAGGATTAGAAGGGAAACTGAGGA

AAAGGAGGAACGCCGACGGACCGAGGACGAACAGAAGGAGAAAGAACGAGATCG

GCGGCGGCACCGGGAGATGTCAAAGCTGCTGGCCACCGTGGTCAGCGGACAGAAAC

AGGACAGACAGGGAGGAGAGCGACGGAGAAGCCAGCTCGACAGGGATCAGTGCGC

ATACTGTAAGGAAAAAGGCCATTGGGCCAAGGATTGCCCCAAAAAGCCAAGAGGAC

CAAGAGGACCAAGACCACAGACATCACTGCTGACCCTGGACGAC
```

Typically in nature, a Gag protein includes a large C-terminal extension which may contain retroviral protease, reverse transcriptase, and integrase enzymatic activity. Assembly of VLPs, however, generally does not require the presence of such components. In some cases, a retroviral Gag protein alone (e.g., lacking a C-terminal extension, lacking one or more of genomic RNA, reverse transcriptase, viral protease, or envelope protein) can self-assemble to form VLPs both in vitro and in vivo (Sharma S et al., 1997 Proc. Natl. Acad. Sci. USA 94: 10803-8). Retroviral Gag polyprotein alone can oligomerize and assemble into VLPs.

In some embodiments, a Gag polypeptide for use in accordance with the present invention lacks a C-terminal extension and/or contains a modified C-terminal extension. A Gag polypeptide may optionally include one or more additional polypeptides (e.g., a heterologous antigen). In some embodiments, a Gag polypeptide is co-expressed with a heterologous antigen (e.g., under separate promoters and/or as separate proteins). In some embodiments, a Gag polypeptide is expressed as a fusion protein with a heterologous antigen. The Gag polypeptide can be linked to a heterologous antigen to create a fusion protein without altering Gag function. For example, a coding sequence for a heterologous antigen may be spliced into the Gag polypeptide coding sequence, e.g., at the 3' end of the Gag polypeptide coding sequence. In some embodiments, a coding sequence for a heterologous antigen may be spliced in frame into the Gag polypeptide coding sequence. In some embodiments, a Gag polypeptide-coding sequence and heterologous antigen may be expressed by a single promoter. In some embodiments, a heterologous antigen is inserted at (e.g., fused to) the C-terminus of a Gag polypeptide. Without wishing to be bound by any theory, it is thought that fusion of a self-assembling Gag polypeptide to a heterologous antigen creates a fusion protein that acts as unmodified Gag and as a result will allow the antigen to be incorporated into the structural components of a resulting VLP. In some embodiments, VLP structural components serve as effective immunogens (e.g., for induction of cellular immune response). For example, provided VLPs may comprise a retroviral Gag polypeptide (e.g., MMLV Gag) and a structural component of HCMV (e.g., pp65). In some such embodiments, pp65 is incorporated into the VLP and serves as an antigen for eliciting an immune response against HCMV.

An exemplary Gag-pp65 fusion polypeptide for use in accordance with the present invention is shown as SEQ ID NO:4 below. In some embodiments, a suitable Gag polypeptide fusion protein includes all or a portion of a Gag polypeptide that is substantially homologous to a known retroviral Gag polypeptide and all or a portion of a pp65 polypeptide that is substantially homologous to a known pp65 polypeptide. For example, a Gag-pp65 polypeptide fusion protein may contain one or more amino acid substitutions, deletions, and/or insertions as compared to a wild-type or naturally-occurring Gag polypeptide and/or pp65 polypeptide, while retaining substantial self-assembly activity. Thus, in some embodiments, a Gag-pp65 polypeptide fusion protein suitable for the present invention is substantially homologous to SEQ ID NO:4. In some embodiments, a Gag-pp65 polypeptide fusion protein suitable for the present invention has an amino acid sequence at least 50%, 55%, 60%, 65%, 70%, 75%, 80%, 85%, 90%, 91%, 92%, 93%, 94%, 95%, 96%, 97%, 98%, 99% or more homologous to SEQ ID NO:4. In some embodiments, a Gag-pp65 polypeptide fusion protein suitable for the present invention is substantially identical to SEQ ID NO:4. In some embodiments, a Gag-pp65 polypeptide fusion protein suitable for the present invention has an amino acid sequence at least 50%, 55%, 60%, 65%, 70%, 75%, 80%, 85%, 90%, 91%, 92%, 93%, 94%, 95%, 96%, 97%, 98%, 99% or more identical to SEQ ID NO:4.

MMLV Gag - CMV pp65 Amino Acid Sequence
(SEQ ID NO: 4)
MGQTVTTPLSLTLGHWKDVERIAHNQSVDVKKRRWVTFCSAEWPTFNVGW

PRDGTFNRDLITQVKIKVFSPGPHGHPDQVPYIVTWEALAFDPPPWVKPF

VHPKPPPPLPPSAPSLPLEPPRSTPPRSSLYPALTPSLGAKPKPQVLSDS

GGPLIDLLTEDPPPYRDPRPPPSDRDGNGGEATPAGEAPDPSPMASRLRG

RREPPVADSTTSQAFPLRAGGNGQLQYWPFSSSDLYNWKNNNPSFSEDPG

KLTALIESVLITHQPTWDDCQQLLGTLLTGEEKQRVLLEARKAVRGDDGR

PTQLPNEVDAAFPLERPDWDYTTQAGRNHLVHYRQLLLAGLQNAGRSPTN

LAKVKGITQGPNESPSAFLERLKEAYRRYTPYDPEDPGQETNVSMSFIWQ

SAPDIGRKLERLEDLKNKTLGDLVREAEKIFNKRETPEEREERIRRETEE

KEERRRTEDEQKEKERDRRRHREMSKLLATVVSGQKQDRQGGERRRSQLD

RDQCAYCKEKGHWAKDCPKKPRGPRGPRPQTSLLTLDDCESRGRRCPEMI

SVLGPISGHVLKAVFSRGDTPVLPHETRLLQTGIHVRVSQPSLILVSQYT

PDSTPCHRGDNQLQVQHTYFTGSEVENVSVNVHNPTGRSICPSQEPMSIY

VYALPLKMLNIPSINVHHYPSAAERKHRHLPVADAVIHASGKQMWQARLT

VSGLAWTRQQNQWKEPDVYYTSAFVFPTKDVALRHVVCAHELVCSMENTR

ATKMQVIGDQYVKVYLESFCEDVPSGKLFMHVTLGSDVEEDLTMTRNPQP

FMRPHERNGFTVLCPKNMIIKPGKISHIMLDVAFTSHEHFGLLCPKSIPG

LSISGNLLMNGQQIFLEVQAIRETVELRQYDPVAALFFFDIDLLLQRGPQ

YSEHPTFTSQYRIQGKLEYRHTWDRHDEGAAQGDDDVWTSGSDSDEELVT

TERKTPRVTGGGAMAGASTSAGRKRKSASSATACTAGVMTRGRLKAESTV

APEEDTDEDSDNEIHNPAVFTWPPWQAGILARNLVPMVATVQGQNLKYQE

FFWDANDIYRIFAELEGVWQPAAQPKRRRHRQDALPGPCIASTPKKHRG*
(SEQ ID NO: 4)
(MMLV Gag amino acid sequence bolded)

MMLV Gag - CMV pp65 Nucleotide Sequence
(SEQ ID NO: 5)
ATGGGCCAGACTGTTACCACTCCCTTAAGTTTGACCTTAGGTCACTGGAA

AGATGTCGAGCGGATCGCTCACAACCAGTCGGTAGATGTCAAGAAGAGAC

GTTGGGTTACCTTCTGCTCTGCAGAATGGCCAACCTTTAACGTCGGATGG

CCGCGAGACGGCACCTTTAACCGAGACCTCATCACCCAGGTTAAGATCAA

GGTCTTTTCACCTGGCCCGCATGGACACCCAGACCAGGTCCCCTACATCG

TGACCTGGGAAGCCTTGGCTTTTGACCCCCCTCCCTGGGTCAAGCCCTTT

GTACACCCTAAGCCTCCGCCTCCTCTTCCTCCATCCGCCCCGTCTCTCCC

CCTTGAACCTCCTCGTTCGACCCCGCCTCGATCCTCCCTTTATCCAGCCC

TCACTCCTTCTCTAGGCGCCAAACCTAAACCTCAAGTTCTTTCTGACAGT

GGGGGGCCGCTCATCGACCTACTTACAGAAGACCCCCCGCCTTATAGGGA

CCCAAGACCACCCCCTTCCGACAGGGACGGAAATGGTGGAGAAGCGACCC

CTGCGGGAGAGGCACCGGACCCCTCCCCAATGGCATCTCGCCTACGTGGG

AGACGGGAGCCCCCTGTGGCCGACTCCACTACCTCGCAGGCATTCCCCCT

CCGCGCAGGAGGAAACGGACAGCTTCAATACTGGCCGTTCTCCTCTTCTG

ACCTTTACAACTGGAAAAATAATAACCCTTCTTTTTCTGAAGATCCAGGT

AAACTGACAGCTCTGATCGAGTCTGTTCTCATCACCCATCAGCCCACCTG

GGACGACTGTCAGCAGCTGTTGGGACTCTGCTGACCGGAGAAGAAAAAC

AACGGGTGCTCTTAGAGGCTAGAAAGGCGGTGCGGGGCGATGATGGGCGC

CCCACTCAACTGCCCAATGAAGTCGATGCCGCTTTTCCCCTCGAGCGCCC

AGACTGGGATTACACCACCCAGGCAGGTAGGAACCACCTAGTCCACTATC

GCCAGTTGCTCCTAGCGGGTCTCCAAAACGCGGGCAGAAGCCCCACCAAT

TTGGCCAAGGTAAAAGGAATAACACAAGGGCCCAATGAGTCTCCCTCGGC

CTTCCTAGAGAGACTTAAGGAAGCCTATCGCAGGTACACTCCTTATGACC

CTGAGGACCCAGGGCAAGAAACTAATGTGTCTATGTCTTTCATTTGGCAG

TCTGCCCCAGACATTGGGAGAAAGTTAGAGAGGTTAGAAGATTTAAAAAA

CAAGACGCTTGGAGATTTGGTTAGAGAGGCAGAAAAGATCTTTAATAAAC

GAGAAACCCCGAAGAAAGAGAGGAACGTATCAGGAGAGAAACAGAGGAA

AAAGAAGAACGCCGTAGGACAGAGGATGAGCAGAAAGAGAAAGAAAGAGA

TCGTAGGAGACATAGAGAGATGAGCAAGCTATTGGCCACTGTCGTTAGTG

GACAGAAACAGGATAGACAGGGAGGAGAACGAAGGAGGTCCCAACTCGAT

CGCGACCAGTGTGCCTACTGCAAAGAAAAGGGGCACTGGGCTAAAGATTG

TCCCAAGAAACCACGAGGACCTCGGGGACCAAGACCCCAGACCTCCCTCC

TGACCCTAGATGACTGTGAGTCGCGCGGTCGCCGTTGTCCCGAAATGATA

TCCGTACTGGGTCCCATTTCGGGGCACGTGCTGAAAGCCGTGTTTAGTCG

CGGCGACACGCCGGTGCTGCCGCACGAGACGCGACTCCTGCAGACGGGTA

TCCACGTGCGCGTGAGCCAGCCCTCGCTGATCCTGGTGTCGCAGTACACG

CCCGACTCGACGCCATGCCACCGCGGCGACAATCAGCTGCAGGTGCAGCA

CACGTACTTTACGGGCAGCGAGGTGGAGAACGTGTCGGTCAACGTGCACA

ACCCCACGGGCCGGAGCATCTGCCCCAGCCAAGAGCCCATGTCGATCTAT

GTGTACGCGCTGCCGCTCAAGATGCTGAACATCCCCAGCATCAACGTGCA

CCACTACCCGTCGGCGGCCGAGCGCAAACACCGACACCTGCCCGTAGCTG

ACGCTGTGATTCACGCGTCGGGCAAGCAGATGTGGCAGGCGCGTCTCACG

GTCTCGGGACTGGCCTGGACGCGTCAGCAGAACCAGTGGAAAGAGCCCGA

CGTCTACTACACGTCAGCGTTCGTGTTTCCCACCAAGGACGTGGCACTGC

GGCACGTGGTGTGCGCGCACGAGCTGGTTTGCTCCATGGAGAACACGCGC

GCAACCAAGATGCAGGTGATAGGTGACCAGTACGTCAAGGTGTACCTGGA

GTCCTTCTGCGAGGACGTGCCCTCCGGCAAGCTCTTTATGCACGTCACGC

TGGGCTCTGACGTGGAAGAGGACCTGACGATGACCCGCAACCCGCAACCC

TTCATGCGCCCCCACGAGCGCAACGGCTTTACGGTGTTGTGTCCCAAAAA
TATGATAATCAAACCGGGCAAGATCTCGCACATCATGCTGGATGTGGCTT
TTACCTCACACGAGCATTTTGGGCTGCTGTGTCCCAAGAGCATCCCGGGC
CTGAGCATCTCAGGTAACCTATTGATGAACGGGCAGCAGATCTTCCTGGA
GGTGCAAGCGATACGCGAGACCGTGGAACTGCGTCAGTACGATCCCGTGG
CTGCGCTCTTCTTTTTCGATATCGACTTGCTGCTGCAGCGCGGGCCTCAG
TACAGCGAACACCCCACCTTCACCAGCCAGTATCGCATCCAGGGCAAGCT
TGAGTACCGACACACCTGGGACCGGCACGACGAGGGTGCCGCCCAGGGCG
ACGACGACGTCTGGACCAGCGGATCGGACTCCGACGAGGAACTCGTAACC
ACCGAGCGCAAGACGCCCCGCGTTACCGGCGGCGGCGCCATGGCGGGCGC
CTCCACTTCCGCGGGCCGCAAACGCAAATCAGCATCCTCGGCGACGGCGT
GCACGGCGGGCGTTATGACACGCGGCCGCCTTAAGGCCGAGTCCACCGTC
GCGCCCGAAGAGGACACCGACGAGGATTCCGACAACGAAATCCACAATCC
GGCCGTGTTCACCTGGCCGCCCTGGCAGGCCGGCATCCTGGCCCGCAACC
TGGTGCCCATGGTGGCTACGGTTCAGGGTCAGAATCTGAAGTACCAGGAG
TTCTTCTGGGACGCCAACGACATCTACCGCATCTTCGCCGAATTGGAAGG
CGTATGGCAGCCCGCTGCGCAACCCAAACGTCGCCGCCACCGGCAAGACG
CCTTGCCCGGGCCATGCATCGCCTCGACGCCCAAAAAGCACCGAGGTTAG
(SEQ ID NO: 5)
(MMLV Gag nucleotide sequence bolded)

Codon Optimized MMLV Gag - CMV pp65 Nucleotide
Sequence
(SEQ ID NO: 6)
**ATGGGACAGACAGTCACTACACCCCTGAGCCTGACACTGGGACATTGGAA
AGACGTGGAGAGGATTGCACATAACCAGAGCGTGGACGTGAAGAAACGGA
GATGGGTCACCTTTTGCTCCGCCGAGTGGCCAACATTCAATGTGGGATGG
CCCCGAGATGGCACCTTCAACCGGGACCTGATCACTCAGGTGAAGATCAA
GGTCTTCTCTCCAGGACCCCACGGCCATCCAGATCAGGTGCCCTACATCG
TCACCTGGGAGGCTCTGGCATTTGACCCCCCTCCATGGGTGAAGCCTTTC
GTCCACCCAAAACCACCTCCACCACTGCCTCCATCTGCCCCTAGTCTGCC
ACTGGAACCCCCTCGGTCAACCCCACCCAGAAGCTCCCTGTATCCCGCAC
TGACACCTAGCCTGGGGGCCAAGCCTAAACCACAGGTGCTGTCTGATAGT
GGCGGGCCTCTGATCGATCTGCTGACCGAGGACCCTCCACCATACCGCGA
CCCACGACCTCCACCAAGCGACCGGGACGGAAACGGAGGAGAGGCTACAC
CCGCAGGCGAAGCCCCCGATCCTAGTCCAATGGCATCAAGGCTGCGCGGG
AGGCGCGAACCTCCAGTGGCCGACTCAACCACAAGCCAGGCATTTCCACT
GAGGGCCGGGGAAATGGACAGCTCCAGTATTGGCCCTTCTCTAGTTCAG
ATCTGTACAACTGGAAGAACAATAACCCTAGCTTCAGCGAGGACCCAGGC
AAACTGACCGCCCTGATCGAATCCGTGCTGATTACCCACCAGCCCACATG
GGACGATTGTCAGCAGCTCCTGGGCACCCTGCTGACCGGAGAGGAAAAGC
AGAGAGTGCTGCTGGAGGCTAGGAAAGCAGTCCGCGGGGACGATGGAAGG
CCAACACAGCTCCCCAATGAGGTGGATGCCGCTTTCCCTCTGGAACGGCC
AGATTGGGACTATACTACCCAGGCTGGACGCAACCACCTGGTGCATTACC**
**GGCAGCTCCTGCTGGCTGGACTGCAGAATGCAGGGCGCAGCCCCACTAAC
CTGGCCAAGGTGAAAGGAATCACCCAGGGCCCCAATGAGTCCCCTTCTGC
ATTCCTGGAGCGGCTGAAGGAAGCCTACCGACGGTATACTCCCTACGATC
CTGAGGACCCAGGCCAGGAAACCAACGTGAGTATGAGCTTCATCTGGCAG
TCCGCTCCTGACATTGGCCGAAAACTGGAGCGGCTGGAAGATCTGAAGAA
CAAGACCCTGGGCGACCTGGTGCGGGAGGCAGAAAAGATCTTCAACAAAA
GGGAGACTCCAGAGGAACGGGAGGAAAGAATTAGAAGGGAAACAGAGGAA
AAGGAGGAACGCCGACGGACTGAGGATGAACAGAAGGAGAAAGAAAGAGA
CCGGCGGCGGCACCGGGAGATGTCTAAGCTGCTGGCCACCGTGGTCAGTG
GCCAGAAACAGGATCGACAGGAGGAGAGCGACGGAGAAGCCAGCTCGAT
CGGGACCAGTGCGCCTATTGTAAGGAAAAAGGGCATTGGGCTAAGGACTG
CCCCAAGAAACCCAGAGGCCCACGCGGGCCCCGACCTCAGACTTCCCTGC
TGACCCTGGACGATTGCGAGAGCCGGGCCGGCCGGTGCCCAGAAATGATC
TCTGTGCTGGGGCCCATTAGTGGACATGTGCTGAAGGCCGTCTTCTCCAG
GGGAGACACCCCCGTGCTGCCTCACGAGACTCGACTGCTGCAGACCGGCA
TCCATGTGCGGGTCTCCCAGCCCTCTCTGATTCTGGTGTCACAGTATACA
CCAGATAGCACTCCCTGCCACAGAGGAGACAATCAGCTCCAGGTGCAGCA
TACCTACTTTACAGGCTCCGAGGTCGAAAACGTGTCTGTCAATGTGCACA
ACCCTACCGGCAGGAGCATCTGTCCTAGCCAGGAGCCAATGAGCATCTAC
GTGTACGCCCTGCCTCTGAAGATGCTGAATATCCCATCAATTAACGTCCA
CCATTACCCTAGCGCAGCCGAACGGAAGCACAGACATCTGCCAGTGGCCG
ACGCTGTCATCCATGCCAGCGGCAAACAGATGTGGCAGGCAAGACTGACC
GTGTCCGGGCTGGCCTGGACAAGGCAGCAGAATCAGTGGAAGGAGCCCGA
CGTGTACTATACCAGCGCCTTCGTGTTCCCTACCAAAGACGTGGCCCTGA
GACATGTGGTGTGCGCACATGAGCTGGTGTGCAGCATGGAAAACACTAGG
GCCACCAAGATGCAGGTCATCGGCGATCAGTATGTCAAAGTGTACCTGGA
GAGTTTTTGCGAAGACGTGCCATCAGGGAAGCTGTTCATGCATGTGACCC
TGGGCAGCGATGTCGAGGAAGACCTGACCATGACAAGAAATCCACAGCCC
TTTATGAGACCCCACGAGAGGAATGGGTTCACTGTGCTGTGCCCCAAGAA
CATGATCATTAAGCCTGGAAAAATCAGTCATATTATGCTGGATGTGGCCT
TTACATCACACGAGCATTTCGGACTGCTGTGCCCCAAATCCATCCCTGGA
CTGAGCATTTCCGGCAATCTGCTGATGAACGGCCAGCAGATCTTCCTGGA
AGTGCAGGCCATCCGGGAGACCGTCGAACTGCGACAGTATGACCCAGTGG
CTGCACTGTTCTTTTTCGACATCGACCTGCTGCTGCAGCGAGGACCACAG
TACAGCGAGCACCCTACTTTTACCTCCCAGTATCGGATTCAGGGGAAGCT
GGAGTACAGGCACACCTGGGATCGCCATGACGAAGGAGCCGCTCAGGGGG
ACGATGACGTGTGGACATCTGGCAGTGATTCAGACGAGGAACTGGTGACA
ACTGAGCGAAAACCCCCGGGTGACAGGAGGAGGGGCAATGGCAGGGGC
CAGCCACCAGCGCAGGGCGGAAGCGAAAAAGCGCCAGCAGCGCCACAGCAT
GTACCGCCGGCGTGATGACTAGAGGAAGGCTGAAGGCCGAGTCTACAGTC
GCTCCCGAGGAAGATACTGACGAGGATAGTGACAATGAAATCCACAACCC**

CGCCGTGTTCACCTGGCCACCTTGGCAGGCAGGGATTCTGGCTCGCAACC

TGGTCCCCATGGTGGCAACCGTCCAGGGACAGAATCTGAAGTATCAGGAG

TTTTTCTGGGATGCTAACGACATCTACCGGATTTTTGCAGAGCTGGAAGG

CGTGTGGCAGCCAGCAGCCCAGCCCAAACGACGGAGACATCGACAGGACG

CTCTGCCAGGACCTTGTATCGCCAGCACACCAAAGAAGCACAGGGGCTAA
(SEQ ID NO: 6)
(MMLV Gag nucleotide sequence bolded)

Codon Optimized MMLV Gag - CMV pp65 Nucleotide
Sequence
(SEQ ID NO: 22)
ATGGGACAGACCGTCACAACACCCCTGAGCCTGACCCTGGGACATTGGAA

AGACGTGGAGAGGATCGCACATAACCAGAGCGTGGACGTGAAGAAACGGA

GATGGGTCACATTCTGCAGTGCTGAGTGGCCAACTTTTAATGTGGGATGG

CCCCGAGACGGCACTTTCAACAGGGATCTGATCACCCAGGTGAAGATCAA

GGTCTTTAGCCCAGGACCTCACGGACATCCAGACCAGGTGCCTTATATCG

TCACCTGGGAGGCACTGGCCTTCGATCCCCCTCCATGGGTGAAGCCATTT

GTCCACCCAAAACCACCTCCACCACTGCCTCCAAGTGCCCCTTCACTGCC

ACTGGAACCACCCCGGAGCACACCACCCCGCAGCTCCCTGTATCCTGCTC

TGACTCCATCTCTGGGCGCAAAGCCAAAACCACAGGTGCTGAGCGACTCC

GGAGGACCACTGATTGACCTGCTGACAGAGGACCCCCCACCATACCGAGA

TCCTCGGCCTCCACCAAGCGACCGCGATGGAAATGGAGGAGAGGCTACTC

CTGCCGGCGAAGCCCCTGACCCATCTCCAATGGCTAGTAGGCTGCGCGGC

AGGCGCGAGCCTCCAGTGGCAGATAGCACCACATCCCAGGCCTTCCCTCT

GAGGGCTGGGGAAATGGGCAGCTCCAGTATTGGCCATTTTCTAGTTCAG

ACCTGTACAACTGGAAGAACAATAACCCCTCTTTCAGTGAGGACCCCGGC

AAACTGACCGCCCTGATCGAATCCGTGCTGATTACCCATCAGCCCACATG

GGACGATTGTCAGCAGCTCCTGGGCACCCTGCTGACCGGAGAGGAAAAGC

AGCGCGTGCTGCTGGAGGCTCGCAAAGCAGTCCGAGGGGACGATGGACGG

CCCACACAGCTCCCTAATGAGGTGGACGCCGCTTTTCCACTGGAAAGACC

CGACTGGGATTATACTACCCAGGCAGGGAGAAACCACCTGGTCCATTACA

GGCAGCTCCTGCTGGCAGGCCTGCAGAATGCCGGGAGATCCCCCACCAAC

CTGGCCAAGGTGAAAGGCATCACACAGGGGCCTAATGAGTCACCAAGCGC

CTTTCTGGAGAGGCTGAAGGAAGCTTACCGACGGTATACCCCATACGACC

CTGAGGACCCCGGACAGGAAACAAACGTCTCCATGTCTTTCATCTGGCAG

TCTGCCCCAGACATTGGGCGGAAGCTGGAGAGACTGGAAGACCTGAAGAA

CAAGACCCTGGGCGACCTGGTGCGGGAGGCTGAAAAGATCTTCAACAAAC

GGGAGACCCCCGAGGAAAGAGAGGAAAGGATTAGAAGGGAAACTGAGGAA

AAGGAGGAACGCCGACGGACCGAGGACGAACAGAAGGAGAAAGAACGAGA

TCGGCGGCGGCACCGGGAGATGTCAAAGCTGCTGGCCACCGTGGTCAGCG

GACAGAAACAGGACAGACAGGGAGGAGAGCGACGGAGAAGCCAGCTCGAC

AGGGATCAGTGCGCATACTGTAAGGAAAAAGGCCATTGGGCCAAGGATTG

CCCCAAAAAGCCAAGAGGACCAAGAGGACCAAGACCACAGACATCACTGC

TGACCCTGGACGACTGCGAGAGCCGGGGCCGGCGGTGCCCAGAAATGATC

TCTGTGCTGGGGCCCATTAGTGGACATGTGCTGAAGGCCGTCTTCTCCAG

GGGAGACACCCCCGTGCTGCCTCACGAGACTCGACTGCTGCAGACCGGCA

TCCATGTGCGGGTCTCCCAGCCCTCTCTGATTCTGGTGTCACAGTATACA

CCAGATAGCACTCCCTGCCACAGAGGAGACAATCAGCTCCAGGTGCAGCA

TACCTACTTTACAGGCTCCGAGGTCGAAAACGTGTCTGTCAATGTGCACA

ACCCTACCGGCAGGAGCATCTGTCCTAGCCAGGAGCCAATGAGCATCTAC

GTGTACGCCCTGCCTCTGAAGATGCTGAATATCCCATCAATTAACGTCCA

CCATTACCCTAGCGCAGCCGAACGGAAGCACAGACATCTGCCAGTGGCCG

ACGCTGTCATCCATGCCAGCGGCAAACAGATGTGGCAGGCAAGACTGACC

GTGTCCGGGCTGGCCTGGACAAGGCAGCAGAATCAGTGGAAGGAGCCCGA

CGTGTACTATACCAGCGCCTTCGTGTTCCCTACCAAAGACGTGGCCCTGA

GACATGTGGTGTGCGCACATGAGCTGGTGTGCAGCATGGAAAACACTAGG

GCCACCAAGATGCAGGTCATCGGCGATCAGTATGTCAAAGTGTACCTGGA

GAGTTTTTGCGAAGACGTGCCATCAGGGAAGCTGTTCATGCATGTGACCC

TGGGCAGCGATGTCGAGGAAGACCTGACCATGACAAGAAATCCACAGCCC

TTTATGAGACCCCACGAGAGGAATGGGTTCACTGTGCTGTGCCCCAAGAA

CATGATCATTAAGCCTGGAAAAATCAGTCATATTATGCTGGATGTGGCCT

TTACATCACACGAGCATTTCGGACTGCTGTGCCCCAAATCCATCCCTGGA

CTGAGCATTTCCGGCAATCTGCTGATGAACGGCCAGCAGATCTTCCTGGA

AGTGCAGGCCATCCGGGAGACCGTCGAACTGCGACAGTATGACCCAGTGG

CTGCACTGTTCTTTTTCGACATCGACCTGCTGCTGCAGCGAGGACCACAG

TACAGCGAGCACCCTACTTTTACCTCCCAGTATCGGATTCAGGGGAAGCT

GGAGTACAGGCACACCTGGGATCGCCATGACGAAGGAGCCGCTCAGGGGG

ACGATGACGTGTGGACATCTGGCAGTGATTCAGACGAGGAACTGGTGACA

ACTGAGCGAAAAACCCCCCGGGTGACAGGAGGAGGGGCAATGGCAGGGGC

CAGCACCAGCGCAGGGCGGAAGCGAAAAAGCGCCAGCAGCGCCACAGCAT

GTACCGCCGGCGTGATGACTAGAGGAAGGCTGAAGGCCGAGTCTACAGTC

GCTCCCGAGGAAGATACTGACGAGGATAGTGACAATGAAATCCACAACCC

CGCCGTGTTCACCTGGCCACCTTGGCAGGCAGGGATTCTGGCTCGCAACC

TGGTCCCCATGGTGGCAACCGTCCAGGGACAGAATCTGAAGTATCAGGAG

TTTTTCTGGGATGCTAACGACATCTACCGGATTTTTGCAGAGCTGGAAGG

CGTGTGGCAGCCAGCAGCCCAGCCCAAACGACGGAGACATCGACAGGACG

CTCTGCCAGGACCTTGTATCGCCAGCACACCAAAGAAGCACAGGGGCTAA
(SEQ ID NO: 22)
(MMLV Gag nucleotide sequence bolded)

In some embodiments, the present invention provides nucleic acids which encode a Gag polypeptide or a characteristic portion of a Gag polypeptide. In certain embodiments, nucleic acids can be DNA or RNA, and can be single stranded or double-stranded. In some embodiments, inventive nucleic acids may include one or more non-natural nucleotides; in other embodiments, inventive nucleic acids include only natural nucleotides.

B. Envelope Proteins

In some embodiments, the present invention utilizes VLPs comprised of one or more envelope polypeptides from HCMV (e.g., gB and/or gH). As used herein, the term "envelope polypeptide" refers to a polypeptide sequence whose amino acid sequence includes at least one characteristic sequence of an envelope glycoprotein. A wide variety of envelope glycoprotein sequences from various viruses, including, but not limited to HCMV, are known in the art and those of ordinary skill in the art, referring to such sequences, can readily identify sequences that are characteristic of envelope glycoproteins generally, and/or of particular envelope glycoproteins. In some embodiments, an envelope polypeptide comprises a cytoplasmic, transmembrane and/or extracellular portion or domain.

In some embodiments, an envelope polypeptide from HCMV includes a transmembrane and cytoplasmic domain that is not found in nature in the HCMV protein. For example, in some embodiments, an envelope polypeptide from HCMV includes a transmembrane and cytoplasmic domain from another HCMV protein (e.g., gB or gH). In some embodiments, an envelope polypeptide from HCMV includes a transmembrane domain and cytoplasmic domain found in nature in vesicular stomatitis virus (VSV). As is known in the art, polypeptides sometimes have transmembrane, cytoplasmic, and/or extracellular domains. In general, a "transmembrane domain", as used herein, refers to a domain that has an attribute of being present in the membrane (e.g., spanning a portion or all of a cellular membrane). As will be appreciated, it is not required that every amino acid in a transmembrane domain be present in the membrane. For example, in some embodiments, a transmembrane domain is characterized in that a designated stretch or portion of a protein is substantially located in the membrane. As is well known in the art, amino acid or nucleic acid sequences may be analyzed using a variety of algorithms to predict protein subcellular localization (e.g., transmembrane localization). Exemplary such programs include psort (PSORT.org), Prosite (prosite.expasy.org), among others. In general, a "cytoplasmic domain", as used herein, refers to a domain that has an attribute of being present in the cytoplasm. As will be appreciated, it is not required that every amino acid in a cytoplasmic domain be present in the cytoplasm. For example, in some embodiments, a cytoplasmic domain is characterized in that a designated stretch or portion of a protein is substantially located in the cytoplasm. As is well known in the art, amino acid or nucleic acid sequences may be analyzed using a variety of algorithms to predict protein subcellular localization (e.g., cytoplasmic localization). Exemplary such programs include psort (PSORT.org), Prosite (prosite.expasy.org), among others.

The transmembrane domain of VSV-G functions to target the viral glycoprotein to the cell membrane (Compton T et al., 1989 Proc Natl Acad Sci USA 86:4112-4116). Swapping the transmembrane and cytoplasmic domains of VSV-G for the transmembrane and cytoplasmic domains of another protein has been used to direct a protein to the cell membrane when the native protein does not naturally do this or requires accessory co-expressed proteins to accomplish this (Garrone P et al., 2011 Sci Transl Med 94:).

Among other things, the present invention encompasses the recognition that VLPs containing a structural component of a virus (e.g., MLV) and one or more heterologous surface antigens (e.g., envelope protein) are especially effective for antigen delivery and induction of an immune response against the heterologous antigen.

C. Heterologous Antigens

Envelope proteins of HCMV, such as glycoproteins gB and gH, are important targets for production of neutralizing antibodies against HCMV, as neutralizing antibodies are generally able to prevent infection. Therapies for HCMV infection, such as a gB subunit vaccine, have been developed and tested in experimental animals and clinical studies. Results from such studies, however, have demonstrated that in humans, the antibody response was not long-lived and not sufficiently effective for the treatment of HCMV in all cases. The reasons which have been suggested for the limited efficacy of subunit vaccines based exclusively on gB of HCMV in turn are strain-specific variations in immune responses, inadequate induction of a cellular immune response, and structural restrictions on antigen used, whose epitopes are thought to be conformation-dependent. The present inventors recognized that development of an HCMV vaccine comprising one or more envelope polypeptide antigens presented in their native conformation on the surface of a VLP leads to induction of neutralizing antibodies (e.g., via a humoral immune response) and an HCMV vaccine comprising one or more structural protein antigens (e.g., tegument protein pp65) leads to induction of helper T cells ($T_H$ lymphocytes) and cytotoxic T cells (CTL) (e.g., via a cell-mediated immune response). Neutralizing antibodies are generally formed against viral envelope proteins, and especially against HCMV glycoproteins gB and gH. $T_H$ cells are stimulated by tegument structural proteins of a virus, such as, for example, HCMV pp65 (ppUL83). In addition, pp65 plays an important role in induction of a CTL response against HCMV.

It will be appreciated that provided VLPs may comprise any heterologous antigen, including heterologous antigens from HCMV. For example, in some embodiments, a VLP in accordance with the present invention comprises one or more HCMV envelope polypeptides. In some embodiments, a VLP in accordance with the present invention comprises one or more HCMV structural polypeptides. In some embodiments, a VLP in accordance with the present invention comprises one or more HCMV envelope polypeptides and one or more HCMV structural polypeptides. A list of exemplary, but non-limiting HCMV antigens is provided below.

gB—Glycoprotein Complex (gC) I

The most fully characterized glycoprotein complex of HCMV is the gB complex (gB;UL55). It has been demonstrated that sera from CMV-seropositive individuals contains antibodies to gB, and up to 70% of the neutralizing antibody response in convalescent sera is gB-specific (Marshall G S et al., 1994 J Med Virol 43:77-83).

An exemplary HCMV gB polypeptide amino acid and nucleic acid sequence is shown below as SEQ ID NO:7 and SEQ ID NO:8, respectively. In some embodiments, a suitable gB polypeptide is substantially homologous to a known HCMV gB polypeptide. For example, a gB polypeptide may be a modified HCMV gB polypeptide containing one or more amino acid substitutions, deletions, and/or insertions as compared to a wild-type or naturally-occurring gB polypeptide (e.g., SEQ ID NO:7). Thus, in some embodiments, a gB polypeptide suitable for the present invention is substantially homologous to an HCMV gB polypeptide (SEQ ID NO:7). In some embodiments, an HCMV polypeptide suitable for the present invention has an amino acid sequence at least 50%, 55%, 60%, 65%, 70%, 75%, 80%, 85%, 90%, 91%, 92%, 93%, 94%, 95%, 96%, 97%, 98%, 99% or more homologous to SEQ ID NO:7. In some embodiments, a gB polypeptide suitable for the present invention is substantially identical to an HCMV gB polypeptide (SEQ ID NO:7). In some embodiments, a gB polypeptide suitable for the present invention has an amino acid sequence at least 50%, 55%, 60%, 65%, 70%, 75%, 80%, 85%, 90%, 91%, 92%, 93%, 94%, 95%, 96%, 97%, 98%, 99% or more identical to SEQ ID NO:7.

HCMV gB Amino Acid Sequence
(SEQ ID NO: 7)
MESRIWCLVVCVNLCIVCLGAAVSSSSTRGTSATHSHHSSHTTSAAHSRS
GSVSQRVTSSQTVSHGVNETIYNTTLKYGDVVGVNTTKYPYRVCSMAQGT
DLIRFERNIVCTSMKPINEDLDEGIMVVYKRNIVAHTFKVRVYQKVLTFR
RSYAYIHTTYLLGSNTEYVAPPMWEIHHINSHSQCYSSYSRVIAGTVFVA
YHRDSYENKTMQLMPDDYSNTHSTRYVTVKDQWHSRGSTWLYRETCNLNC
MVTITTARSKYPYHFFATSTGDVVDISPFYNGTNRNASYFGENADKFFIF
PNYTIVSDFGRPNSALETHRLVAFLERADSVISWDIQDEKNVTCQLTFWE
ASERTIRSEAEDSYHFSSAKMTATFLSKKQEVNMSDSALDCVRDEAINKL
QQIFNTSYNQTYEKYGNVSVFETTGGLVVFWQGIKQKSLVELERLANRSS
LNLTHNRTKRSTDGNNATHLSNMESVHNLVYAQLQFTYDTLRGYINRALA
QIAEAWCVDQRRTLEVFKELSKINPSAILSAIYNKPIAARFMGDVLGLAS
CVTINQTSVKVLRDMNVKESPGRCYSRPVVIFNFANSSYVQYGQLGEDNE
ILLGNHRTEECQLPSLKIFIAGNSAYEYVDYLFKRMIDLSSISTVDSMIA
LDIDPLENTDFRVLELYSQKELRSINVFDLEEIMREFNSYKQRVKYVEDK
VVDPLPPYLKGLDDLMSGLGAAGKAVGVAIGAVGGAVASVVEGVATFLKN
<u>PFGAFTIILVAIAVVIIIYLIYTRQRRLCMQPLQNLFPYLVSADGTTVTS</u>
<u>GNTKDTSLQAPPSYEESVYNSGRKGPGPPSSDASTAAPPYTNEQAYQMLL</u>
<u>ALVRLDAEQRAQQNGTDSLDGQTGTQDKGQKPNLLDRLRHRKNGYRHLKD</u>
<u>SDEEENV</u>*
(SEQ ID NO: 7)
(TM and CD underlined)

HCMV gB Nucleotide Sequence
(SEQ ID NO: 8)
ATGGAATCCAGGATCTGGTGCCTGGTAGTCTGCGTTAACTTGTGTATCGT
CTGTCTGGGTGCTGCGGTTTCCTCATCTTCTACTCGTGGAACTTCTGCTA
CTCACAGTCACCATTCCTCTCATACGACGTCTGCTGCTCATTCTCGATCC
GGTTCAGTCTCTCAACGCGTAACTTCTTCCCAAACGGTCAGCCATGGTGT
TAACGAGACCATCTACAACACTACCCTCAAGTACGGAGATGTGGTGGGGG
TCAACACCACCAAGTACCCCTATCGCGTGTGTTCTATGGCACAGGGTACG
GATCTTATTCGCTTTGAACGTAATATCGTCTGCACCTCGATGAAGCCCAT
CAATGAAGACCTGGACGAGGGCATCATGGTGGTCTACAAACGCAACATCG
TCGCGCACACCTTTAAGGTACGAGTCTACCAGAAGGTTTTGACGTTTCGT
CGTAGCTACGCTTACATCCACACCACTTATCTGCTGGGCAGCAACACGGA
ATACGTGGCGCCTCCTATGTGGGAGATTCATCATATCAACAGTCACAGTC
AGTGCTACAGTTCCTACAGCCGCGTTATAGCAGGCACGGTTTTCGTGGCT
TATCATAGGGACAGCTATGAAAACAAAACCATGCAATTAATGCCCGACGA
TTATTCCAACACCCACAGTACCCGTTACGTGACGGTCAAGGATCAATGGC
ACAGCCGCGGCAGCACCTGGCTCTATCGTGAGACCTGTAATCTGAATTGC
ATGGTGACCATCACTACTGCGCGCTCCAAGTATCCCTATCATTTTTTCGC AACTTCCACGGGTGATGTGGTTGACATTTCTCCTTTCTACAACGGAACTA
ATCGCAATGCCAGCTATTTTGGAGAAAACGCCGACAAGTTTTTTCATTTTT
CCGAACTACACTATCGTCTCCGACTTTGGAAGACCGAATTCTGCGTTAGA
GACCCACAGGTTGGTGGCTTTTCTTGAACGTGCGGACTCAGTGATCTCCT
GGGATATACAGGACGAGAAGAATGTTACTTGTCAACTCACTTTCTGGGAA
GCCTCGGAACGCACCATTCGTTCCGAAGCCGAGGACTCGTATCACTTTTC
TTCTGCCAAAATGACCGCCACTTTCTTATCTAAGAAGCAAGAGGTGAACA
TGTCCGACTCTGCGCTGGACTGTGTACGTGATGAGGCCATAAATAAGTTA
CAGCAGATTTTCAATACTTCATACAATCAAACATATGAAAAATATGGAAA
CGTGTCCGTCTTTGAAACCACTGGTGGTTTGGTGGTGTTCTGGCAAGGTA
TCAAGCAAAAATCTCTGGTGGAACTCGAACGTTTGGCCAACCGCTCCAGT
CTGAATCTTACTCATAATAGAACCAAAAGAAGTACAGATGGCAACAATGC
AACTCATTTATCCAACATGGAGTCGGTGCACAATCTGGTCTACGCCCAGC
TGCAGTTCACCTATGACACGTTGCGCGGTTACATCAACCGGGCGCTGGCG
CAAATCGCAGAAGCCTGGTGTGTGGATCAACGGCGCACCCTAGAGGTCTT
CAAGGAACTTAGCAAGATCAACCCGTCAGCTATTCTCTCGGCCATCTACA
ACAAACCGATTGCCGCGCGTTTCATGGGTGATGTCCTGGGTCTGGCCAGC
TGCGTGACCATTAACCAAACCAGCGTCAAGGTGCTGCGTGATATGAATGT
GAAGGAATCGCCAGGACGCTGCTACTCACGACCAGTGGTCATCTTTAATT
TCGCCAACAGCTCGTACGTGCAGTACGGTCAACTGGGCGAGGATAACGAA
ATCCTGTTGGGCAACCACCGCACTGAGGAATGTCAGCTTCCCAGCCTCAA
GATCTTCATCGCCGGCAACTCGGCCTACGAGTACGTGGACTACCTCTTCA
AACGCATGATTGACCTCAGCAGCATCTCCACCGTCGACAGCATGATCGCC
CTAGACATCGACCCGCTGGAAAACACCGACTTCAGGGTACTGGAACTTTA
CTCGCAGAAAGAATTGCGTTCCATCAACGTTTTTGATCTCGAGGAGATCA
TGCGCGAGTTCAATTCGTATAAGCAGCGGGTAAAGTACGTGGAGGACAAG
GTAGTCGACCCGCTGCCGCCCTACCTCAAGGGTCTGGACGACCTCATGAG
CGGGCCTGGGCGCCGCGGGAAAGGCCGTTGGCGTAGCCATTGGGGCCGTGG
GTGGCGCGGTGGCCTCCGTGGTCGAAGGCGTTGCCACCTTCCTCAAAAAC
CCC<u>TTCGGAGCCTTCACCATCATCCTCGTGGCCATAGCCGTCGTCATTAT</u>
<u>CATTTATTTGATCTATACTCGACAGCGGCGTCTCTGCATGCAGCCGCTGC</u>
<u>AGAACCTCTTTCCCTATCTGGTGTCCGCCGACGGGACCACCGTGACGTCG</u>
<u>GGCAACACCAAAGACACGTCGTTACAGGCTCCGCCTTCCTACGAGGAAAG</u>
<u>TGTTTATAATTCTGGTCGCAAAGGACCGGGACCACCGTCGTCTGATGCAT</u>
<u>CCACGGCGGCTCCGCCTTACACCAACGAGCAGGCTTACCAGATGCTTCTG</u>
<u>GCCCTGGTCCGTCTGGACGCAGAGCAGCGAGCGCAGCAGAACGGTACAGA</u>
<u>TTCTTTGGACGGACAGACTGGCACGCAGGACAAGGGACAGAAGCCCAACC</u>
<u>TGCTAGACCGACTGCGACACCGCAAAAACGGCTACCGACACTTGAAAGAC</u>
<u>TCCGACGAAGAAGAGAACGTCTGA</u>
(SEQ ID NO: 8)
(TM and CD underlined)

Codon Optimized HCMV gB Nucleotide Sequence (SEQ ID NO: 9)
ATGGAGTCAAGGATTTGGTGCCTGGTCGTGTGCGTCAATCTGTGCATCGT

CTGTCTGGGGGCTGCCGTGTCATCAAGTTCTACAAGAGGCACCAGCGCCA

CCCACTCACACCATAGCTCCCATACCACATCCGCCGCTCACTCCCGGTCT

GGCAGCGTGAGCCAGAGAGTCACATCTAGTCAGACCGTGAGCCACGGGGT

CAACGAGACCATCTACAATACTACCCTGAAGTATGGCGACGTGGTCGGGG

TGAACACAACTAAATACCCATATAGGGTCTGCAGTATGGCCCAGGGCACT

GATCTGATTAGATTCGAAAGGAACATCGTGTGCACCAGCATGAAGCCCAT

TAATGAGGACCTGGATGAAGGGATCATGGTGGTCTACAAACGCAATATTG

TGGCCCATACCTTCAAGGTGCGAGTCTATCAGAAAGTGCTGACATTTCGG

AGATCTTACGCATATATCCACACCACATACCTGCTGGGGAGTAACACCGA

GTATGTGGCTCCCCCTATGTGGGAAATTCACCATATCAATAGCCATTCCC

AGTGCTACTCAAGCTACAGCAGAGTGATCGCTGGAACAGTGTTCGTCGCA

TACCACAGAGACTCTTATGAGAACAAGACTATGCAGCTCATGCCCGACGA

TTACAGCAATACACATTCCACTAGATATGTGACAGTCAAAGATCAGTGGC

ACTCAAGGGGCAGCACCTGGCTGTACCGCGAGACATGCAACCTGAATTGT

ATGGTGACTATCACTACCGCTAGATCCAAGTACCCCTATCACTTCTTTGC

AACTTCCACCGGGGACGTGGTCGATATTTCTCCTTTCTACAACGGCACAA

ACCGGAATGCATCTTATTTTGGGGAGAACGCCGACAAGTTCTTTATTTTC

CCAAATTACACCATCGTGTCTGATTTTGGCAGACCCAACAGTGCCCTGGA

GACACATCGACTGGTGGCATTCCTGGAACGGGCCGACTCCGTCATTTCTT

GGGACATCCAGGATGAGAAGAATGTGACCTGCCAGCTCACCTTCTGGGAG

GCCAGCGAACGCACCATCCGATCCGAGGCTGAAGATTCTTACCACTTCTC

CTCTGCCAAAATGACAGCTACTTTTCTGAGCAAGAAACAGGAGGTGAACA

TGTCTGACAGTGCTCTGGATTGCGTGCGGGACGAAGCAATTAATAAGCTG

CAGCAGATCTTCAACACATCATACAACCAGACTTACGAGAAGTACGGAAA

CGTGAGCGTCTTCGAAACAACTGGCGGGCTGGTGGTCTTTTGGCAGGGCA

TCAAGCAGAAATCCCTGGTGGAGCTGGAAAGGCTGGCCAATCGCAGTTCA

CTGAACCTGACTCATAATCGGACCAAGAGATCTACAGACGGAAACAATGC

CACACATCTGTCTAACATGGAGAGTGTGCACAATCTGGTCTACGCTCAGC

TCCAGTTTACCTACGACACACTGAGAGGCTATATTAACAGGGCACTGGCC

CAGATCGCTGAAGCATGGTGCGTGGATCAGAGGCGCACCCTGGAGGTCTT

CAAGGAACTGTCCAAAATCAACCCTTCAGCAATTCTGAGCGCCATCTACA

ATAAGCCAATTGCAGCCAGGTTTATGGGAGACGTGCTGGGCCTGGCCAGT

TGCGTCACTATCAACCAGACCTCAGTGAAGGTCCTGCGCGATATGAATGT

GAAAGAGAGTCCCGGCAGATGCTATTCACGGCCTGTGGTCATCTTCAACT

TTGCTAATAGCTCCTACGTGCAGTATGGACAGCTCGGCGAGGACAACGAA

ATTCTGCTGGGGAATCACAGGACCGAGGAATGTCAGCTCCCTAGCCTGAA

GATTTTCATCGCTGGAAACTCCGCATACGAGTATGTGGATTACCTGTTCA

AGCGGATGATTGACCTGTCTAGTATCTCCACTGTGGATTCTATGATTGCC

CTGGACATCGATCCACTGGAAAATACCGACTTCAGGGTGCTGGAGCTGTA

TAGCCAGAAGGAACTGCGCTCCATCAACGTGTTCGATCTGGAGGAAATTA

TGAGAGAGTTTAATAGCTACAAGCAGAGGGTGAAATATGTCGAAGATAAG

GTGGTCGACCCCCTGCCACCCTACCTGAAAGGCCTGGACGATCTGATGAG

CGGGCTGGGAGCTGCAGGGAAGGCAGTGGGAGTCGCTATCGGCGCAGTGG

GAGGAGCCGTGGCCAGCGTGGTCGAGGGAGTGGCAACATTCCTGAAAAAC

CCC<u>TTCGGGGCCTTCACCATCATTCTGGTGGCAATCGCCGTGGTCATCAT

TATCTACCTGATCTACACAAGGCAGCGGCGGCTGTGCATGCAGCCTCTGC

AGAACCTGTTTCCATACCTGGTGAGCGCCGACGGGACCACAGTCACCTCA

GGAAATACTAAGGATACCTCTCTGCAGGCCCCCCCAAGTTACGAGGAATC

AGTGTATAACAGCGGCAGAAAAGGACCAGGACCACCTTCAAGCGACGCCA

GCACTGCCGCTCCACCCTACACCAATGAGCAGGCCTATCAGATGCTGCTG

GCTCTGGTGCGCCTGGATGCCGAACAGCGAGCTCAGCAGAACGGGACCGA

CTCCCTGGATGGACAGACCGGAACACAGGACAAGGGACAGAAACCTAATC

TGCTGGATCGGCTGCGGCACAGAAAAAACGGGTATAGGCACCTGAAGGAC

TCCGACGAAGAAGAAAATGTCTAA</u>
(SEQ ID NO: 9)
(TM and CD underlined)

In some embodiments, a gB polypeptide for use in accordance with the present invention lacks a transmembrane domain and/or cytoplasmic domain and/or contains a modified transmembrane domain and/or cytoplasmic domain. A gB polypeptide may optionally include one or more additional polypeptides (e.g., a heterologous transmembrane domain and/or cytoplasmic domain polypeptide). In some embodiments, a gB polypeptide is expressed as a fusion protein with a heterologous polypeptide. The gB polypeptide can be linked to a heterologous polypeptide to create a fusion protein without altering gB function and/or antigenicity. For example, a coding sequence for a heterologous polypeptide may be spliced into the gB polypeptide coding sequence, e.g., at the 3' end of the gB polypeptide coding sequence. In some embodiments, a coding sequence for a heterologous polypeptide may be spliced in frame into the gB polypeptide coding sequence. In some embodiments, a gB polypeptide-coding sequence and heterologous polypeptide may be expressed by a single promoter. In some embodiments, a heterologous polypeptide is inserted at (e.g., fused to) the C-terminus of a gB polypeptide.

In some embodiments, a heterologous polypeptide is or comprises a transmembrane domain and/or cytoplasmic domain found in Vesicular Stomatitis Virus (VSV). In some embodiments, a gB that is lacking a transmembrane domain and/or cytoplasmic domain is fused to a transmembrane domain and/or cytoplasmic domain from VSV. An exemplary gB-VSV fusion polypeptide for use in accordance with the present invention is shown below as SEQ ID NO:10. In some embodiments, a suitable gB-VSV polypeptide fusion protein includes all or a portion of a gB polypeptide that is substantially homologous to a known gB polypeptide and all or a portion of a VSV polypeptide that is substantially homologous to a known VSV polypeptide. For example, a gB-VSV polypeptide fusion protein may contain one or more amino acid substitutions, deletions, and/or insertions as compared to a wild-type or naturally-occurring gB and/or VSV polypeptide. Thus, in some embodiments, a gB-VSV polypeptide fusion protein suitable for the present invention is substantially homologous to SEQ ID NO:10. In some embodiments, a gB-VSV polypeptide fusion protein suitable for the present invention has an amino acid sequence at least 50%, 55%, 60%, 65%, 70%, 75%, 80%, 85%, 90%, 91%, 92%, 93%, 94%, 95%, 96%, 97%, 98%, 99% or more homologous to SEQ ID NO:10. In some embodiments, a gB-VSV polypeptide fusion protein suitable for the present invention is substantially identical to SEQ ID NO:10. In some embodiments, a gB-VSV polypeptide fusion protein suitable for the present invention has an amino acid sequence at least 50%, 55%, 60%, 65%, 70%, 75%, 80%, 85%, 90%, 91%, 92%, 93%, 94%, 95%, 96%, 97%, 98%, 99% or more identical to SEQ ID NO:10. As used herein, "gB-G" refers to a HMCV gB-VSV TM/CTD fusion protein.

HCMV gB-G Amino Acid Sequence
(SEQ ID NO: 10)
MESRIWCLVVCVNLCIVCLGAAVSSSSTRGTSATHSHHSSHTTSAAHSRS
GSVSQRVTSSQTVSHGVNETIYNTTLKYGDVVGVNTTKYPYRVCSMAQGT
DLIRFERNIVCTSMKPINEDLDEGIMVVYKRNIVAHTFKVRVYQKVLTFR
RSYAYIHTTYLLGSNTEYVAPPMWEIHHINSHSQCYSSYSRVIAGTVFVA
YHRDSYENKTMQLMPDDYSNTHSTRYVTVKDQWHSRGSTWLYRETCNLNC
MVTITTARSKYPYHFFATSTGDVVDISPFYNGTNRNASYFGENADKFFIF
PNYTIVSDFGRPNSALETHRLVAFLERADSVISWDIQDEKNVTCQLTFWE
ASERTIRSEAEDSYHFSSAKMTATFLSKKQEVNMSDSALDCVRDEAINKL
QQIFNTSYNQTYEKYGNVSVFETTGGLVVFWQGIKQKSLVELERLANRSS
LNLTHNRTKRSTDGNNATHLSNMESVHNLVYAQLQFTYDTLRGYINRALA
QIAEAWCVDQRRTLEVFKELSKINPSAILSAIYNKPIAARFMGDVLGLAS
CVTINQTSVKVLRDMNVKESPGRCYSRPVVIFNFANSSYVQYGQLGEDNE
ILLGNHRTEECQLPSLKIFIAGNSAYEYVDYLFKRMIDLSSISTVDSMIA
LDIDPLENTDFRVLELYSQKELRSINVFDLEEIMREFNSYKQRVKYVEDK
VVDPLPPYLKGLDDLMSGLGAAGKAVGVAIGAVGGAVASVVEGVATFLKN
<u>PFFFIIGLIIGLFLVLRVGIHLCIKLKHTKKRQIYTDIEMNRLGK</u>*
(SEQ ID NO: 10)
(TM and CTD underlined)

HCMV gB - G Nucleotide Sequence
(SEQ ID NO: 11)
ATGGAATCCAGGATCTGGTGCCTGGTAGTCTGCGTTAACTTGTGTATCGT
CTGTCTGGGTGCTGCGGTTTCCTCATCTTCTACTCGTGGAACTTCTGCTA
CTCACAGTCACCATTCCTCTCATACGACGTCTGCTGCTCATTCTCGATCC
GGTTCAGTCTCTCAACGCGTAACTTCTTCCCAAACGGTCAGCCATGGTGT
TAACGAGACCATCTACAACACTACCCTCAAGTACGGAGATGTGGTGGGGG
TCAACACCACCAAGTACCCCTATCGCGTGTGTTCTATGGCACAGGGTACG
GATCTTATTCGCTTTGAACGTAATATCGTCTGCACCTCGATGAAGCCCAT
CAATGAAGACCTGGACGAGGGCATCATGGTGGTCTACAAACGCAACATCG
TCGCGCACACCTTTAAGGTACGAGTCTACCAGAAGGTTTTGACGTTTCGT
CGTAGCTACGCTTACATCCACACCACTTATCTGCTGGGCAGCAACACGGA
ATACGTGGCGCCTCCTATGTGGGAGATTCATCATATCAACAGTCACAGTC
AGTGCTACAGTTCCTACAGCCGCGTTATAGCAGGCACGGTTTTCGTGGCT
TATCATAGGGACAGCTATGAAAACAAAACCATGCAATTAATGCCCGACGA
TTATTCCAACACCCACAGTACCCGTTACGTGACGGTCAAGGATCAATGGC
ACAGCCGCGGCAGCACCTGGCTCTATCGTGAGACCTGTAATCTGAATTGT
ATGGTGACCATCACTACTGCGCGCTCCAAGTATCCCTATCATTTTTTCGC
AACTTCCACGGGTGATGTGGTTGACATTTCTCCTTTCTACAACGGAACTA
ATCGCAATGCCAGCTATTTTGGAGAAAACGCCGACAAGTTTTTCATTTTT
CCGAACTACACTATCGTCTCCGACTTTGGAAGACCGAATTCTGCGTTAGA
GACCCACAGGTTGGTGGCTTTTCTTGAACGTGCGGACTCAGTGATCTCCT
GGGATATACAGGACGAGAAGAATGTTACTTGTCAACTCACTTTCTGGGAA
GCCTCGGAACGCACCATTCGTTCCGAAGCCGAGGACTCGTATCACTTTTC
TTCTGCCAAAATGACCGCCACTTTCTTATCTAAGAAGCAAGAGGTGAACA
TGTCCGACTCTGCGCTGGACTGTGTACGTGATGAGGCCATAAATAAGTTA
CAGCAGATTTTCAATACTTCATACAATCAAACATATGAAAAATATGGAAA
CGTGTCCGTCTTTGAAACCACTGGTGGTTTGGTGGTGTTCTGGCAAGGTA
TCAAGCAAAAATCTCTGGTGGAACTCGAACGTTTGGCCAACCGCTCCAGT
CTGAATCTTACTCATAATAGAACCAAAAGAAGTACAGATGGCAACAATGC
AACTCATTTATCCAACATGGAGTCGGTGCACAATCTGGTCTACGCCCAGC
TGCAGTTCACCTATGACACGTTGCGCGGTTACATCAACCGGGCGCTGGCG
CAAATCGCAGAAGCCTGGTGTGTGGATCAACGGCGCACCCTAGAGGTCTT
CAAGGAACTTAGCAAGATCAACCCGTCAGCTATTCTCTCGGCCATCTACA
ACAAACCGATTGCCGCGCGTTTCATGGGTGATGTCCTGGGTCTGGCCAGC
TGCGTGACCATTAACCAAACCAGCGTCAAGGTGCTGCGTGATATGAATGT
GAAGGAATCGCCAGGACGCTGCTACTCACGACCAGTGGTCATCTTTAATT
TCGCCAACAGCTCGTACGTGCAGTACGGTCAACTGGGCGAGGATAACGAA
ATCCTGTTGGGCAACCACCGCACTGAGGAATGTCAGCTTCCCAGCCTCAA
GATCTTCATCGCCGGCAACTCGGCCTACGAGTACGTGGACTACCTCTTCA
AACGCATGATTGACCTCAGCAGCATCTCCACCGTCGACAGCATGATCGCC
CTAGACATCGACCCGCTGGAAAACACCGACTTCAGGGTACTGGAACTTTA
CTCGCAGAAAGAATTGCGTTCCATCAACGTTTTTGATCTCGAGGAGATCA
TGCGCGAGTTCAATTCGTATAAGCAGCGGGTAAAGTACGTGGAGGACAAG
GTAGTCGACCCGCTGCCGCCCTACCTCAAGGGTCTGGACGACCTCATGAG
CGGCCTGGGCGCCGCGGGAAAGGCCGTTGGCGTAGCCATTGGGGCCGTGG
GTGGCGCGGTGGCCTCCGTGGTCGAAGGCGTTGCCACCTTCCTCAAAAAC
<u>CCCTTTTTCTTTATCATAGGGTTAATCATTGGACTATTCTTGGTTCTCCG</u>
<u>AGTTGGTATCCATCTTTGCATTAAATTAAAGCACACCAAGAAAAGACAGA</u>
<u>TTTATACAGACATAGAGATGAACCGACTTGGAAAGTAA</u>
(SEQ ID NO: 11)
TM and CTD underlined)

Codon Optimized HCMV gB - G Nucleotide Sequence
(SEQ ID NO: 12)
ATGGAGTCAAGGATTTGGTGTCTGGTCGTCTGCGTCAACCTGTGCATTGT
CTGCCTGGGAGCCGCCGTCTCATCATCATCTACCCGAGGCACATCCGCCA
CTCACTCTCACCATAGCTCCCATACCACATCCGCCGCTCACTCAAGAAGC

```
GGGTCCGTGTCTCAGAGGGTCACATCTAGTCAGACCGTGAGCCATGGAGT

CAACGAGACAATCTACAATACTACCCTGAAGTATGGAGACGTGGTCGGCG

TGAACACAACTAAATACCCCTATAGGGTCTGCTCTATGGCCCAGGGGACA

GATCTGATCCGATTTGAACGGAACATCGTGTGCACTAGCATGAAGCCTAT

CAATGAGGACCTGGATGAAGGAATTATGGTGGTCTACAAACGAAATATCG

TGGCCCATACTTTTAAGGTGAGAGTCTATCAGAAAGTGCTGACCTTCCGG

AGAAGCTACGCTTATATTCACACCACATACCTGCTGGGGTCCAACACCGA

GTATGTGGCACCCCCTATGTGGGAAATCCACCATATTAATAGTCATTCAC

AGTGCTACTCAAGCTACAGCAGAGTGATCGCTGGAACCGTGTTCGTCGCA

TACCACAGAGACAGTTATGAGAACAAGACAATGCAGCTCATGCCCGACGA

TTACAGTAATACCCATTCAACAAGATATGTGACCGTCAAAGATCAGTGGC

ACTCTCGCGGCAGTACCTGGCTGTACCGAGAGACATGCAACCTGAATTGT

ATGGTGACAATTACTACCGCCAGAAGCAAGTACCCTTATCACTTCTTTGC

TACCTCAACAGGGGACGTGGTCGACATCAGCCCCTTCTACAACGGAACAA

ACCGGAATGCCTCCTATTTCGGCGAGAACGCTGACAAATTCTTTATCTTC

CCCAACTACACTATCGTGAGCGATTTCGGCAGACCTAACAGTGCCCTGGA

GACCCATCGGCTGGTGGCATTTCTGGAAAGAGCCGACAGCGTGATCTCCT

GGGACATTCAGGATGAGAAGAATGTGACCTGCCAGCTCACCTTCTGGGAG

GCCAGCGAAAGAACCATCAGGTCCGAGGCAGAAGATTCTTACCACTTTTC

CTCTGCAAAAATGACTGCCACCTTCCTGTCCAAGAAACAGGAGGTGAACA

TGAGCGACTCCGCACTGGATTGCGTGCGGGACGAAGCCATCAATAAGCTG

CAGCAGATCTTCAACACATCTTACAACCAGACTTACGAGAAGTACGGCAA

CGTGAGTGTCTTTGAAACAACTGGCGGGCTGGTGGTCTTCTGGCAGGGGA

TCAAGCAGAAATCTCTGGTGGAGCTGGAACGGCTGGCCAATAGAAGTTCA

CTGAACCTGACTCATAATCGCACCAAGCGATCCACAGACGGAAACAATGC

AACTCATCTGAGCAACATGGAGTCCGTGCACAATCTGGTCTACGCCCAGC

TCCAGTTCACTTACGACACCCTGCGAGGCTATATCAACCGGGCCCTGGCT

CAGATTGCAGAAGCCTGGTGCGTGGATCAGAGGCGCACCCTGGAGGTCTT

TAAGGAACTGAGCAAAATTAACCCATCTGCTATCCTGAGTGCAATCTACA

ATAAGCCCATCGCAGCCAGGTTCATGGGGACGTGCTGGGACTGGCCTCC

TGCGTCACTATCAACCAGACCTCTGTGAAGGTCCTGCGCGATATGAATGT

GAAAGAGAGTCCTGGCAGGTGTTATTCACGCCCAGTGGTCATCTTCAACT

TCGCTAATAGCTCCTACGTGCAGTATGGCCAGCTCGGGGAGGACAACGAA

ATCCTGCTGGGAAATCACAGGACCGAGGAATGTCAGCTCCCAAGTCTGAA

GATCTTTATTGCCGGCAACTCAGCTTACGAGTATGTGGATTACCTGTTCA

AACGCATGATCGACCTGTCTAGTATTTCAACAGTGGATAGCATGATCGCC

CTGGACATTGATCCCCTGGAAAATACTGACTTCAGGGTGCTGGAGCTGTA

TAGCCAGAAGGAACTGCGCTCCATTAACGTGTTTGATCTGGAGGAAATCA

TGAGGGAGTTCAATTCCTACAAGCAGCGCGTGAAATATGTCGAAGATAAG

GTGGTCGACCCTCTGCCACCCTACCTGAAAGGCCTGGACGATCTGATGAG
```
```
CGGGCTGGGAGCTGCAGGCAAGGCAGTGGGAGTCGCCATCGGAGCTGTGG

GAGGCGCTGTCGCATCCGTGGTCGAGGGAGTGGCTACCTTTCTGAAGAAC

CCATTCTTTTTCATCATCGGCCTGATCATTGGGCTGTTCCTGGTGCTGAG

AGTCGGCATCCACCTGTGCATTAAGCTGAAGCACACCAAGAAGAGGCAGA

TCTACACCGATATTGAAATGAACAGACTGGGCAAGTGA
```
(SEQ ID NO: 12)
(TM and CTD underlined)

gH—Glycoprotein Complex (gC) III

The gc III complex contains glycoproteins gH (UL75), gL (UL115) and gO (UL74) (Urban M et al., 1996 J Gen Virol 77:1537-47). Like gB, gH is conserved among human pathogenic herpesviruses and plays an important role in a number of steps during HCMV replication. HCMV encodes two gH/gL complexes: gH/gL/gO and a gH/gL/UL128/UL130/UL131 complex (Wang D and Shenk T 2005 Proc Natl Acad USA 102:18153-8). The gO-containing complex is generally sufficient for fibroblast infection with HCMV, whereas the UL128/UL130/UL131-containing complex is needed in order for HCMV to infect endothelial and epithelial cells (Wang D and Shenk T 2005 J Virol 79 10330-8). Natural infection with HCMV typically elicits high titer neutralizing antibodies specific for epithelial cell entry and it has been demonstrated that antibodies against gH/gL/UL128/UL130/UL131 epitopes may comprise a significant component of this activity (Macagno A et al., 2010 J Virol 84:1005-13). Immunological studies on gH have demonstrated that in mammalian cells the protein requires additional polypeptides (like gL) for correct processing and transport to the cellular membrane (Urban Metal., 1996 J Gen Virol 77:1537-1547). If expressed alone, gH is found exclusively in the cytoplasm and/or nuclear membrane (Cranage M P et al., 1988 J Virol 62: 1416-1422).

An exemplary HCMV gH polypeptide amino acid and nucleic acid sequence is shown below as SEQ ID NO:13 and SEQ ID NO:14, respectively. In some embodiments, a suitable gH polypeptide is substantially homologous to a known HCMV gH polypeptide. For example, a gH polypeptide may be a modified HCMV gH polypeptide containing one or more amino acid substitutions, deletions, and/or insertions as compared to a wild-type or naturally-occurring gH polypeptide (e.g., SEQ ID NO:13). Thus, in some embodiments, a gH polypeptide suitable for the present invention is substantially homologous to an HCMV gH polypeptide (SEQ ID NO:13). In some embodiments, an HCMV gH polypeptide suitable for the present invention has an amino acid sequence at least 50%, 55%, 60%, 65%, 70%, 75%, 80%, 85%, 90%, 91%, 92%, 93%, 94%, 95%, 96%, 97%, 98%, 99% or more homologous to SEQ ID NO:13. In some embodiments, a gH polypeptide suitable for the present invention is substantially identical to an HCMV gH polypeptide (SEQ ID NO:13). In some embodiments, a gH polypeptide suitable for the present invention has an amino acid sequence at least 50%, 55%, 60%, 65%, 70%, 75%, 80%, 85%, 90%, 91%, 92%, 93%, 94%, 95%, 96%, 97%, 98%, 99% or more identical to SEQ ID NO:13.

HCMV gH Amino Acid Sequence
(SEQ ID NO: 13)
MRPGLPSYLIVLAVCLLSHLLSSRYGAEAISEPLDKAFHLLLNTYGRPIR

FLRENTTQCTYNSSLRNSTVVRENAISFNFFQSYNQYYVFHMPRCLFAGP

LAEQFLNQVDLTETLERYQQRLNTYALVSKDLASYRSFSQQLKAQDSLGE

QPTTVPPPIDLSIPHVWMPPQTTPHGWTESHTTSGLHRPHFNQTCILFDG

HDLLFSTVTPCLHQGFYLIDELRYVKITLTEDFFVVTVSIDDDTPMLLIF

GHLPRVLFKAPYQRDNFILRQTEKHELLVLVKKDQLNRHSYLKDPDFLDA

ALDFNYLDLSALLRNSFHRYAVDVLKSGRCQMLDRRTVEMAFAYALALFA

AARQEEAGAQVSVPRALDRQAALLQIQEFMITCLSQTPPRTTLLLYPTAV

DLAKRALWTPNQITDITSLVRLVYILSKQNQQHLIPQWALRQIADFALKL

HKTHLASFLSAFARQELYLMGSLVHSMLVHTTERREIFIVETGLCSLAEL

SHFTQLLAHPHHEYLSDLYTPCSSSGRRDHSLERLTRLFPDATVPTTVPA

ALSILSTMQPSTLETFPDLFCLPLGESFSALTVSEHVSYVVTNQYLIKGI

SYPVSTTVVGQSLIITQTDSQTKCELTRNMHTTHSITAALNISLENCAFC

QSALLEYDDTQGVINIMYMHDSDDVLFALDPYNEVVSSPRTHYLMLLKN

GTVLEVTDVVVDATDSR<u>LLMMSVYALSAIIGIYLLYRMLKTC</u>*
(SEQ ID NO: 13)
(TM and CTD underlined)

HCMV gH Nucleotide Sequence
(SEQ ID NO: 14)
ATGCGGCCAGGCCTCCCCTCCTACCTCATCGTCCTCGCCGTCTGTCTCCT

CAGCCACCTACTTTCGTCACGATATGGCGCAGAAGCCATATCCGAACCGC

TGGACAAAGCGTTTCACCTACTGCTCAACACCTACGGGAGACCCATCCGC

TTCCTGCGTGAAAACACCACCCAGTGTACCTACAATAGCAGCCTCCGTAA

CAGCACGGTCGTCAGGGAAAACGCCATCAGTTTCAACTTTTTCCAAAGCT

ATAATCAATACTATGTATTCCATATGCCTCGATGTCTTTTTGCGGGTCCT

CTGGCGGAGCAGTTTCTGAACCAGGTAGATCTGACCGAAACCCTGGAAAG

ATACCAACAGAGACTTAACACTTACGCGCTGGTATCCAAAGACCTGGCCA

GCTACCGATCTTTTTCGCAGCAGCTAAAGGCACAGGACAGCCTAGGTGAA

CAGCCCACCACTGTGCCACCACCCATTGACCTGTCAATACCTCACGTTTG

GATGCCACCGCAAACCACTCCACACGGCTGGACAGAATCACATACCACCT

CAGGACTACACCGACCACACTTTAACCAGACCTGTATCCTCTTTGATGGA

CACGATCTACTATTCAGCACCGTCACACCTTGTTTGCACCAAGGCTTTTA

CCTCATCGACGAACTACGTTACGTTAAAATAACACTGACCGAGGACTTCT

TCGTAGTTACGGTGTCCATAGACGACGACACACCCATGCTGCTTATCTTC

GGCCATCTTCCACGCGTACTCTTTAAAGCGCCCTATCAACGCGACAACTT

TATACTACGACAAACTGAAAAACACGAGCTCCTGGTGCTAGTTAAGAAAG

ATCAACTGAACCGTCACTCTTATCTCAAAGACCCGGACTTTCTTGACGCC

GCACTTGACTTCAACTACCTGGACCTCAGCGCACTACTACGTAACAGCTT

TCACCGTTACGCCGTGGATGTACTCAAAAGCGGTCGATGTCAGATGCTGG

ACCGCCGCACGGTAGAAATGGCCTTCGCCTACGCATTAGCACTGTTCGCA

GCAGCCCGACAAGAAGAGGCCGGCGCCCAAGTCTCCGTCCCACGGGCCCT

AGACCGCCAGGCCGCACTCTTACAAATACAAGAATTTATGATCACCTGCC

TCTCACAAACACCACCACGCACCACGTTGCTGCTGTATCCCACGGCCGTG

GACCTGGCCAAACGAGCCCTTTGGACACCGAATCAGATCACCGACATCAC

CAGCCTCGTACGCCTGGTCTACATACTCTCTAAACAGAATCAGCAACATC

TCATCCCCCAGTGGGCACTACGACAGATCGCCGACTTTGCCCTAAAACTA

CACAAAACGCACCTGGCCTCTTTTCTTTCAGCCTTCGCGCGTCAAGAACT

CTACCTCATGGGCAGCCTCGTCCACTCCATGCTAGTACATACGACGGAGA

GACGCGAAATCTTCATCGTAGAAACGGGCCTCTGTTCATTAGCCGAGCTA

TCACACTTTACGCAGTTGCTAGCTCATCCGCACCACGAATACCTCAGCGA

CCTGTACACACCCTGTTCCAGTAGCGGGCGACGCGATCACTCGCTCGAAC

GCCTCACACGTCTCTTCCCCGATGCCACCGTCCCCACTACCGTTCCCGCC

GCCCTCTCCATCCTATCTACCATGCAACCAAGCACGCTAGAAACCTTCCC

CGACCTGTTTTGTCTGCCGCTCGGCGAATCCTTCTCCGCGCTGACCGTCT

CCGAACACGTCAGTTATGTCGTAACAAACCAGTACCTGATCAAAGGTATC

TCCTACCCTGTCTCCACCACCGTCGTAGGCCAGAGCCTCATCATCACCCA

GACGGACAGTCAAACTAAATGCGAACTGACGCGCAACATGCATACCACAC

ACAGCATCACAGCGGCGCTCAACATTTCCCTAGAAAACTGCGCCTTTTGC

CAAAGCGCCCTACTAGAATACGACGACACGCAAGGCGTCATCAACATCAT

GTACATGCACGACTCGGACGACGTCCTTTTCGCCCTGGATCCCTACAACG

AAGTGGTGGTCTCATCTCCGCGAACTCACTACCTCATGCTTTTGAAAAAC

GGTACGGTCCTAGAAGTAACTGACGTCGTCGTGGACGCTACCGACAGTCG

<u>TCTCCTCATGATGTCCGTCTACGCGTATCGGCCATCATCGGCATCTATC</u>

<u>TGCTCTACCGCATGCTCAAGACATGCTGA</u>
(SEQ ID NO: 14)
(TM and CTD underlined)

Codon Optimized HCMV gH Nucleotide Sequence
(SEQ ID NO: 15)
ATGAGACCTGGACTGCCTTCTTATCTGATTGTGCTGGCCGTCTGCCTGCT

GTCACATCTGCTGAGTTCACGCTATGGGCTGAGGCTATCTCCGAGCCAC

TGGACAAGGCTTTTCACCTGCTGCTGAACACCTACGGGAGACCCATTAGG

TTCCTGCGCGAGAATACCACACAGTGCACATATAACAGCTCCCTGCGGAA

CAGCACTGTGGTCCGCGAAAACGCCATCTCTTTTAATTTCTTTCAGAGTT

ACAACCAGTACTACGTGTTCCATATGCCACGCTGTCTGTTTGCAGGACCC

CTGGCCGAGCAGTTCCTGAACCAGGTGGACCTGACCGAGACACTGGAAAG

ATACCAGCAGAGGCTGAATACCTATGCCCTGGTGAGTAAGGATCTGGCTT

CATATCGGTCTTTCAGTCAGCAGCTCAAGGCCCAGGACTCACTGGGCGAG

CAGCCTACTACCGTGCCCCCTCCAATCGATCTGAGCATTCCACACGTCTG

GATGCCCCCTCAGACAACTCCCCACGGCTGGACCGAAAGCCATACCACAT

CCGGGCTGCACAGACCCCATTTCAACCAGACATGCATCCTGTTTGATGGG

CACGACCTGCTGTTCAGCACTGTGACCCCTTGTCTGCATCAGGGATTCTA

CCTGATCGATGAGCTGAGATATGTGAAAATTACACTGACTGAAGACTTCT

TTGTGGTCACCGTGAGCATCGACGATGACACACCAATGCTGCTGATTTTT

GGACACCTGCCCCGGGTGCTGTTCAAGGCCCCCTACCAGCGAGACAACTT

TATTCTGCGGCAGACCGAGAAACACGAACTGCTGGTGCTGGTCAAGAAAG

ATCAGCTCAACAGGCATAGCTATCTGAAGGACCCCGACTTTCTGGATGCC

GCTCTGGACTTCAACTACCTGGACCTGTCAGCACTGCTGCGGAATAGCTT

```
CCACAGATATGCCGTGGATGTCCTGAAATCCGGAAGATGCCAGATGCTGG

ACCGGAGAACCGTGGAGATGGCATTTGCCTACGCTCTGGCACTGTTCGCA

GCCGCTAGGCAGGAGGAAGCAGGCGCTCAGGTGTCCGTCCCTCGCGCACT

GGATCGACAGGCAGCCCTGCTGCAGATCCAGGAGTTCATGATTACCTGTC

TGTCTCAGACACCACCCAGAACTACCCTGCTGCTGTACCCCACTGCCGTG

GACCTGGCTAAGAGGGCACTGTGGACCCCTAACCAGATCACTGATATTAC

CTCTCTGGTGCGCCTGGTCTATATCCTGAGTAAACAGAATCAGCAGCACC

TGATCCCACAGTGGGCCCTGCGACAGATTGCCGACTTCGCTCTGAAGCTG

CACAAAACCCATCTGGCTTCCTTCCTGTCTGCATTTGCCCGCCAGGAGCT

GTACCTGATGGGCTCTCTGGTGCACAGTATGCTGGTCCATACAACTGAGA

GGCGCGAAATCTTTATTGTGGAGACAGGGCTGTGCAGCCTGGCTGAACTG

TCCCACTTCACTCAGCTCCTGGCCCATCCTCACCATGAGTACCTGTCCGA

TCTGTATACCCCATGTTCTAGTTCAGGCCGACGGGACCACTCTCTGGAAC

GACTGACTCGGCTGTTTCCTGATGCAACCGTGCCTACCACCGTGCCCGCC

GCCCTGAGTATCCTGTCAACAATGCAGCCAAGCACACTGGAGACTTTCCC

CGACCTGTTTTGCCTGCCTCTGGGGGAGTCATTCAGCGCCCTGACCGTGT

CAGAACATGTCAGCTACGTGGTCACAAACCAGTATCTGATCAAGGGAATT

TCCTACCCCGTGTCTACTACCGTGGTCGGCCAGAGTCTGATCATTACCCA

GACAGATTCACAGACTAAATGTGAGCTGACCCGGAATATGCACACAACTC

ATAGCATCACCGCCGCTCTGAACATTTCCCTGGAGAATTGCGCTTTTTGT

CAGAGTGCACTGCTGGAATACGATGACACACAGGGCGTGATCAACATTAT

GTATATGCACGATAGCGATGACGTGCTGTTCGCTCTGGACCCCTACAACG

AGGTGGTCGTGAGCTCCCCTCGCACTCATTATCTGATGCTGCTGAAGAAT

GGAACAGTGCTGGAAGTCACTGATGTCGTGGTCGATGCCACAGACTCCCG

GCTGCTGATGATGTCTGTGTACGCACTGTCCGCCATCATCGGCATCTATC

TGCTGTATCGAATGCTGAAAACCTGTTGA
(SEQ ID NO: 15)
(TM and CTD underlined)
```

In some embodiments, a gH polypeptide for use in accordance with the present invention lacks a transmembrane domain and/or cytoplasmic domain and/or contains a modified transmembrane domain and/or cytoplasmic domain. A gH polypeptide may optionally include one or more additional polypeptides (e.g., a heterologous transmembrane domain and/or cytoplasmic domain polypeptide). In some embodiments, a gH polypeptide is expressed as a fusion protein with a heterologous polypeptide. The gH polypeptide can be linked to a heterologous polypeptide to create a fusion protein without altering gH function and/or antigenicity. For example, a coding sequence for a heterologous polypeptide may be spliced into the gH polypeptide coding sequence, e.g., at the 3' end of the gH polypeptide coding sequence. In some embodiments, a coding sequence for a heterologous polypeptide may be spliced in frame into the gH polypeptide coding sequence. In some embodiments, a gH polypeptide-coding sequence and heterologous polypeptide may be expressed by a single promoter. In some embodiments, a heterologous polypeptide is inserted at (e.g., fused to) the C-terminus of a gH polypeptide.

In some embodiments, a heterologous polypeptide is or comprises a transmembrane domain and/or cytoplasmic domain found in Vesicular Stomatitis Virus (VSV). In some embodiments, a gH that is lacking a transmembrane domain and/or cytoplasmic domain is fused to a transmembrane domain and/or cytoplasmic domain from VSV. An exemplary gH-VSV fusion polypeptide for use in accordance with the present invention is shown below as SEQ ID NO:16. In some embodiments, a suitable gH-VSV polypeptide fusion protein includes all or a portion of a gH polypeptide that is substantially homologous to a known HCMV gH polypeptide and all or a portion of a VSV polypeptide that is substantially homologous to a known VSV polypeptide. For example, a gH-VSV polypeptide fusion protein may contain one or more amino acid substitutions, deletions, and/or insertions as compared to a wild-type or naturally-occurring gH and/or VSV polypeptide. Thus, in some embodiments, a gH-VSV polypeptide fusion protein suitable for the present invention is substantially homologous to SEQ ID NO:16. In some embodiments, a gH-VSV polypeptide fusion protein suitable for the present invention has an amino acid sequence at least 50%, 55%, 60%, 65%, 70%, 75%, 80%, 85%, 90%, 91%, 92%, 93%, 94%, 95%, 96%, 97%, 98%, 99% or more homologous to SEQ ID NO:16. In some embodiments, a gH-VSV polypeptide fusion protein suitable for the present invention is substantially identical to SEQ ID NO:16. In some embodiments, a gH-VSV polypeptide fusion protein suitable for the present invention has an amino acid sequence at least 50%, 55%, 60%, 65%, 70%, 75%, 80%, 85%, 90%, 91%, 92%, 93%, 94%, 95%, 96%, 97%, 98%, 99% or more identical to SEQ ID NO:16. As used herein, "gH-G" refers to a HMCV gH-VSV TM/CTD fusion protein.

```
HCMV gH - G Amino Acid Sequence
                                        (SEQ ID NO: 16)
MRPGLPSYLIVLAVCLLSHLLSSRYGAEAISEPLDKAFHLLLNTYGRPIR

FLRENTTQCTYNSSLRNSTVVRENAISFNFFQSYNQYYVFHMPRCLFAGP

LAEQFLNQVDLTETLERYQQRLNTYALVSKDLASYRSFSQQLKAQDSLGE

QPTTVPPPIDLSIPHVWMPPQTTPHGWTESHTTSGLHRPHFNQTCILFDG

HDLLFSTVTPCLHQGFYLIDELRYVKITLTEDFFVVTVSIDDDTPMLLIF

GHLPRVLFKAPYQRDNFILRQTEKHELLVLVKKDQLNRHSYLKDPDFLDA

ALDFNYLDLSALLRNSFHRYAVDVLKSGRCQMLDRRTVEMAFAYALALFA

AARQEEAGAQVSVPRALDRQAALLQIQEFMITCLSQTPPRTTLLLYPTAV

DLAKRALWTPNQITDITSLVRLVYILSKQNQQHLIPQWALRQ1ADFALKL

HKTHLASFLSAFARQELYLMGSLVHSMLVHTTERREIFIVETGLCSLAEL

SHFTQLLAHPHHEYLSDLYTPCSSSGRRDHSLERLTRLFPDATVPTTVPA

ALSILSTMQPSTLETFPDLFCLPLGESFSALTVSEHVSYVVTNQYLIKGI

SYPVSTTVVGQSLIITQTDSQTKCELTRNMHTTHSITAALNISLENCAFC

QSALLEYDDTQGVINIMYMHDSDDVLFALDPYNEVVVSSPRTHYLMLLKN

GTVLEVTDVVVDATDSRFFFIIGLIIGLFLVLRVGIHLCIKLKHTKKRQI

YTDIEMNRLGK*
(SEQ ID NO: 16)
(TM and CTD underlined)

HCMV gH - G Nucleotide Sequence
                                        (SEQ ID NO: 17)
ATGCGGCCAGGCCTCCCCTCCTACCTCATCGTCCTCGCCGTCTGTCTCCT

CAGCCACCTACTTTCGTCACGATATGGCGCAGAAGCCATATCCGAACCGC
```

-continued

TGGACAAAGCGTTTCACCTACTGCTCAACACCTACGGGAGACCCATCCGC
TTCCTGCGTGAAAACACCACCCAGTGTACCTACAATAGCAGCCTCCGTAA
CAGCACGGTCGTCAGGGAAAACGCCATCAGTTTCAACTTTTTCCAAAGCT
ATAATCAATACTATGTATTCCATATGCCTCGATGTCTTTTTGCGGGTCCT
CTGGCGGAGCAGTTTCTGAACCAGGTAGATCTGACCGAAACCCTGGAAAG
ATACCAACAGAGACTTAACACTTACGCGCTGGTATCCAAAGACCTGGCCA
GCTACCGATCTTTTTCGCAGCAGCTAAAGGCACAGGACAGCCTAGGTGAA
CAGCCCACCACTGTGCCACCACCCATTGACCTGTCAATACCTCACGTTTG
GATGCCACCGCAAACCACTCCACACGGCTGGACAGAATCACATACCACCT
CAGGACTACACCGACCACACTTTAACCAGACCTGTATCCTCTTTGATGGA
CACGATCTACTATTCAGCACCGTCACACCTTGTTTGCACCAAGGCTTTTA
CCTCATCGACGAACTACGTTACGTTAAAATAACACTGACCGAGGACTTCT
TCGTAGTTACGGTGTCCATAGACGACGACACACCCATGCTGCTTATCTTC
GGCCATCTTCCACGCGTACTCTTTAAAGCGCCCTATCAACGCGACAACTT
TATACTACGACAAACTGAAAAACACGAGCTCCTGGTGCTAGTTAAGAAAG
ATCAACTGAACCGTCACTCTTATCTCAAAGACCCGGACTTTCTTGACGCC
GCACTTGACTTCAACTACCTGGACCTCAGCGCACTACTACGTAACAGCTT
TCACCGTTACGCCGTGGATGTACTCAAAGCGGTCGATGTCAGATGCTGG
ACCGCCGCACGGTAGAAATGGCCTTCGCCTACGCATTAGCACTGTTCGCA
GCAGCCCGACAAGAAGAGGCCGGCGCCCAAGTCTCCGTCCCACGGGCCCT
AGACCGCCAGGCCGCACTCTTACAAATACAAGAATTTATGATCACCTGCC
TCTCACAAACACCACCACGCACCACGTTGCTGCTGTATCCCACGGCCGTG
GACCTGGCCAAACGAGCCCTTTGGACACCGAATCAGATCACCGACATCAC
CAGCCTCGTACGCCTGGTCTACATACTCTCTAAACAGAATCAGCAACATC
TCATCCCCCAGTGGGCACTACGACAGATCGCCGACTTTGCCCTAAAACTA
CACAAAACGCACCTGGCCTCTTTTCTTTCAGCCTTCGCGCGTCAAGAACT
CTACCTCATGGGCAGCCTCGTCCACTCCATGCTAGTACATACGACGGAGA
GACGCGAAATCTTCATCGTAGAAACGGGCCTCTGTTCATTAGCCGAGCTA
TCACACTTTACGCAGTTGCTAGCTCATCCGCACCACGAATACCTCAGCGA
CCTGTACACACCCTGTTCCAGTAGCGGGCGACGCGATCACTCGCTCGAAC
GCCTCACACGTCTCTTCCCGATGCCACCGTCCCACTACCGTTCCCGCC
GCCCTCTCCATCCTATCTACCATGCAACCAAGCACGCTAGAAACCTTCCC
CGACCTGTTTTGTCTGCCGCTCGGCGAATCCTTCTCCGCGCTGACCGTCT
CCGAACACGTCAGTTATGTCGTAACAAACCAGTACCTGATCAAAGGTATC
TCCTACCCTGTCTCCACCACCGTCGTAGGCCAGAGCCTCATCATCACCCA
GACGGACAGTCAAACTAAATGCGAACTGACGCGCAACATGCATACCACAC
ACAGCATCACAGCGGCGCTCAACATTTCCCTAGAAAACTGCGCCTTTTGC
CAAAGCGCCCTACTAGAATACGACGACACGCAAGGCGTCATCAACATCAT
GTACATGCACGACTCGGACGACGTCCTTTTCGCCCTGGATCCCTACAACG
AAGTGGTGGTCTCATCTCCGCGAACTCACTACCTCATGCTTTTGAAAAAC

-continued

GGTACGGTCCTAGAAGTAACTGACGTCGTCGTGGACGCTACCGACAGTCG
<u>TTTTTTCTTTATCATAGGGTTAATCATTGGACTATTCTTGGTTCTCCGAG</u>
<u>TTGGTATCCATCTTTGCATTAAATTAAAGCACACCAAGAAAAGACAGATT</u>
<u>TATACAGACATAGAGATGAACCGACTTGGAAAGTAA</u>
(SEQ ID NO: 17)
(TM and CTD underlined)

Codon Optimized HCMV gH - G Nucleotide Sequence
(SEQ ID NO: 18)
ATGCGACCCGGACTGCCAAGCTACCTGATTGTCCTGGCTGTCTGTCTGCT
GTCACACCTGCTGAGTTCAAGATATGGGGCCGAAGCCATCAGCGAGCCAC
TGGACAAGGCTTTCCACCTGCTGCTGAACACCTACGGCAGACCCATTAGG
TTTCTGCGCGAGAATACCACACAGTGCACATATAACAGCTCCCTGAGGAA
TAGCACTGTGGTCCGCGAAAACGCCATCTCTTTCAATTTCTTTCAGAGTT
ACAACCAGTACTACGTGTTCCATATGCCACGCTGTCTGTTCGCAGGACCC
CTGGCCGAGCAGTTTCTGAACCAGGTGGACCTGACCGAGACACTGGAAAG
ATACCAGCAGAGGCTGAATACCTATGCCCTGGTGAGTAAGGATCTGGCTT
CATATCGGTCTTTCAGTCAGCAGCTCAAGGCCCAGGACTCTCTGGGAGAG
CAGCCTACTACCGTGCCCCCTCCAATCGATCTGAGTATTCCACACGTCTG
GATGCCCCCTCAGACAACTCCCCACGGATGGACCGAAAGCCATACCACAT
CCGGCCTGCACAGACCCCACTTCAACCAGACATGCATCCTGTTCGATGGC
CACGACCTGCTGTTTTCCACTGTGACCCCTTGTCTGCATCAGGGGTTCTA
CCTGATCGATGAGCTGAGATATGTGAAGATTACACTGACTGAAGACTTCT
TTGTGGTCACCGTGTCTATCGACGATGACACACCAATGCTGCTGATTTTC
GGACACCTGCCCCGGGTGCTGTTCAAGGCCCCCTACCAGCGAGACAACTT
CATCCTGCGGCAGACCGAGAAACACGAACTGCTGGTGCTGGTCAAGAAAG
ATCAGCTCAACCGGCATTCCTATCTGAAGGACCCCGACTTCCTGGATGCC
GCTCTGGACTTTAACTACCTGGACCTGTCAGCACTGCTGCGGAATAGCTT
TCACAGATATGCCGTGGATGTCCTGAAATCTGGGCGCTGCCAGATGCTGG
ACCGGAGAACCGTGGAGTGGCATTCGCCTACGCTCGGCACTGTTTGCA
GCCGCTCGGCAGGAGGAAGCAGGAGCTCAGGTGAGTGTCCCTCGCGCACT
GGATCGACAGGCAGCCCTGCTGCAGATCCAGGAGTTCATGATTACCTGTC
TGAGCCAGACACCACCCAGAACTACCCTGCTGCTGTACCCCACTGCCGTG
GACCTGGCTAAGAGGGCACTGTGGACCCTAACCAGATCACTGATATTAC
CAGCCTGGTGAGACTGGTCTATATCCTGTCCAAACAGAATCAGCAGCACC
TGATCCCACAGTGGGCCCTGAGGCAGATTGCCGACTTTGCTCTGAAGCTG
CACAAACCCATCTGGCTTCCTTTCTGTCTGCATTCGCCAGACAGGAGCT
GTACCTGATGGGATCTCTGGTGCACAGTATGCTGGTCCATACAACTGAGA
GGCGCGAAATCTTCATTGTGGAGACAGGCCTGTGCAGCCTGGCTGAACTG
TCCCACTTTACTCAGCTCCTGGCCCATCCTCACCATGAGTACCTGTCAGA
TCTGTATACCCCATGTTCTAGTTCAGGACGACGGGACCACAGCCTGGAAC
GACTGACTCGGCTGTTCCCTGATGCAACCGTGCCTACCACCGTGCCCGCC
GCCCTGAGTATCCTGTCAACAATGCAGCCAAGCACACTGGAGACTTTTCC
CGACCTGTTCTGCCTGCCTCTGGGCGAGAGCTTCAGCGCCCTGACCGTGA -continued

GCGAACATGTCAGCTACGTGGTCACAAACCAGTATCTGATCAAGGGGATT

TCCTACCCCGTGTCTACTACCGTGGTCGGACAGTCCCTGATCATTACCCA

GACAGATTCTCAGACTAAATGTGAGCTGACCAGAAATATGCACACAACTC

ATAGTATCACCGCCGCTCTGAACATTTCACTGGAGAATTGCGCTTTCTGT

CAGTCCGCACTGCTGGAATACGATGACACACAGGGCGTGATCAACATTAT

GTATATGCACGATTCTGATGACGTGCTGTTTGCTCTGGACCCCTACAACG

AGGTGGTCGTGAGCTCCCCCAGAACTCATTATCTGATGCTGCTGAAGAAT

GGCACAGTGCTGGAAGTCACTGATGTCGTGGTCGATGCCACAGACTCCCG

CTTCTTTTTCATCATTGGCCTGATCATTGGGCTGTTCCTGGTGCTGCGAG

TCGGCATCCACCTGTGCATCAAGCTGAAGCATACAAAGAAGAGACAGATC

TACACCGATATTGAAATGAACAGGCTGGGCAAATGA
(SEQ ID NO: 18)
(TM and CTD underlined)

In some embodiments, a gH polypeptide includes a transmembrane domain and/or cytoplasmic domain found in gB. An exemplary nucleotide encoding an HCMV gH-HCMV gB TM/CTD fusion polypeptide for use in accordance with the present invention is shown below as SEQ ID NO:20. In some embodiments, an HCMV gH-HCMV gB TM/CTD polypeptide suitable for the present invention is substantially homologous to the polypeptide encoded by SEQ ID NO:20. In some embodiments, an HCMV gH-HCMV gB TM/CTD polypeptide suitable for the present invention has an amino acid sequence at least 50%, 55%, 60%, 65%, 70%, 75%, 80%, 85%, 90%, 91%, 92%, 93%, 94%, 95%, 96%, 97%, 98%, 99% or more homologous to the polypeptide encoded by SEQ ID NO:20. In some embodiments, an HCMV gH-HCMV gB TM/CTD polypeptide suitable for the present invention is substantially identical to the polypeptide encoded by SEQ ID NO:20. In some embodiments, an HCMV gH-HCMV gB TM/CTD polypeptide suitable for the present invention has an amino acid sequence at least 50%, 55%, 60%, 65%, 70%, 75%, 80%, 85%, 90%, 91%, 92%, 93%, 94%, 95%, 96%, 97%, 98%, 99% or more identical to the polypeptide encoded by SEQ ID NO:20.

HCMV gH - HCMV gB TM/CTD Nucleotide Sequence
(SEQ ID NO: 20)
ATGCGGCCAGGCCTCCCCTCCTACCTCATCGTCCTCGCCGTCTGTCTCCT

CAGCCACCTACTTTCGTCACGATATGGCGCAGAAGCCATATCCGAACCGC

TGGACAAAGCGTTTCACCTACTGCTCAACACCTACGGGAGACCCATCCGC

TTCCTGCGTGAAAACACCACCCAGTGTACCTACAATAGCAGCCTCCGTAA

CAGCACGGTCGTCAGGGAAAACGCCATCAGTTTCAACTTTTTCCAAAGCT

ATAATCAATACTATGTATTCCATATGCCTCGATGTCTTTTTGCGGGTCCT

CTGGCGGAGCAGTTTCTGAACCAGGTAGATCTGACCGAAACCCTGGAAAG

ATACCAACAGAGACTTAACACTTACGCGCTGGTATCCAAAGACCTGGCCA

GCTACCGATCTTTTTCGCAGCAGCTAAAGGCACAGGACAGCCTAGGTGAA

CAGCCCACCACTGTGCCACCACCCATTGACCTGTCAATACCTCACGTTTG

GATGCCACCGCAAACCACTCCACACGGCTGGACAGAATCACATACCACCT

CAGGACTACACCGACCACACTTTAACCAGACCTGTATCCTCTTTGATGGA

CACGATCTACTATTCAGCACCGTCACACCTTGTTTGCACCAAGGCTTTTA

CCTCATCGACGAACTACGTTACGTTAAAATAACACTGACCGAGGACTTCT

TCGTAGTTACGGTGTCCATAGACGACGACACACCCATGCTGCTTATCTTC

GGCCATCTTCCACGCGTACTCTTTAAAGCGCCCTATCAACGCGACAACTT

TATACTACGACAAACTGAAAAACACGAGCTCCTGGTGCTAGTTAAGAAAG

ATCAACTGAACCGTCACTCTTATCTCAAAGACCCGGACTTTCTTGACGCC

GCACTTGACTTCAACTACCTGGACCTCAGCGCACTACTACGTAACAGCTT

TCACCGTTACGCCGTGGATGTACTCAAAAGCGGTCGATGTCAGATGCTGG

ACCGCCGCACGGTAGAAATGGCCTTCGCCTACGCATTAGCACTGTTCGCA

GCAGCCCGACAAGAAGAGGCCGGCGCCCAAGTCTCCGTCCCACGGGCCCT

AGACCGCCAGGCCGCACTCTTACAAATACAAGAATTTATGATCACCTGCC

TCTCACAAACACCACCACGCACCACGTTGCTGCTGTATCCCACGGCCGTG

GACCTGGCCAAACGAGCCCTTTGGACACCGAATCAGATCACCGACATCAC

CAGCCTCGTACGCCTGGTCTACATACTCTCTAAACAGAATCAGCAACATC

TCATCCCCCAGTGGGCACTACGACAGATCGCCGACTTTGCCCTAAAACTA

CACAAAACGCACCTGGCCTCTTTTCTTTCAGCCTTCGCGCGTCAAGAACT

CTACCTCATGGGCAGCCTCGTCCACTCCATGCTAGTACATACGACGGAGA

GACGCGAAATCTTCATCGTAGAAACGGGCCTCTGTTCATTAGCCGAGCTA

TCACACTTTACGCAGTTGCTAGCTCATCCGCACCACGAATACCTCAGCGA

CCTGTACACACCCTGTTCCAGTAGCGGGCGACGCGATCACTCGCTCGAAC

GCCTCACACGTCTCTTCCCCGATGCCACCGTCCCCACTACCGTTCCCGCC

GCCCTCTCCATCCTATCTACCATGCAACCAAGCACGCTAGAAACCTTCCC

CGACCTGTTTTGTCTGCCGCTCGGCGAATCCTTCTCCGCGCTGACCGTCT

CCGAACACGTCAGTTATGTCGTAACAAACCAGTACCTGATCAAAGGTATC

TCCTACCCTGTCTCCACCACCGTCGTAGGCCAGAGCCTCATCATCACCCA

GACGGACAGTCAAACTAAATGCGAACTGACGCGCAACATGCATACCACAC

ACAGCATCACAGCGGCGCTCAACATTTCCCTAGAAAACTGCGCCTTTTGC

CAAAGCGCCCTACTAGAATACGACGACACGCAAGGCGTCATCAACATCAT

GTACATGCACGACTCGGACGACGTCCTTTTCGCCCTGGATCCCTACAACG

AAGTGGTGGTCTCATCTCCGCGAACTCACTACCTCATGCTTTTGAAAAAC

GGTACGGTCCTAGAAGTAACTGACGTCGTCGTGGACGCTACCGACAGTCG

TTTCGGAGCCTTCACCATCATCCTCGTGGCCATAGCCGTCGTCATTATCA

TTTATTTGATCTATACTCGACAGCGGCGTCTCTGCATGCAGCCGCTGCAG

AACCTCTTTCCCTATCTGGTGTCCGCCGACGGGACCACCGTGACGTCGGG

CAACACCAAAGACACGTCGTTACAGGCTCCGCCTTCCTACGAGGAAAGTG

TTTATAATTCTGGTCGCAAAGGACCGGGACCACCGTCGTCTGATGCATCC

ACGGCGGCTCCGCCTTACACCAACGAGCAGGCTTACCAGATGCTTCTGGC

CCTGGTCCGTCTGGACGCAGAGCAGCGAGCGCAGCAGAACGGTACAGATT

CTTTGGACGGACAGACTGGCACGCAGGACAAGGGACAGAAGCCCAACCTG

CTAGACCGACTGCGACACCGCAAAAACGGCTACCGACACTTGAAAGACTC

CGACGAAGAAGAGAACGTCTGA

-continued
(SEQ ID NO: 20)
(gH peptide signal underlined; gB TM-CTD bolded)

Others (Including gN and gM—Glycoprotein Complex (gC) II)

In addition to gB and gH, other envelope glycoproteins may be useful in vaccine development. For example, the gcII complex, containing gN (UL73) and gM (UL100), is of particular interest. Proteomic analyses of HCMV virions has demonstrated that gcII is the most abundantly expressed glycoprotein in virus particles, emphasizing its potential importance in protective immunity (Varnum S M et al., 2005 Human Gene Ther 16:1143-50). HCMV infection elicits a gcII-specific antibody response in a majority of seropositive individuals (Shimamura M et al., 2006 J Virol 80:4591-600), and DNA vaccines containing gcII antigens gM and gN have been shown to elicit neutralizing antibody responses in rabbits and mice (Shen S et al., 2007 Vaccine 25:3319-27).

pp65

The cellular immune response to HCMV includes MHC class II restricted $CD4^+$ and MHC class I restricted, cytotoxic $CD8^+$ T-lymphocyte responses to a number of viral antigens, many of which are found in the viral tegument, the region of the viral particle that lies between the envelope and nucleocapsid. For example, HCMV pp65 protein (UL83) has been shown to elicit a significant $CD8^+$ T-lymphocyte response following HCMV infection (McLaughlin-Taylor E 1994 J Med Virol 43:103-10). This 65 kDa viral protein is one of the most abundantly expressed structural proteins of HCMV. Exemplary pp65 sequences are described herein.

Others (Including IE1, pp150)

Other proteins that elicit T-lymphocyte responses include the immediate early-1 (IE1) protein (UL123) and pp150 (UL32) (Gibson L et al., 2004 J Immunol 172:2256-64; La Rosa C et al., 2005 Human Immunol 66:116-26).

As described above, a Gag polypeptide may optionally include one or more addition al polypeptides (e.g., a heterologous antigen). In some embodiments, a Gag polypeptide is co-expressed with a heterologous antigen (e.g., under separate promoters and/or as separate proteins). The Gag polypeptide can be co-expressed with a heterologous antigen without altering Gag function. Without wishing to be bound by any theory, it is thought that co-expression of a self-assembling Gag polypeptide with a heterologous envelope antigen will allow the antigen to be incorporated into the envelope or lipid bilayer of a resulting VLP. In some embodiments, VLP envelope components serve as effective immunogens (e.g., for induction of humoral immune response). In some embodiments, a Gag polypeptide is expressed as a fusion protein with a heterologous antigen. For example, a coding sequence for a heterologous antigen may be spliced into the Gag polypeptide coding sequence, e.g., at the 3' end of the Gag polypeptide coding sequence. In some embodiments, a coding sequence for a heterologous antigen may be spliced in frame into the Gag polypeptide coding sequence. In some embodiments, a Gag polypeptide-coding sequence and heterologous antigen may be expressed by a single promoter. In some embodiments, a heterologous antigen is inserted at (e.g., fused to) the C-terminus of a Gag polypeptide. Without wishing to be bound by any theory, it is thought that fusion of a self-assembling Gag polypeptide to a heterologous antigen will allow the antigen to be incorporated into the structural components of a resulting VLP. In some embodiments, VLP structural components serve as effective immunogens (e.g., for induction of cellular immune response). For example, provided VLPs may comprise a retroviral gag polypeptide (e.g., MLV gag) and a structural component of HCMV (e.g., pp65). In some such embodiments, pp65 is incorporated into the VLP and serves as an antigen for eliciting an immune response against HCMV.

Provided VLPs may contain a structural retroviral protein (e.g., Gag polypeptide) that is arranged and constructed such that it self-assembles to form the VLP and is positioned in the VLP interior. In some embodiments, provided VLPs contain an envelope protein (e.g., gB and/or gH) that is arranged and constructed such that one or more epitopes of the envelope protein (e.g., gB and/or gH) is positioned on the VLP surface. In some embodiments, provided VLPs contain a fusion structural protein (e.g., Gag/pp65) that is arranged and constructed such that one or more epitopes of the structural protein (e.g., pp65) is positioned in the VLP interior.

II. Production of VLPs

It will be appreciated that a composition comprising VLPs will typically include a mixture of VLPs with a range of sizes. It is to be understood that the diameter values listed below correspond to the most frequent diameter within the mixture. In some embodiments >90% of the vesicles in a composition will have a diameter which lies within 50% of the most frequent value (e.g., 1000±500 nm). In some embodiments the distribution may be narrower, e.g., >90% of the vesicles in a composition may have a diameter which lies within 40, 30, 20, 10 or 5% of the most frequent value. In some embodiments, sonication or ultra-sonication may be used to facilitate VLP formation and/or to alter VLP size. In some embodiments, filtration, dialysis and/or centrifugation may be used to adjust the VLP size distribution.

In general, VLPs produced in accordance with the methods of the present disclosure may be of any size. In certain embodiments, the composition may include VLPs with diameter in range of about 20 nm to about 300 nm. In some embodiments, a VLP is characterized in that it has a diameter within a range bounded by a lower limit of 20, 30, 40, 50, 60, 70, 80, 90, or 100 nm and bounded by an upper limit of 300, 290, 280, 270, 260, 250, 240, 230, 220, 210, 200, 190, 180, or 170 nm. In some embodiments, VLPs within a population show an average diameter within a range bounded by a lower limit of 20, 30, 40, 50, 60, 70, 80, 90, or 100 nm and bounded by an upper limit of 300, 290, 280, 270, 260, 250, 240, 230, 220, 210, 200, 190, 180, or 170 nm. In some embodiments, VLPs in a population have a polydispersity index that is less than 0.5 (e.g., less than 0.45, less than 0.4, or less than 0.3). In some embodiments, VLP diameter is determined by nanosizing. In some embodiments, VLP diameter is determined by electron microscopy.

A. In Vitro/Ex Vivo VLP Production

Provided VLPs in accordance with the present invention may be prepared according to general methodologies known to the skilled person. For example, various nucleic acid molecules, genomes or reconstituted vectors or plasmids may be prepared using sequences of known viruses. Such sequences are available from banks, and material may be obtained from various collections, published plasmids, etc. These elements can be isolated and manipulated using techniques well known to the skilled artisan, or isolated from plasmids available in the art. Various synthetic or artificial sequences may also be produced from computer analysis or through (high throughput) screening of libraries. Recombinant expression of the polypeptides for VLPs requires construction of an expression vector containing a polynucleotide that encodes one or more polypeptide(s). Once a polynucleotide encoding one or more polypeptides has been obtained, the vector for production of the polypeptide may be produced by recombinant DNA technology using techniques known in the art. Expression vectors that may be utilized in accordance with the present invention include, but are not limited to mammalian expression vectors, baculovirus expression vectors, plant expression vectors (e.g., Cauliflower Mosaic Virus (CaMV), Tobacco Mosaic Virus (TMV)), plasmid expression vectors (e.g., Ti plasmid), among others.

An exemplary VLP expression plasmid that may be used in accordance with the present invention is shown below as SEQ ID NO:19:

Propol II Expression Plasmid
(SEQ ID NO: 19)
CTAGAGAGCTTGGCCCATTGCATACGTTGTATCCATATCATAATATGTAC

ATTTATATTGGCTCATGTCCAACATTACCGCCATGTTGACATTGATTATT

GACTAGTTATTAATAGTAATCAATTACGGGGTCATTAGTTCATAGCCCAT

ATATGGAGTTCCGCGTTACATAACTTACGGTAAATGGCCCGCCTGGCTGA

CCGCCCAACGACCCCCGCCCATTGACGTCAATAATGACGTATGTTCCCAT

AGTAACGCCAATAGGGACTTTCCATTGACGTCAATGGGTGGAGTATTTAC

GGTAAACTGCCCACTTGGCAGTACATCAAGTGTATCATATGCCAAGTACG

CCCCCTATTGACGTCAATGACGGTAAATGGCCCGCCTGGCATTATGCCCA

GTACATGACCTTATGGGACTTTCCTACTTGGCAGTACATCTACGTATTAG

TCATCGCTATTACCATGGTGATGCGGTTTTGGCAGTACATCAATGGGCGT

GGATAGCGGTTTGACTCACGGGGATTTCCAAGTCTCCACCCCATTGACGT

CAATGGGAGTTTGTTTTGGCACCAAAATCAACGGGACTTTCCAAAATGTC

GTAACAACTCCGCCCCATTGACGCAAATGGGCGGTAGGCGTGTACGGTGG

GAGGTCTATATAAGCAGAGCTCGTTTAGTGAACCGTCAGATCGCCTGGAG

ACGCCATCCACGCTGTTTTGACCTCCATAGAAGACACCGGGACCGATCCA

GCCTCCGGTCGACCGATCCTGAGAACTTCAGGGTGAGTTTGGGGACCCTT

GATTGTTCTTTCTTTTTCGCTATTGTAAAATTCATGTTATATGGAGGGGG

CAAAGTTTTCAGGGTGTTGTTTAGAATGGGAAGATGTCCCTTGTATCACC

ATGGACCCTCATGATAATTTTGTTTCTTTCACTTTCTACTCTGTTGACAA

CCATTGTCTCCTCTTATTTTCTTTTCATTTTCTTGTAACTTTTTCGTTAA

ACTTTAGCTTGCATTTGTAACGAATTTTTAAATTCACTTTTGTTTATTTG

TCAGATTGTAAGTACTTTCTCTAATCACTTTTTTTTCAAGGCAATCAGGG

TATATTATATTGTACTTCAGCACAGTTTTAGAGAACAATTGTTATAATTA

AATGATAAGGTAGAATATTTCTGCATATAAATTCTGGCTGGCGTGGAAAT

ATTCTTATTGGTAGAAACAACTACATCCTGGTCATCATCCTGCCTTTCTC

TTTATGGTTACAATGATATACACTGTTTGAGATGAGGATAAAATACTCTG

AGTCCAAACCGGGCCCCTCTGCTAACCATGTTCATGCCTTCTTCTTTTTC

CTACAGCTCCTGGGCAACGTGCTGGTTATTGTGCTGTCTCATCATTTTGG

CAAAGAATTCCTCGAGCGTACGCCTAGGGGATCCAGCGCTATTTAAATGC

TAGCATGCATGTTAACCCTGCAGGGGTACCGCGGCCGCAAGCTTAGATCC

GTCGAGGAATTCACTCCTCAGGTGCAGGCTGCCTATCAGAAGGTGGTGGC

TGGTGTGGCCAATGCCCTGGCTCACAAATACCACTGAGATCTTTTTCCCT

CTGCCAAAAATTATGGGGACATCATGAAGCCCCTTGAGCATCTGACTTCT

GGCTAATAAAGGAAATTTATTTTCATTGCAATAGTGTGTTGGAATTTTTT

GTGTCTCTCACTCGGAAGGACATATGGGAGGGCAAATCATTTAAAACATC

AGAATGAGTATTTGGTTTAGAGTTTGGCAACATATGCCCATATGCTGGCT

GCCATGAACAAAGGTTGGCTATAAAGAGGTCATCAGTATATGAAACAGCC

CCCTGCTGTCCATTCCTTATTCCATAGAAAAGCCTTGACTTGAGGTTAGA

TTTTTTTTATATTTTGTTTTGTGTTATTTTTTCTTTAACATCCCTAAAA

TTTTCCTTACATGTTTTACTAGCCAGATTTTCCTCCTCTCCTGACTACT

CCCAGTCATAGCTGTCCCTCTTCTCTTATGGAGATCCCTCGACGGATCGG

CCGCAATTCGTAATCATGTCATAGCTGTTTCCTGTGTGAAATTGTTATCC

GCTCACAATTCCACACAACATACGAGCCGGAAGCATAAAGTGTAAAGCCT

GGGGTGCCTAATGAGTGAGCTAACTCACATTAATTGCGTTGCGCTCACTG

CCCGCTTTCCAGTCGGGAAACCTGTCGTGCCAGCTGCATTAATGAATCGG

CCAACGCGCGGGGAGAGGCGGTTTGCGTATTGGGCGCTCTTCCGCTTCCT

CGCTCACTGACTCGCTGCGCTCGGTCGTTCGGCTGCGGCGAGCGGTATCA

GCTCACTCAAAGGCGGTAATACGGTTATCCACAGAATCAGGGGATAACGC

AGGAAAGAACATGTGAGCAAAAGGCCAGCAAAAGGCCAGGAACCGTAAAA

AGGCCGCGTTGCTGGCGTTTTTCCATAGGCTCCGCCCCCCTGACGAGCAT

CACAAAAATCGACGCTCAAGTCAGAGGTGGCGAAACCCGACAGGACTATA

AAGATACCAGGCGTTTCCCCCTGGAAGCTCCCTCGTGCGCTCTCCTGTTC

CGACCCTGCCGCTTACCGGATACCTGTCCGCCTTTCTCCCTTCGGGAAGC

GTGGCGCTTTCTCATAGCTCACGCTGTAGGTATCTCAGTTCGGTGTAGGT

CGTTCGCTCCAAGCTGGGCTGTGTGCACGAACCCCCCGTTCAGCCCGACC

GCTGCGCCTTATCCGGTAACTATCGTCTTGAGTCCAACCCGGTAAGACAC

GACTTATCGCCACTGGCAGCAGCCACTGGTAACAGGATTAGCAGAGCGAG

GTATGTAGGCGGTGCTACAGAGTTCTTGAAGTGGTGGCCTAACTACGGCT

ACACTAGAAGAACAGTATTTGGTATCTGCGCTCTGCTGAAGCCAGTTACC

TTCGGAAAAAGAGTTGGTAGCTCTTGATCCGGCAAACAAACCACCGCTGG

TAGCGGTGGTTTTTTTGTTTGCAAGCAGCAGATTACGCGCAGAAAAAAAG

GATCTCAAGAAGATCCTTTGATCTTTTCTACGGGGTCTGACGCTCAGTGG

AACGAAAACTCACGTTAAGGGATTTTGGTCATGAGATTATCAAAAGGAT

CTTCACCTAGATCCTTTTAAATTAAAAATGAAGTTTTAAATCAATCTAAA

GTATATATGAGTAAACTTGGTCTGACAGTTACCAATGCTTAATCAGTGAG

GCACCTATCTCAGCGATCTGTCTATTTCGTTCATCCATAGTTGCCTGACT

CCCCGTCGTGTAGATAACTACGATACGGGAGGGCTTACCATCTGGCCCCA

GTGCTGCAATGATACCGCGAGACCCACGCTCACCGGCTCCAGATTTATCA

GCAATAAACCAGCCAGCCGGAAGGGCCGAGCGCAGAAGTGGTCCTGCAAC

TTTATCCGCCTCCATCCAGTCTATTAATTGTTGCCGGGAAGCTAGAGTAA

GTAGTTCGCCAGTTAATAGTTTGCGCAACGTTGTTGCCATTGCTACAGGC

ATCGTGGTGTCACGCTCGTCGTTTGGTATGGCTTCATTCAGCTCCGGTTC

```
-continued
CCAACGATCAAGGCGAGTTACATGATCCCCATGTTGTGCAAAAAGCGG

GTTAGCTCCTTCGGTCCTCCGATCGTTGTCAGAAGTAAGTTGGCCGCAGT

GTTATCACTCATGGTTATGGCAGCACTGCATAATTCTCTTACTGTCATGC

CATCCGTAAGATGCTTTTCTGTGACTGGTGAGTACTCAACCAAGTCATTC

TGAGAATAGTGTATGCGGCGACCGAGTTGCTCTTGCCCGGCGTCAATACG

GGATAATACCGCGCCACATAGCAGAACTTTAAAAGTGCTCATCATTGGAA

AACGTTCTTCGGGGCGAAAACTCTCAAGGATCTTACCGCTGTTGAGATCC

AGTTCGATGTAACCCACTCGTGCACCCAACTGATCTTCAGCATCTTTTAC

TTTCACCAGCGTTTCTGGGTGAGCAAAAACAGGAAGGCAAATGCCGCAA

AAAAGGGAATAAGGGCGACACGGAAATGTTGAATACTCATACTCTTCCTT

TTTCAATATTATTGAAGCATTTATCAGGGTTATTGTCTCATGAGCGGATA

CATATTTGAATGTATTTAGAAAAATAAACAAATAGGGGTTCCGCGCACAT

TTCCCCGAAAAGTGCCACCTAAATTGTAAGCGTTAATATTTTGTTAAAAT

TCGCGTTAAATTTTTGTTAAATCAGCTCATTTTTTAACCAATAGGCCGAA

ATCGGCAAAATCCCTTATAAATCAAAAGAATAGACCGAGATAGGGTTGAG

TGTTGTTCCAGTTTGGAACAAGAGTCCACTATTAAAGAACGTGGACTCCA

ACGTCAAAGGGCGAAAAACCGTCTATCAGGGCGATGGCCCACTACGTGAA

CCATCACCCTAATCAAGTTTTTTGGGGTCGAGGTGCCGTAAAGCACTAAA

TCGGAACCCTAAAGGGAGCCCCCGATTTAGAGCTTGACGGGGAAAGCCGG

CGAACGTGGCGAGAAAGGAAGGGAAGAAAGCGAAAGGAGCGGGCGCTAGG

GCGCTGGCAAGTGTAGCGGTCACGCTGCGCGTAACCACCACACCCGCCGC

GCTTAATGCGCCGCTACAGGGCGCGTCCCATTCGCCATTCAGGCTGCGCA

ACTGTTGGGAAGGGCGATCGGTGCGGGCCTCTTCGCTATTACGCCAGCTG

GCGAAAGGGGGATGTGCTGCAAGGCGATTAAGTTGGGTAACGCCAGGGTT

TTCCCAGTCACGACGTTGTAAAACGACGGCCAGTGAGCGCGCGTAATACG

ACTCACTATAGGGCGAATTGGAGCTCCACCGCGGTGGCGGCCGCT
(SEQ ID NO: 19)
```

Provided VLPs may be prepared according to techniques known in the art. For example, in some embodiments, provided VLPs may be produced in any available protein expression system. Typically, the expression vector is transferred to a host cell by conventional techniques and the transfected cells are then cultured by conventional techniques to produce VLPs. In some embodiments, VLPs are produced using transient transfection of cells. In some embodiments, VLPs are produced using stably transfected cells. Typical cell lines that may be utilized for VLP production include, but are not limited to, mammalian cell lines such as human embryonic kidney (HEK) 293, WI 38, Chinese hamster ovary (CHO), monkey kidney (COS), HT1080, C10, HeLa, baby hamster kidney (BHK), 3T3, C127, CV-1, HaK, NS/O, and L-929 cells. Specific non-limiting examples include, but are not limited to, BALB/c mouse myeloma line (NSo/1, ECACC No: 85110503); human retinoblasts (PER.C6 (CruCell, Leiden, The Netherlands)); monkey kidney CV1 line transformed by SV40 (COS-7, ATCC CRL 1651); human embryonic kidney line (293 or 293 cells subcloned for growth in suspension culture, Graham et al., *J. Gen Virol.*, 36:59 (1977)); baby hamster kidney cells (BHK, ATCC CCL 10); Chinese hamster ovary cells+/−DHFR (CHO, Urlaub and Chasin, *Proc. Natl. Acad. Sci. USA,* 77:4216 (1980)); mouse sertoli cells (TM4, Mather, *Biol. Reprod.,* 23:243-251 (1980)); monkey kidney cells (CV1 ATCC CCL 70); African green monkey kidney cells (VERO-76, ATCC CRL-1 587); human cervical carcinoma cells (HeLa, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TRI cells (Mather et al., *Annals N.Y. Acad. Sci.,* 383:44-68 (1982)); MRC 5 cells; FS4 cells; and a human hepatoma line (Hep G2). In some embodiments, cell lines that may be utilized for VLP production include insect (e.g., Sf-9, Sf-21, Tn-368, Hi5) or plant (e.g., Leguminosa, cereal, or tobacco) cells. It will be appreciated in some embodiments, particularly when glycosylation is important for protein function, mammalian cells are preferable for protein expression and/or VLP production (see, e.g., Roldao A et al., 2010 Expt Rev Vaccines 9:1149-76).

It will be appreciated that a cell strain may be chosen which modulates the expression of the inserted sequences, or modifies and processes the gene product in a specific way. Such modifications (e.g., glycosylation) and processing (e.g., cleavage or transport to the membrane) of protein products may be important for generation of a VLP or function of a VLP polypeptide or additional polypeptide (e.g., an adjuvant or additional antigen). Different cells have characteristic and specific mechanisms for post-translational processing and modification of proteins and gene products. Appropriate cell lines or host systems can be chosen to ensure the correct modification and processing of the foreign protein expressed. Generally, eukaryotic host cells (also referred to as packaging cells (e.g., 293T human embryo kidney cells) which possess appropriate cellular machinery for proper processing of the primary transcript, glycosylation and phosphorylation of the gene product may be used in accordance with the present invention.

VLPs may be purified according to known techniques, such as centrifugation, gradients, sucrose-gradient ultracentrifugation, tangential flow filtration and chromatography (e.g., ion exchange (anion and cation), affinity and sizing column chromatography), or differential solubility, among others. Alternatively or additionally, cell supernatant may be used directly, with no purification step. Additional entities, such as additional antigens or adjuvants may be added to purified VLPs.

In some embodiments, provided polynucleotide sequences are codon optimized. Codon optimization is well known in the art and involves modification of codon usage so that higher levels of protein are produced.

B. In Vivo VLP Production

Provided VLPs in accordance with the present invention may be prepared as DNA vaccines according to methods well known in the art. For example, in some embodiments, one or more vectors or plasmids, e.g., such as those described above, is administered to a subject such that recipient cells express polypeptides encoded by the vector or plasmid. In some embodiments, recipient cells expressing such polypeptides produce VLPs comprising the polypeptides.

C. Mono-, Di-, Trivalent eVLPs

In accordance with the present invention, cells may be transfected with a single expression vector as described herein. In some embodiments, a single expression vector encodes more than one element of a VLP (e.g., more than one of structural polyprotein, CMV tegument polypeptide, CMV glycoprotein, etc.). For example, in some embodiments, a single expression vector encodes two or more elements of a VLP. In some embodiments, a single expression vector encodes three of more elements of a VLP.

In some embodiments, cells are transfected with two or more expression vectors. For example, in some embodiments, cells are transfected with a first vector encoding a Gag polypeptide and a second vector encoding an HCMV envelope glycoprotein (e.g., gB or gB-G or gH-G). In some such embodiments, "monovalent" VLPs comprising an HCMV envelope glycoprotein (e.g., gB or gB-G or gH-G) are produced. In some embodiments, cells are transfected with a first vector encoding a Gag polypeptide, a second vector encoding an HCMV envelope glycoprotein (e.g., gB or gB-G or gH-G) and a third vector encoding another HCMV envelope glycoprotein (e.g., gB or gB-G or gH-G). In some such embodiments, "bivalent" VLPs comprising 2 HCMV envelope glycoproteins (e.g., gB and gH-G or gB-G and gH-G) are produced. In some embodiments, cells are transfected with a first vector encoding a Gag-pp65 fusion polypeptide and a second vector encoding an HCMV envelope glycoprotein (e.g., gB or gB-G or gH-G). In some such embodiments, "bivalent" VLPs comprising an HCMV structural protein and an HCMV envelope glycoprotein (e.g., gB or gB-G or gH-G) are produced. In some embodiments, cells are transfected with a first vector encoding a Gag-pp65 fusion polypeptide, a second vector encoding an HCMV envelope glycoprotein (e.g., gB or gB-G or gH-G), and a third vector encoding another HCMV envelope glycoprotein (e.g., gB or gB-G or gH-G). In some such embodiments, "trivalent" VLPs comprising an HCMV structural protein and 2 HCMV envelope glycoproteins (e.g., gB and gH-G or gB-G and gH-G) are produced.

In some embodiments, monovalent, bivalent, or trivalent VLPs are admixed. For example, in some embodiments, monovalent and bivalent VLPs are admixed to form a trivalent VLP mixture. In some embodiments two bivalent VLPs are admixed to form a trivalent VLP mixture.

III. HCMV Infection and Treatment

Human cytomegalovirus (HCMV), a β-herpesvirus, is a ubiquitously occurring pathogen. In general, entry of herpesviruses into cells is a complex process initiated by adsorption and receptor binding and followed by fusion of the virus envelope with a cell membrane. Fusion generally occurs at either the plasma membrane or an endosomal membrane. HCMV infects multiple cell types in vivo, including epithelial cells, endothelial cells and fibroblasts (Plachter B et al., 1996 Adv Virus Res 46:195-261). It fuses with the plasma membranes of fibroblasts (Compton T et al., 1992 Virology 191:387-395), but enters retinal pigmented epithelial cells and umbilical vein endothelial cells via endocytosis (Bodaghi B et al., 1999 J Immunol 162:957-964; Ryckman B J et al., 2006 J Virol 80:710-722). The mechanism by which herpesviruses' choose their route of entry remains unclear. It is generally assumed that entry pathways are mainly determined by the host cell, but there is evidence for tropic roles of virion glycoproteins (Wang X et al., 1998 J Virol 72:5552-5558). As mentioned previously, HCMV encodes two gH/gL complexes: gH/gL/gO and gH/gL/UL128/UL130/UL131. The gO-containing complex is sufficient for fibroblast infection, whereas the pUL128/UL130/UL131-containing complex is important for HCMV infection of endothelial and epithelial cells.

HCMV infects 50-85% of adults by 40 years of age (Gershon A A et al., 1997 in *Viral Infections of Humans, 4$^{th}$* edition, New York; Plenum Press: 229-251). Most healthy individuals who acquire HCMV after birth develop few, if any, symptoms. However, HCMV disease is the cause of significant morbidity and mortality in immunocompromised individuals, such as recipients of hematopoietic cell transplants (HCT) and solid-organ transplants (SOT) (Pass RF 2001 Cytomegalovirus. In Fields Virology. 4$^{th}$ edition, Philadelphia; Lippincott Williams & Wilkens: 2675-2705). In SOT or HCT populations, HCMV disease can occur either from new infection transmitted from the donor organ or HCT, or can recur as a result of reactivation of latent virus in the recipient. In HIV-infected individuals, HCMV infection accelerates progression to AIDS and death, despite availability of antiretroviral therapy (Deayton J R et al., 2004 Lancet 363:2116-2121). In addition in the US, HCMV is the most common intrauterine infection and causes congenital abnormalities resulting in death or severe birth defects, including deafness and mental retardation, in approximately 8000 infants each year (Stagon S et al., 1986 JAMA 256:1904-1908).

Immune responses which control HCMV are incompletely understood. By analogy to other human herpesviruses it can be assumed that both cellular and humoral immune responses play an important role (Kohl S 1992 Current topics in Microbiology and Immunology 179:75-88). For murine CMV it was shown that either a cytotoxic T cell response or the passive transfer of neutralizing antibodies is sufficient to protect against a lethal challenge (Rapp M et al., 1993 Multidisciplinary Approach to Understanding Cytomegalovirus Disease: 327-332; Reddehase M J et al., 198 J Virology 61:3102-3108).

Control of CMV in immunocompromised persons is primarily associated with cellular immune responses; both $CD8^+$ and $CD4^+$ T lymphocytes appear to be important for protection against CMV disease (Gamadia L E et al., 2003 Blood 101:2686-2692; Cobbold M et al., 2005 J Exp Med 202:379-386). The cellular immune response to CMV includes $CD4^+$ helper T-lymphocyte and $CD8^+$ Cytotoxic T-lymphocyte responses to a number of antigens, found in the viral tegument, the region of the viral particle between the envelope and capsid. A recent study of CMV-specific $CD4^+$ and $CD8^+$ T cells from healthy donors used overlapping peptides from a series of CMV open reading frames to identify antigens recognized after CMV infection (Sylwester A W et al., 2005 J Exp Med 202:673-685). The CMV tegument phosphoprotein 65 (pp65) and surface glycoprotein gB were the antigens most frequently recognized by CD4 T cells, and pp65 was also one of the antigens most frequently recognized by CD8 T cells.

In contrast to the transplant setting, the maternal humoral immune response against the virus seems to be important in preventing HCMV disease in the newborn. Antibodies to surface glycoproteins, especially gB, appear to be critical for protection against the maternal-fetal transfer of CMV (Fowler K B et al., 2003 JAMA 289:1008-1011). Moreover, in an earlier vaccination study it was shown that protection from re-infection is correlated with neutralizing antibodies (Adler S P et al., 1995 J Infectious Diseases 171:26-32). The humoral immune response to CMV is dominated by responses to viral envelope glycoproteins present in the outer envelope of the virus particle (e.g., gB and gH).

In the case of HCMV, direct evaluation of immunological effector functions is difficult since the virus is strictly species specific and no animal model system is available. However, murine CMV and guinea pig CMV have been used to evaluate vaccine strategies in these host species.

A CMV vaccine that induces both protective T cell and neutralizing antibody responses has the potential to prevent infection or ameliorate CMV disease due to congenital infection or transplantation.

The first live, attenuated HCMV vaccine candidate tested in humans was based on the laboratory-adapted AD169 strain. Subsequent trials with another laboratory-adapted clinical isolate, the Towne strain, confirmed that live attenuated vaccines could elicit neutralizing antibodies, as well as CD4+ and CD8+ T lymphocyte responses. The efficacy of the Towne vaccine was assessed in a series of studies in renal transplant recipients. Although the Towne vaccine did provide a protective impact on HCMV disease it failed to prevent HCMV infection after transplantation (Plotkin S A et al., 1984 Lancet 1:528-530). Towne vaccine was also evaluated in a placebo-controlled study of seronegative mothers who had children attending group daycare where it failed to prevent these women from acquiring infection from their HCMV-infected children (Adler S P et al., 1995 J Infectious Diseases 171:26-32). An interpretation of these studies was that the Towne vaccine was overattenuated. To explore this possibility a series of genetic recombinants in which regions of the unattenuated "Toledo" strain of CMV were substituted for the corresponding regions of the Towne genome, resulting in the construction of Towne/Toledo "chimeras" that contain some, but not all, of the mutations that contribute to the Towne vaccine attenuation (Heineman T C et al. 2006 J Infect Disease 193:1350-1360). The safety and tolerability of four Towne/Toledo "chimeras" is being tested in a Phase I trial. Long-term safety concerns about the potential risk of establishing a latent HCMV infection have hindered the further development of live, attenuated vaccines.

The leading subunit CMV vaccine candidate is based on the envelope glycoprotein, gB, (purified recombinant gB vaccine is manufactured by Sanofi-Pasteur Vaccines) due to this protein's ability to elicit high-titer, virus-neutralizing antibody responses during natural infection. The recombinant gB vaccine elicits neutralizing antibody responses and has an excellent safety profile, however, it excludes other glycoprotein targets of neutralizing antibody response and more importantly T-lymphocyte targets. The vaccine requires MF59 adjuvant to optimize immunogenicity. In the most recent trial, this vaccine provided an overall 50% efficacy for prevention of CMV infection in a Phase 2 clinical trial in young woman (Pass R F et al., 2009 N Engl J Med 360:1191-1199). Other viral proteins being evaluated as subunit vaccine candidates include pp65 and IE1, both of which elicit T-cell responses.

DNA vaccines elicit robust cellular and humoral immune responses in animals and are well suited to specificity and precision in vaccine design. DNA vaccines have been developed for CMV and have focused on gB, IE1 and pp65 proteins as the candidate target immunogens. A bivalent CMV DNA vaccine candidate (Wloch MK 2008 J Infectious Diseases 297:1634-1642), using plasmid DNA encoding pp65 and gB and a trivalent vaccine candidate (Jacobson M A 2009 Vaccine 27:1540-1548) that also includes a third plasmid encoding the IE1 gene product have been developed by Vical Vaccines (U.S. Pat. No. 7,410,795). The trivalent DNA vaccine alone had minimal immunogenicity irrespective of route of administration. However the CMV DNA vaccine did appear to safely prime for a memory response to CMV antigens observed after administration of a live, attenuated CMV (Towne).

In a vectored vaccine approach, the gene product of interest is expressed in the context of a non-replicating (usually viral) carrier. One example of this is a canarypox vector called ALVAC developed by Virogenetics and Sanofi-Pasteur Vaccines, which is an attenuated poxvirus that replicates abortively in mammalian cells. ALVAC expressing CMV gB and ALVAC expressing pp65 (U.S. Pat. No. 6,267,965) have been tested in clinical trials. ALVAC-CMV (gB) did not induce neutralizing antibodies but did prime for higher neutralizing antibody titers after subsequent infection with the Towne strain CMV (Adler S P et al. 1999 J Infectious Diseases 180:843-846), although it did not appear to boost neutralizing antibody titers after subsequent immunization with gB subunit/MF59 vaccine (Bernstein D I et al. 2002 J Infectious Diseases 185:686-690). A canarypox vector expressing pp65, ALVAC-CMV(pp64), induced long-lasting CTL responses in all originally seronegative volunteers, at frequencies comparable to naturally seropositive individuals (Berencsi K et al. 2001 J Infectious Diseases 183:1171-1179). Another approach used to express gB as a vectored vaccine is the use of an alphavirus replicon system by AlphaVax Inc (U.S. Pat. No. 7,419,674). This approach involves a propagation-defective single-cycle RNA replicon vector system derived from an attenuated strain of an alphavirus, Venezuelan Equine Encephalitis (VEE) virus, to produce virus-like replicon particles (VRPs) expressing pp65, IE1 or gB protein (Berstein et al., 2010 Vaccine 28:484-493). A two component alphavirus replicon vaccine was used to express the three CMV proteins as a soluble form of CMV gB (Towne strain) and a pp65/IE1 fusion protein (Reap E A et al. 2007 Vaccine 25:7441-7449) was found to be safe and induced high levels of neutralizing antibody and polyfunctional CD4+ and CD8+ antigen-specific T cell responses. The Geometric Mean Titre (GMT) for the high dose group was about half the GMT in 12 naturally infected, CMV seropositive individuals tested in the assay.

A novel candidate for vaccination against HCMV currently in preclinical development is the "dense body" vaccine. Dense bodies (DBs) are enveloped, replication-defective particles formed during the replication of CMVs in cell culture. They contain both envelope glycoproteins and large quantities of pp65 protein. DBs are non-infectious and immunogenic but incapable of establishing latent HCMV infection in the vaccine recipient. DBs have been shown to be capable of inducing virus neutralizing antibodies and T-cell responses in mice in the absence of viral gene expression (Pepperl S et al., 2000 J Virol 74:6132-6146—WO 00/53729 and U.S. Pat. No. 6,713,070).

IV. Pharmaceutical Compositions

The present invention provides pharmaceutical compositions comprising provided VLPs and/or provided glycoprotein variants. In some embodiments, the present invention provides a VLP and at least one pharmaceutically acceptable excipient. Such pharmaceutical compositions may optionally comprise and/or be administered in combination with one or more additional therapeutically active substances. In some embodiments, provided pharmaceutical compositions are useful in medicine. In some embodiments, provided pharmaceutical compositions are useful as prophylactic agents (i.e., vaccines) in the treatment or prevention of HCMV or of negative ramifications associated or correlated with HCMV infection. In some embodiments, provided pharmaceutical compositions are useful in therapeutic applications, for example in individuals suffering from or susceptible to HCMV infection. In some embodiments, pharmaceutical compositions are formulated for administration to humans.

For example, pharmaceutical compositions provided here may be provided in a sterile injectible form (e.g., a form that is suitable for subcutaneous injection or intravenous infusion). For example, in some embodiments, pharmaceutical compositions are provided in a liquid dosage form that is suitable for injection. In some embodiments, pharmaceutical compositions are provided as powders (e.g. lyophilized and/or sterilized), optionally under vacuum, which are reconstituted with an aqueous diluent (e.g., water, buffer, salt solution, etc.) prior to injection. In some embodiments, pharmaceutical compositions are diluted and/or reconstituted in water, sodium chloride solution, sodium acetate solution, benzyl alcohol solution, phosphate buffered saline, etc. In some embodiments, powder should be mixed gently with the aqueous diluent (e.g., not shaken).

In some embodiments, provided pharmaceutical compositions comprise one or more pharmaceutically acceptable excipients (e.g., preservative, inert diluent, dispersing agent, surface active agent and/or emulsifier, buffering agent, etc.). Suitable excipients include, for example, water, saline, dextrose, sucrose, trehalose, glycerol, ethanol, or similar, and combinations thereof. In addition, if desired, the vaccine may contain auxiliary substances such as wetting or emulsifying agents, pH buffering agents, or adjuvants which enhance the effectiveness of the vaccines. In some embodiments, pharmaceutical compositions comprise one or more preservatives. In some embodiments, pharmaceutical compositions comprise no preservative.

In some embodiments, pharmaceutical compositions are provided in a form that can be refrigerated and/or frozen. In some embodiments, pharmaceutical compositions are provided in a form that cannot be refrigerated and/or frozen. In some embodiments, reconstituted solutions and/or liquid dosage forms may be stored for a certain period of time after reconstitution (e.g., 2 hours, 12 hours, 24 hours, 2 days, 5 days, 7 days, 10 days, 2 weeks, a month, two months, or longer). In some embodiments, storage of VLP formulations for longer than the specified time results in VLP degradation.

Liquid dosage forms and/or reconstituted solutions may comprise particulate matter and/or discoloration prior to administration. In some embodiments, a solution should not be used if discolored or cloudy and/or if particulate matter remains after filtration.

Formulations of the pharmaceutical compositions described herein may be prepared by any method known or hereafter developed in the art of pharmacology. In some embodiments, such preparatory methods include the step of bringing active ingredient into association with one or more excipients and/or one or more other accessory ingredients, and then, if necessary and/or desirable, shaping and/or packaging the product into a desired single- or multi-dose unit.

A pharmaceutical composition in accordance with the invention may be prepared, packaged, and/or sold in bulk, as a single unit dose, and/or as a plurality of single unit doses. As used herein, a "unit dose" is discrete amount of the pharmaceutical composition comprising a predetermined amount of the active ingredient. The amount of the active ingredient is generally equal to a dose which would be administered to a subject and/or a convenient fraction of such a dose such as, for example, one-half or one-third of such a dose.

Relative amounts of active ingredient, pharmaceutically acceptable excipient, and/or any additional ingredients in a pharmaceutical composition in accordance with the invention may vary, depending upon the identity, size, and/or condition of the subject treated and/or depending upon the route by which the composition is to be administered. By way of example, the composition may comprise between 0.1% and 100% (w/w) active ingredient.

Pharmaceutical compositions of the present invention may additionally comprise a pharmaceutically acceptable excipient, which, as used herein, may be or comprise solvents, dispersion media, diluents, or other liquid vehicles, dispersion or suspension aids, surface active agents, isotonic agents, thickening or emulsifying agents, preservatives, solid binders, lubricants and the like, as suited to the particular dosage form desired. Remington's The Science and Practice of Pharmacy, 21st Edition, A. R. Gennaro, (Lippincott, Williams & Wilkins, Baltimore, Md., 2006) discloses various excipients used in formulating pharmaceutical compositions and known techniques for the preparation thereof. Except insofar as any conventional excipient medium is incompatible with a substance or its derivatives, such as by producing any undesirable biological effect or otherwise interacting in a deleterious manner with any other component(s) of the pharmaceutical composition, its use is contemplated to be within the scope of this invention.

In some embodiments, a pharmaceutical composition is sufficiently immunogenic as a vaccine (e.g., in the absence of an adjuvant). In some embodiments, immunogenicity of a pharmaceutical composition is enhanced by including an adjuvant. Any adjuvant may be used in accordance with the present invention. A large number of adjuvants are known; a useful compendium of many such compounds is prepared by the National Institutes of Health and can be found (www.niaid.nih.gov/daids/vaccine/pdf/compendium.pdf). See also Allison (1998, Dev. Biol. Stand., 92:3-11; incorporated herein by reference), Unkeless et al. (1998, Annu. Rev. Immunol., 6:251-281; incorporated herein by reference), and Phillips et al. (1992, Vaccine, 10:151-158; incorporated herein by reference). Hundreds of different adjuvants are known in the art and may be employed in the practice of the present invention. Exemplary adjuvants that can be utilized in accordance with the invention include, but are not limited to, cytokines, gel-type adjuvants (e.g., aluminum hydroxide, aluminum phosphate, calcium phosphate, etc.); microbial adjuvants (e.g., immunomodulatory DNA sequences that include CpG motifs; endotoxins such as monophosphoryl lipid A; exotoxins such as cholera toxin, *E. coli* heat labile toxin, and pertussis toxin; muramyl dipeptide, etc.); oil-emulsion and emulsifier-based adjuvants (e.g., Freund's Adjuvant, MF59 [Novartis], SAF, etc.); particulate adjuvants (e.g., liposomes, biodegradable microspheres, saponins, etc.); synthetic adjuvants (e.g., nonionic block copolymers, muramyl peptide analogues, polyphosphazene, synthetic polynucleotides, etc.); and/or combinations thereof. Other exemplary adjuvants include some polymers (e.g., polyphosphazenes; described in U.S. Pat. No. 5,500,161, which is incorporated herein by reference), Q57, QS21, squalene, tetrachlorodecaoxide, etc. Pharmaceutically acceptable excipients have been previously described in further detail in the above section entitled "Pharmaceutical Compositions."

V. Administration

Provided compositions and methods of the present disclosure are useful for prophylaxis and/or treatment of HCMV infection in a subject, including human adults and children. In general however they may be used with any animal. In certain embodiments, the methods herein may be used for veterinary applications, e.g., canine and feline applications. If desired, the methods herein may also be used with farm animals, such as ovine, avian, bovine, porcine and equine breeds.

As used herein, the terms "subject," "individual" or "patient" refer to a human or a non-human mammalian subject. The individual (also referred to as "patient" or "subject") being treated is an individual (fetus, infant, child, adolescent, or adult) suffering from a disease, for example, HCMV infection. In some embodiments, the subject is at risk for HCMV infection. In some embodiments, the subject is an immunosuppressed subject. For example, in some embodiments, the immunosuppressed subject is selected from the group consisting of an HIV-infected subject, an AIDS patient, a transplant recipient, a pediatric subject, and a pregnant subject. In some embodiments, the subject has been exposed to HCMV infection. In some embodiments, the subject is a human.

Compositions described herein will generally be administered in such amounts and for such a time as is necessary or sufficient to induce an immune response. Dosing regimens may consist of a single dose or a plurality of doses over a period of time. The exact amount of an immunogenic composition (e.g., VLP) to be administered may vary from subject to subject and may depend on several factors. Thus, it will be appreciated that, in general, the precise dose used will be as determined by the prescribing physician and will depend not only on the weight of the subject and the route of administration, but also on the age of the subject and the severity of the symptoms and/or the risk of infection. In certain embodiments a particular amount of a VLP composition is administered as a single dose. In certain embodiments, a particular amount of a VLP composition is administered as more than one dose (e.g., 1-3 doses that are separated by 1-12 months). In certain embodiments a particular amount of a VLP composition is administered as a single dose on several occasions (e.g., 1-3 doses that are separated by 1-12 months).

In some embodiments, a provided composition is administered in an initial dose and in at least one booster dose. In some embodiments, a provided composition is administered in an initial dose and two booster doses. In some embodiments, a provided composition is administered in an initial dose and three booster doses. In some embodiments, a provided composition is administered in an initial dose and four booster doses. In some embodiments, a provided composition is administered in an initial dose and in at least one booster dose about one month, about two months, about three months, about four months, about five months, or about six months following the initial dose. In some embodiments, a provided composition is administered in a second booster dose about six months, about seven months, about eight months, about nine months, about ten months, about eleven months, or about one year following the initial dose. In some embodiments, a provided composition is administered in a booster dose every 1 year, 2 years, 3 years, 4 years, 5 years, 6 years, 7 years, 8 years, 9 years, or 10 years.

In certain embodiments, provided compositions may be formulated for delivery parenterally, e.g., by injection. In such embodiments, administration may be, for example, intravenous, intramuscular, intradermal, or subcutaneous, or via by infusion or needleless injection techniques. In certain embodiments, the compositions may be formulated for peroral delivery, oral delivery, intranasal delivery, buccal delivery, sublingual delivery, transdermal delivery, transcutaneous delivery, intraperitoneal delivery, intravaginal delivery, rectal delivery or intracranial delivery.

EXAMPLES

The following examples describe some exemplary modes of making and practicing certain compositions that are described herein. It should be understood that these examples are for illustrative purposes only and are not meant to limit the scope of the compositions and methods described herein.

Example 1: Construction of DNA Expression Plasmids

This Example describes development of expression plasmids and constructs for expression of recombinant HCMV gene sequences (e.g., gB, gB-G, gH-G, and Gag/pp65 fusion gene sequences). A standard expression plasmid generally consists of a promoter sequence of mammalian origin, an intron sequence, a PolyAdenylation signal sequence (PolyA), a pUC origin of replication sequence (pUC-pBR322 is a colE1 origin/site of replication initiation and is used to replicate plasmid in bacteria such as *E Coli* (DH5α)), and an antibiotic resistance gene as a selectable marker for plasmid plaque selection. Within the plasmid following the Intron are a variety of restriction enzyme sites that can be used to splice in a gene or partial gene sequence of interest.

The Propol II expression plasmid contains the pHCMV (early promoter for HCMV), a Beta-Globin Intron (BGL Intron), a rabbit Globin polyAdenylation signal sequence (PolyA), a pUC origin of replication sequence (pUC-pBR322 is a colE1 origin/site of replication initiation and is used to replicate plasmid in bacteria such as *E. coli* (DH5α)), and an ampicillin resistance gene β-lactamase (Amp R—selectable marker for plasmid confers resistance to ampicillin) (100 µg/ml) (FIG. 1A).

FIG. 1B depicts exemplary recombinant expression plasmids. For example, to develop a pHCMV-Gag MMLV expression construct ("MLV-Gag"), a complementary DNA (cDNA) sequence encoding a Gag polyprotein of MMLV (Gag without its C terminus Pol sequence) was cloned in a Propol II (pHCMV) expression vector. To develop a gB expression construct ("gB"), the full-length sequence of gB was codon-optimized for human expression (GenScript) and was cloned in a Propol II expression vector including the extracellular portion, transmembrane domain (TM) and cytoplasmic portion (Cyto) of gB. To develop a gH-G expression construct ("gH-G"), the truncated sequence of gH encoding only the extracellular portion was fused together with TM and Cyto portions of VSV-G and codon-optimized for human expression (GenScript) and cloned in a Propol II expression vector. Similarly, to develop a gB-G expression construct ("gB-G"), the truncated sequence of gB encoding only the extracellular portion was fused together with TM and Cyto portions of VSV-G and codon-optimized for human expression (GenScript) and cloned in a Propol II expression vector. To develop a Gag/pp65 expression construct ("Gag/pp65"), a sequence encoding the Gag polyprotein of MMLV (Gag without its C terminus Pol sequence) was fused with the full-length sequence of pp65 and codon-optimized for human expression (GenScript) and cloned in a Propol II expression vector.

DNA plasmids were amplified in competent *E. coli* (DH5α) and purified with endotoxin-free preparation kits according to standard protocols.

Example 2: Production of Virus-Like Particles (VLPs)

This Example describes methods for production of virus-like particles (VLPs) containing various recombinant HCMV antigens described in Example 1.

Figure 2:
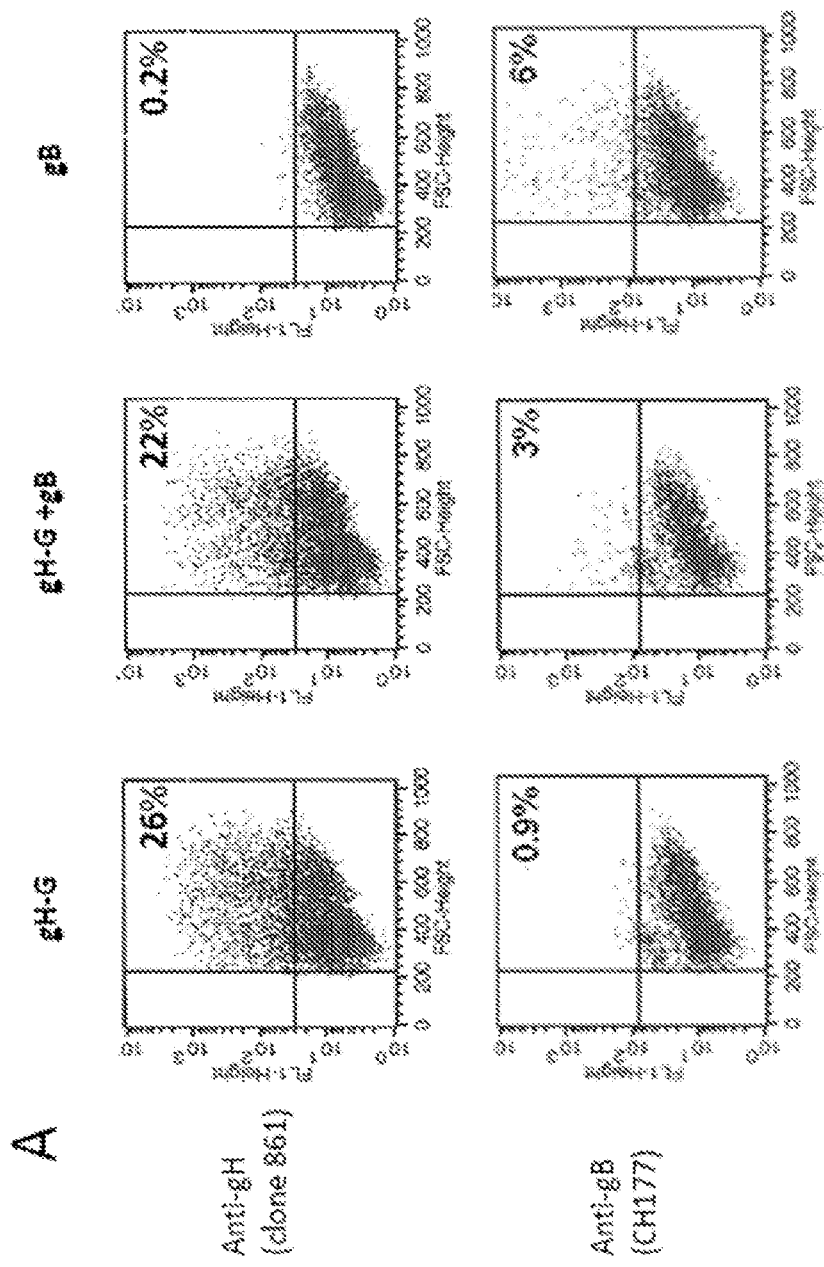
FIG. 2 shows FACS analysis of exemplary heterologous surface antigens on HEK 293 packaging cells (A) and western blot analysis of heterologous antigen expression in exemplary VLP compositions (B).
Figure 2:
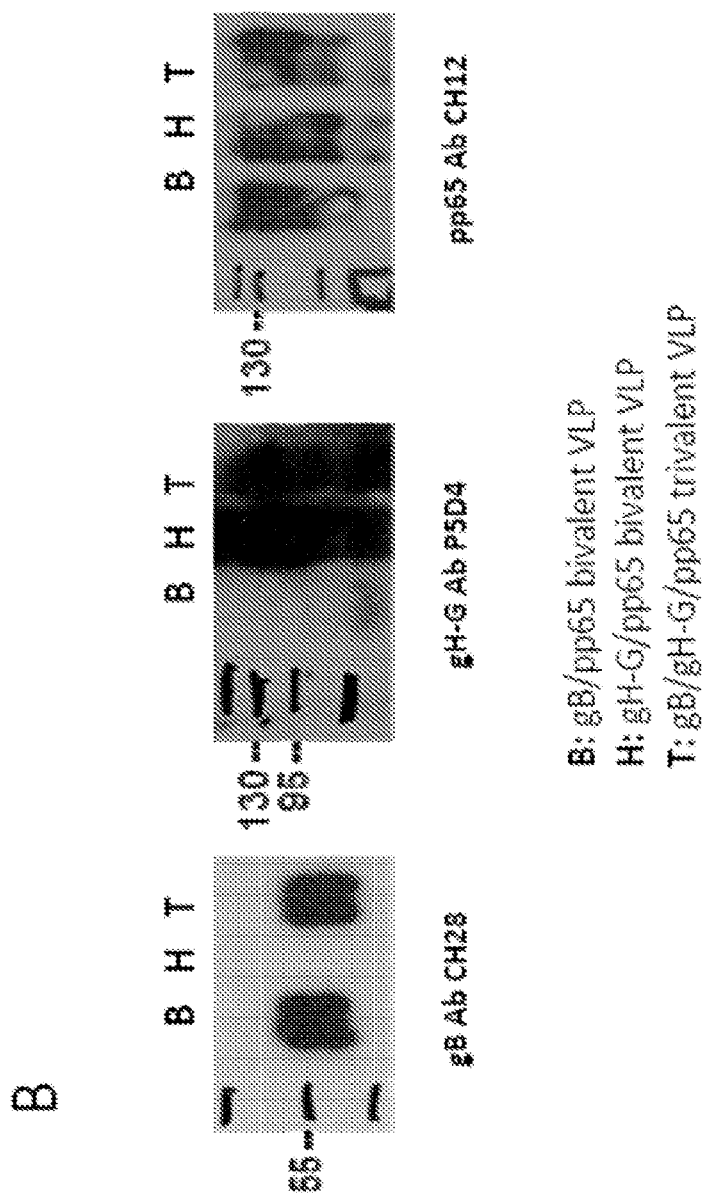

HEK 293T cells (ATCC, CRL-11268) were transiently transfected using calcium phosphate methods with an MMLV-Gag DNA expression plasmid and co-transfected with either a gB or a gB-G (data not shown) or a gH-G DNA expression plasmid. Alternatively cells were transfected with a Gag/pp65 DNA expression plasmid and co-transfected with either a gB or a gB-G (data not shown) or a gH-G DNA expression plasmid. It will be appreciated that cells can be transfected with an MMLV-Gag DNA expression plasmid and cotransfected with both a gB and a gH-G or gB-G and a gH-G DNA expression plasmid. Expression of various HCMV antigens by the HEK 293 cells was confirmed by flow cytometry (FIG. 2A). After 48 to 72 hours of transfection, supernatants containing the VLPs were harvested and filtered through 0.45 μm pore size membranes and further concentrated and purified by ultracentrifugation through a 20% sucrose cushion in a SW32 Beckman rotor (25,000 rpm, 2 hours, 4° C.). Pellets were resuspended in sterile endotoxin-free PBS (GIBCO) to obtain 500 times concentrated VLP stocks. Total protein was determined on an aliquot by a Bradford assay quantification kit (BioRad). Purified VLPs were stored at −80° C. until used. Each lot of purified VLPs was analyzed for the expression of MMLV-Gag, gB, gH-G and/or MMLV-Gag/pp65 fusion protein by SDS-Page and Western Blot with specific antibodies to gB (CH 28 mouse monoclonal antibody to gB; Virusys Corporation; Pereira, L et al. 1984 Virology 139:73-86), gH-G (mouse monoclonal antibody to Anti-VSV-G tag antibody P5D4; Abcam plc) and pp65 (CH12 mouse monoclonal antibody to UL83/pp65; Virusys Corporation; Pereira, L. et al. 1982 Infect Immun 36: 924-932) (FIG. 2B). Antibodies were detected using enhanced chemilluminescence (ECL).

Example 3: Physico-Chemical Characterization of Virus-Like Particles (VLPs)

Figure 3:
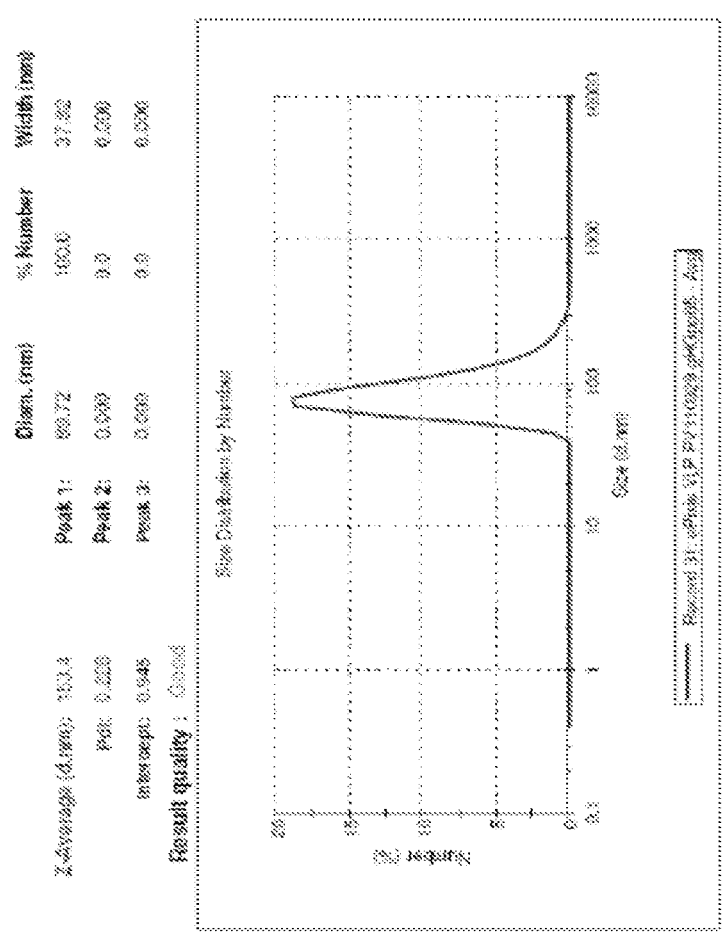
FIGS. 3(A) and (B) show particle size determination and polydispersity index for two exemplary VLP compositions.
Figure 3:
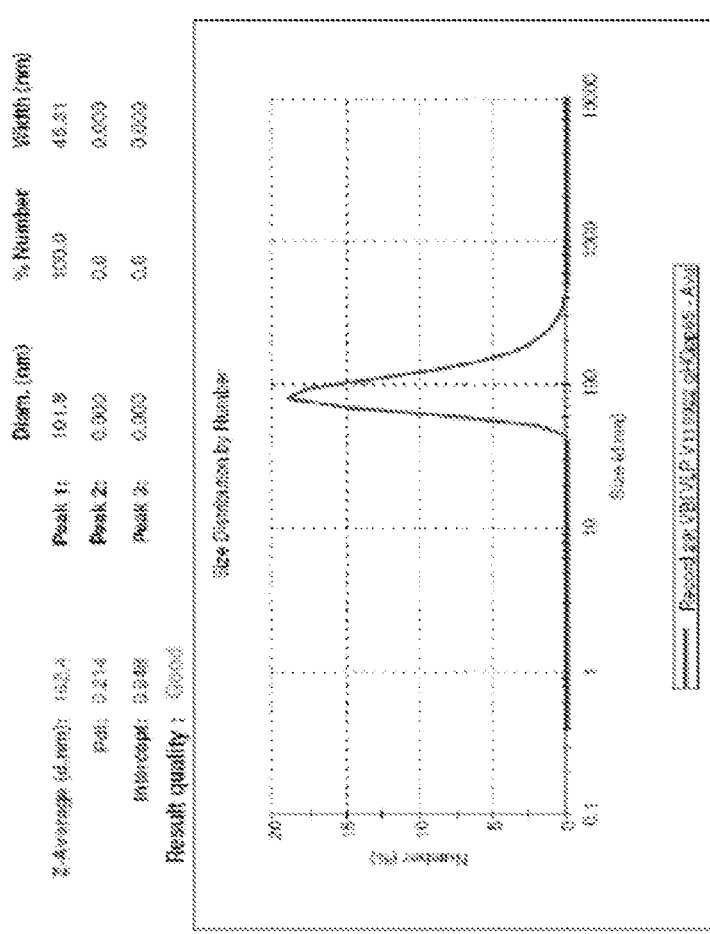

Physico-chemical analysis of VLPs included particle size determination and Polydispersity Index assessment using a Malvern Instrument Zeta-Sizer Nano series (ZEN3600). Exemplary results obtained from nanosizing analysis are shown in FIGS. 3A and 3B. An exemplary VLP composition (gH-G/pp65 bivalent VLP composition) was produced in two different labs using the same recombinant expression vectors and both VLP preparations gave an average particle size of 150-180 nm in diameter. This is consistent with the size of a CMV virion which is reported to be 150-200 nm in size (1997 J Pathol 182: 273-281). The low Polydispersity Index (PdI) of 0.214-0.240 indicates product homogeneity or a narrow size distribution.

Example 4: Immunogenicity and Neutralization Activity of VLPs in Mice

VLP compositions prepared as described in Example 2 were tested in female BALB/C mice 6-8 weeks old (minimum 6 animals per test group). Mice were immunized intraperitoneally with 200 μl of VLP compositions twice, once on day 0 (Prime) and once on day 56 (week 8 Boost). Mice were treated with 10 μg, 25 μg or 50 μg (total protein) of a bivalent gB/Gag/pp65, a bivalent gH-G/Gag/pp65 or a trivalent gB/gH-G/Gag/pp65 VLP composition. To assess humoral immune responses in mice, blood was collected from all mice in the study groups pre-immunization and then post-1$^{st}$ and -2$^{nd}$ immunizations at 0, 2, 3, 4, 6, 8, 9, 10, 12 and 14 weeks. The study design is summarized in Table 1.

TABLE 1

| Test Article # | Dose Test Article Description | Immunization Schedule (weeks) |
|---|---|---|
| 1 | 50 μg pp65/gB bivalent VLPs | 0, 8 |
| 2 | 25 μg pp65/gB bivalent VLPs | 0, 8 |
| 3 | 10 μg pp65/gB bivalent VLPs | 0, 8 |
| 4 | 50 μg pp65/gH-G bivalent VLPs | 0, 8 |
| 5 | 25 μg pp65/gH-G bivalent VLPs | 0, 8 |
| 6 | 10 μg pp65/gH-G bivalent VLPs | 0, 8 |
| 7 | 50 μg Trivalent pp65/gB/gH-G VLPs | 0, 8 |
| 8 | 25 μg Trivalent pp65/gB/gH-G VLPs | 0, 8 |
| 9 | 10 μg Trivalent pp65/gB/gH-G VLPs | 0, 8 |

Figure 4:
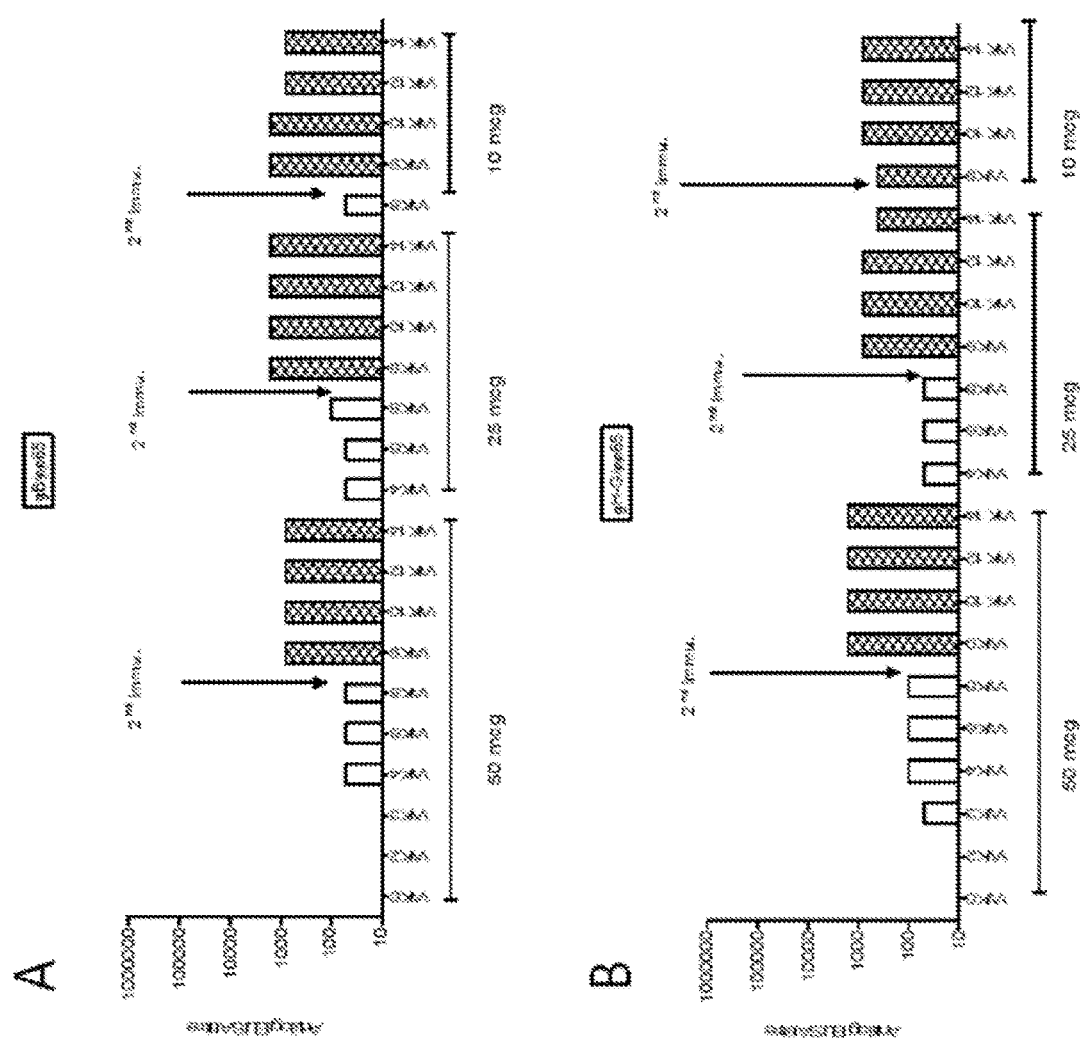
FIG. 4 shows ELISA titers in mice treated with exemplary gB/pp65 (A), gH-G/pp65 (B), or gB/gH-G/pp65 (C) VLP compositions.
Figure 4:
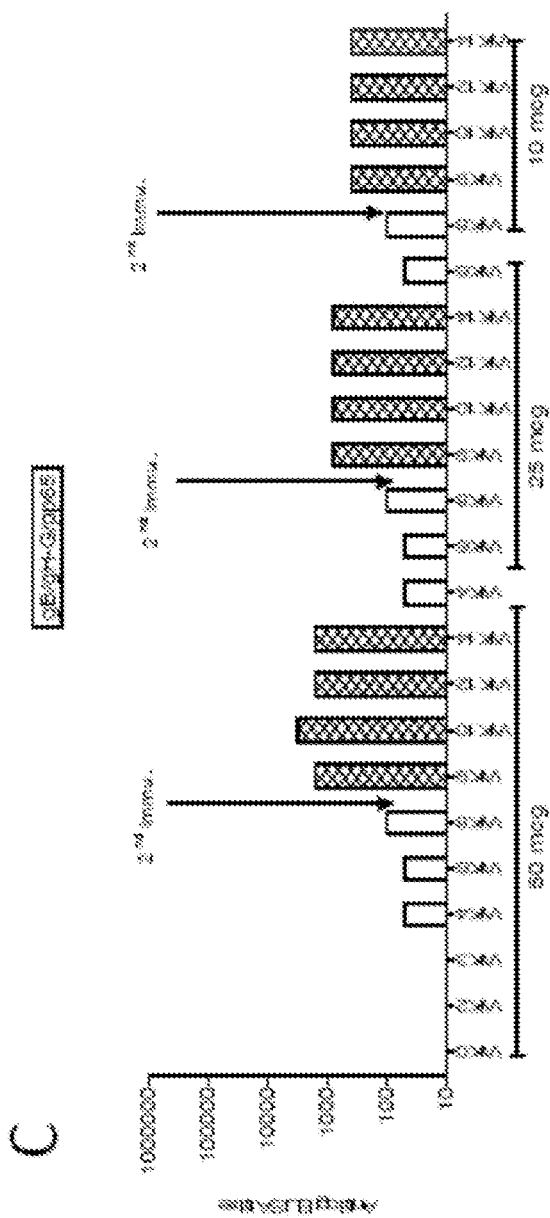

Enzyme-linked Immunosorbent Assay (ELISA) was performed using commercially available ELISA plates (IBL International) coated with lysates derived from MRC-5 cells infected with HCMV strain AD169. Crude commercial HCMV lysate, which contains all CMV related antigens and is useful to detect IgG immune responses, was used as a positive control to determine mouse serum HCMV IgG content by ELISA. Serial dilutions of mouse sera (dilution in TBS-T/BSA/DMEM 10% FCS) were incubated with the coated plates for 2 hours at room temperature. After the plates were washed, anti-mouse Horse Radish Peroxidase (HRP) conjugated secondary antibody was added at a dilution of 1/10,000 and incubated for 1 hour, followed by the addition of Tetramethylbenzidine (TMB) substrate solution. The reaction was stopped by addition of HCL 1N and absorbance was read at 450 nm in an ELISA microwell plate reader. FIG. 4 shows evidence of persistent antibodies and strong boosting of mice after 2$^{nd}$ immunization at 8 weeks for each of the bivalent and the trivalent VLP compositions.

Figure 5:
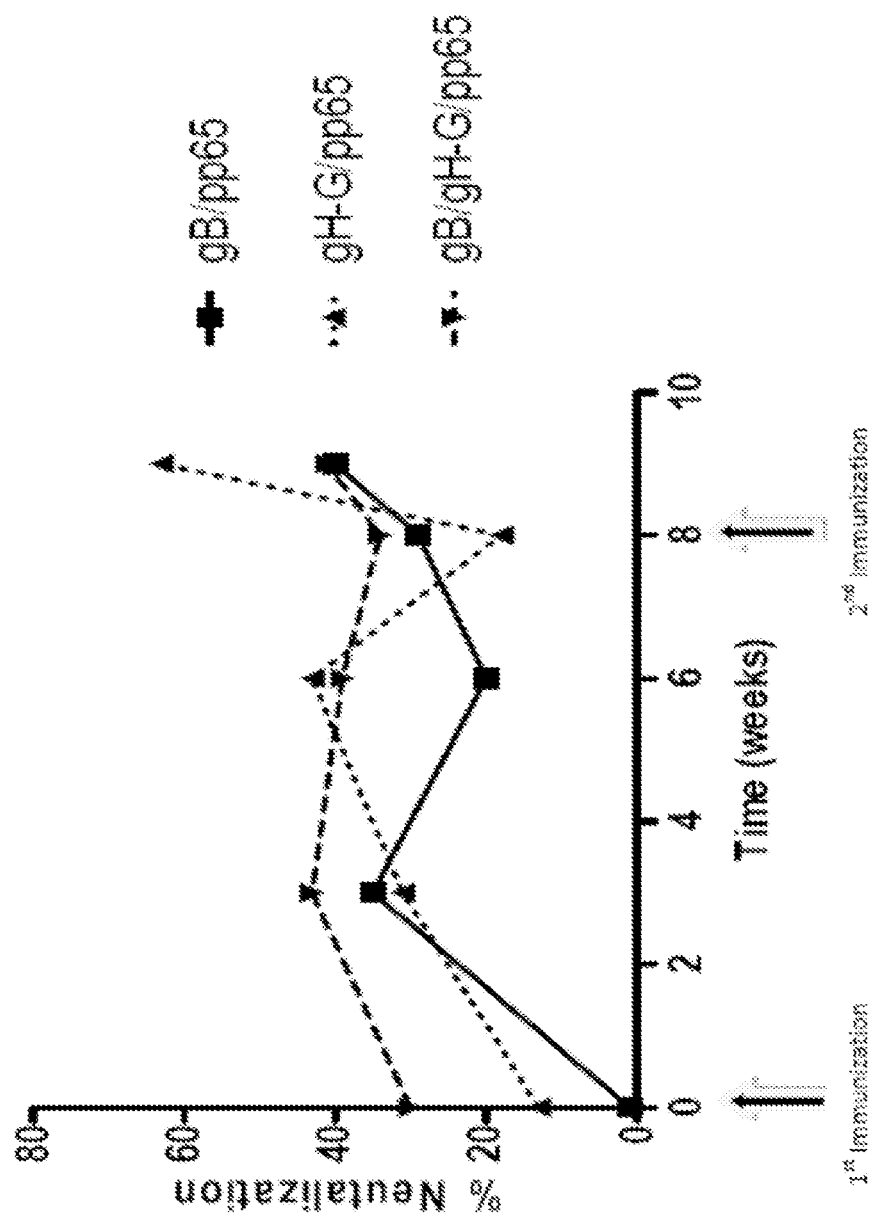
FIG. 5 shows neutralizing antibody activity in mice treated with exemplary VLP compositions (assayed in human fibroblast cells).
Figure 6:
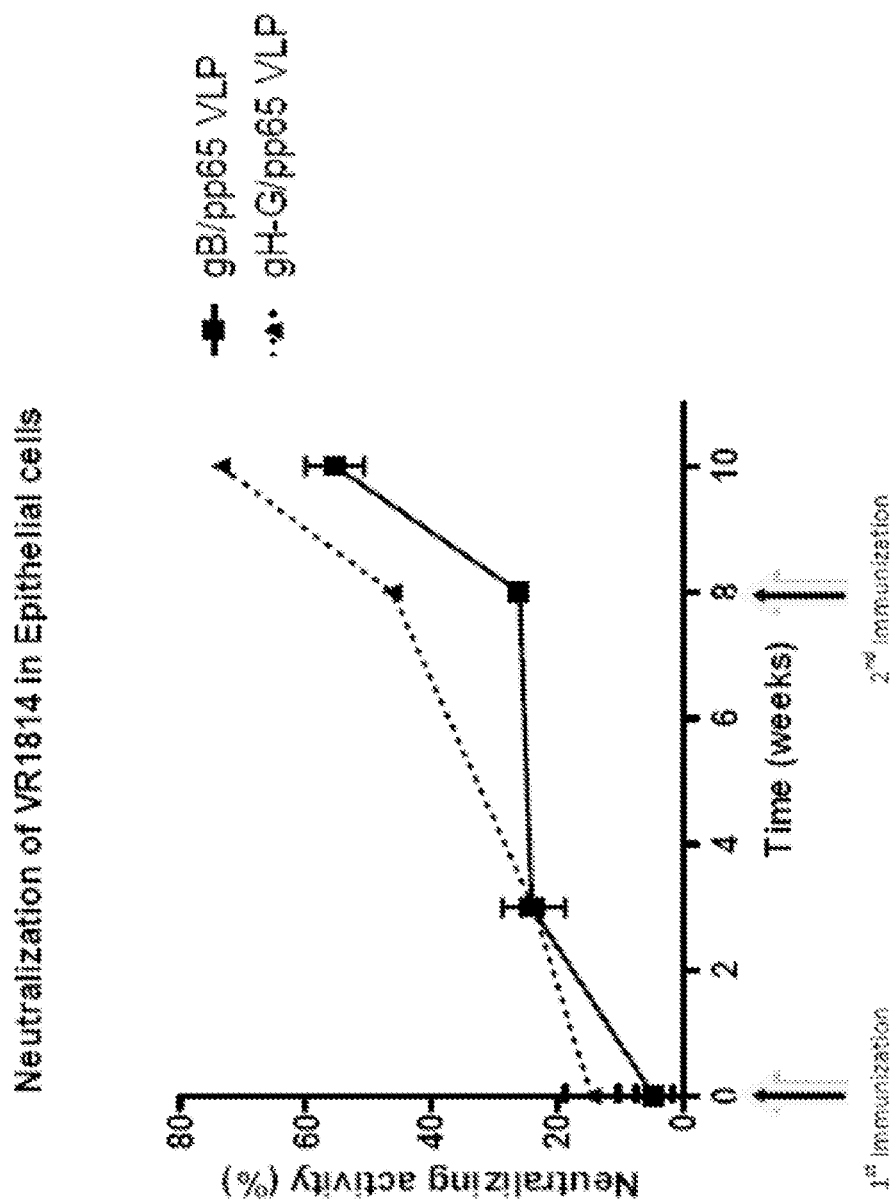
FIG. 6 shows neutralizing antibody activity in mice treated with exemplary VLP compositions (assayed in human epithelial cells).

Neutralizing antibody responses to HCMV were determined using a microneutralization assay. A standard amount of HCMV strain VR1814 (an endothelial cell-tropic CMV strain—Revello M G et al. J Gen Virol 82:1429-1438) was diluted with infection medium (DME containing 1% heat-inactivated FBS, 1% amino acid mixture, 1% Penicillin-Streptomycin and Ca$^{+2}$ and Mg$^{+2}$ free PBS), and added to an equal volume of serial dilutions of heat-inactivated test serum and incubated for 1 hour at 37° C. on a rotator. The serum/HCMV mixtures were added to human foreskin fibroblasts (HFF) or retinal pigmented epithelial cells (ARPE-19 cells) grown on coverslips in 24 well tissue culture plates and incubated for 2 hours at 37° C., 5% $CO_2$. The plates were washed with PBS twice and then cultured for 48 hours at 37° C., 5% $CO_2$. Cells were fixed with 4% paraformaldehyde, reacted with an anti-IE1 monoclonal antibody (CH160 Mouse Monoclonal antibody to IE1/2 or CH443 Monoclonal antibody to IE1; Virusys Corporation) for 1 hour at room temperature followed by FITC-labelled goat anti-mouse antibody for 45 minutes at room temperature. The number of cells expressing IE1 was determined by fluorescent microscopy. Pooled mouse sera (1:6 dilution) was tested for neutralizing activity at each bleed time point (0, 3, 6, 8 and 9 weeks) in duplicate. FIG. 5 shows induction of neutralizing antibodies in mice (assayed in fibroblast cells) after 2$^{nd}$ immunization at 8 weeks for each of the bivalent and the trivalent VLP compositions. FIG. 6 shows induction of neutralizing antibodies in mice (assayed in epithelial cells) after 2$^{nd}$ immunization at 8 weeks for each of the bivalent VLP compositions.

In another study, monovalent gB-G VLP compositions prepared as described in Example 2 were tested in female BALB/C mice 6-8 weeks old (minimum 8 animals per test group). Mice were immunized intraperitoneally with 200 μl of VLP compositions twice, once on day 0 (Prime) and once on day 56 (week 8 Boost). Mice were treated with equivalent amounts of 20 µg of gB content (determined by ELISA) per injection. To assess humoral immune responses in mice, blood was collected from all mice in the study groups pre-1$^{st}$ immunization and then post-1$^{st}$ immunization at 3 and 6 weeks and pre-2$^{nd}$ immunization at 8 weeks and then post 2$^{nd}$ immunization at 9 weeks from study start. The study design is summarized in Table 2.

TABLE 2

| Test Article # | Dose | Test Article Description | Immunization Schedule (weeks) |
|---|---|---|---|
| 1 | 20 µg | gB-G monovalent VLPs | 0, 8 |
| 2 | 20 µg | Recombinant gB | 0, 8 |

Figure 7:
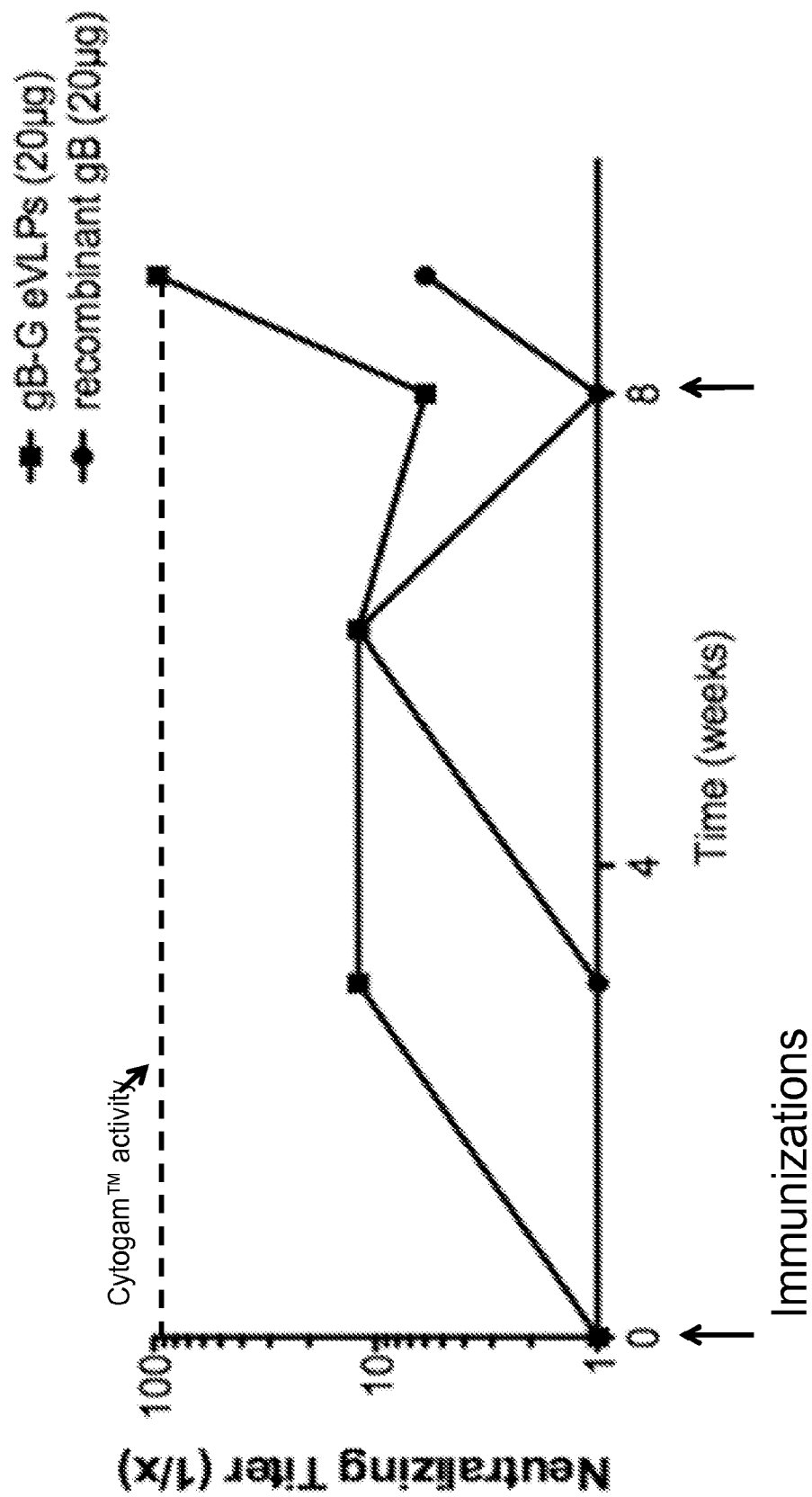
FIG. 7 shows neutralizing antibody activity in mice treated with exemplary VLP compositions versus a recombinant gB protein (assayed in human fibroblast cells).

Neutralizing antibody responses to HCMV were determined using a microneutralization assay in fibroblast cells based on a green fluorescent protein (GFP)-expressing HCMV virus (TB40) and flow cytometric analysis of infected (GFP+) HFF cells. To assess the presence of neutralizing antibodies in serum samples, the serum was pre-incubated with GFP-expressing HCMV for a period of time sufficient for neutralizing antibodies to reduce the infectivity of HCMV. Serial dilutions of the pre-incubated mixture of serum and HCMV were used to contact a host cell (fibroblast or epithelial) susceptible to infection by HCMV. The number of cells that express the reporter gene construct (GFP) were determined by flow cytometry to calculate the infectious titer of the virus preparation. FIG. 7 depicts Neutralizing Antibody titers for mice immunized twice at 0 and 8 weeks with monovalent gB-G VLPs versus recombinant gB. Sera collected pre- and post-immunizations as described were pooled and tested relative to a positive control CMV hyperglobulin, Cytogam™, in the presence of 10% guinea pig complement. As shown in FIG. 7, the monovalent gB-G VLP composition elicited a more rapid and potent neutralization of fibroblast cell infection than that elicited by a recombinant gB protein.

As can be seen (or as will be appreciated by those skilled in the art having read the present specification), the data demonstrate, among other things, surprisingly good activity of VLPs, such as by VLPs that include gB-G as compared with recombinant gB.

Figure 8:
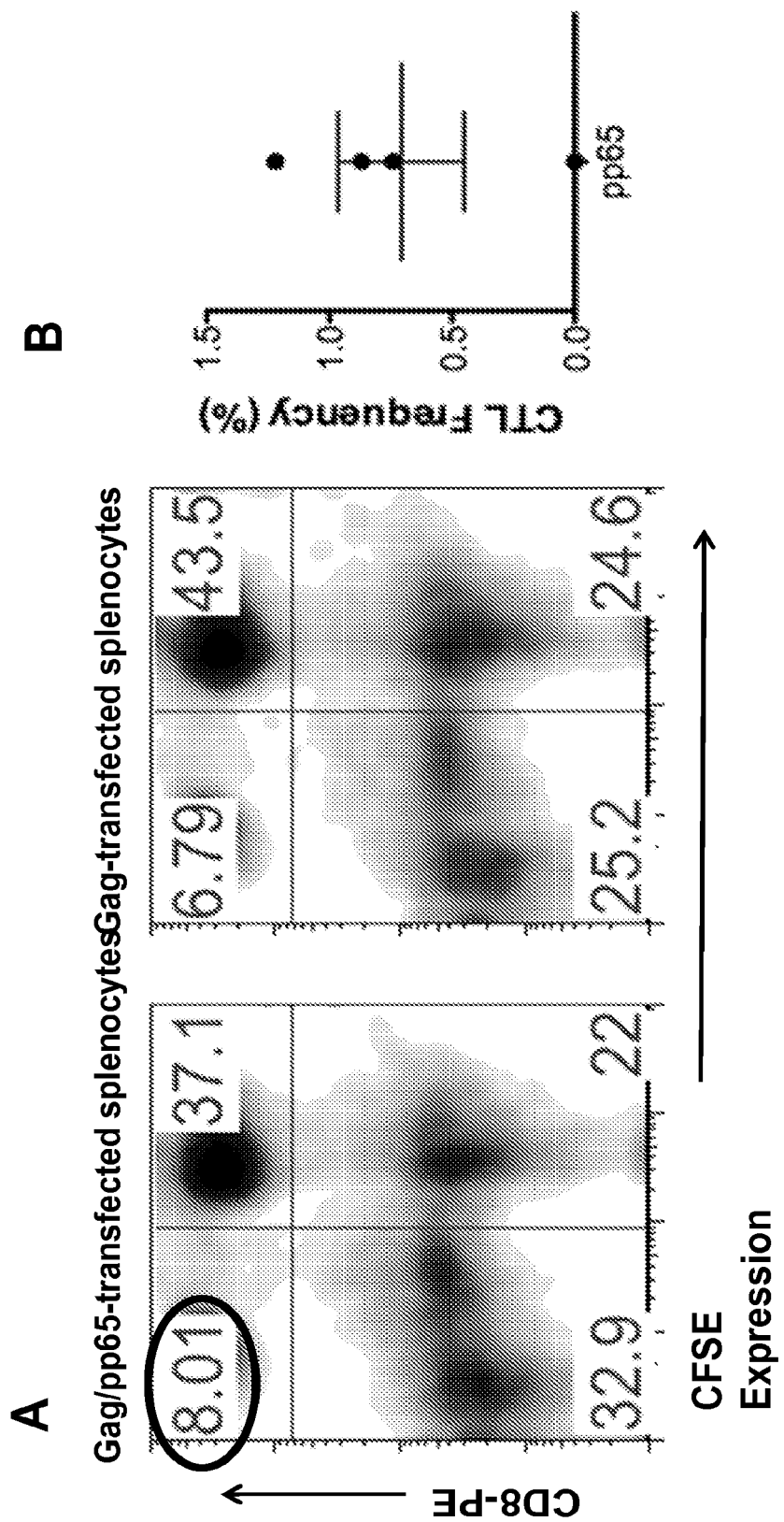
FIG. 8 shows antigen-specific CTL responses in mice treated with exemplary VLP compositions expressed in HEK 293 cells, depicted as CTL frequency based on CFSE decay, gating on CD3+ CD8+ T cells (A) or frequency of proliferating pp65-specific CTLs (B).

In another study, bivalent gB/Gag/pp65 VLP compositions prepared as described in Example 2 were tested in female BALB/C mice 6-8 weeks old (minimum 4 animals per test group). Mice were immunized intraperitoneally with 200 µl of VLP compositions twice, once on day 0 (Prime) and once on day 56 (week 8 Boost). Mice were treated with bivalent gB/Gag/pp65 VLPs and splenocytes were collected 14 days later. Enriched CD8$^+$ T cells were stimulated (1:5 ratio) with splenocytes transfected for 24 hours with plasmid encoding Gag/pp65 or Gag to determine frequencies of CTLs directed against pp65 or Gag. CTL frequencies were determined based on CFSE decay, gating on CD3$^+$ CD8$^+$ T cells (FIG. 8A). The scatter plot shows the frequency of proliferating, pp65-specific CTLs after subtracting responses directed against Gag (FIG. 8B). As depicted in FIG. 8, bivalent gB/Gag/pp65 VLPs elicited pp65-specific CTLs in immunized mice.

Example 5: Immunogenicity and Neutralization Activity of VLPs in Rabbits

Bivalent gB/Gag/pp65 and gH-G/Gag/pp65 VLP compositions prepared as described in Example 2 were tested in New Zealand White rabbits 6-8 weeks old (minimum 6 animals per test group). Rabbits were immunized intramuscularly with 0.5 ml of VLP compositions three times, once on day 0 (Prime) and once on day 56 (week 8 Boost) and once on day 168 (week 24 Boost). Rabbits were treated with 25 µg or 50 µg or 100 µg (total protein) of either a bivalent gB/Gag/pp65, a bivalent gH-G/Gag/pp65 or a trivalent gB/gH-G/Gag/pp65 (bivalent gB/Gag/pp65 and gH-G/Gag/pp65 mixed together at a 1:1 ratio) VLP composition. To assess humoral immune responses in rabbits, blood was collected from all rabbits in the study groups pre-1$^{st}$ immunization and then post-1$^{st}$ immunization at 2, 4, 6 and 8 weeks and post-2$^{nd}$ immunization at 10, 13, 16, 20 and 24 weeks from study start and then post-3$^{rd}$ immunization at 26 and 28 weeks from study start. The study design is summarized in Table 3.

TABLE 3

| Test Article # | Dose | Test Article Description | Immunization Schedule (weeks) |
|---|---|---|---|
| 1 | 100 µg | gB/pp65 bivalent VLPs | 0, 8, 24 |
| 2 | 50 µg | gB/pp65 bivalent VLPs | 0, 8, 24 |
| 3 | 25 µg | gB/pp65 bivalent VLPs | 0, 8, 24 |
| 4 | 100 µg | gH-G/pp65 bivalent VLPs | 0, 8, 24 |
| 5 | 25 µg | gH-G/pp65 bivalent VLPs | 0, 8, 24 |
| 6 | 100 µg each | gB/pp65 bivalent VLPs + gH-G/pp65 bivalent VLPs (1:1 ratio) | 0, 8, 24 |
| 7 | 25 µg each | gB/pp65 bivalent VLPs + gH-G/pp65 bivalent VLPs (1:1 ratio) | 0, 8, 24 |

Figure 9:
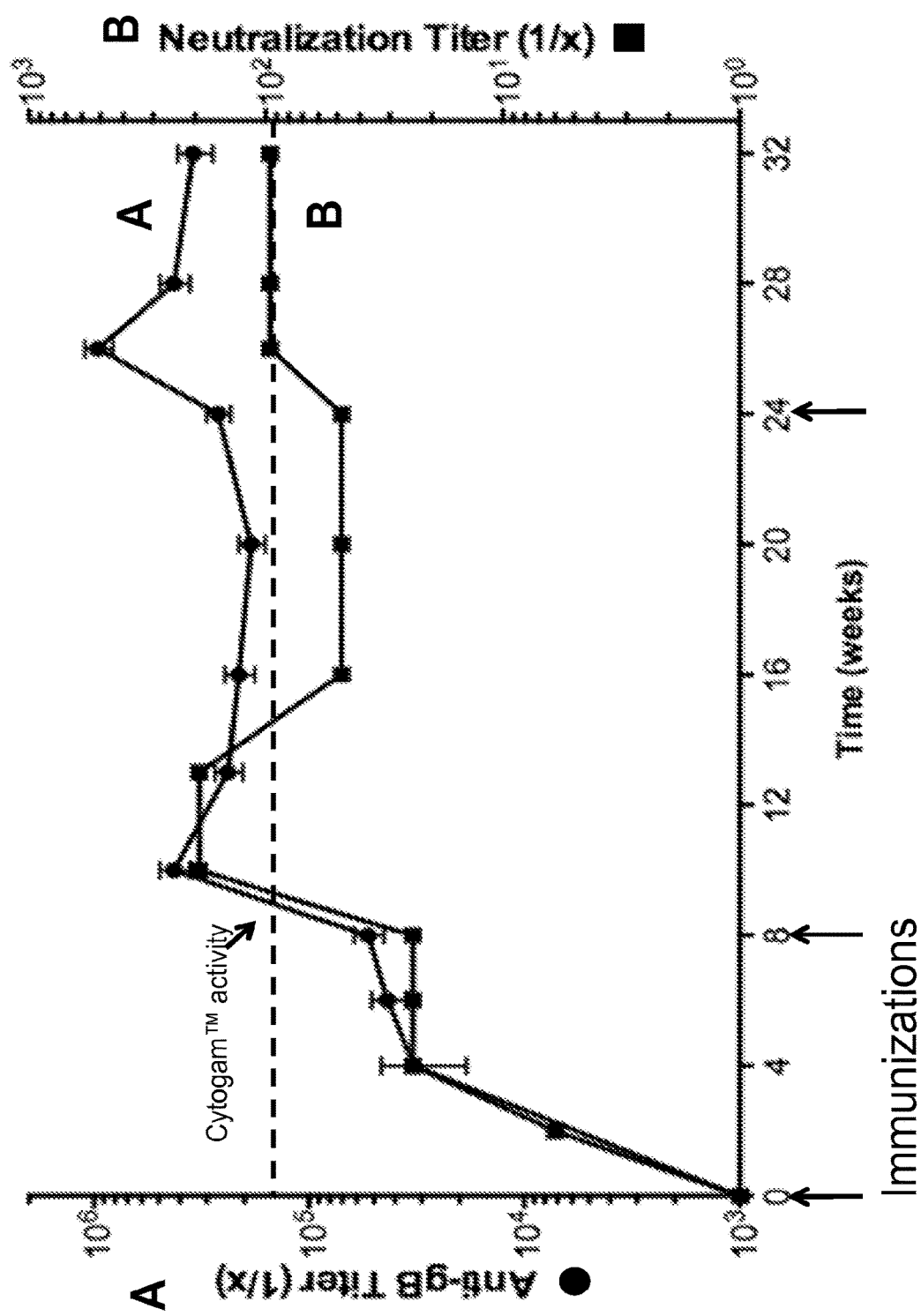
FIG. 9 shows anti-gB and neutralizing antibody titers in rabbits treated with exemplary VLP compositions expressed in HEK 293 cells (assayed in human fibroblast cells).

Individual rabbit sera was tested for reactivity against recombinant gB antigen by ELISA (plotted on left axis FIG. 9A). Neutralizing antibody responses to HCMV was determined using a microneutralization assay in fibroblast cells based on a GFP-expressing CMV virus (TB40) and flow cytometric analysis of infected (GFP+) HFF cells as described in Example 4 (plotted on right axis FIG. 9B). Rabbit sera collected pre- and post-immunizations as described were pooled and tested for neutralizing activity in the presence of complement against HCMV expressing GFP in HFF fibroblasts relative to a positive control CMV hyperglobulin, Cytogam™. Endpoint titers are plotted and represent a 50% reduction in CMV-infected cells relative to matched pre-immunization sera (plotted on left axis FIG. 9A). 50,000 cells were collected during flow cytometric analysis of infected (GFP$^+$) cells (plotted on right axis FIG. 9B). As shown in FIG. 9, the bivalent gB/Gag/pp65 VLP composition elicited high titer binding (A) and high titer neutralizing antibody (B) responses in rabbits against fibroblast cell infection.

Figure 10:
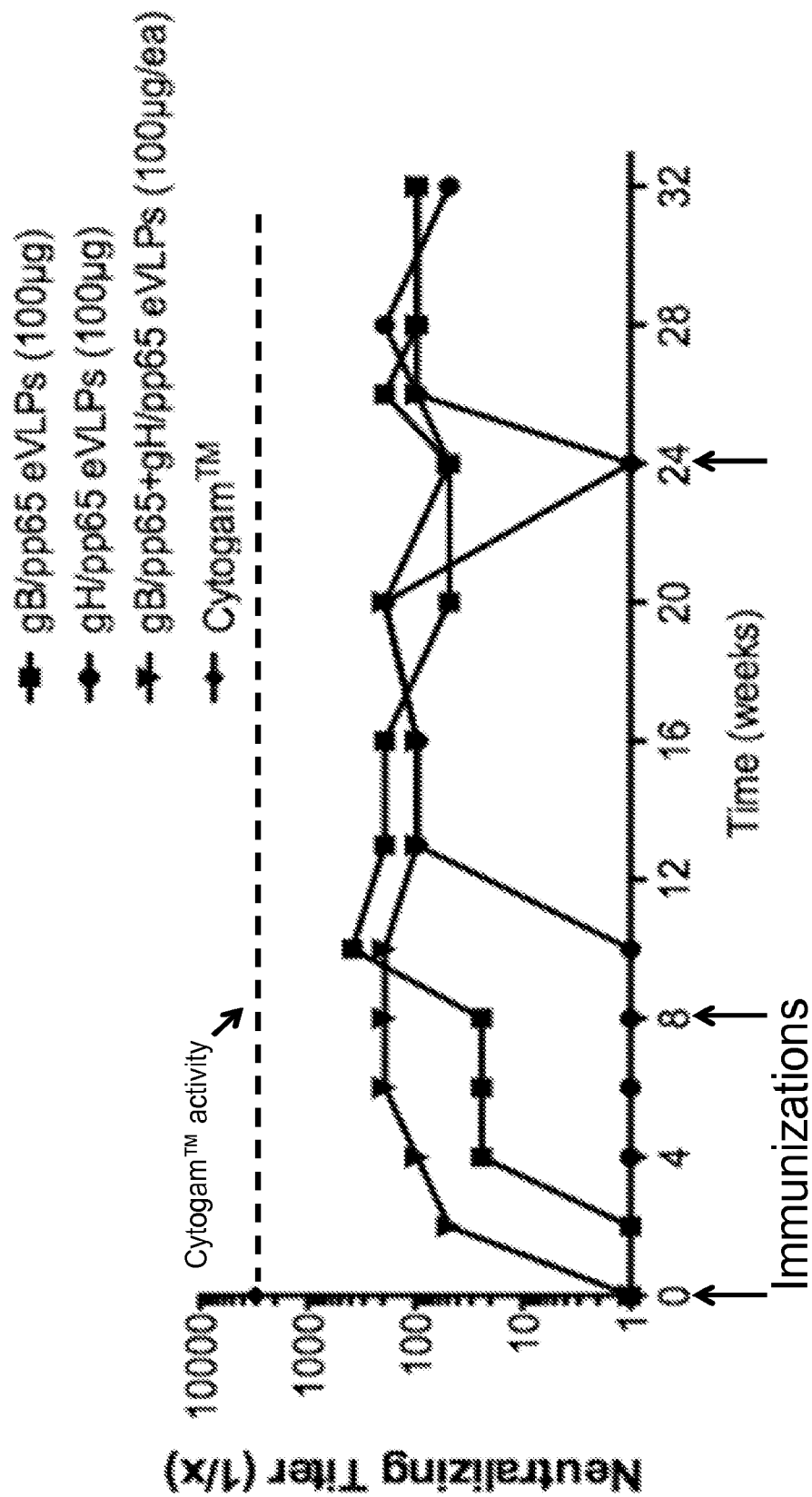
FIG. 10 shows neutralizing antibody titers in rabbits treated with exemplary VLP compositions expressed in HEK 293 cells (assayed in human epithelial cells).

Pooled rabbit sera was also tested for neutralizing antibody responses to HCMV using a microneutralization assay in epithelial cells based on a GFP-expressing HCMV virus (Towne TS15-rR) and flow cytometric analysis of infected (GFP+) ARPE-19 cells. Rabbit sera collected pre- and post-immunizations as described were pooled and tested for neutralizing activity in the presence of complement against HCMV expressing GFP in ARPE-19 epithelial cells relative to a positive control CMV hyperglobulin, Cytogam™. As shown in FIG. 10, surprisingly, the combination of bivalent gB/Gag/pp65 and bivalent gH-G/Gag/pp65 VLP composition elicited a synergistic and more rapid neutralizing antibody response in rabbits against epithelial cell infection, relative to gB/Gag/pp65 or gH/Gag/pp65.

As can be seen (or as will be appreciated by those skilled in the art having read the present specification), the data demonstrate, among other things, surprisingly good activity of VLPs, such as by a combination of VLPs that include gB/Gag/pp65 and VLPs that include gH-G/Gag/pp65, even as compared with VLPs that include gB/Gag/pp65 or VLPs that include gH-G/Gag/pp65.

Example 6: Scaled-Up Production and Purification of Virus-Like Particles (VLPs)

VLPs were produced and purified as follows. CHO cells were transfected at a cell density between 1.5E06 to 2.0E06 cells/mL with plasmids of choice (prepared as described in Example 1) at predetermined concentrations and ratios. Stuffer DNA was added to make total DNA concentration up to 1 µg/mL cell culture. The plasmids used for transfection were first purified by MaxiPrep or GigaPrep plasmid purification kits (Qiagen). The PEIMAX used for transfection to deliver DNA to the cells was provided at a ratio of 6:1 (PEI: DNA wt/wt). The cells were cultured for 72 hours, and then the cultures were centrifuged at 4000 rpm for 20 minutes, using rotor JS-4.2A by Beckman Coulter, in 1 L bottles. The supernatant was filtered through 0.8/0.45 µm filter (AcroPak 500 Capsule, Pall). The filtered supernatant was then concentrated by Tangential Flow Filtration (TFF) and diafiltered against histidine-containing buffer. The diafiltered material was loaded onto an anion exchange chromatography column (AEX) where the flowthrough was collected. The flowthrough was then sterile filtered through 0.45 µm to be aliquoted in different volumes.

The TFF procedure involved overnight sanitization of two TFF membranes (Pellicon 2 Mini 500 kDa cutoff, 0.1 m² surface area) in 0.5 M NaOH by fixing them in parallel in a stainless-steel housing. After running water to neutral pH on the retentate as well as on the permeate side, the phosphate buffer (PBS) was used to equilibrate the membrane. The filtered supernatant was then loaded into the TFF retentate recirculation loop. The starting inlet pressure was 10.5 psi at a permeate flow rate of 400 mL/min that reduced to about 200 mL/min at the end of concentration. After concentration to about 10 to 20 times, diafiltration with 5 volumes of 20 mM Histidine+150 mM NaCl, pH 5.5 was done. The diafiltered material was collected and rinsed with an equal volume of his-buffer after recirculating for another 5 minutes with permeate flow closed. The retentate was then collected and pooled with the previously collected retentate. To maintain the functionality of the membranes, the membranes were rinsed with PBS for 10 minutes; with 0.5 M NaOH for 40 minutes (after flushing 200 mL to waste through permeate and retentate); and finally with water to neutral pH in retentate and permeate. The membranes were then stored in 0.1 M NaOH solution in a refrigerator.

AEX column chromatography was used to reduce DNA content, using a 20 mL HiLoad 16/10 Sepharose HP column at a flow rate of 1.6 mL/min for equilibration with equilibration buffer (20 mM Histidine+150 mM NaCl, pH 5.5), and a flow rate of 3.2 mL/min for the loading, washing and stripping steps. Cleaning procedures were performed at 0.8 mL/min. A chart recorder was used to monitor the UV absorbance at 280 nm. A Gradifrac chromatography system (GE Healthcare) was used, which was sanitized before use. First ethanol (20% v/v present in the column as a storage buffer) was removed from the column using 5 column volumes of Super Q Water (low endotoxins). The equilibrium buffer was passed for 5 column volumes, followed by 5 column volumes of stripping buffer (20 mM Histidine+ 1000 mM NaCl, pH 5.5) to condition the column. The equilibration buffer was passed for 5 column volumes again to prepare the column for loading. Loading was performed at 3.2 mL/min, after which the column was washed with 5 column volumes of equilibration buffer, or until the base line was observed. The flowthrough was collected from the onset of the UV peak until the drop of UV peak to about 10% of the maximum peak height of the UV absorbance during the loading of the material. The column was then stripped by 5 column volumes of stripping buffer (20 mM Histidine+1000 mM NaCl, pH 5.5) and the peak was collected. This was followed by 5 column volumes of another stripping buffer (20 mM Histidine+2000 mM NaCl, pH 5.5) to remove any strongly bound proteins and nucleic acids and the peak was collected. The column was then cleaned with 1M NaOH to remove any precipitated proteins at 0.8 mL/min for 4 column volumes. The column was then rinsed with water at 0.8 ml/min to neutral pH (normally 4-5 column volumes). The column was then passed by 20% ethanol (4 column volumes at 0.8 mL/min) to remove any lipoproteins or lipids (2 column volumes). At this stage the column was either stored or rinsed with water (4 column volumes) to restart the cycle for a second batch.

Figure 11:
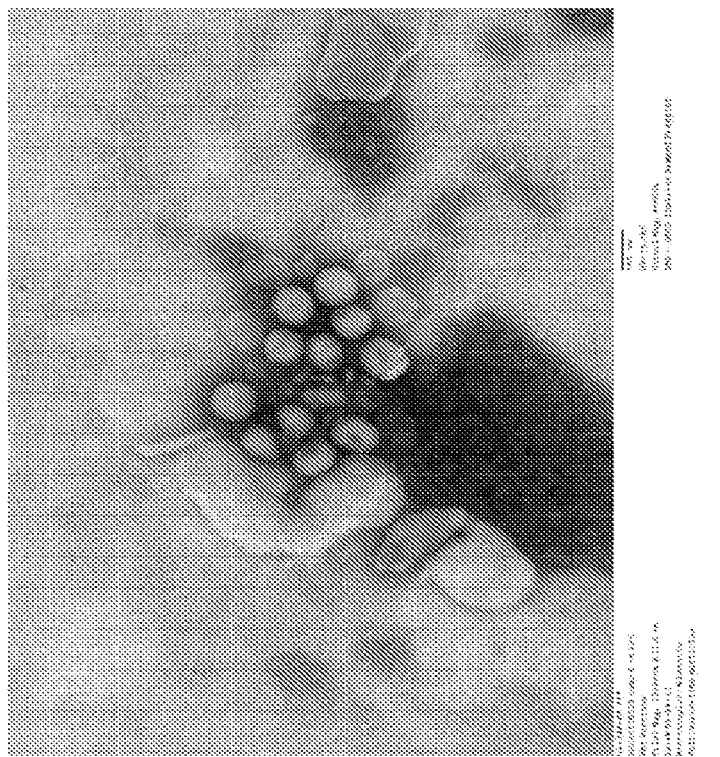
FIG. 11 shows negative-staining Electron Microscopy (EM) images of exemplary VLP compositions expressed in CHO cells purified by (A) Tangential Flow Filtration (TFF) or (B) Anion Exchange (AEX) Chromatography.
Figure 11:
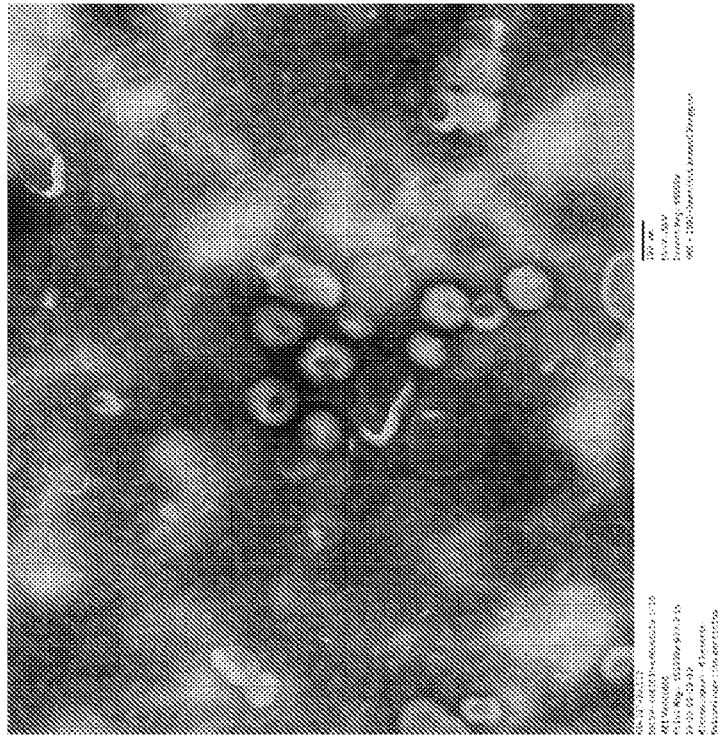

FIG. 11 depicts images of a purified gB-G monovalent VLP produced from CHO cells and then subjected to TFF (FIG. 11A) and AEX (FIG. 11B) purification methods followed by negative staining Electron Microscopy analytical methods. As shown in FIG. 11, intact gB-G monovalent VLPs are present after TFF (FIG. 11A) and AEX purification (FIG. 11B).

Example 7: Immunogenicity and Neutralization Activity of Purified VLPs in Rabbits Monovalent gB-G VLP compositions prepared as described in Example 6 were tested in New Zealand White rabbits 6-8 weeks old (minimum 6 animals per test group). Rabbits were immunized intramuscularly with 0.5 ml (50 µg gB content) of VLP compositions three times, once on day 0 (Prime) and once on day 56 (week 8 Boost) and once on day 168 (week 24 Boost). To assess humoral immune responses in rabbits, blood was collected from all rabbits in the study groups pre-1$^{st}$ immunization and then post-1$^{st}$ immunization at 2, 4, 6 and 8 weeks and post-2$^{nd}$ immunization at 10, 13, 16, 20 and 24 weeks from study start. The study design is summarized in Table 4.

TABLE 4

| Test Article # | Dose | Test Article Description | Immunization Schedule (weeks) |
|---|---|---|---|
| 1 | 50 µg gB content | gB-G monovalent VLPs (TFF & AEX purified) | 0, 8, 24 |

Figure 12:
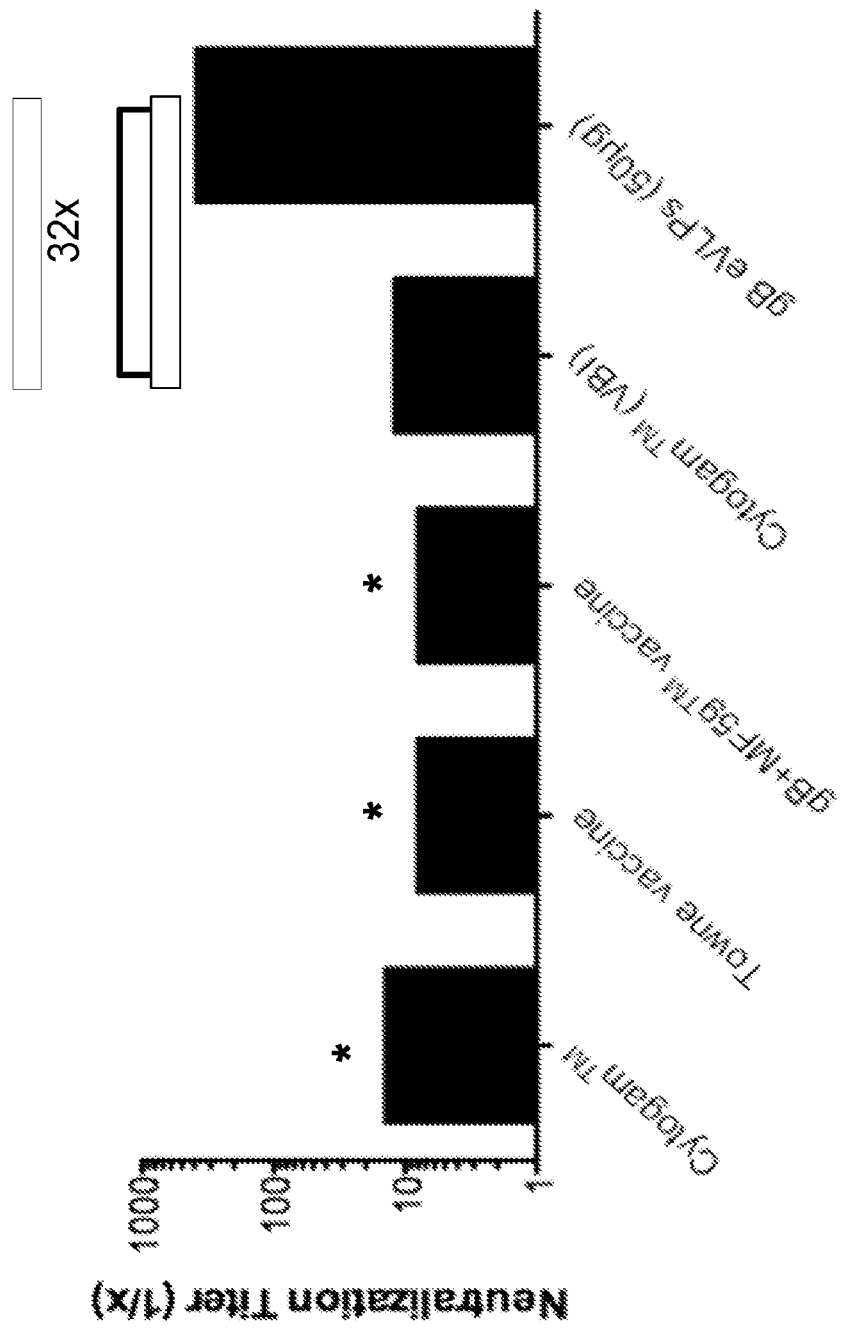
FIG. 12 shows neutralizing antibody titers in rabbits treated with exemplary VLP compositions expressed in CHO cells and purified by Tangential Flow Filtration (TFF) and Anion Exchange (AEX) Chromatography (assayed in human fibroblast cells).

FIG. 12 depicts the potent neutralization of fibroblast cell infection that was elicited by serum from rabbits immunized with TFF/AEX purified CHO cell-produced gB-G monovalent VLPs ("gB eVLPs" in FIG. 12). This neutralization was superior to that achieved with a positive control CMV hyperglobulin, Cytogam™. FIG. 12 also includes published neutralization titer data for Towne Vaccine and adjuvanted gB subunit vaccine (gB+MF59™) (Cui X et al. 2008 Vaccine 26:5760-5766).

Figure 13:
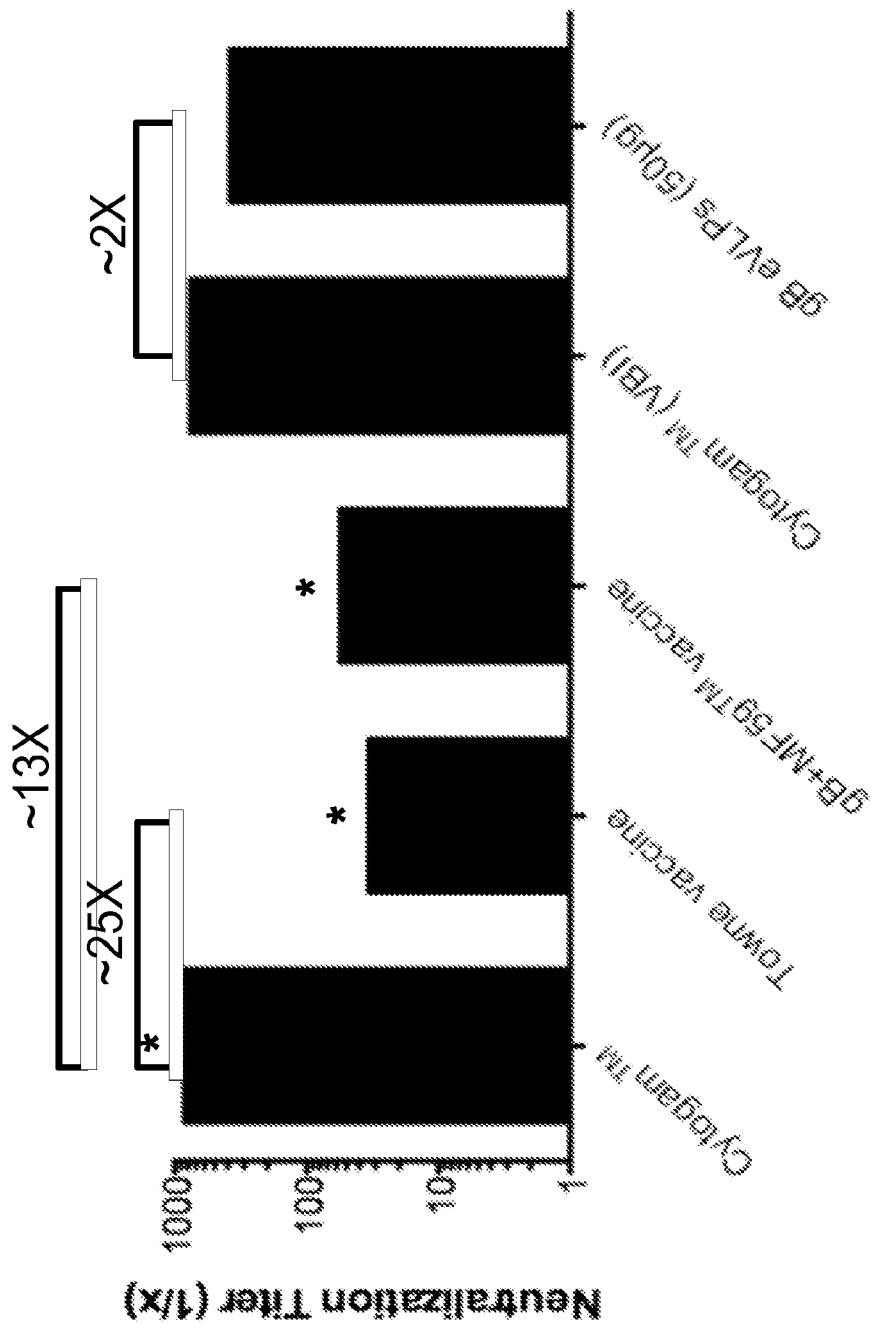
FIG. 13 shows neutralizing antibody titers in rabbits treated with exemplary VLP compositions expressed in CHO cells purified by Tangential Flow Filtration (TFF) and Anion Exchange (AEX) Chromatography (assayed in human epithelial cells).

FIG. 13 illustrates potent neutralization of epithelial cell infection that was elicited by serum from rabbits immunized with TFF/AEX purified CHO cell-produced gB-G monovalent VLPs ("gB eVLPs" in FIG. 13). This neutralization was comparable to that achieved with a positive control CMV hyperglobulin, Cytogam™. FIG. 13 also includes published neutralization titer data for Towne Vaccine and adjuvanted gB subunit vaccine (gB+MF59™) (Cui X et al. 2008 Vaccine 26:5760-5766).

Figure 14:
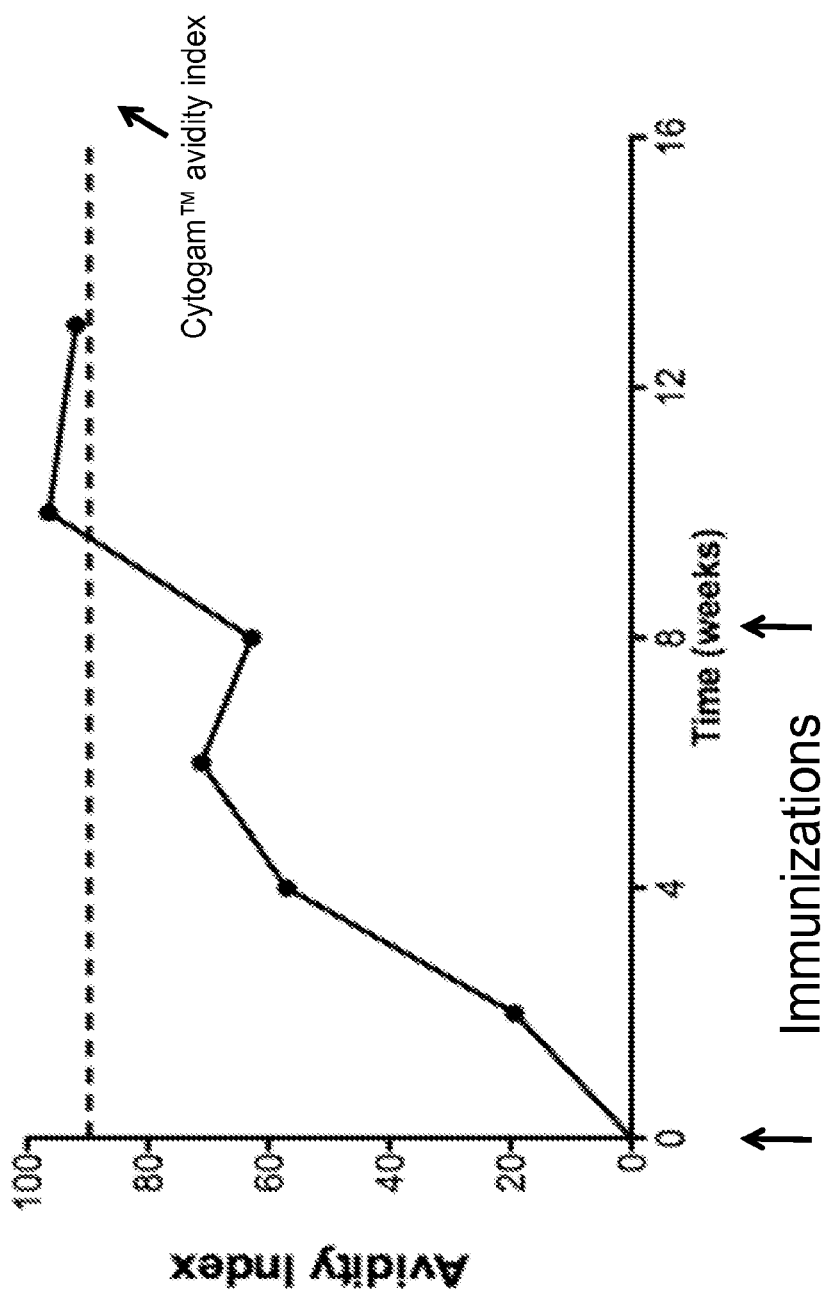
FIG. 14 shows the avidity index of antibodies produced in rabbits treated with exemplary VLP compositions expressed in CHO cells and purified by Tangential Flow Filtration (TFF) and Anion Exchange (AEX) Chromatography.

FIG. 14 depicts the avidity index of antibodies elicited in rabbits immunized with TFF/AEX purified CHO cell-produced gB-G monovalent VLP compositions. Pooled rabbit sera and a positive control CMV hyperglobulin, Cytogam™ were diluted 1:600,000 and tested against full length recombinant gB antigen by ELISA in the presence or absence of 5M urea. Antibody avidity was determined as previously described (Marshall BC and Adler S 2003 Viral Immunol 16:491-500). As shown in FIG. 14, a rapid induction of high avidity neutralizing antibodies was elicited in rabbits by immunization with TFF/AEX purified CHO cell-produced gB-G monovalent VLPs. Maximal antibody avidity was achieved after two gB-G VLP immunizations.

Other Embodiments

Other embodiments of the disclosure will be apparent to those skilled in the art from a consideration of the specification or practice of the disclosure disclosed herein. It is intended that the specification and examples be considered as exemplary only, with the true scope of the disclosure being indicated by the following claims. The contents of any reference that is referred to herein are hereby incorporated by reference in their entirety.

BRIEF DESCRIPTION OF SEQUENCE LISTING

SEQ ID NO:1 depicts an MMLV Gag Amino Acid Sequence.
SEQ ID NO:2 depicts an MMLV Gag Nucleotide Sequence.
SEQ ID NO:3 depicts a Codon Optimized MMLV Gag Nucleotide Sequence.
SEQ ID NO:4 depicts an MMLV Gag-CMV pp65 Amino Acid Sequence.
SEQ ID NO:5 depicts an MMLV Gag-CMV pp65 Nucleotide Sequence.
SEQ ID NO:6 depicts a Codon Optimized MMLV Gag-CMV pp65 Nucleotide Sequence.
SEQ ID NO:7 depicts an HCMV gB Amino Acid Sequence.
SEQ ID NO:8 depicts an HCMV gB Nucleotide Sequence.
SEQ ID NO:9 depicts a Codon Optimized HCMV gB Nucleotide Sequence.
SEQ ID NO:10 depicts an HCMV gB-G Amino Acid Sequence.
SEQ ID NO:11 depicts an HCMV gB-G Nucleotide Sequence.
SEQ ID NO:12 depicts a Codon Optimized HCMV gB-G Nucleotide Sequence.
SEQ ID NO:13 depicts an HCMV gH Amino Acid Sequence.
SEQ ID NO:14 depicts an HCMV gH Nucleotide Sequence.
SEQ ID NO:15 depicts a Codon Optimized HCMV gH Nucleotide Sequence.
SEQ ID NO:16 depicts an HCMV gH-G Amino Acid Sequence.
SEQ ID NO:17 depicts an HCMV gH-G Nucleotide Sequence.
SEQ ID NO:18 depicts a Codon Optimized HCMV gH-G Nucleotide Sequence.
SEQ ID NO:19 depicts a Propol II Expression Plasmid Nucleotide Sequence.
SEQ ID NO:20 depicts an HCMV gH-HCMV gB TM/CTD Nucleotide Sequence.
SEQ ID NO:21 depicts a Codon Optimized MMLV Gag Nucleotide Sequence.
SEQ ID NO:22 depicts a Codon Optimized MMLV Gag-CMV pp65 Nucleotide Sequence.

What is claimed is:

1. A virus-like particle (VLP) comprising:
   a first polypeptide comprising an amino acid sequence that is at least 95% identical to the amino acid sequence of SEQ ID NO:1; and
   a second polypeptide comprising the amino acid sequence of SEQ ID NO:10.

2. The VLP of claim 1, wherein the second polypeptide consists of the amino acid sequence of SEQ ID NO: 10.

3. The VLP of claim 1, wherein the first polypeptide comprises the amino acid sequence of SEQ ID NO: 1.

4. The VLP of claim 1, wherein the first polypeptide consists of the amino acid sequence of SEQ ID NO: 1.

5. A pharmaceutical composition comprising the VLP of claim 1 and a pharmaceutically acceptable carrier.

6. The pharmaceutical composition of claim 5, further comprising an adjuvant selected from the group consisting of a cytokine, a gel-type adjuvant, a microbial adjuvant, an oil-emulsion adjuvant, an emulsifier-based adjuvant, a particulate adjuvant, a synthetic adjuvant, a polymer adjuvant, and a combination thereof.

7. A method of producing a VLP, the method comprising:
   co-transfecting a host cell with a vector comprising a nucleotide sequence encoding a first polypeptide comprising an amino acid sequence that is at least 95% identical to the amino acid sequence of SEQ ID NO: 1 and a vector comprising a nucleotide sequence encoding a second polypeptide comprising the amino acid sequence of SEQ ID NO: 10; and
   cultivating the host cell in a suitable medium under conditions allowing the expression of the proteins encoded by the vectors.

8. A method of reducing frequency or severity or delaying onset of symptoms of HCMV infection in a subject, the method comprising administering to the subject the pharmaceutical composition of claim 5.

9. The VLP of claim 1, wherein the first polypeptide comprises an amino acid sequence that is at least 96% identical to the amino acid sequence of SEQ ID NO: 1.

10. The VLP of claim 1, wherein the first polypeptide comprises an amino acid sequence that is at least 97% identical to the amino acid sequence of SEQ ID NO: 1.

11. The VLP of claim 1, wherein the first polypeptide comprises an amino acid sequence that is at least 98% identical to the amino acid sequence of SEQ ID NO: 1.

12. The VLP of claim 1, wherein the first polypeptide comprises an amino acid sequence that is at least 99% identical to the amino acid sequence of SEQ ID NO: 1.

13. The method of claim 7, wherein the first polypeptide comprises an amino acid sequence that is at least 96% identical to the amino acid sequence of SEQ ID NO: 1.

14. The method of claim 7, wherein the first polypeptide comprises an amino acid sequence that is at least 97% identical to the amino acid sequence of SEQ ID NO: 1.

15. The method of claim 7, wherein the first polypeptide comprises an amino acid sequence that is at least 98% identical to the amino acid sequence of SEQ ID NO: 1.

16. The method of claim 7, wherein the first polypeptide comprises an amino acid sequence that is at least 99% identical to the amino acid sequence of SEQ ID NO: 1.

17. The method of claim 8, wherein the first polypeptide comprises an amino acid sequence that is at least 96% identical to the amino acid sequence of SEQ ID NO: 1.

18. The method of claim 8, wherein the first polypeptide comprises an amino acid sequence that is at least 97% identical to the amino acid sequence of SEQ ID NO: 1.

19. The method of claim 8, wherein the first polypeptide comprises an amino acid sequence that is at least 98% identical to the amino acid sequence of SEQ ID NO: 1.

20. The method of claim 8, wherein the first polypeptide comprises an amino acid sequence that is at least 99% identical to the amino acid sequence of SEQ ID NO: 1.

* * * * *